(12) United States Patent
Claremon et al.

(10) Patent No.: US 8,138,178 B2
(45) Date of Patent: Mar. 20, 2012

(54) CYCLIC INHIBITORS OF 11BETA-HYDROXYSTEROID DEHYDROGENASE 1

(75) Inventors: David A. Claremon, Maple Glen, PA (US); Linghang Zhuang, Chalfont, PA (US); Katerina Leftheris, Skillman, NJ (US); Colin M. Tice, Ambler, PA (US); Zhenrong Xu, Chalfont, PA (US); Yuanjie Ye, Ambler, PA (US); Suresh B. Singh, Kendall Park, NJ (US); Salvacion Cacatian, Blue Bell, PA (US); Wei Zhao, Eagleville, PA (US)

(73) Assignees: Vitae Pharmaceuticals, Inc., Fort Washington, PA (US); Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 12/741,522

(22) PCT Filed: Apr. 30, 2009

(86) PCT No.: PCT/US2009/002653
§ 371 (c)(1),
(2), (4) Date: Sep. 30, 2010

(87) PCT Pub. No.: WO2009/134400
PCT Pub. Date: Nov. 5, 2009

(65) Prior Publication Data
US 2011/0021512 A1    Jan. 27, 2011

Related U.S. Application Data

(60) Provisional application No. 61/137,148, filed on Jul. 25, 2008, provisional application No. 61/206,785, filed on Feb. 4, 2009, provisional application No. 61/049,650, filed on May 1, 2008.

(51) Int. Cl.
C07D 413/10    (2006.01)
C07D 413/14    (2006.01)
A61K 31/5355   (2006.01)

(52) U.S. Cl. ........................ 514/228.8; 544/96
(58) Field of Classification Search ............ 544/96; 514/228.8
See application file for complete search history.

(56) References Cited

U.S. PATENT DOCUMENTS

| | | |
|---|---|---|
| 3,341,538 A | 9/1967 | Block et al. |
| 3,681,349 A | 8/1972 | Schwan et al. |
| 4,136,145 A | 1/1979 | Fuchs et al. |
| 4,136,162 A | 1/1979 | Fuchs et al. |
| 5,089,506 A | 2/1992 | Gray et al. |
| 5,098,916 A | 3/1992 | Gray et al. |
| 5,215,992 A | 6/1993 | Gray et al. |
| 5,393,735 A | 2/1995 | Lange et al. |
| 5,410,081 A | 4/1995 | Kunde et al. |
| 5,432,175 A | 7/1995 | Piwinski et al. |
| 5,480,899 A | 1/1996 | Yano et al. |
| 5,502,027 A | 3/1996 | Lange et al. |
| 5,631,209 A | 5/1997 | Lange et al. |
| 5,776,959 A | 7/1998 | Covey et al. |
| 5,780,466 A | 7/1998 | Emonds-Alt et al. |
| 5,811,422 A | 9/1998 | Lam et al. |
| 5,856,273 A | 1/1999 | Kay et al. |
| 5,866,702 A | 2/1999 | Mackman et al. |
| 5,936,124 A | 8/1999 | Hilborn et al. |
| 5,981,436 A | 11/1999 | Drewes et al. |
| 6,066,666 A | 5/2000 | Covey et al. |
| 6,159,990 A | 12/2000 | Lagu et al. |
| 6,242,637 B1 | 6/2001 | Emonds-Alt et al. |
| 6,251,897 B1 | 6/2001 | Ina et al. |
| 6,559,163 B2 | 5/2003 | Cai et al. |
| 6,620,815 B1 | 9/2003 | Lagu et al. |
| 6,635,630 B2 | 10/2003 | Shih et al. |
| 6,638,935 B2 | 10/2003 | Emig et al. |
| 6,653,315 B2 | 11/2003 | Tulshian et al. |
| 6,706,722 B2 | 3/2004 | Emig et al. |
| 6,794,390 B2 | 9/2004 | Lum et al. |
| 6,841,671 B2 | 1/2005 | Noe et al. |
| 6,890,926 B2 | 5/2005 | Emig et al. |
| 6,900,201 B2 | 5/2005 | Noe et al. |

(Continued)

FOREIGN PATENT DOCUMENTS

DE    1801556 A1    5/1970

(Continued)

OTHER PUBLICATIONS

U.S. Appl. No. 12/670,205, filed Jul. 25, 2008, Vitae Pharmaceuticals, Inc.

(Continued)

*Primary Examiner* — Kahsay T Habte
(74) *Attorney, Agent, or Firm* — McCarter & English LLP

(57) ABSTRACT

Disclosed is a compound represented by Formula (Im¹)

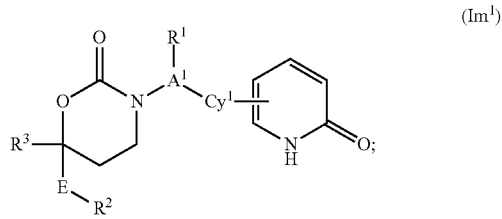

or a pharmaceutically acceptable salt, enantiomer or diastereomer thereof. Also disclosed are pharmaceutical compositions comprising the compound of Formula (Im¹) or a pharmaceutically acceptable salt, enantiomer or diastereomer thereof and methods of inhibiting 11β-HSD1 activity comprising the step of administering to a mammal in need of such treatment an effective amount of a compound of Formulas (Im¹), or a pharmaceutically acceptable salt, enantiomer or diastereomer thereof.

24 Claims, No Drawings

U.S. PATENT DOCUMENTS

| | | |
|---|---|---|
| 6,916,807 B2 | 7/2005 | Freeman-Cook et al. |
| 6,936,615 B2 | 8/2005 | Emig et al. |
| 7,026,310 B2 | 4/2006 | Emig et al. |
| 7,056,912 B2 | 6/2006 | Emig et al. |
| 7,132,551 B2 | 11/2006 | Aquila et al. |
| 7,186,844 B2 | 3/2007 | Ikemoto |
| 7,208,487 B2 | 4/2007 | Bergnes et al. |
| 7,253,198 B2 | 8/2007 | Demont et al. |
| 7,256,005 B2 | 8/2007 | Zitzmann et al. |
| 7,262,212 B2 | 8/2007 | Tsubouchi et al. |
| 7,294,637 B2 | 11/2007 | Aquila et al. |
| 7,417,045 B2 | 8/2008 | Anilkumar et al. |
| 7,566,718 B2 | 7/2009 | Wong et al. |
| 2001/0039286 A1 | 11/2001 | Dinnell et al. |
| 2006/0063819 A1 | 3/2006 | Lanter et al. |
| 2006/0089349 A1 | 4/2006 | Gundertofte et al. |
| 2006/0116382 A1 | 6/2006 | Yao et al. |
| 2006/0194780 A1 | 8/2006 | Nargund et al. |
| 2006/0276457 A1 | 12/2006 | Yu et al. |
| 2006/0276479 A1 | 12/2006 | Kim et al. |
| 2006/0276480 A1 | 12/2006 | Wong et al. |
| 2007/0021611 A1 | 1/2007 | McGuinness et al. |
| 2007/0054919 A1 | 3/2007 | Rosenblum et al. |
| 2007/0082913 A1 | 4/2007 | Kim et al. |
| 2007/0129345 A1 | 6/2007 | Zhuo et al. |
| 2007/0208001 A1 | 9/2007 | Zhuo et al. |
| 2007/0219182 A1 | 9/2007 | Lubisch et al. |
| 2007/0254875 A1 | 11/2007 | Zhi et al. |
| 2007/0254901 A1 | 11/2007 | Bilodeau et al. |
| 2007/0259891 A1 | 11/2007 | Strobel et al. |
| 2008/0004300 A1 | 1/2008 | Strobel et al. |
| 2008/0021029 A1 | 1/2008 | Strobel et al. |
| 2008/0045518 A1 | 2/2008 | Commons et al. |
| 2008/0045578 A1 | 2/2008 | Commons et al. |
| 2008/0045579 A1 | 2/2008 | Commons et al. |
| 2008/0124384 A1 | 5/2008 | Blum |
| 2008/0188482 A1 | 8/2008 | Rice et al. |
| 2008/0249087 A1 | 10/2008 | Rotstein et al. |
| 2008/0269295 A1 | 10/2008 | Haurand et al. |
| 2008/0280933 A1 | 11/2008 | Efremov et al. |
| 2008/0312271 A1 | 12/2008 | Efremov et al. |
| 2009/0018054 A1 | 1/2009 | Ali et al. |
| 2009/0264650 A1 | 10/2009 | Cho et al. |
| 2010/0041637 A1 | 2/2010 | Claremon et al. |
| 2010/0197675 A1 | 8/2010 | Claremon et al. |
| 2010/0256363 A1 | 10/2010 | Xu |
| 2010/0324045 A1 | 12/2010 | Claremon et al. |
| 2011/0009402 A1 | 1/2011 | Himmelsbach |
| 2011/0015157 A1 | 1/2011 | Claremon et al. |
| 2011/0021512 A1 | 1/2011 | Claremon et al. |
| 2011/0028445 A1 | 2/2011 | Eckhardt et al. |
| 2011/0071139 A1 | 3/2011 | Claremon et al. |
| 2011/0098320 A1 | 4/2011 | Claremon et al. |
| 2011/0105504 A1 | 5/2011 | Claremon et al. |
| 2011/0112082 A1 | 5/2011 | Claremon et al. |
| 2011/0124635 A1 | 5/2011 | Claremon et al. |
| 2011/0190262 A1 | 8/2011 | Himmelsbach et al. |
| 2011/0224242 A1 | 9/2011 | Giethlen et al. |

FOREIGN PATENT DOCUMENTS

| | | |
|---|---|---|
| DE | 19918725 A1 | 10/2000 |
| DE | 19929348 A1 | 12/2000 |
| DE | 100 34 623 | 1/2002 |
| DE | 10034623 | 1/2002 |
| EP | 0415642 A1 | 3/1991 |
| EP | 0454444 A1 | 10/1991 |
| EP | 0640594 A1 | 3/1995 |
| EP | 0645387 A | 3/1995 |
| EP | 0471591 B1 | 5/1995 |
| EP | 0928789 A1 | 7/1999 |
| EP | 1156049 A | 11/2001 |
| EP | 1270724 A2 | 1/2003 |
| EP | 1852425 A | 11/2007 |
| EP | 1864971 A | 12/2007 |
| EP | 1935420 | 6/2008 |
| GB | 1077711 | 8/1967 |
| JP | 6092945 A | 4/1994 |
| JP | 7157681 | 6/1995 |
| JP | 2009110842 A2 | 4/1997 |
| JP | 09151179 | 6/1997 |
| JP | 2002179572 A2 | 6/2002 |
| JP | 2003096058 | 4/2003 |
| JP | 2003300884 A2 | 10/2003 |
| JP | 2005-206503 A | 8/2005 |
| JP | 2005239670 | 9/2005 |
| JP | 2005272321 A | 10/2005 |
| JP | 2007 140188 | 6/2007 |
| JP | 2007 254409 | 10/2007 |
| WO | WO 92/07838 | 5/1992 |
| WO | WO 93/07128 | 4/1993 |
| WO | WO 93/13103 | 7/1993 |
| WO | WO 95/31440 | 11/1995 |
| WO | WO 96/14297 A | 5/1996 |
| WO | WO 96/23787 | 8/1996 |
| WO | WO 97/36605 | 10/1997 |
| WO | WO 98/57940 | 12/1998 |
| WO | WO 99/05125 | 2/1999 |
| WO | WO 99/06395 | 2/1999 |
| WO | WO 01/00595 A1 | 1/2001 |
| WO | WO 01/44200 A2 | 6/2001 |
| WO | WO 01/55063 | 8/2001 |
| WO | WO 02/06244 A1 | 1/2002 |
| WO | WO 02/06277 A1 | 1/2002 |
| WO | WO 02/22572 A2 | 3/2002 |
| WO | WO 03/043988 A1 | 5/2003 |
| WO | WO 03/057673 A | 7/2003 |
| WO | WO 03/093261 A1 | 11/2003 |
| WO | WO 2004/004722 A1 | 1/2004 |
| WO | WO 2004/009559 A2 | 1/2004 |
| WO | WO 2004/014859 A2 | 2/2004 |
| WO | WO 2004/046137 A | 6/2004 |
| WO | WO 2004/094375 A | 11/2004 |
| WO | WO 2005/000845 | 1/2005 |
| WO | WO 2005/086700 A2 | 9/2005 |
| WO | WO 2005/108361 | 11/2005 |
| WO | WO 2005/108361 A | 11/2005 |
| WO | WO 2005/113525 A1 | 12/2005 |
| WO | WO 2006/003494 A2 | 1/2006 |
| WO | WO 2006/014357 A | 2/2006 |
| WO | WO 2006/024627 A2 | 3/2006 |
| WO | WO 2006/024628 A | 3/2006 |
| WO | WO 2006/031715 A | 3/2006 |
| WO | WO 2006/040329 | 4/2006 |
| WO | WO 2006/044174 | 4/2006 |
| WO | WO 2006/049952 A | 5/2006 |
| WO | WO 2006/066924 A2 | 6/2006 |
| WO | WO 2006/066948 A1 | 6/2006 |
| WO | WO 2006/090792 A1 | 8/2006 |
| WO | WO 2006/104280 A | 10/2006 |
| WO | WO 2006/109056 A1 | 10/2006 |
| WO | WO 2007/008529 A2 | 1/2007 |
| WO | WO 2007/048595 A1 | 5/2007 |
| WO | WO 2007/051810 | 5/2007 |
| WO | WO 2007/061661 A2 | 5/2007 |
| WO | WO 2007/068330 A1 | 6/2007 |
| WO | WO 2007/079186 A2 | 7/2007 |
| WO | WO 2007/081569 A2 | 7/2007 |
| WO | WO 2007/081570 A | 7/2007 |
| WO | WO 2007/081571 A2 | 7/2007 |
| WO | WO 2007/084314 A2 | 7/2007 |
| WO | WO 2007/109456 A2 | 9/2007 |
| WO | WO 2007/118185 A2 | 10/2007 |
| WO | WO 2007/124254 | 11/2007 |
| WO | WO 2007/124329 A1 | 11/2007 |
| WO | WO 2007/124337 | 11/2007 |
| WO | WO 2007/127693 A | 11/2007 |
| WO | WO 2008/000951 | 1/2008 |
| WO | WO 2008/031227 A1 | 3/2008 |
| WO | WO 2008/036715 A1 | 3/2008 |
| WO | WO 2008/046758 A | 4/2008 |
| WO | WO 2008/059948 A | 5/2008 |
| WO | WO 2008/106128 | 9/2008 |
| WO | WO 2008/106128 A | 9/2008 |
| WO | WO 2008/118332 A2 | 10/2008 |
| WO | WO 2009/017664 | 2/2009 |
| WO | WO 2009/017664 A1 | 2/2009 |

| WO | WO 2009/017671 | 2/2009 |
| WO | WO 2009/061498 | 5/2009 |
| WO | WO 2009/063061 | 5/2009 |
| WO | WO 2009/075835 | 6/2009 |
| WO | WO 2009/088997 | 7/2009 |
| WO | WO 2009/094169 A | 7/2009 |
| WO | WO 2009/100872 | 8/2009 |
| WO | WO 2009/102428 | 8/2009 |
| WO | WO 2009/102460 | 8/2009 |
| WO | WO 2009/117109 | 9/2009 |
| WO | WO 2009/134384 | 11/2009 |
| WO | WO 2009/134387 | 11/2009 |
| WO | WO 2009/134392 | 11/2009 |
| WO | WO 2009/134400 | 11/2009 |
| WO | WO 2009/138386 | 11/2009 |
| WO | WO 2010/010149 | 1/2010 |
| WO | WO 2010/010150 A1 | 1/2010 |
| WO | WO 2010/010157 | 1/2010 |
| WO | WO 2010/010174 | 1/2010 |
| WO | WO 2010/011314 | 1/2010 |
| WO | WO 2010/023161 | 3/2010 |
| WO | WO 2010/046445 | 4/2010 |
| WO | WO 2010/091067 | 8/2010 |
| WO | WO 2010/127237 | 11/2010 |

OTHER PUBLICATIONS

U.S. Appl. No. 12/670,209, filed Jul. 25, 2008, Vitae Pharmaceuticals, Inc.
U.S. Appl. No. 12/990,309, filed Apr. 30, 2009, Vitae Pharmaceuticals, Inc.
U.S. Appl. No. 12/990,296, filed Apr. 30, 2009, Vitae Pharmaceuticals, Inc.
U.S. Appl. No. 12/745,663, filed Nov. 7, 2008, Vitae Pharmaceuticals, Inc.
U.S. Appl. No. 12/811,577, filed Jan. 7, 2009, Vitae Pharmaceuticals, Inc.
U.S. Appl. No. 12/747,391, filed Dec. 10, 2008, Vitae Pharmaceuticals, Inc.
U.S. Appl. No. 12/863,634, filed Jan. 21, 2009, Vitae Pharmaceuticals, Inc.
U.S. Appl. No. 12/867,374, filed Feb. 13, 2009, Vitae Pharmaceuticals, Inc.
U.S. Appl. No. 12/933,027, filed Mar. 18, 2009, Vitae Pharmaceuticals, Inc.
U.S. Appl. No. 12/741,532, filed Sep. 27, 2010, Vitae Pharmaceuticals, Inc.
U.S. Appl. No. 12/771,499, filed Apr. 30, 2010, Vitae Pharmaceuticals, Inc.
MS Bitar, "Glucocorticoid Dynamics and Impaired Wound Healing in Diabetes Mellitus", Am J Pathol., 1998, vol. 152, pp. 547-554.
MS Bitar, et al., "Heat-Shock Protein 72/73 and Impaired Wound Healing in Diabetic and Hypercortisolemic States", Sugery, 1999, vol. 125, pp. 594-601.
MS Bitar, et al., "Glucocorticoid-Dependent Impairment of Wound Healing in Experimental Diabetes: Amelioration by Adrenalectomy and RU 486", J Surg Res., 1999, vol. 82, pp. 234-243.
MS Bitar, "Insulin and Glucocorticoid-Dependent Suppression of the IGF-I System in Diabetic Wounds", Sugery, 2000, vol. 127, pp. 687-695.
Database Caplus [Online] Chemical Abstracts Service, Maillard et al., "Spiroheterocyclic Cycloalkane Compounds. II. Synthesis of 6-Substituted-Tetrahydro-2H-1,3-Oxazine-2-Ones", XP002516521, retrieved from STN Database accession No. 1969:68280 CAS RN: 20057-45-8 abstract, (1969).
Chimica Therapeutica, 1968, vol. 3(5), pp. 321-324, 1968.
Database Caplus [Online] Chemical Abstracts Service, Slyusarenko et al., "Synthesis based on Thionylamides.IV. 2-Alkoxy-5,6-Dihydro-1,3-Oxazines", XP002516522, retrieved from STN Database accession No. 1978:563520 CAS RN: 67868-26-2 abstract, (1978).
Zhurnal Organicheskoi Khimii, 1978, vol. 14(5), pp. 1092-1094.
Database CA [Online], Chemical Abstracts Service, Fukushima et al., "Preparation of Imidazolidinone Derivatives as 11.beta.-HSD1 Inhibitors", Oct. 6, 2009, XP 002531878.

"Khimiia Elementoorganicheskikh Soedineni", 1982, vol. 1982 pp. 22-26.
"Zhurnal Organicheskoi Khimii", 1982, vol. 18, PT 11, p. 2468.
Chemical Abstracts, vol. 98, No. 11, 1983, Columbus, Ohio, US; abstract No. 89280k, Lapkin, et al., "Synthesis of 1,3-oxazin-2,4-diones", p. 552 col. 1, XP002504063 abstract.
Chemical Abstracts, vol. 99, No. 23, 1983, Columbus, Ohio, US; abstract No. 195067b, Saitkulova, et al., "Synthesis involving bromozinc alcoholates of carboxylic acid esters", p. 764 col. 1, XP002504064 abstract.
Goubet, et al., "Conversion of a Thiohydantoin to the Corresponding Hydantoin via a Ring-Opening/Ring Closure Mechanism", Tetrahedron Letters, Elsevier, Amsterdam, 1996, vol. 37, pp. 7727-7730.
Ho-Jane Shue et al., "Cyclic Urea Derivatives as Potent NK1 Selective Antagonists", Bioorganic & Medicinal Chemistry Letters, 2005, vol. 15, pp. 3896-3899.
Ho-Jane Shue et al., "Cyclic Urea Derivatives as Potent NK1 Selective Antagonists. Part II: Effects of Fluoro and Benzylic Methyl Substitutions", Bioorganic & Medicinal Chemistry Letters, 2006, vol. 16, pp. 1065-1069.
Kashima, et al., "Preparation of N-Aryl-2,4-diaminopentanes by the Ring Opening Reaction of 1-Aryl-3,4,5,6-tetrahydro-2-(1H)pyrimidinones", Journal of Heterocyclic Chemistry, vol. 18, 1981, pp. 1595-1596, XP002517485.
Lohray et al., "Enantiospecific Synthesis of 6-Substituted N-Aryl-1,3-Oxazin-2-Ones", Tetrahedron Letters, 1998, vol. 39, pp. 6555-6556.
Malgorzata Wamil and Jonathan R. Seckl, "Inhibition of 11β-hydroxysteroid Dehydrogenase Type 1 as a Promising Therapeutic Target", Drug Discovery Today, 2007, vol. 12, pp. 504-520.
Muehlstadt, et al., "Cyclisation reactions of beta, gamma-unsaturated derivatives of carbonic acid. IX.", Journal Fuer Praktische Chemie, vol. 328, 1986, pp. 163-172, XP002504062 p. 164, compound 4j.
Schoellkopf, et al., "Umsetzungen Alphametalliertier Isocyanide Mit Einigen 1,3-Dipolen//Reactions of Alpha-Metalated Osicyanides with Some 1,3-Dipoles", Liebigs Annalen Der Chemie, Verlag Chemie GMBH. Weinheim, DE, 1980, vol. 4, pp. 600-610.
Suga, Seiji et al., ""N-Acyliminium Ion Pool" as a Heterodiene in [4+2] Cycloaddition Reaction", Organic Letters, 2003, vol. 5, pp. 945-947.
Suga, Seiji et al., "Cycloaddition of "N-Acyliminium Ion Pools" with Carbon-Carbon Multiple Bonds", Bulletin of the Chemical Society of Japan, Chemical Society of Japan, 2005, vol. 78, pp. 1206-1217.
Tamaru et al., "Urea as the Most Reactive and Versatile Nitrogen Nucleophile for the Palladium(2+)- Catalyzed Cyclization of Unsaturated Amines", Journal of the American Chemical Society, 1988, vol. 110, pp. 3994-4002.
Yoshida, Masaaki et al., "Selective synthesis of five- and six-membered cyclic carbamates by the reaction of 2-(1-haloalkyl)oxiranes with carbon dioxide and aliphatic primary amines", Heterocycles, Elsevier Science Ltd., 1993, vol. 35 (2), pp. 623-626.
Yoshinao Tamaru, "Palladium(2+)-Catalyzed Intramolecular Aminocarbonylation of 3-Hydroxy-4-pentenylamines and 4-Hydroxy-5-hexenylamines", J. Org. Chem., 1988, pp. 5731-5741.
International Search Report & Written Opinion—(PCT/US2008/009017) Date of Mailing Apr. 12, 2008.
International Search Report & Written Opinion—(PCT/US2008/002517) Date of Mailing Dec. 29, 2008.
International Search Report—(PCT/US2009/002653) Date of Mailing Jul. 3, 2009.
International Search Report—(PCT/US2009/002641) Date of Mailing Jul. 3, 2009.
International Search Report—(PCT/US2009/002629) Date of Mailing Jul. 3, 2009.
International Search Report—(PCT/US2009/002633) Date of Mailing Jul. 3, 2009.
International Search Report—(PCT/US2008/012618) Date of Mailing Dec. 3, 2009.
International Search Report—(PCT/US2009/000057) Date of Mailing Mar. 25, 2009.
International Search Report—(PCT/US2008/013539) Date of Mailing Mar. 19, 2009.

International Search Report—(PCT/US2009/000853) Date of Mailing Sep. 2, 2009.
International Search Report—(PCT/US2009/000421) Date of Mailing Apr. 15, 2009.
International Search Report—(PCT/US2009/000908) Date of Mailing Sep. 17, 2009.
International Search Report—(PCT/US2009/001712) Date of Mailing Jul. 14, 2009.
Database File Registry [Online], Chemical Abstracts Service, Columbus, Ohio, US, 2007, Database accession No. 958700-63-5, Abstract, XP002556893.
Database File Registry [Online], Chemical Abstracts Service, Columbus, Ohio, US, 2007, Database accession No. 958696-39-4, Abstract, XP002556894.
Database File Registry [Online], Chemical Abstracts Service, Columbus, Ohio, US, 2007, Database accession No. 958696-32-7, Abstract, XP002556895.
Database File Registry [Online], Chemical Abstracts Service, Columbus, Ohio, US, 2007, Database accession No. 958629-39-5, Abstract, XP002556896.
Database File Registry [Online], Chemical Abstracts Service, Columbus, Ohio, US, 2007, Database accession No. 958629-22-6, Abstract, XP002556897.
Database File Registry [Online], Chemical Abstracts Service, Columbus, Ohio, US, 2007, Database accession No. 958629-14-6, Abstract, XP002556898.
Database File Registry [Online], Chemical Abstracts Service, Columbus, Ohio, US, 2007, Database accession No. 958625-83-7, Abstract, XP002556899.
Database File Registry [Online], Chemical Abstracts Service, Columbus, Ohio, US, 2007, Database accession No. 958599-31-0, Abstract, XP002556900.
International Search Report—(PCT/US2010/023021) Date of Mailing Aug. 5, 2010.
International Search Report and Written Opinion—(PCT/US2008/009048) Date of Mailing Dec. 4, 2008.
International Search Report—(PCT/US2009/004261) Date of Mailing Oct. 21, 2009.
Shibata, et al., "Cycloaddition of Oxetanes with Heterocumulenes Catalysed by Organotin Iodine-Lewis Base Complex", Journal of Heterocyclic Chemistry, vol. 24, 1987, pp. 361-363.
Database CA [Online], Chemical Abstracts Service, Fukushima et al., "Preparation of Imidazolidinone Derivatives as 11.beta.-HSD1 Inhibitors", 2007, XP 002531878.
Gavezzotti, "Are Crystal Structures Predictable?", Accounts of Chemical Research, 1994, vol. 27, pp. 309-314.
Vippagunta, et al., "Crystalline Solids", Advanced Drug Deliver Reviews, 2001, vol. 48, pp. 3-26.
Office Action for U.S. Appl. No. 12/741,532, date of mailing Dec. 15, 2010.
Office Action for U.S. Appl. No. 12/771,499, date of mailing Dec. 21, 2010.
CA 154: 284276, (Mar. 17, 2011).
CA 1267843-31-1, (Aug. 10, 2009).
Sullivan, John M. and Efner, Howard F., "The Preparation of 6-Aryltetrahydro-1,3-oxazin-2-ones and Their Hydrolysis to 3-Substituted Propylamines," *The Journal of Organic Chemistry*, 33 (5): 2134-2136 (1968).
Wolfling, Janos et al., "Neighboring Group Participation Part 15. Stereoselective.Synthesis of Some Steroidal Tetrahydrooxaziin-2-ones, as Novel Presumed Inhibitors of Human 5α-Reductase," *Steroids*, 69: 451-460 (2004).
U.S. Appl. No. 12/747,391, filed Nov. 11, 2010, Claremon et al.
U.S. Appl. No. 12/990,296, filed Mar. 1, 2011, Claremon et al.
U.S. Appl. No. 12/990,306, filed Jun. 6, 2011, Claremon et al.
U.S. Appl. No. 12/991,722, filed Jan. 5, 2011, Peters, Stefan.
U.S. Appl. No. 13/054,949, filed Feb. 23, 2011, Eckhardt et al.
U.S. Appl. No. 13/054,954, filed Jan. 20, 2011, Himmelsbach et al.
U.S. Appl. No. 13/059,233, filed Feb. 16, 2011, Eckhardt et al.
U.S. Appl. No. 13/124,259, filed May 17, 2011, Eckhardt et al.
U.S. Appl. No. 13/147,637, filed Aug. 3, 2011, Claremon et al.
U.S. Appl. No. 13/054,959, filed Feb. 23, 2011, Fandrick et al.

CYCLIC INHIBITORS OF 11BETA-HYDROXYSTEROID DEHYDROGENASE 1

RELATED APPLICATIONS

This application is the United States National Application of International Application No. PCT/US2009/002653, filed Apr. 30, 2009, which claims the benefit of U.S. Provisional Application No. 61/206,785, filed on Feb. 4, 2009, U.S. Provisional Application No. 61/137,148, filed on Jul. 25, 2008, and U.S. Provisional Application No. 61/049,650, filed May 1, 2008. International Application No. PCT/US2009/002653 also claims priority to International Application No. PCT/2008/009017, which designated the United States and was filed on Jul. 25, 2008, published in English, which claims the benefit of U.S. Provisional Application No. 61/049,650, filed May 1, 2008.

The entire teachings of the above applications are incorporated herein by reference.

FIELD OF THE INVENTION

The present invention relates to inhibitors of 11β-hydroxysteroid dehydrogenase type 1 (11β-HSD1), pharmaceutical compositions thereof and methods of using the same.

BACKGROUND OF THE INVENTION

Glucocorticoids, such as cortisol (hydrocortisone), are steroid hormones that regulate fat metabolism, function and distribution, and play a role in carbohydrate, protein and fat metabolism. Glucocorticoids are also known to have physiological effects on development, neurobiology, inflammation, blood pressure, metabolism, and programmed cell death. Cortisol and other corticosteroids bind both the glucocorticoid receptor (GR) and the mineralocorticoid receptor (MR), which are members of the nuclear hormone receptor superfamily and have been shown to mediate cortisol function in vivo. These receptors directly modulate transcription via DNA-binding zinc finger domains and transcriptional activation domains.

Until recently, the major determinants of glucocorticoid action were attributed to three primary factors: (1) circulating levels of glucocorticoid (driven primarily by the hypothalamic-pituitary-adrenal (HPA) axis); (2) protein binding of glucocorticoids in circulation; and (3) intracellular receptor density inside target tissues. Recently, a fourth determinant of glucocorticoid function has been identified: tissue-specific pre-receptor metabolism by glucocorticoid-activating and -inactivating enzymes. These 11β-hydroxysteroid dehydrogenase (11β-HSD) pre-receptor control enzymes modulate activation of GR and MR by regulation of glucocorticoid hormones. To date, two distinct isozymes of 11-beta-HSD have been cloned and characterized: 11β-HSD1 (also known as 11-beta-HSD type 1, 11betaHSD1, HSD11B1, HDL, and HSD11L) and 11β-HSD2. 11β-HSD1 is a bi-directional oxidoreductase that regenerates active cortisol from inactive 11-keto forms, whereas 11β-HSD2 is a unidirectional dehydrogenase that inactivates biologically active cortisol by converting it into cortisone.

The two isoforms are expressed in a distinct tissue-specific fashion, consistent with the differences in their physiological roles. 11β-HSD1 is widely distributed in rat and human tissues; expression of the enzyme and corresponding mRNA have been detected in human liver, adipose tissue, lung, testis, bone and ciliary epithelium. In adipose tissue, increased cortisol concentrations stimulate adipocyte differentiation and may play a role in promoting visceral obesity. In the eye, 11β-HSD1 may regulate intraocular pressure and may contribute to glaucoma; some data suggest that inhibition of 11β-HSD1 may cause a drop in intraocular pressure in patients with intraocular hypertension (Kotelevstev et al. (1997), Proc. Natl. Acad. Sci. USA 94(26):14924-9). Although 11β-HSD1 catalyzes both 11-beta-dehydrogenation and the reverse 11-oxoreduction reaction, 11β-HSD1 acts predominantly as a NADPH-dependent oxoreductase in intact cells and tissues, catalyzing the formation of active cortisol from inert cortisone (Low et al. (1994) J. Mol. Endocrin. 13: 167-174). In contradistinction, 11β-HSD2 expression is found mainly in mineralocorticoid target tissues such as kidney (cortex and medulla), placenta, sigmoid and rectal colon, salivary gland and colonic epithelial cell lines. 11β-HSD2 acts as an NAD-dependent dehydrogenase catalyzing the inactivation of cortisol to cortisone (Albiston et al. (1994) Mol. Cell. Endocrin. 105: R11-R17), and has been shown to protect the MR from glucocorticoid excess (e.g., high levels of receptor-active cortisol) (Blum, et al. (2003) Prog. Nucl. Acid Res. Mol. Biol. 75:173-216).

Mutations in either the 11β-HSD1 or the 11β-HSD2 genes result in human pathology. For example, individuals with mutations in 11β-HSD2 are deficient in this cortisol-inactivation activity and, as a result, present with a syndrome of apparent mineralocorticoid excess (also referred to as 'SAME') characterized by hypertension, hypokalemia, and sodium retention (Edwards et al. (1988) Lancet 2: 986-989; Wilson et al. (1998) Proc. Natl. Acad. Sci. 95: 10200-10205). Similarly, mutations in 11β-HSD1 and in the gene encoding a co-localized NADPH-generating enzyme, hexose 6-phosphate dehydrogenase (H6PD), can result in cortisone reductase deficiency (CRD); these individuals present with ACTH-mediated androgen excess (hirsutism, menstrual irregularity, hyperandrogenism), a phenotype resembling polycystic ovary syndrome (PCOS) (Draper et al. (2003) Nat. Genet. 34: 434-439).

Notably, disruption of homeostasis in the HPA axis by either deficient or excess secretion or action results in Cushing's syndrome or Addison's disease, respectively (Miller and Chrousos (2001) Endocrinology and Metabolism, eds. Felig and Frohman (McGraw-Hill, New York), 4$^{th}$ Ed.: 387-524). Patients with Cushing's syndrome or receiving glucocorticoid therapy develop reversible visceral fat obesity. The phenotype of Cushing's syndrome patients closely resembles that of Reaven's metabolic syndrome (also known as Syndrome X or insulin resistance syndrome), the symptoms of which include visceral obesity, glucose intolerance, insulin resistance, hypertension, type 2 diabetes and hyperlipidemia (Reaven (1993) Ann. Rev. Med. 44: 121-131). Although the role of glucocorticoids in human obesity is not fully characterized, there is mounting evidence that 11β-HSD1 activity plays an important role in obesity and metabolic syndrome (Bujaiska et al. (1997) Lancet 349: 1210-1213); (Livingstone et al. (2000) Endocrinology 131: 560-563; Rask et al. (2001) J. Clin. Endocrinol. Metab. 86: 1418-1421; Lindsay et al. (2003) J. Clin. Endocrinol. Metab. 88: 2738-2744; Wake et al. (2003) J. Clin. Endocrinol. Metab. 88: 3983-3988).

Data from studies in mouse transgenic models supports the hypothesis that adipocyte 11β-HSD1 activity plays a central role in visceral obesity and metabolic syndrome (Alberts et al. (2002) Diabetologia. 45(11): 1526-32). Over-expression in adipose tissue of 11β-HSD1 under the control of the aP2 promoter in transgenic mice produced a phenotype remarkably similar to human metabolic syndrome (Masuzaki et al. (2001) Science 294: 2166-2170; Masuzaki et al. (2003) J.

Clinical Invest. 112: 83-90). Moreover, the increased activity of 11β-HSD1 in these mice is very similar to that observed in human obesity (Rask et al. (2001) J. Clin. Endocrinol. Metab. 86: 1418-1421). In addition, data from studies with 11β-HSD1-deficient mice produced by homologous recombination demonstrate that the loss of 11β-HSD1 leads to an increase in insulin sensitivity and glucose tolerance due to a tissue-specific deficiency in active glucocorticoid levels (Kotelevstev et al. (1997) Proc. Natl. Acad. Sci. 94: 14924-14929; Morton et al. (2001) J. Biol. Chem. 276: 41293-41300; Morton et al. (2004) Diabetes 53: 931-938).

The published data supports the hypothesis that increased expression of 11β-HSD1 contributes to increased local conversion of cortisone to cortisol in adipose tissue and hence that 11β-HSD1 plays a role in the pathogenesis of central obesity and the appearance of the metabolic syndrome in humans (Engeli, et al., (2004) Obes. Res. 12: 9-17). Therefore, 11β-HSD1 is a promising pharmaceutical target for the treatment of the metabolic syndrome (Masuzaki, et al., (2003) Curr. Drug Targets Immune Endocr. Metabol. Disord. 3: 255-62). Furthermore, inhibition of 11β-HSD1 activity may prove beneficial in treating numerous glucocorticoid-related disorders. For example, 11β-HSD1 inhibitors could be effective in combating obesity and/or aspects of the metabolic syndrome cluster, including glucose intolerance, insulin resistance, hyperglycemia, hypertension, and/or hyperlipidemia (Kotelevstev et al. (1997) Proc. Natl. Acad. Sci. 94: 14924-14929; Morton et al. (2001) J. Biol. Chem. 276: 41293-41300; Morton et al. (2004) Diabetes 53: 931-938). In addition, inhibition of 11β-HSD1 activity may have beneficial effects on the pancreas, including the enhancement of glucose-stimulated insulin release (Billaudel and Sutter (1979) Horm. Metab. Res. 11: 555-560; Ogawa et al. (1992) J. Clin. Invest. 90: 497-504; Davani et al. (2000) J. Biol. Chem. 275: 34841-34844).

Furthermore, given that inter-individual differences in general cognitive function have been linked to variability in the long-term exposure to glucocorticoids (Lupien et al. (1998) Nat. Neurosci. 1: 69-73) and dysregulation of the HPA axis resulting in chronic exposure to glucocorticoid excess in certain brain subregions has been theorized to contribute to the decline of cognitive function (McEwen and Sapolsky (1995) Curr. Opin. Neurobiol. 5: 205-216), one might predict that inhibition of 1113-HSD1 could reduce exposure to glucocorticoids in the brain and thereby protect against deleterious glucocorticoid effects on neuronal function, including cognitive impairment, dementia, and/or depression. Notably, it is known that stress and glucocorticoids influence cognitive function (de Quervain et al. (1998) Nature 394: 787-790); and it has been shown that 11β-HSD1, through its control of glucocorticoid action in the brain, may have effects on neurotoxicity (Rajan et al. (1996) Neuroscience 16: 65-70; Seckl (2000) Neuroendocrinol. 18:49-99).

There is also evidence that glucocorticoids and 11β-HSD1 play a role in regulation of in intra-ocular pressure (IOP) (Stokes et al. (2000) Invest. Opthalmol. Vis. Sci. 41: 1629-1683; Rauz et al. (2001) Invest. Opthalmol. Vis. Sci. 42: 2037-2042); if left untreated, elevated IOP can lead to partial visual field loss and eventually blindness. Thus, inhibition of 11β-HSD1 in the eye could reduce local glucocorticoid concentrations and IOP, and 11β-HSD1 hence could potentially be used to treat glaucoma and other visual disorders.

Transgenic aP2-11βHSD1 mice exhibit high arterial blood pressure and have increased sensitivity to dietary salt. Moreover, plasma angiotensinogen levels are elevated in the transgenic mice, as are angiotensin II and aldosterone; and treatment of the mice with an angiotensin II antagonist alleviates the hypertension (Masuzaki et al. (2003) J. Clinical Invest. 112: 83-90). This suggests that hypertension may be caused or exacerbated by 11β-HSD1 activity. Thus, 11β-HSD1 inhibitors may be useful for treatment of hypertension and hypertension-related cardiovascular disorders. Inhibition of 11β-HSD1 in mature adipocytes is also expected to attenuate secretion of plasminogen activator inhibitor 1 (PAI-1), which is an independent cardiovascular risk factor (Halleux et al. (1999) J. Clin. Endocrinol. Metabl. 84: 4097-4105).

Glucocorticoids can have adverse effects on skeletal tissues; and prolonged exposure to even moderate glucocorticoid doses can result in osteoporosis (Cannalis (1996) J. Clin. Endocrinol. Metab. 81: 3441-3447). In addition, 11β-HSD1 has been shown to be present in cultures of human primary osteoblasts as well as cells from adult bone (Cooper et al. (2000) Bone 27: 375-381), and the 11β-HSD1 inhibitor carbenoxolone has been shown to attenuate the negative effects of glucocorticoids on bone nodule formation (Bellows et al. (1998) Bone 23: 119-125). Thus, inhibition of 11β-HSD1 is predicted to decrease the local glucocorticoid concentration within osteoblasts and osteoclasts, thereby producing beneficial effects in various forms of bone disease, including osteoporosis.

11β-HSD1 inhibitors may also be useful for immunomodulation. Although glucocorticoids are perceived to suppress the immune system, in actuality, there is a complex, dynamic interaction between the HPA axis and the immune system (Rook (1999) Baillier's Clin. Endocrinol. Metabl. 13: 576-581). Glucocorticoids play a role in modulating the balance between cell-mediated and humoral immune response, with high glucocorticoid activity normally associated with a humoral response. Inhibition of 11β-HSD1 therefore can be used a means of shifting the immune response towards a cell-mediated response. Certain disease states, such as tuberculosis, leprosy (Hansen's disease) and psoriasis, trigger immune responses that are biased towards a humoral response whereas the more effective immune response may be a cell-mediated response. Hence, 11β-HSD1 inhibitors may be useful for treating such diseases.

It has been reported that glucocorticoids inhibit wound healing, especially in diabetic patients with ulcers (Bitar et al. (1999) J. Surg. Res. 82: 234-243; Bitar et al. (1999) Surgery 125: 594-601; Bitar (2000) Surgery 127: 687-695; Bitar (1998) Am. J. Pathol. 152: 547-554). Patients that exhibit impaired glucose tolerance and/or type 2 diabetes often also have impaired wound healing. Glucocorticoids have been shown to increase the risk of infection and delay wound healing (Anstead (1998) Adv. Wound Care 11:277-285). Moreover, there is a correlation between elevated levels of cortisol in wound fluid and non-healing wounds (EP Patent App. No. 0 902 288). Recent published patent applications have suggested that certain 11β-HSD1 inhibitors may be useful for promoting wound healing (PCT/US2006/043, 951).

As evidenced herein, there is a continuing need for new and improved drugs that inhibit 11β-HSD1. The novel compounds of the instant invention are effective inhibitors of 11β-HSD1.

SUMMARY OF THE INVENTION

It has now been found that compounds of Formula Im[1] or pharmaceutically acceptable salts thereof, are effective inhibitors of 11β-HSD1.

The invention is a compound represented by Formula (Im¹)

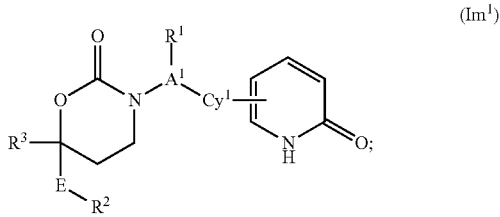

(Im¹)

or a pharmaceutically acceptable salt, enantiomer or diastereomer thereof.

In a first embodiment of the invention, Formula Im¹ and its constituent members are defined herein as follows:

$R^1$ is (a) absent or (b) is selected from $(C_1-C_6)$alkyl, $(C_2-C_6)$alkenyl, $(C_2-C_6)$alkynyl, $(C_1-C_3)$alkoxy$(C_1-C_3)$alkoxy, or $(C_1-C_3)$alkoxy$(C_1-C_3)$alkyl and is optionally substituted with up to four groups independently selected from fluorine, cyano, oxo, $R^4$, $R^4O-$, $(R^4)_2N-$, $R^4O_2C-$, $R^4S$, $R^4S(=O)-$, $R^4S(=O)_2-$, $R^4C(=O)NR^4-$, $(R^4)_2NC(=O)-$, $(R^4)_2NC(=O)O-$, $(R^4)_2NC(=O)NR^4-$, $R^4OC(=O)NR^4-$, $(R^4)_2NC(=NCN)NR^4-$, $(R^4O)_2P(=O)O-$, $(R^{40})_2P(=O)NR^4-$, $R^4OS(=O)_2NR^4-$, $(R^4)_2NS(=O)_2O-$, $(R^4)_2NS(=O)_2NR^4-$, $R^4S(=O)_2NR^4-$, $R^4S(=O)_2NHC(=O)-$, $R^4S(=O)_2NHC(=O)O-$, $R^4S(=O)_2NHC(=O)NR^4-$, $R^4OS(=O)_2NHC(=O)-$, $R^4OS(=O)_2NHC(=O)O-$, $R^4OS(=O)_2NHC(=O)NR^4-$, $(R^4)_2NS(=O)_2NHC(=O)-$, $(R^4)_2NS(=O)_2NHC(=O)O-$, $(R^4)_2NS(=O)_2NHC(=O)NR^4-$, $R^4C(=O)NHS(=O)_2-$, $R^4C(=O)NHS(=O)_2O-$, $R^4C(=O)NHS(=O)_2NR^4-$, $R^4OC(=O)NHS(=O)_2-$, $R^4OC(=O)NHS(=O)_2O-$, $R^4OC(=O)NHS(=O)_2NR^4-$, $(R^4)_2NC(=O)NHS(=O)_2-$, $(R^4)_2NC(=O)NHS(=O)_2O-$, $(R^4)_2NC(=O)NHS(=O)_2NR^4-$, heterocyclyl, heteroaryl, arylamino and heteroarylamino;

$A^1$ is (a) a bond, or (b) $(C_1-C_3)$alkylene, $CH_2CH_2O$, wherein the oxygen is attached to $Cy^1$, or $CH_2C(=O)$, wherein the carbonyl carbon is attached to $Cy^1$;

$Cy^1$ is aryl, heteroaryl, monocyclic cycloalkyl or monocyclic heterocyclyl and is optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylhio, $(C_4-C_7)$cycloalkylalkylthio, halo$(C_1-C_6)$alkylthio, halo$(C_3-C_6)$cycloalkylhio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclylsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkylamino$(C_2-C_6)$alkoxy, $(C_1-C_6)$alkylamino$(C_2-C_6)$alkoxy, di$(C_1-C_6)$alkylamino$(C_2-C_6)$alkoxy, $(C_1-C_6)$alkylcarbonyl, $(C_3-C_6)$cycloalkylcarbonyl, $(C_3-C_6)$cycloalkylaminocarbonyl, {$(C_3-C_6)$cycloalkyl}{$(C_1-C_6)$alkyl}aminocarbonyl, di$(C_3-C_6)$cycloalkylaminocarbonyl, $(C_3-C_6)$cycloalkylaminosulfonyl, {$(C_3-C_6)$cycloalkyl}{$(C_1-C_6)$alkyl}aminosulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$alkyl, $(C_3-C_6)$cycloalkylaminocarbonyl$(C_1-C_6)$alkyl, {$(C_3-C_6)$cycloalkyl}{$(C_1-C_6)$alkyl}aminocarbonyl$(C_1-C_6)$alkyl and di$(C_3-C_6)$cycloalkylaminocarbonyl$(C_1-C_6)$alkyl;

The oxodihydropyridyl ring in Formula Im¹ is optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylhio, $(C_4-C_7)$cycloalkylalkylthio, halo$(C_1-C_6)$alkylthio, halo$(C_3-C_6)$cycloalkylhio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_r-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclylsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkylamino$(C_2-C_6)$alkoxy, $(C_1-C_6)$alkylamino$(C_2-C_6)$alkoxy, di$(C_1-C_6)$alkylamino$(C_2-C_6)$alkoxy, $(C_1-C_6)$alkylcarbonyl, $(C_3-C_6)$cycloalkylcarbonyl, $(C_3-C_6)$cycloalkylaminocarbonyl, {$(C_3-C_6)$cycloalkyl}{$(C_1-C_6)$alkyl}aminocarbonyl, di$(C_3-C_6)$cycloalkylaminocarbonyl, $(C_3-C_6)$cycloalkylaminosulfonyl, {$(C_3-C_6)$cycloalkyl}{$(C_1-C_6)$alkyl}aminosulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$alkyl, $(C_3-C_6)$cycloalkylaminocarbonyl$(C_1-C_6)$alkyl, {$(C_3-C_6)$cycloalkyl}{$(C_1-C_6)$alkyl}aminocarbonyl$(C_1-C_6)$alkyl and di$(C_3-C_6)$cycloalkylaminocarbonyl$(C_1-C_6)$alkyl;

E is (a) a bond or (b) $(C_1-C_3)$alkylene or $(C_1-C_2)$alkylenyloxy, wherein the O is attached to $R^2$, each of which is optionally substituted with 1 to 4 groups independently selected from methyl, ethyl, trifluoromethyl or oxo;

$R^2$ is $(C_1-C_6)$alkyl, aryl, heteroaryl, cycloalkyl or heterocyclyl and is optionally substituted with up to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylhio, $(C_4-C_7)$cycloalkylalkylthio, halo$(C_1-C_6)$alkylthio, halo$(C_3-C_6)$cycloalkylhio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkyl-alkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclylsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkylamino$(C_2-C_6)$alkoxy, $(C_1-C_6)$alkylamino$(C_2-C_6)$alkoxy, di$(C_1-C_6)$alkylamino$(C_2-C_6)$alkoxy, $(C_1-C_6)$alkylcarbonyl, $(C_3-C_6)$cycloalkylcarbonyl, $(C_3-C_6)$cycloalkylaminocarbonyl, $\{(C_3-C_6)$cycloalkyl$\}\{(C_1-C_6)$alkyl$\}$aminocarbonyl, di$(C_3-C_6)$cycloalkylaminocarbonyl, $(C_3-C_6)$cycloalkylaminosulfonyl, $\{(C_3-C_6)$cycloalkyl$\}\{(C_1-C_6)$alkyl$\}$aminosulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$alkyl, $(C_3-C_6)$cycloalkylaminocarbonyl$(C_1-C_6)$alkyl, $\{(C_3-C_6)$cycloalkyl$\}\{(C_1-C_6)$alkyl$\}$aminocarbonyl$(C_1-C_6)$alkyl and di$(C_3-C_6)$cycloalkylaminocarbonyl$(C_1-C_6)$alkyl;

$R^3$ is selected from $(C_1-C_6)$alkyl, $(C_2-C_6)$alkenyl, $(C_2-C_6)$alkynyl, $(C_3-C_5)$cycloalkyl$(C_1-C_4)$alkyl, $(C_1-C_3)$alkoxy$(C_1-C_3)$alkoxy, or $(C_1-C_3)$alkoxy$(C_1-C_3)$alkyl and is optionally substituted with up to four groups independently selected from fluorine, cyano, oxo, $R^4$, $R^4O$—, $(R^4)_2N$—, $R^4O_2C$—, $R^4C(=O)O$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$—, $(R^{40})_2P(=O)O$—, $(R^{40})_2P(=O)NR^4$—, $R^4OS(=O)_2NR^4$—, $(R^4)_2NS(=O)_2O$—, $(R^4)_2NS(=O)_2NR^4$—, $R^4S(=O)_2NR^4$—, $R^4S(=O)_2NHC(=O)$—, $R^4S(=O)_2NHC(=O)O$—, $R^4S(=O)_2NHC(=O)NR^4$—, $R^4OS(=O)_2NHC(=O)$—, $R^4OS(=O)_2NHC(=O)O$—, $R^4OS(=O)_2NHC(=O)NR^4$—, $(R^4)_2NS(=O)_2NHC(=O)$—, $(R^4)_2NS(=O)_2NHC(=O)O$—, $(R^4)_2NS(=O)_2NHC(=O)NR^4$—, $R^4C(=O)NHS(=O)_2$—, $R^4C(=O)NHS(=O)_2O$—, $R^4C(=O)NHS(=O)_2NR^4$—, $R^4OC(=O)NHS(=O)_2$—, $R^4OC(=O)NHS(=O)_2O$—, $R^4OC(=O)NHS(=O)_2NR^4$—, $(R^4)_2NC(=O)NHS(=O)_2$—, $(R^4)_2NC(=O)NHS(=O)_2O$—, $(R^4)_2NC(=O)NHS(=O)_2NR^4$—, spirocycloalkyl; heterocyclyl (which in turn may be optionally substituted with alkyl, haloalkyl, halogen or oxo), heteroaryl (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo), arylamino (which in turn may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido) and heteroarylamino (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo); and $R^4$ is independently selected from H, $(C_1-C_6)$alkyl, halo$(C_1-C_6)$alkyl, amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl and $(C_1-C_6)$alkoxy$(C_1-C_6)$alkyl.

Alternatively, the first embodiment above excludes the compounds of structural formulas PR-221 and PR-313, or a pharmaceutically acceptable salt, enantiomer or diastereomer thereof.

Another embodiment of the invention is a pharmaceutical composition comprising i) a pharmaceutically acceptable carrier or diluent, and ii) a compound of Formulas Ik, $Im^1$, $Im^2$, $Im^5$, $In^1$, $In^2$, $In^5$, $Io^1$, $Io^2$, $Io^5$, $Ip^1$ or $Ip^3$, or a pharmaceutically acceptable salt, enantiomer or diastereomer thereof.

Another embodiment of the invention is a method of inhibiting 11β-HSD1 activity comprising the step of administering to a mammal in need of such treatment an effective amount of a compound of Formulas Ik, $Im^1$, $Im^2$, $Im^5$, $In^1$, $In^2$, $In^5$, $Io^1$, $Io^2$, $Io^5$, $Ip^1$ or $Ip^3$, or a pharmaceutically acceptable salt, enantiomer or diastereomer thereof.

Another embodiment of the invention is a method of treating a subject with a disease associated with the activity or expression of 11β-HSD1, comprising the step of administering to the subject an effective amount of a compound of Formulas Ik, $Im^1$, $Im^2$, $Im^5$, $In^1$, $In^2$, $In^5$, $Io^1$, $Io^2$, $Io^5$, $Ip^1$ or $Ip^3$, or a pharmaceutically acceptable salt, enantiomer or diastereomer thereof.

Another embodiment of the invention is the use of a compound of Formulas Ik, $Im^1$, $Im^2$, $Im^5$, $In^1$, $In^2$, $In^5$, $Io^1$, $Io^2$, $Io^5$, $Ip^1$ or $Ip^3$, or a pharmaceutically acceptable salt, enantiomer or diastereomer thereof for the manufacture of a medicament for inhibiting 11β-HSD1 activity in a mammal in need of such treatment.

Another embodiment of the invention is the use of a compound of Formulas Ik, $Im^1$, $Im^2$, $Im^5$, $In^1$, $In^2$, $In^5$, $Io^1$, $Io^2$, $Io^5$, $Ip^1$ or $Ip^3$, or a pharmaceutically acceptable salt, enantiomer or diastereomer thereof for the manufacture of a medicament for treating a subject with a disease associated with the activity or expression of 11β-HSD1.

Another embodiment of the invention is a compound of Formulas Ik, $Im^1$, $Im^2$, $Im^5$, $In^1$, $In^2$, $In^5$, $Io^1$, $Io^2$, $Io^5$, $Ip^1$ or $Ip^3$, or a pharmaceutically acceptable salt, enantiomer or diastereomer thereof for use in inhibiting 11β-HSD1 activity in a mammal in need of such treatment.

Another embodiment of the invention is a compound of Ik, $Im^1$, $Im^2$, $Im^5$, $In^1$, $In^2$, $In^5$, $Io^1$, $Io^2$, $Io^5$, $Ip^1$ or $Ip^3$, or a pharmaceutically acceptable salt, enantiomer or diastereomer thereof for use in for treating a subject with a disease associated with the activity or expression of 11β-HSD1.

DETAILED DESCRIPTION OF THE INVENTION

Another embodiment of the invention is a compound of Formula Ik:

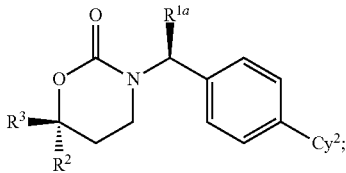

or a pharmaceutically acceptable salt, enantiomer or diastereomer thereof;

$R^{1a}$ is absent or is methyl or ethyl;

$Cy^2$ is 2-oxo-1,2-dihydropyridyl optionally substituted by 1 to 4 groups independently selected from halo, hydroxy, methoxy, hydroxymethyl, methoxycarbonyl, amino, carbamoyl, methylcarbamoyl, dimethylcarbamoyl, (2-methoxyethyl)aminocarbonyl, acetylaminomethyl, methylsulfonyl, methylsulfonylamino, methylaminosulfonyl, isopropylaminosulfonyl, dimethylaminosulfonyl, pyrrolidine-1-sulfonyl, methylsulfonylaminomethyl, tetrazolyl, methyl, trifluoromethyl, acetyl, 2-hydroxyethyl and 1-aminoethyl;

$R^2$ is phenyl, thienyl, pyridyl or isopropyl each optionally substituted with halo, methyl, methylthio or (4-morpholino)methyl; and $R^3$ is methyl, ethyl, propyl, butyl, vinyl, allyl or ethoxyethyl each optionally substituted with up to two groups independently selected from Methyl, HO—, MeO—, $H_2N$—, MeC(=O)NH—, MeS(=O)$_2$NH—, $H_2$NC(=O)—, MeNHC(=O)—, $HO_2$C—, $(HO)_2$P(=O)O—, $H_2$NS(=O)$_2$O—, $H_2$NS(=O)$_2$NH—, MeNHC(=O)NH—, MeNHC(=O)O—, oxo, cyano, $HO_2$C—, HOCH$_2$CH$_2$NH—, 4-morpholino, HOCH$_2$C(=O)NH—, $H_2$NCH$_2$C(=O)NH—, EtNHC(=O)NH, MeOC(=O)NH—, MeNHC(=NC≡N)NH—, Me-, MeS—, MeSO$_2$— MeSO$_2$N(Me)-, MeS(=O)$_2$NHC(=O)—, imidazolylamino-, imidazolyl, tetrazolyl, $H_2$NCONH—, $H_2$NCO$_2$—, HOCH$_2$CH$_2$O—, MeNH—, Me$_2$N— and MeCONMe.

Another embodiment of the invention is a compound of any one of Formulas Im$^1$, Im$^2$ and Im$^5$ or a pharmaceutically acceptable salt, enantiomer or diastereomer thereof:

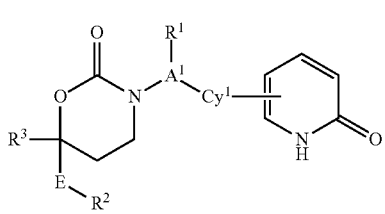

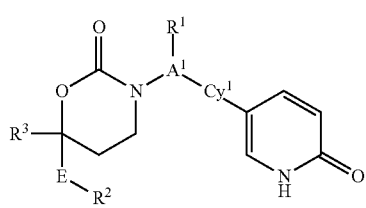

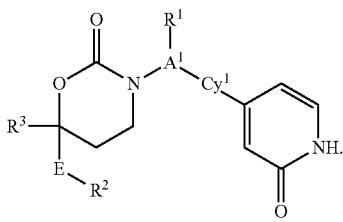

In Formulas Im$^1$, Im$^2$ and Im$^5$, the oxodihydropyridyl ring is optionally substituted (substitution at ring carbons bonded to hydrogen and ring nitrogen atoms bonded to hydrogen atoms are encompassed, i.e., a "substitutable ring nitrogen atom") with up to four substituents as described above. Suitable substituents for the oxodihydropyridyl ring and suitable values for $R^1$, $R^2$, $R^3$, $A^2$, $Cy^1$ and E are as defined above in the first embodiment. Alternatively, suitable substituents for $Cy^1$ and the oxodihydropyridyl ring in Formulas Im$^1$, Im$^2$ and Im$^5$ are independently fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylthio, $(C_4-C_7)$cycloalkylalkylthio, halo$(C_1-C_6)$alkylthio, halo$(C_3-C_6)$cycloalkylthio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkyl-alkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2$NCO, $H_2$NSO$_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclylsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, amino$(C_1-C_6)$alkyl, $(C_1-C_6)$alkylamino$(C_1-C_6)$alkyl, di$(C_1-C_6)$alkylamino$(C_1-C_6)$alkylamino$(C_2-C_6)$alkoxy, $(C_1-C_6)$alkylamino$(C_2-C_6)$alkoxy, di$(C_1-C_6)$alkylamino$(C_2-C_6)$alkoxy, $(C_1-C_6)$alkylcarbonyl, $(C_3-C_6)$cycloalkylcarbonyl, $(C_3-C_6)$cycloalkylaminocarbonyl, {$(C_3-C_6)$cycloalkyl}{$(C_1-C_6)$alkyl}aminocarbonyl, di$(C_3-C_6)$cycloalkylaminocarbonyl, $(C_3-C_6)$cycloalkylaminosulfonyl, {$(C_3-C_6)$cycloalkyl}{$(C_1-C_6)$alkyl}aminosulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$alkyl, $(C_3-C_6)$cycloalkylaminocarbonyl$(C_1-C_6)$alkyl, {$(C_3-C_6)$cycloalkyl}{$(C_1-C_6)$alkyl}aminocarbonyl$(C_1-C_6)$alkyl and di$(C_3-C_6)$cycloalkylaminocarbonyl$(C_1-C_6)$alkyl; and values for $R^1$, $R^2$, $R^3$, $A^1$, $Cy^1$ and E are as defined above in the first embodiment. Alternatively, suitable substituents for $Cy^1$ include $(C_1-C_4)$alkyl, $(C_1-C_4)$alkoxy, $(C_1-C_4)$haloalkyl, $(C_1-C_4)$haloalkoxy, halogen, cyano and nitro; suitable substituents for a substitutable ring nitrogen atom in the oxodihydropyridyl ring in Formulas $Im^1$, $Im^2$ and $Im^5$ include $(C_1-C_4)$alkyl, $(C_3-C_4)$cycloalkyl, $(C_3-C_4)$cycloalkyl$(C_1-C_2)$alkyl, and $(C_1-C_4)$haloalkyl; suitable substituents for a ring carbon atom in the oxodihydropyridyl ring in Formulas $Im^1$, $Im^2$ and $Im^5$ include fluorine, chlorine, cyano, hydroxy, amino, $(C_1-C_4)$alkyl, $(C_3-C_4)$cycloalkyl, $(C_3-C_4)$cycloalkyl$(C_1-C_2)$alkyl, halo$(C_1-C_4)$alkyl, $(C_1-C_4)$alkoxy, $(C_1-C_4)$haloalkoxy, $CONH_2$, $(C_1-C_4)$alkylaminocarbonyl, di$(C_1-C_4)$alkylaminocarbonyl and $(C_1-C_4)$alkylcarbonylamino; and suitable values for $R^1$, $R^2$, $R^3$, $A^1$, $Cy^1$ and E are as defined above in the first embodiment. In another alternative, the embodiments in this paragraph exclude the following compounds:

(R)-6-(3-hydroxypropyl)-3-((S)-1-(4-(6-oxo-1,6-dihydropyridin-3-yl)phenyl)ethyl)-6-phenyl-1,3-oxazinan-2-one (PR-221)

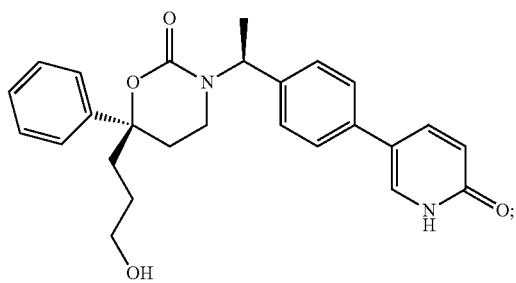

and (R)-6-(3-hydroxypropyl)-3-((S)-1-(4-(1-methyl-6-oxo-1,6-dihydropyridin-3-yl)phenyl)ethyl)-6-phenyl-1,3-oxazinan-2-one (PR-313)

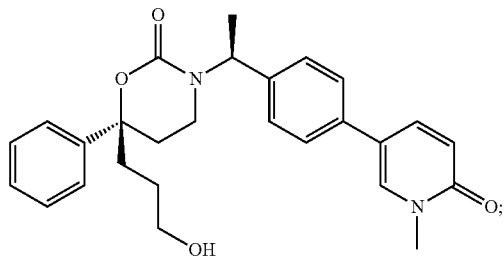

or a pharmaceutically acceptable salt, enantiomer or diastereomer thereof.

For each of the embodiments described in the previous paragraph, $R^1$ is preferably methyl or ethyl.

For each of the embodiments described in the paragraph immediately following Formulas $Im^1$, $Im^2$ and $Im^5$, $R^1$ is preferably methyl or ethyl; and $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl.

For each of the embodiments described in the paragraph immediately following Formulas $Im^1$, $Im^2$ and $Im^5$, $R^1$ is preferably methyl or ethyl; and $R^3$ is $H_2NC(=O)CMe_2CH_2$, 3-hydroxy-3-methylbutyl, 2-hydroxy-2-methylpropyl or 2-cyano-2-methylpropyl.

For each of the embodiments described in the paragraph immediately following Formulas $Im^1$, $Im^2$ and $Im^5$, $R^1$ is preferably methyl or ethyl; $R^2$ is phenyl optionally substituted with 1, 2 or 3 substituents selected from halo, cyano, $CONH_2$, $(C_1-C_4)$alkyl, $(C_1-C_4)$haloalkyl, and $SO_2Me$; and $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl.

For each of the embodiments described in the paragraph immediately following Formulas $Im^1$, $Im^2$ and $Im^5$, $R^1$ is preferably methyl or ethyl; $R^2$ is phenyl optionally substituted with 1, 2 or 3 substituents selected from halo, cyano, $CONH_2$, $(C_1-C_4)$alkyl, $(C_1-C_4)$haloalkyl, and $SO_2Me$; and $R^3$ is $H_2NC(=O)CMe_2CH_2$, 3-hydroxy-3-methylbutyl, 2-hydroxy-2-methylpropyl or 2-cyano-2-methylpropyl.

For each of the embodiments described in the paragraph immediately following Formulas $Im^1$, $Im^2$ and $Im^5$, $R^1$ is preferably methyl or ethyl; and $R^3$ is 2-hydroxy-2-methylpropyl or 2-cyano-2-methylpropyl.

For each of the embodiments described in the paragraph immediately following Formulas $Im^1$, $Im^2$ and $Im^5$, $R^1$ is preferably methyl or ethyl; $R^2$ is phenyl or fluorophenyl; and $R^3$ is 2-hydroxy-2-methylpropyl or 2-cyano-2-methylpropyl.

For each of the embodiments described in the paragraph immediately following Formulas $Im^1$, $Im^2$ and $Im^5$, $R^1$ is preferably methyl or ethyl; $R^2$ is phenyl or fluorophenyl; $R^3$ is 2-hydroxy-2-methylpropyl or 2-cyano-2-methylpropyl; the substituent on the substitutable ring nitrogen atom in the oxodihydropyridyl ring in Formulas $Im^1$, $Im^2$ and $Im^5$ is $(C_1-C_4)$alkyl, $(C_3-C_4)$cycloalkyl, $(C_3-C_4)$cycloalkyl$(C_1-C_2)$alkyl, or $(C_1-C_2)$haloalkyl; and one or two ring carbon atoms in the oxodihydropyridyl ring in Formulas $Im^1$, $Im^2$ and $Im^5$ are optionally substituted with methyl or ethyl.

Another embodiment of the invention is a compound of any one of Formulas $In^1$, $In^2$ and $In^5$, or a pharmaceutically acceptable salt, enantiomer or diastereomer thereof:

$In^1$

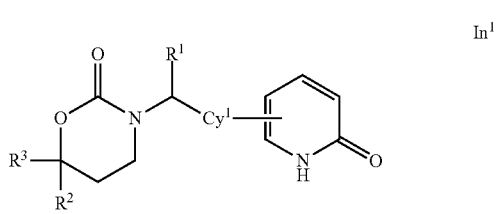

$In^2$

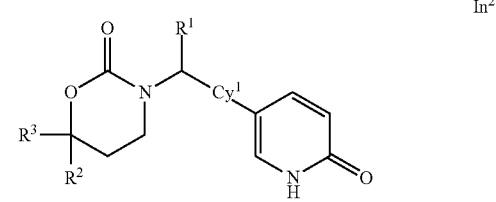

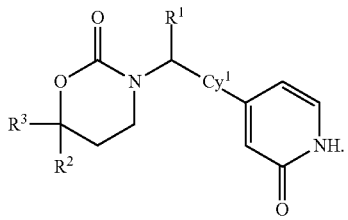

In Formulas In¹, In² and In⁵, the oxodihydropyridyl ring is optionally substituted (substitution at ring carbons bonded to hydrogen and at nitrogen atoms bonded to hydrogen atoms are encompassed, i.e., a "substitutable ring nitrogen atom") with up to four substituents as described above for $Cy^2$. Suitable substituents for the oxodihydropyridyl ring and suitable values for $R^1$, $R^2$, $R^3$ and $Cy^1$ are as defined above in the first embodiment. Alternatively, suitable substituents for $Cy^1$ and the oxodihydropyridyl ring in Formulas In¹, In² and In⁵ are independently fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylthio, $(C_4-C_7)$cycloalkylalkylthio, halo$(C_1-C_6)$alkylthio, halo$(C_3-C_6)$cycloalkylthio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclylsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, amino$(C_1-C_6)$alkyl, $(C_1-C_6)$alkylamino$(C_1-C_6)$alkyl, di$(C_1-C_6)$alkylamino$(C_1-C_6)$alkylamino$(C_2-C_6)$alkoxy, $(C_1-C_6)$alkylamino$(C_2-C_6)$alkoxy, di$(C_1-C_6)$alkylamino$(C_2-C_6)$alkoxy, $(C_1-C_6)$alkylcarbonyl, $(C_3-C_6)$cycloalkylcarbonyl, $(C_3-C_6)$cycloalkylaminocarbonyl, $\{(C_3-C_6)$cycloalkyl$\}\{(C_1-C_6)$alkyl$\}$aminocarbonyl, di$(C_3-C_6)$cycloalkylaminocarbonyl, $(C_3-C_6)$cycloalkylaminosulfonyl, $\{(C_3-C_6)$cycloalkyl$\}\{(C_1-C_6)$alkyl$\}$aminosulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, $C_6)$alkylaminocarbonyl$(C_1-C_6)$alkyl, $(C_3-C_6)$cycloalkylaminocarbonyl$(C_1-C_6)$alkyl, $\{(C_3-C_6)$cycloalkyl$\}\{(C_1-C_6)$alkyl$\}$aminocarbonyl$(C_1-C_6)$alkyl and di$(C_3-C_6)$cycloalkylaminocarbonyl$(C_1-C_6)$alkyl; and values for $R^1$, $R^2$, $R^3$ and $Cy^1$ are as defined above in the first embodiment. Alternatively, suitable substituents for $Cy^1$ include $(C_1-C_4)$alkyl, $(C_1-C_4)$alkoxy, $(C_1-C_4)$haloalkyl, $(C_1-C_4)$haloalkoxy, halogen, cyano and nitro; suitable substituents for a substitutable ring nitrogen atom in the oxodihydropyridyl ring in Formulas In¹, In² and In⁵ include $(C_1-C_4)$alkyl, $(C_3-C_4)$cycloalkyl, $(C_3-C_4)$cycloalkyl$(C_1-C_2)$alkyl and $(C_1-C_4)$haloalkyl; suitable substituents for a ring carbon atom in the oxodihydropyridyl ring in Formulas In¹, In² and In⁵ include fluorine, chlorine, cyano, hydroxy, amino, $(C_1-C_4)$alkyl, $(C_3-C_4)$cycloalkyl, $(C_3-C_4)$cycloalkyl$(C_1-C_2)$alkyl, halo$(C_1-C_4)$alkyl, $(C_1-C_4)$alkoxy, $(C_1-C_4)$haloalkoxy, $CONH_2$, $(C_1-C_4)$alkylaminocarbonyl, di$(C_1-C_4)$alkylaminocarbonyl and $(C_1-C_4)$alkylcarbonylamino; and suitable values for $R^1$, $R^2$, $R^3$, and $Cy^1$ are as defined above in the first embodiment. In another alternative, the embodiments described in this paragraph exclude the compounds PR-221 and PR-313; or a pharmaceutically acceptable salt, enantiomer or diastereomer thereof.

For each of the embodiments described in the previous paragraph, $R^1$ is preferably methyl or ethyl.

For each of the embodiments described in the paragraph immediately following Formulas In¹, In² and In⁵, $R^1$ is preferably methyl or ethyl; and $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl.

For each of the embodiments described in the paragraph immediately following Formulas In¹, In² and In⁵, $R^1$ is preferably methyl or ethyl; and $R^3$ is $H_2NC(=O)CMe_2CH_2$, 3-hydroxy-3-methylbutyl, 2-hydroxy-2-methylpropyl or 2-cyano-2-methylpropyl.

For each of the embodiments described in the paragraph immediately following Formulas In¹, In² and In⁵, $R^1$ is preferably methyl or ethyl; $R^2$ is phenyl optionally substituted with 1, 2 or 3 substituents selected from halo, cyano, $CONH_2$, $(C_1-C_4)$alkyl, $(C_1-C_4)$haloalkyl and $SO_2Me$; and $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl.

For each of the embodiments described in the paragraph immediately following Formulas In¹, In² and In⁵, $R^1$ is preferably methyl or ethyl; $R^2$ is phenyl optionally substituted with 1, 2 or 3 substituents selected from halo, cyano, $CONH_2$, $(C_1-C_4)$alkyl, $(C_1-C_4)$haloalkyl and $SO_2Me$; and $R^3$ is $H_2NC(=O)CMe_2CH_2$, 3-hydroxy-3-methylbutyl, 2-hydroxy-2-methylpropyl or 2-cyano-2-methylpropyl.

For each of the embodiments described in the paragraph immediately following Formulas In¹, In² and In⁵, $R^1$ is preferably methyl or ethyl; and $R^3$ is 2-hydroxy-2-methylpropyl or 2-cyano-2-methylpropyl.

For each of the embodiments described in the paragraph immediately following Formulas In¹, In² and In⁵, $R^1$ is preferably methyl or ethyl; $R^2$ is phenyl or fluorophenyl; and $R^3$ is 2-hydroxy-2-methylpropyl or 2-cyano-2-methylpropyl.

For each of the embodiments described in the paragraph immediately following Formulas In¹, In² and In⁵, $R^1$ is preferably methyl or ethyl; $R^2$ is phenyl or fluorophenyl; $R^3$ is 2-hydroxy-2-methylpropyl or 2-cyano-2-methylpropyl; the substituent on the substitutable ring nitrogen atom in the oxodihydropyridyl rings in Formulas In¹, In² and In⁵ is $(C_1-C_4)$alkyl, $(C_3-C_4)$cycloalkyl, $(C_3-C_4)$cycloalkyl$(C_1-C_2)$alkyl, or $(C_1-C_2)$haloalkyl; and one or two ring carbon atoms in the oxodihydropyridyl rings in Formulas In¹, In² and In⁵ are optionally substituted with methyl or ethyl.

Another embodiment of the invention is a compound of any one of Formulas Io¹, Io² and Io⁵, or a pharmaceutically acceptable salt thereof:

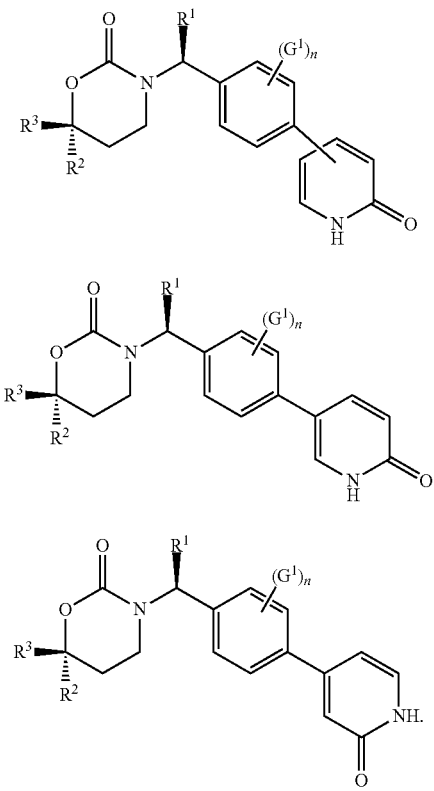

In Formulas Io¹, Io² and Io⁵, the oxodihydropyridyl ring in Formulas Io¹, Io² and Io⁵ is optionally substituted (substitution at ring carbons bonded to hydrogen and at nitrogen atoms bonded to hydrogen atoms are encompassed, i.e., a "substitutable ring nitrogen atom") with up to four substituents as described above in the first embodiment; suitable values for $G^1$ are fluorine, chlorine, bromine, iodine, cyano, nitro, amino, hydroxy, carboxy, $(C_1-C_6)$alkyl, hydroxy$(C_1-C_6)$ alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl $(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylthio, $(C_4-C_7)$cycloalkyl-alkylthio, halo$(C_1-C_6)$alkylthio, halo$(C_3-C_6)$cycloalkylthio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkyl-aminocarbonyl, di$(C_1-C_6)$alkylaminocarbonyl, $(C_1-C_3)$alkoxy$(C_1-C_3)$alkyl-aminocarbonyl, heterocyclylcarbonyl, $(C_1-C_6)$alkylaminosulfonyl, di$(C_1-C_6)$alkylamino-sulfonyl, heterocyclylsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, amino$(C_1-C_6)$alkyl, $(C_1-C_6)$alkylamino$(C_1-C_6)$alkyl, di$(C_1-C_6)$alkylamino$(C_1-C_6)$alkylamino$(C_2-C_6)$alkyl, $(C_1-C_6)$alkylamino$(C_2-C_6)$alkoxy, di$(C_1-C_6)$alkylamino$(C_2-C_6)$alkoxy, $(C_1-C_6)$alkylcarbonyl, $(C_3-C_6)$cycloalkylcarbonyl, $(C_3-C_6)$cycloalkylaminocarbonyl, $\{(C_3-C_6)$cycloalkyl$\}\{(C_1-C_6)$alkyl$\}$aminocarbonyl, di$(C_3-C_6)$cycloalkylaminocarbonyl, $(C_3-C_6)$cycloalkylaminosulfonyl, $\{(C_3-C_6)$cycloalkyl$\}\{(C_1-C_6)$alkyl$\}$aminosulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$ alkyl, di$(C_1-C_6)$alkylaminocarbonyl$(C_1-C_6)$alkyl, $(C_3-C_6)$cycloalkylaminocarbonyl$(C_1-C_6)$alkyl, $\{(C_3-C_6)$cycloalkyl$\}\{(C_1-C_6)$alkyl$\}$aminocarbonyl$(C_1-C_6)$alkyl and di$(C_3-C_6)$cycloalkylaminocarbonyl$(C_1-C_6)$alkyl; n is 0, 1, 2 or 3; and suitable substituents for the oxodihydropyridyl ring and suitable values for $R^1$, $R^2$ and $R^3$ are as defined above in the first embodiment. Alternatively, n is 0, 1, 2 or 3; suitable values for $G^1$ and substituents for the oxodihydropyridyl ring in Formulas Io¹, Io² and Io⁵ are independently fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylthio, $(C_4-C_7)$cycloalkylalkylthio, halo$(C_1-C_6)$alkylthio, halo$(C_3-C_6)$cycloalkylthio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkyl-alkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclylsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$ alkyl, hydroxy$(C_1-C_6)$alkoxy, heteroaryl, amino$(C_1-C_6)$ alkyl, $(C_1-C_6)$alkylamino$(C_1-C_6)$alkyl, di$(C_1-C_6)$alkylamino $(C_1-C_6)$alkylamino$(C_2-C_6)$alkoxy, $(C_1-C_6)$alkylamino$(C_2-C_6)$alkoxy, di$(C_1-C_6)$alkylamino$(C_2-C_6)$alkoxy and $(C_1-C_6)$ alkylcarbonyl; and values for $R^1$, $R^2$ and $R^3$ are as defined above in the first embodiment. Alternatively, n is 0, 1, 2 or 3; suitable values for $G^1$ include $(C_1-C_4)$alkyl, $(C_1-C_4)$alkoxy, $(C_1-C_4)$haloalkyl, $(C_1-C_4)$haloalkoxy, halogen, cyano and nitro; suitable substituents for a substitutable ring nitrogen atom in the oxodihydropyridyl ring in Formulas Io¹, Io² and Io⁵ include $C_1-C_4$ alkyl, $(C_3-C_4)$cycloalkyl, $(C_3-C_4)$cycloalkyl$(C_1-C_2)$alkyl and $C_1-C_4$ haloalkyl; suitable substituents for a ring carbon atom in the oxodihydropyridyl ring in Formulas Io¹, Io² and Io⁵ include fluorine, chlorine, cyano, hydroxy, amino, $(C_1-C_4)$alkyl, $(C_3-C_4)$cycloalkyl, $(C_3-C_4)$cycloalkyl$(C_1-C_2)$alkyl, halo$(C_1-C_4)$alkyl, $(C_1-C_4)$alkoxy, $(C_1-C_4)$haloalkoxy, $CONH_2$, $(C_1-C_4)$alkylaminocarbonyl, di$(C_1-C_4)$alkylaminocarbonyl and $(C_1-C_4)$alkylcarbonylamino; and suitable values for $R^1$, $R^2$ and $R^3$ are as defined above in the first embodiment. In another alternative, the embodiments described in this paragraph exclude the compounds PR-221 and PR-313; or a pharmaceutically acceptable salt, enantiomer or diastereomer thereof.

For each of the embodiments described in the previous paragraph, $R^1$ is preferably methyl or ethyl.

For each of the embodiments described in the paragraph immediately following Formulas Io$^1$, Io$^2$ and Io$^5$, $R^1$ is preferably methyl or ethyl; and $R^3$ is MeSO$_2$NHCH$_2$CH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl.

For each of the embodiments described in the paragraph immediately following Formulas Io$^1$, Io$^2$ and Io$^5$, $R^1$ is preferably methyl or ethyl; and $R^3$ is H$_2$NC(=O)CMe$_2$CH$_2$, 3-hydroxy-3-methylbutyl, 2-hydroxy-2-methylpropyl or 2-cyano-2-methylpropyl.

For each of the embodiments described in the paragraph immediately following Formulas Io$^1$, Io$^2$ and Io$^5$, $R^1$ is preferably methyl or ethyl; $R^2$ is phenyl optionally substituted with 1, 2 or 3 substituents selected from halo, cyano, CONH$_2$, (C$_1$-C$_4$)alkyl, (C$_1$-C$_4$)haloalkyl and SO$_2$Me; and $R^3$ is MeSO$_2$NHCH$_2$CH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl.

For each of the embodiments described in the paragraph immediately following Formulas Io$^1$, Io$^2$ and Io$^5$, $R^1$ is preferably methyl or ethyl; $R^2$ is phenyl optionally substituted with 1, 2 or 3 substituents selected from halo, cyano, CONH$_2$, (C$_1$-C$_4$)alkyl, (C$_1$-C$_4$)haloalkyl and SO$_2$Me; and $R^3$ is H$_2$NC(=O)CMe$_2$CH$_2$, 3-hydroxy-3-methylbutyl, 2-hydroxy-2-methylpropyl or 2-cyano-2-methylpropyl.

For each of the embodiments described in the paragraph immediately following Formulas Io$^1$, Io$^2$ and Io$^5$, $R^1$ is preferably methyl or ethyl; and $R^3$ is 2-hydroxy-2-methylpropyl or 2-cyano-2-methylpropyl.

For each of the embodiments described in the paragraph immediately following Formulas Io$^1$, Io$^2$ and Io$^5$, $R^1$ is preferably methyl or ethyl; $R^2$ is phenyl or fluorophenyl; and $R^3$ is 2-hydroxy-2-methylpropyl or 2-cyano-2-methylpropyl.

For each of the embodiments described in the paragraph immediately following Formulas Io$^1$, Io$^2$ and Io$^5$, $R^1$ is preferably methyl or ethyl; $R^2$ is phenyl or fluorophenyl; $R^3$ is 2-hydroxy-2-methylpropyl or 2-cyano-2-methylpropyl; the substituent on the substitutable ring nitrogen atom in the oxodihydropyridyl ring in Formulas Io$^1$, Io$^2$ and Io$^5$ is (C$_1$-C$_4$)alkyl, (C$_3$-C$_4$)cycloalkyl, (C$_3$-C$_4$)cycloalkyl(C$_1$-C$_2$) alkyl, or (C$_1$-C$_2$)haloalkyl; and one or two ring carbon atoms in the oxodihydropyridyl rings in Formulas Io$^1$, Io$^2$ and Io$^5$ are optionally substituted with methyl or ethyl.

Another embodiment of the invention (referred to herein as the "First Alternate Embodiment") is a compound represented by Structural Formulas Io$^1$, Io$^2$ and Io$^5$, wherein: n is 0 or 1, preferably 0; each G$^1$ is independently (C$_1$-C$_4$)alkyl, (C$_1$-C$_4$)alkoxy, (C$_1$-C$_4$)haloalkyl, (C$_1$-C$_4$)haloalkoxy, halogen, cyano or nitro; the oxodihydropyridyl is substituted at its ring nitrogen atom with hydroxy(C$_1$-C$_6$)alkyl, (C$_1$-C$_6$)alkylcarbonylamino(C$_1$-C$_6$)alkyl, (C$_1$-C$_6$)alkylsulfonylamino(C$_1$-C$_6$)alkyl, (C$_1$-C$_6$)alkoxy(C$_1$-C$_6$)alkyl, amino(C$_1$-C$_6$)alkyl, (C$_1$-C$_6$)alkylamino(C$_1$-C$_6$)alkyl, di(C$_1$-C$_6$)alkylamino(C$_1$-C$_6$)alkyl, cyano(C$_1$-C$_6$)alkyl, aminocarbonyl(C$_1$-C$_6$)alkyl, (C$_1$-C$_6$)alkylaminocarbonyl(C$_1$-C$_6$)alkyl, di(C$_1$-C$_6$)alkylaminocarbonyl(C$_1$-C$_6$)alkyl, (C$_3$-C$_6$)cycloalkylaminocarbonyl(C$_1$-C$_6$)alkyl, {(C$_3$-C$_6$)cycloalkyl}{(C$_1$-C$_6$)alkyl}aminocarbonyl(C$_1$-C$_6$)alkyl or di(C$_3$-C$_6$)cycloalkylaminocarbonyl(C$_1$-C$_6$)alkyl; the oxodihydropyridyl is optionally substituted at one or more substitutable ring carbon atoms with a group independently selected from fluorine, chlorine, cyano, hydroxy, amino, (C$_1$-C$_4$)alkyl, (C$_3$-C$_4$)cycloalkyl, (C$_3$-C$_4$)cycloalkyl(C$_1$-C$_2$) alkyl, halo(C$_1$-C$_4$)alkyl, (C$_1$-C$_4$)alkoxy, (C$_1$-C$_4$)haloalkoxy, CONH$_2$, (C$_1$-C$_4$)alkylaminocarbonyl, di(C$_1$-C$_4$)alkylaminocarbonyl and (C$_1$-C$_4$)alkylcarbonylamino; $R^1$ is methyl or ethyl; $R^2$ is phenyl, thienyl, pyridyl or isopropyl each optionally substituted with up to three groups independently selected from halo, methyl, methylthio, (4-morpholino)methyl or cyclopropyl; and $R^3$ is methyl, ethyl, propyl, butyl, vinyl, allyl or ethoxyethyl each optionally substituted with up to two groups independently selected from methyl, HO—, MeO—, H$_2$N—, MeC(=O)NH—, MeS(=O)$_2$NH—, H$_2$NC(=O)—, MeNHC(=O)—, HO$_2$C—, (HO)$_2$P(=O)O—, H$_2$NS(=O)$_2$O—, H$_2$NS(=O)$_2$NH—, MeNHC(=O)NH—, MeNHC(=O)O—, oxo, cyano, HO$_2$C—, HOCH$_2$CH$_2$NH—, 4-morpholino, HOCH$_2$C(=O)NH—, H$_2$NCH$_2$C(=O)NH—, EtNHC(=O)NH, MeOC(=O)NH—, MeNHC(=NC≡N)NH—, Me-, MeS—, MeSO$_2$-MeSO$_2$N(Me)—, MeS(=O)$_2$NHC(=O)—, imidazolylamino-, imidazolyl, tetrazolyl, H$_2$NCONH—, H$_2$NCO$_2$—, HOCH$_2$CH$_2$O—, MeNH—, Me$_2$N— and MeCONMe.

Alternatively for Structural Formulas Io$^1$, Io$^2$ and Io$^5$, $R^2$ is phenyl optionally substituted with 1, 2 or 3 substituents independently selected from halo, cyano, CONH$_2$, (C$_1$-C$_4$)alkyl, (C$_1$-C$_4$)haloalkyl and SO$_2$Me; and $R^3$ is MeSO$_2$NHCH$_2$CH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl; and the remainder of the variables are as described above for the First Alternate Embodiment.

Alternatively for Structural Formulas Io$^1$, Io$^2$ and Io$^5$, $R^3$ is H$_2$NC(=O)CMe$_2$CH$_2$, 3-hydroxy-3-methylbutyl, 2-hydroxy-2-methylpropyl or 2-cyano-2-methylpropyl; and the remainder of the variables are as described above for the First Alternate Embodiment.

Alternatively for Structural Formulas Io$^1$, Io$^2$ and Io$^5$, $R^2$ is phenyl optionally substituted with 1, 2 or 3 substituents independently selected from halo, cyano, CONH$_2$, (C$_1$-C$_4$)alkyl, (C$_1$-C$_4$)haloalkyl and SO$_2$Me; and $R^3$ is H$_2$NC(=O)CMe$_2$CH$_2$, 3-hydroxy-3-methylbutyl, 2-hydroxy-2-methylpropyl or 2-cyano-2-methylpropyl; and the remainder of the variables are as described in the First Alternate Embodiment.

Alternatively for Structural Formulas Io$^1$, Io$^2$ and Io$^5$, $R^3$ is 2-hydroxy-2-methylpropyl or 2-cyano-2-methylpropyl; and the remainder of the variables are as described in the First Alternate Embodiment.

Alternatively for Structural Formulas Io$^1$, Io$^2$ and Io$^5$, $R^2$ is phenyl or fluorophenyl; and $R^3$ is 2-hydroxy-2-methylpropyl or 2-cyano-2-methylpropyl; and the remainder of the variables are as described in the First Alternate Embodiment.

Alternatively for Structural Formulas Io$^1$, Io$^2$ and Io$^5$, $R^2$ is phenyl or fluorophenyl; $R^3$ is 2-hydroxy-2-methylpropyl or 2-cyano-2-methylpropyl; one or two ring carbon atoms in the oxodihydropyridyl rings are optionally substituted with fluorine, methyl or ethyl; and the remainder of the variables are as described in the First Alternate Embodiment.

For the embodiment described in the previous seven paragraphs, n is 0 and all of the substitutable ring carbons in the oxodihydropyridyl are preferably unsubstituted.

Another embodiment of the invention is a compound represented by any one of Formulas Ip$^1$ and Ip$^3$, or a pharmaceutically acceptable salt thereof:

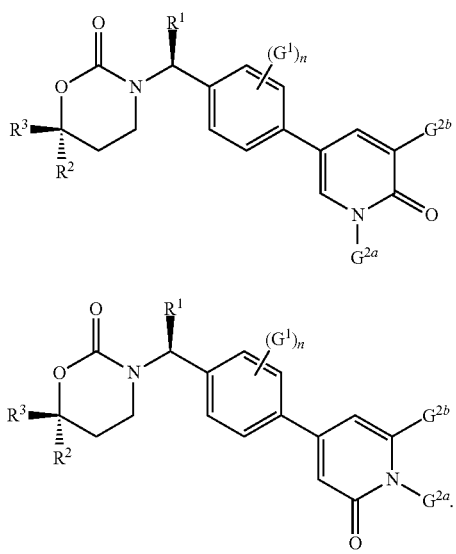

In Formulas Ip¹ and Ip³, G¹ is $(C_1-C_4)$alkyl, $(C_1-C_4)$alkoxy, $(C_1-C_4)$haloalkyl, $(C_1-C_4)$haloalkoxy, halogen, cyano or nitro; n is 0, 1 or 2; $G^{2a}$ is $(C_1-C_4)$alkyl, $(C_3-C_4)$cycloalkyl, $(C_3-C_4)$cycloalkyl$(C_1-C_2)$alkyl or $(C_1-C_4)$haloalkyl; $G^{2b}$ is hydrogen, fluorine, chlorine, cyano, hydroxy, amino, $(C_1-C_4)$ alkyl, $(C_3-C_4)$cycloalkyl, $(C_3-C_4)$cycloalkyl$(C_1-C_2)$alkyl, halo$(C_1-C_4)$alkyl, $(C_1-C_4)$alkoxy, $(C_1-C_4)$haloalkoxy, $CONH_2$, $(C_1-C_4)$alkylaminocarbonyl, di$(C_1-C_4)$alkylaminocarbonyl or $(C_1-C_4)$alkylcarbonylamino; and suitable values for $R^1$, $R^2$ and $R^3$ are as defined above in the first embodiment. In another alternative, the embodiments described in this paragraph exclude the compounds PR-221 and PR-313; or a pharmaceutically acceptable salt, enantiomer or diastereomer thereof.

For each of the embodiments described in the previous paragraph, $R^1$ is preferably methyl or ethyl.

For each of the embodiments described in the paragraph immediately following Formulas Ip¹ and Ip³, $R^1$ is preferably methyl or ethyl; and $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methyl butyl, 2-hydroxyethyl, 2-hydroxy-2-methylpropyl or 2-cyano-2-methylpropyl.

For each of the embodiments described in the paragraph immediately following Formulas Ip¹ and Ip³, $R^1$ is preferably methyl or ethyl; and $R^3$ is $H_2NC(=O)CMe_2CH_2$, 3-hydroxy-3-methylbutyl, 2-hydroxy-2-methylpropyl or 2-cyano-2-methylpropyl.

For each of the embodiments described in the paragraph immediately following Formulas Ip¹ and Ip³, $R^1$ is preferably methyl or ethyl; $R^2$ is phenyl optionally substituted with 1, 2 or 3 substituents selected from halo, cyano, $CONH_2$, $(C_1-C_4)$alkyl, $(C_1-C_4)$haloalkyl and $SO_2Me$; and $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl.

For each of the embodiments described in the paragraph immediately following Formulas Ip¹ and Ip³, $R^1$ is preferably methyl or ethyl; $R^2$ is phenyl optionally substituted with 1, 2 or 3 substituents selected from halo, cyano, $CONH_2$, $(C_1-C_4)$ alkyl, $(C_1-C_4)$haloalkyl and $SO_2Me$; and $R^3$ is $H_2NC(=O)CMe_2CH_2$, 3-hydroxy-3-methylbutyl, 2-hydroxy-2-methylpropyl or 2-cyano-2-methylpropyl.

For each of the embodiments described in the paragraph immediately following Formulas Ip¹ and Ip³, $R^1$ is preferably methyl or ethyl; and $R^3$ is 2-hydroxy-2-methylpropyl or 2-cyano-2-methylpropyl.

For each of the embodiments described in the paragraph immediately following Formulas Ip¹ and Ip³, $R^1$ is preferably methyl or ethyl; $R^2$ is phenyl or fluorophenyl; and $R^3$ is 2-hydroxy-2-methylpropyl or 2-cyano-2-methylpropyl.

For each of the embodiment described in the paragraph immediately following Formulas Ip¹ and Ip³, $R^1$ is preferably methyl or ethyl; $R^2$ is phenyl or fluorophenyl; $R^3$ is 2-hydroxy-2-methylpropyl or 2-cyano-2-methylpropyl; the substituent $G^{2a}$ is selected from $(C_1-C_4)$alkyl, $(C_3-C_4)$cycloalkyl, $(C_3-C_4)$cycloalkyl$(C_1-C_2)$alkyl, and $(C_1-C_2)$haloalkyl; and $G^{2b}$ is optionally selected from hydrogen, methyl or ethyl.

For each of the embodiment described in the paragraph immediately following Formulas Ip¹ and Ip³, $R^1$ is preferably methyl or ethyl; $R^2$ is phenyl or fluorophenyl; $R^3$ is 2-hydroxy-2-methylpropyl or 2-cyano-2-methylpropyl; the substituent $G^{2a}$ is selected from haloalkyl, $(C_1-C_4)$alkyl, $(C_3-C_4)$cycloalkyl, $(C_3-C_4)$cycloalkyl$(C_1-C_2)$alkyl, and $(C_1-C_2)$haloalkyl; and $G^{2b}$ is optionally selected from hydrogen, methyl or ethyl.

For each of the embodiment described in the paragraph immediately following Formulas Ip¹ and Ip³, $R^1$ is preferably methyl or ethyl; $R^2$ is phenyl or fluorophenyl; $R^3$ is 2-hydroxy-2-methylpropyl or 2-cyano-2-methylpropyl; the substituent $G^{2a}$ is selected from difluoromethyl, ethyl substituted with one to three fluorine (preferably, 2-fluoroethyl or 2,2,2-fluoroethyl), $(C_1-C_4)$alkyl, $(C_3-C_4)$cycloalkyl, $(C_3-C_4)$cycloalkyl$(C_1-C_2)$alkyl, and $(C_1-C_2)$haloalkyl; and $G^{2b}$ is optionally selected from hydrogen, methyl or ethyl.

Another embodiment of the invention (referred to herein as the "Second Alternate Embodiment") is a compound represented by Structural Formulas Ip¹ and Ip³, wherein: n is 0 or 1, preferably 0; each G¹ is independently $(C_1-C_4)$alkyl, $(C_1-C_4)$ alkoxy, $(C_1-C_4)$haloalkyl, $(C_1-C_4)$haloalkoxy, halogen, cyano or nitro; $G^{2a}$ is hydroxy$(C_1-C_6)$alkyl, $(C_1-C_6)$alkylcarbonylamino$(C_1-C_6)$alkyl, $(C_1-C_6)$alkyl-sulfonylamino$(C_1-C_6)$alkyl, $(C_1-C_6)$alkoxy$(C_1-C_6)$alkyl, amino$(C_1-C_6)$alkyl, $(C_1-C_6)$alkylamino$(C_1-C_6)$alkyl, di$(C_1-C_6)$alkylamino$(C_1-C_6)$alkyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$alkyl, $(C_3-C_6)$cycloalkylaminocarbonyl$(C_1-C_6)$alkyl, {$(C_3-C_6)$cycloalkyl}{$(C_1-C_6)$alkyl}aminocarbonyl$(C_1-C_6)$alkyl or di$(C_3-C_6)$cycloalkylaminocarbonyl$(C_1-C_6)$alkyl; $G^{2b}$ is hydrogen, fluorine, chlorine, cyano, hydroxy, amino, $(C_1-C_4)$alkyl, $(C_3-C_4)$cycloalkyl, $(C_3-C_4)$cycloalkyl$(C_1-C_2)$alkyl, halo$(C_1-C_4)$alkyl, $(C_1-C_4)$alkoxy, $(C_1-C_4)$haloalkoxy, $CONH_2$, $(C_1-C_4)$alkylaminocarbonyl, di$(C_1-C_4)$alkylaminocarbonyl or $(C_1-C_4)$alkylcarbonylamino; $R^1$ is methyl or ethyl; $R^2$ is phenyl, thienyl, pyridyl or isopropyl each optionally substituted with up to three groups independently selected from halo, methyl, methylthio or (4-morpholino)methyl; and $R^3$ is methyl, ethyl, propyl, butyl, vinyl, allyl or ethoxyethyl each optionally substituted with up to two groups independently selected from methyl, HO—, MeO—, $H_2N$—, $MeC(=O)NH$—, $MeS(=O)_2NH$—, $H_2NC(=O)$—, $MeNHC(=O)$—, $HO_2C$—, $(HO)_2P(=O)O$—, $H_2NS(=O)_2O$—, $H_2NS(=O)_2NH$—, $MeNHC(=O)NH$—, $MeNHC(=O)O$—, oxo, cyano, $HO_2C$—, $HOCH_2CH_2NH$—, 4-morpholino, $HOCH_2C(=O)NH$—, $H_2NCH_2C(=O)NH$—, $EtNHC(=O)NH$, $MeOC(=O)NH$—, $MeNHC(=NC\equiv N)NH$—, Me-, MeS—, $MeSO_2$— $MeSO_2N(Me)$—, $MeS(=O)_2NHC(=O)$—, imidazolylamino-, imidazolyl, tetrazolyl, $H_2NCONH-$, $H_2NCO_2-$, $HOCH_2CH_2O-$, MeNH—, $Me_2N-$ and MeCONMe.

Alternatively for Structural Formulas $Ip^1$ and $Ip^3$, $R^2$ is phenyl optionally substituted with 1, 2 or 3 substituents independently selected from halo, cyano, $CONH_2$, $(C_1-C_4)$alkyl, $(C_1-C_4)$haloalkyl and $SO_2Me$; and $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl; and the remainder of the variables are as described above for the Second Alternate Embodiment.

Alternatively for Structural Formulas $Ip^1$ and $Ip^3$, $R^3$ is $H_2NC(=O)CMe_2CH_2$, 3-hydroxy-3-methylbutyl, 2-hydroxy-2-methylpropyl or 2-cyano-2-methylpropyl; and the remainder of the variables are as described above for the Second Alternate Embodiment.

Alternatively for Structural Formulas $Ip^1$ and $Ip^3$, $R^2$ is phenyl optionally substituted with 1, 2 or 3 substituents independently selected from halo, cyano, $CONH_2$, $(C_1-C_4)$alkyl, $(C_1-C_4)$haloalkyl and $SO_2Me$; and $R^3$ is $H_2NC(=O)CMe_2CH_2$, 3-hydroxy-3-methylbutyl, 2-hydroxy-2-methylpropyl or 2-cyano-2-methylpropyl; and the remainder of the variables are as described in the Second Alternate Embodiment.

Alternatively for Structural Formulas $Ip^1$ and $Ip^3$, $R^3$ is 2-hydroxy-2-methylpropyl or 2-cyano-2-methylpropyl; and the remainder of the variables are as described in the Second Alternate Embodiment.

Alternatively for Structural Formulas $Ip^1$ and $Ip^3$, $R^2$ is phenyl or fluorophenyl; and $R^3$ is 2-hydroxy-2-methylpropyl or 2-cyano-2-methylpropyl; and the remainder of the variables are as described in the Second Alternate Embodiment.

Alternatively for Structural Formulas $Ip^1$ and $Ip^3$, $R^2$ is phenyl or fluorophenyl; $R^3$ is 2-hydroxy-2-methylpropyl or 2-cyano-2-methylpropyl; one or two substitutable ring carbon atoms in the oxodihydropyridyl rings are optionally substituted with fluorine, methyl or ethyl; and the remainder of the variables are as described in the Second Alternate Embodiment.

For the embodiment described in the previous seven paragraphs, n is 0 and $G^{2b}$ is preferably —H.

Another embodiment of the invention is a hydrate or monohydrate of (S)-6-(2-hydroxy-2-methylpropyl)-3-((S)-1-(4-(1-methyl-6-oxo-1,6-dihydropyridin-3-yl)phenyl)ethyl)-6-phenyl-1,3-oxazinan-2-one, (S)-6-(2-hydroxy-2-methylpropyl)-3-((S)-1-(4-(1-methyl-2-oxo-1,2-dihydropyridin-4-yl)phenyl)ethyl)-6-phenyl-1,3-oxazinan-2-one, 3-{(S)-1-[4-(1-Cyclopropyl-2-oxo-1,2-dihydropyridin-4-yl)-phenyl]-ethyl}-(S)-6-(2-hydroxy-2-methyl-propyl)-6-phenyl-[1,3]oxazinan-2-one and pharmaceutically acceptable salts thereof. Both, neutral and salt forms of the hydrate and monohydrate are also included. Preferably, the salt form is pharmaceutically acceptable.

Compounds of the invention are also disclosed in INHIBITORS OF 11β-HYDROXYSTEROID DEHYDOGENASE I, U.S. Provisional Application No. 61/61/135,933, filed Jul. 25, 2008; Cyclic Inhibitors Of 11β-Hydroxysteroid Dehydrogenase 1, U.S. Provisional Application No. 61/135,933, filed May 1, 2008; Cyclic Inhibitors Of 11β-Hydroxysteroid Dehydrogenase 1, U.S. Provisional Application No. 61/137, 148, filed Jul. 25, 2008; and Cyclic Inhibitors Of 11β-Hydroxysteroid Dehydrogenase 1, International Application No. PCT/US2008/009017, filed Jul. 25, 2008; the entire teachings of these applications are incorporated herein by reference in their entirety.

DEFINITIONS

The term "alkyl" means a straight or branched hydrocarbon radical having 1-10 carbon atoms and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like.

The term "cycloalkyl" means a monocyclic, bicyclic or tricyclic, saturated hydrocarbon ring having 3-10 carbon atoms and includes, for example, cyclopropyl (c-Pr), cyclobutyl, cyclopentyl, cyclohexyl, cycloheptyl, cyclooctyl, bicyclo[2.2.2]octyl, bicyclo[2.2.1]heptyl, spiro[4.4]nonane, adamantyl and the like.

The term "aryl" means an aromatic radical which is a phenyl group, a naphthyl group, an indanyl group or a tetrahydronaphthalene group. An aryl group is optionally substituted with 1-4 substituents. Exemplary substituents include alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido.

The term "heteroaryl" means a 5- and 6-membered heteroaromatic radical which may optionally be fused to a saturated or unsaturated ring containing 0-4 heteroatoms selected from N, O, and S and includes, for example, a heteroaromatic radical which is 2- or 3-thienyl, 2- or 3-furanyl, 2- or 3-pyrrolyl, 2-, 3-, or 4-pyridyl, 2-pyrazinyl, 2-, 4-, or 5-pyrimidinyl, 3- or 4-pyridazinyl, 1H-indol-6-yl, 1H-indol-5-yl, 1H-benzimidazol-6-yl, 1H-benzimidazol-5-yl, 2-, 4-, 5-, 6-, 7- or 8-quinazolinyl, 2-, 3-, 5-, 6-, 7- or 8-quinoxalinyl, 2-, 3-, 4-, 5-, 6-, 7- or 8-quinolinyl, 1-, 3-, 4-, 5-, 6-, 7- or 8-isoquinolinyl, 2-, 4-, or 5-thiazolyl, 2-, 3-, 4-, or 5-pyrazolyl, 2-, 3-, 4-, or 5-imidazolyl. A heteroaryl is optionally substituted. Exemplary substituents include alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido, or by oxo to form an N-oxide.

The term "heterocyclyl" means a 4-, 5-, 6- and 7-membered saturated or partially unsaturated heterocyclic ring containing 1 to 4 heteroatoms independently selected from N, O, and S. Exemplary heterocyclyls include pyrrolidine, pyrrolidin-2-one, 1-methylpyrrolidin-2-one, piperidine, piperidin-2-one, dihydropyridine, tetrahydropyridine, piperazine, 1-(2, 2,2-trifluoroethyl)piperazine, 1,2-dihydro-2-oxopyridine, 1,4-dihydro-4-oxopyridine, piperazin-2-one, 3,4,5,6-tetrahydro-4-oxopyrimidine, 3,4-dihydro-4-oxopyrimidine, tetrahydrofuran, tetrahydropyran, tetrahydrothiophene, tetrahydrothiopyran, isoxazolidine, 1,3-dioxolane, 1,3-dithiolane, 1,3-dioxane, 1,4-dioxane, 1,3-dithiane, 1,4-dithiane, oxazolidin-2-one, imidazolidin-2-one, imidazolidine-2,4-dione, tetrahydropyrimidin-2(1H)-one, morpholine, N-methylmorpholine, morpholin-3-one, 1,3-oxazinan-2-one, thiomorpholine, thiomorpholine 1,1-dioxide, tetrahydro-1,2,5-thiaoxazole 1,1-dioxide, tetrahydro-2H-1,2-thiazine 1,1-dioxide, hexahydro-1,2,6-thiadiazine 1,1-dioxide, tetrahydro-1,2,5-thiadiazole 1,1-dioxide isothiazolidine 1,1-dioxide, 6-oxo-1, 6-dihydropyridazin-3-yl, 6-oxo-1,6-dihydropyridazin-4-yl, 5-oxo-4,5-dihydro-1H-1,2,4-triazol-3-yl and 5-oxo-4,5-dihydro-1H-imidazol-2-yl. A heterocyclyl can be optionally substituted with 1-4 substituents. Exemplary substituents include alkyl, haloalkyl, halogen and oxo.

The term "spirocycloalkyl" means a cycloalkyl group which shares one ring carbon with another alkyl or cycloalkyl group.

As used herein the terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

When a disclosed compound or its pharmaceutically acceptable salt is named or depicted by structure, it is to be understood that solvates or hydrates of the compound or its pharmaceutically acceptable salts are also included. "Solvates" refer to crystalline forms wherein solvent molecules are incorporated into the crystal lattice during crystallization. Solvate may include water or nonaqueous solvents such as ethanol, isopropanol, DMSO, acetic acid, ethanolamine, and EtOAc. Solvates, wherein water is the solvent molecule incorporated into the crystal lattice, are typically referred to as "hydrates." Hydrates include stoichiometric hydrates as well as compositions containing variable amounts of water. Some of the compounds disclosed in the exemplification may be in the anhydrous form.

The term "compound" also includes labeling at one or more positions with deuterium. "Labeled with deuterium at a position" means that the amount deuterium at the position is greater than the amount that is present at natural abundance. In certain instances, the deuterium at each position in a "compound" is at natural abundance.

Certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. The symbol "*" in a structural formula represents the presence of a chiral carbon center. "R" and "S" represent the configuration of substituents around one or more chiral carbon atoms. Thus, "R*" and "S*" denote the relative configurations of substituents around one or more chiral carbon atoms.

"Racemate" or "racemic mixture" means a compound of equimolar quantities of two enantiomers, wherein such mixtures exhibit no optical activity; i.e., they do not rotate the plane of polarized light.

"Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration.

"R," "S," "St," "R*," "E," "Z," "cis," and "trans," indicate configurations relative to the core molecule.

The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

When the stereochemistry of a disclosed compound is named or depicted by structure, the named or depicted stereoisomer is at least 60%, 70%, 80%, 90%, 99% or 99.9% by weight pure relative to the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer over the weight of the enantiomer plus the weight of its optical isomer.

When a disclosed compound is named or depicted by structure without indicating the stereochemistry, and the compound has at least one chiral center, it is to be understood that the name or structure encompasses one enantiomer of compound free from the corresponding optical isomer, a racemic mixture of the compound and mixtures enriched in one enantiomer relative to its corresponding optical isomer.

When a disclosed compound is named or depicted by structure without indicating the stereochemistry and has at least two chiral centers, it is to be understood that the name or structure encompasses a diastereomer free of other diastereomers, a pair of diastereomers free from other diastereomeric pairs, mixtures of diastereomers, mixtures of diastereomeric pairs, mixtures of diastereomers in which one diastereomer is enriched relative to the other diastereomer(s) and mixtures of diastereomeric pairs in which one diastereomeric pair is enriched relative to the other diastereomeric pair(s).

The compounds of the invention may be present in the form of pharmaceutically acceptable salts. For use in medicines, the salts of the compounds of the invention refer to non-toxic "pharmaceutically acceptable salts." Pharmaceutically acceptable salt forms include pharmaceutically acceptable acidic/anionic or basic/cationic salts.

Pharmaceutically acceptable basic/cationic salts include, the sodium, potassium, calcium, magnesium, diethanolamine, n-methyl-D-glucamine, L-lysine, L-arginine, ammonium, ethanolamine, piperazine and triethanolamine salts.

Pharmaceutically acceptable acidic/anionic salts include, the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, malonate, mandelate, mesylate, methylsulfate, mucate, napsylate, nitrate, pamoate, pantothenate, phosphate/diphospate, polygalacturonate, salicylate, stearate, subacetate, succinate, sulfate, hydrogensulfate, tannate, tartrate, teoclate, tosylate, and triethiodide salts.

The following abbreviations have the indicated meanings:

| Abbreviation | Meaning |
|---|---|
| A % | Area percentage |
| Boc | tert-butoxy carbonyl or t-butoxy carbonyl |
| (Boc)$_2$O | di-tert-butyl dicarbonate |
| Cbz | Benzyloxycarbonyl |
| CbzCl | Benzyl chloroformate |
| c-Pr | cyclopropyl |
| DAST | diethylaminosulfur trifluoride |
| DBU | 1,8-diazabicyclo[5.4.0]undec-7-ene |
| DCC | N,N'-dicyclohexylcarbodiimide |
| DCU | N,N'-dicyclohexylurea |
| DIAD | diisopropyl azodicarboxylate |
| DIBAL-H | diisobutylaluminum hydride |

-continued

| Abbreviation | Meaning |
|---|---|
| DIEA | N,N-diisopropylethylamine |
| DMAP | 4-(dimethylamino)pyridine |
| DMF | N,N-dimethylformamide |
| DMPU | 1,3-dimethyl-3,4,5,6-tetrahydro-2(1H)-pyrimidinone |
| 2,4-DNP | 2,4-dinitrophenylhydrazine |
| dppf | 1,1'-Bis(diphenylphosphino)ferrocene |
| DPTBS | Diphenyl-t-butylsilyl |
| dr | diastereomer ratio |
| EDC•HCl, EDCl | 1-[3-(dimethylamino)propyl]-3-ethylcarbodiimide hydrochloride |
| Equiv | equivalents |
| EtOAc | Ethyl acetate |
| Fmoc | 1-[[(9H-fluoren-9-ylmethoxy)carbonyl]oxy]- |
| Fmoc-OSu | 1-[[(9H-fluoren-9-ylmethoxy)carbonyl]oxy]-2,5-pyrrolidinedione |
| h, hr | hour(s) |
| HOBt | 1-hydroxybenzotriazole |
| HATU | 2-(7-Aza-1H-benzotriazole-1-yl)-1,1,3,3-tetramethyluronium hexafluorophosphate |
| HBTU | 2-(1H-Benzotriazol-1-yl)-1,1,3,3-tetramethyluronium hexafluorophosphate |
| KHMDS | potassium hexamethyldisilazane |
| LAH or LiAlH$_4$ | lithium aluminum hydride |
| LC-MS | liquid chromatography-mass spectroscopy |
| LHMDS | lithium hexamethyldisilazane |
| m-CPBA | meta-chloroperoxybenzoic acid |
| Me | methyl |
| MsCl | methanesulfonyl chloride |
| Min | minute |
| MS | mass spectrum |
| NaH | sodium hydride |
| NaHCO$_3$ | sodium bicarbonate |
| NaN$_3$ | sodium azide |
| NaOH | sodium hydroxide |
| Na$_2$SO$_4$ | sodium sulfate |
| NMM | N-methylmorpholine |
| NMP | N-methylpyrrolidinone |
| Pd$_2$(dba)$_3$ | tris(dibenzylideneacetone)dipalladium(0) |
| PE | petroleum ether |
| Quant | quantitative yield |
| rt | room temperature |
| Satd | saturated |
| SOCl$_2$ | thionyl chloride |
| SFC | supercritical fluid chromatography |
| SPA | scintillation proximity assay |
| SPE | solid phase extraction |
| TBAF | tetrabutylammonium fluoride |
| TBS | t-butyldimethylsilyl |
| TBDPS | t-butyldiphenylsilyl |
| TBSCl | t-butyldimethylsilyl chloride |
| TBDPSCl | t-butyldiphenylsilyl chloride |
| TEA | triethylamine or Et$_3$N |
| TEMPO | 2,2,6,6-tetramethyl-1-piperidinyloxy free radical |
| Teoc | 1-[2-(trimethylsilyl)ethoxycarbonyloxy]- |
| Teoc-OSu | 1-[2-(trimethylsilyl)ethoxycarbonyloxy]pyrrolidin-2,5-dione |
| T$_{ext}$ | External temperature |
| T$_{int}$ | Internal temperature |
| TFA | trifluoroacetic acid |
| Tlc, TLC | thin layer chromatography |
| TMS | trimethylsilyl |
| TMSCl | chlorotrimethylsilane or trimethylsilyl chloride |
| t$_R$ | retention time |
| TsOH | p-toluenesulfonic acid |

General Description of Synthetic Methods

Compounds of Formula I* can be prepared by several processes. In the discussion below, $A^1$, $Cy^1$, E, $R^1$, $R^2$, $R^3$, Y and n have the meanings indicated above unless otherwise noted. $Cy^2$ is an optionally substituted 2-oxo-1,2-dihydropyridyl group. In cases where the synthetic intermediates and final products of Formula I* described below contain potentially reactive functional groups, for example amino, hydroxyl, thiol and carboxylic acid groups, that may interfere with the desired reaction, it may be advantageous to employ protected forms of the intermediate. Methods for the selection, introduction and subsequent removal of protecting groups are well known to those skilled in the art. (T. W. Greene and P. G. M. Wuts "Protective Groups in Organic Synthesis" John Wiley & Sons, Inc., New York 1999). Such protecting group manipulations are assumed in the discussion below and not described explicitly. Generally, reagents in the reaction schemes are used in equimolar amounts; however, in certain cases it may be desirable to use an excess of one reagent to drive a reaction to completion. This is especially the case when the excess reagent can be readily removed by evaporation or extraction. Bases employed to neutralize HCl in reaction mixtures are generally used in slight to substantial excess (1.05-5 equivalents).

In a first process a compound of Formula I*, can be prepared by reaction of an aminoalcohol intermediate of Formula II with a reagent of Formula III, wherein $Z^1$ and $Z^2$ are leaving groups such as chloride, 1-imidazolyl or aryloxide in an inert solvent such as THF, CH$_2$Cl$_2$, toluene or MeCN, usually in the presence of an organic or inorganic base such as triethylamine or NaHCO$_3$ respectively, at −10° C. to 120° C.:

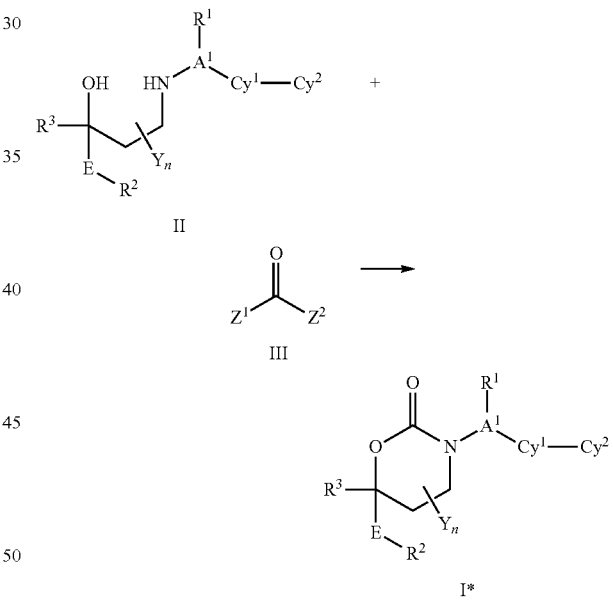

Certain instances of reagent III are especially convenient because they are commercially available. For example when $Z^1$ and $Z^2$ are both chloride, III is phosgene. When $Z^1$ and $Z^2$ are both 1-imidazolyl, III is carbonyl diimidazole. When $Z^1$ is chloride and $Z^2$ is p-nitrophenoxide, III is p-nitrophenyl chloroformate. When $Z^1$ and $Z^2$ are both OCCl$_3$, III is triphosgene and as little as one third of molar equivalent can be used.

Aminoalcohol intermediates of Formula II can be prepared by reduction of amides of Formula IV using a hydride reagent such as BH$_3$.THF solution, BH$_3$.Me$_2$S or LiAlH$_4$ in an inert solvent ethereal such as THF or DME at 20° C. to 100° C. for between 1 h and 48 h:

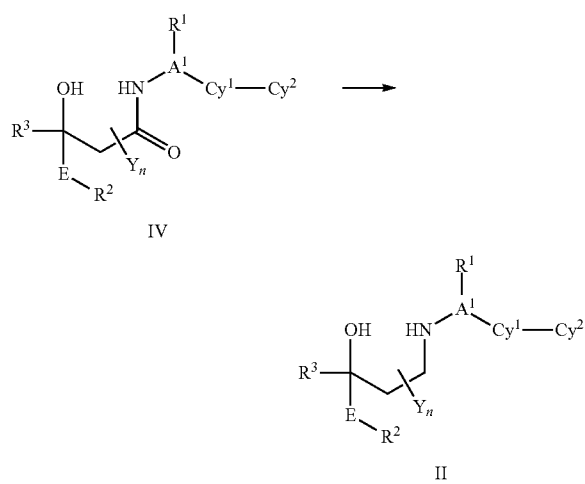

IV

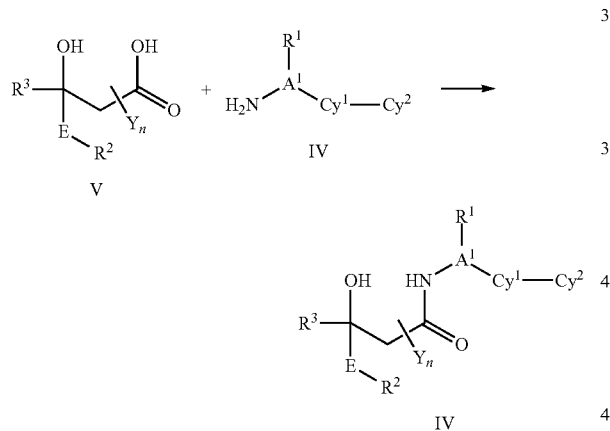

II

Intermediates of Formula IV can be prepared by coupling of a β-hydroxyacid of Formula V with an amine of Formula VI using standard peptide coupling reagents such as EDC in the presence of HOBt and N,N-diisopropylethylamine in an inert solvent such as CH$_2$Cl$_2$ at 0-30° C. for between 1 h and 24 h:

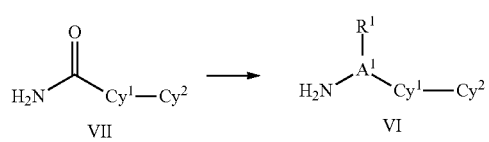

Amine intermediates of Formula VI, wherein A$^1$=CH$_2$ and R$^1$ is absent, can be prepared by reduction of amides of Formula VII using a hydride reagent such as BH$_3$.THF solution, BH$_3$.Me$_2$S or LiAlH$_4$ in an inert solvent ethereal such as THF or DME at 20° C. to 100° C. for between 1 h and 48 h:

Amine intermediates of Formula VI, wherein A$^1$ is a bond, R$^1$ is absent and Cy$^1$ is not an aromatic or heteroaromatic ring, can be prepared from ketones of formula VIII via oximes of Formula IX or by reductive amination of a ketone of Formula VIII with ammonia:

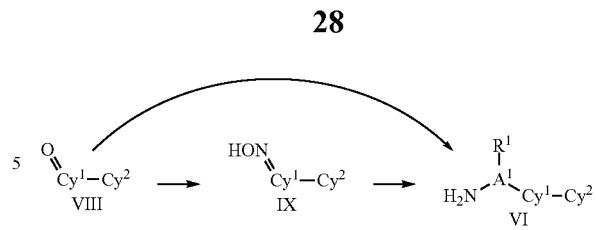

Methods for the conversion of ketones to oximes are described in Smith, M. B. and March, J. "March's Advanced Organic Chemistry" pp 1194-1195, 5$^{th}$ Edition, Wiley, New York, N.Y., 2001. Methods for the reduction of oximes to primary amines are described in Smith, M. B. and March, J. "March's Advanced Organic Chemistry" p 1555, 5$^{th}$ Edition, Wiley, New York, N.Y., 2001. Methods for the reductive amination of ketones are described in Baxter, E. W. and Reitz, A. B. "Organic Reactions" Volume 59, Ed. Overman, L. E., Wiley Interscience, 2002.

Similarly amine intermediates of Formula VI, wherein A$^1$ is CH and R$^1$ is methyl or ethyl, can be prepared by reduction t-butylsulfinylimines of Formula VIIIb which can be prepared from ketones of Formula VIIIa and t-butylsulfinamide or by addition of organometallic reagents of Formula R$^1$M, wherein R1 is Me or Et and M is Li, MgCl, MgBr or MgI, to t-butylsulfinylimines of Formula VIIId which can be prepared from aldehydes of Formula VIIIc.

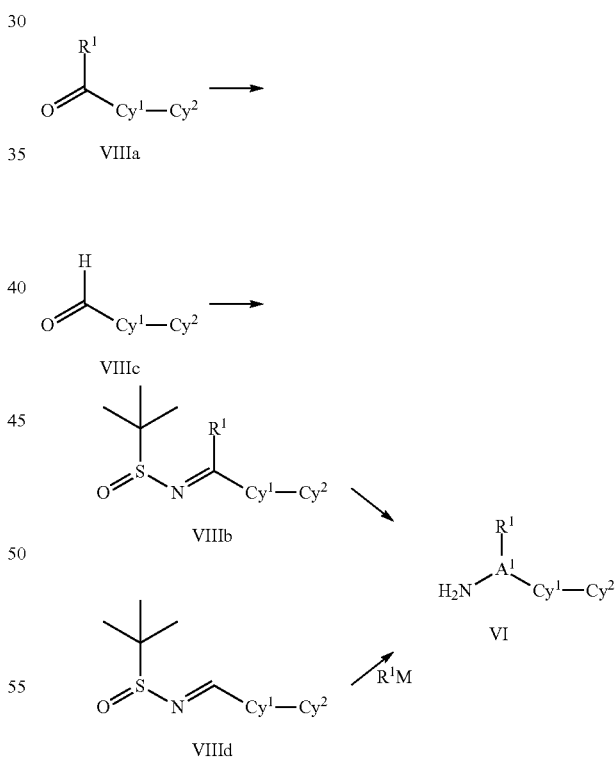

High stereoselectivity is often achieved in such reactions using chiral t-butylsulfinylimines.

Intermediates of Formula II, wherein n=0, can be prepared by reaction of oxetanes of Formula X with amines of Formula VI as described in Smith, M. B. and March, J. "March's Advanced Organic Chemistry" p 505, 5$^{th}$ Edition, Wiley, New York, N.Y., 2001:

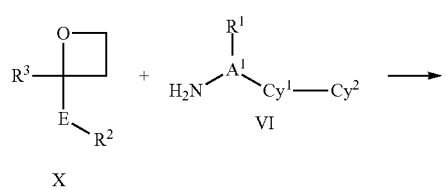

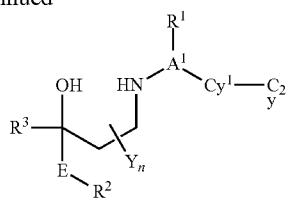

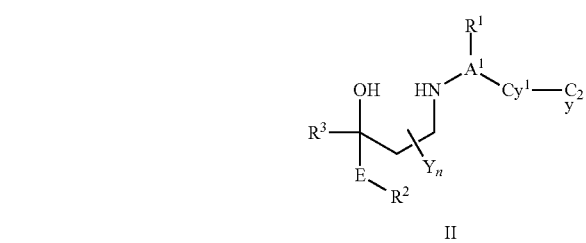

Amide intermediates of Formula XI can be prepared by reaction of an amino-alcohol intermediate of Formula XII with activated carboxylic acid of Formula XIII wherein $Z^3$=chloride or an activated ester, such as an N-hydroxysuccinimide ester:

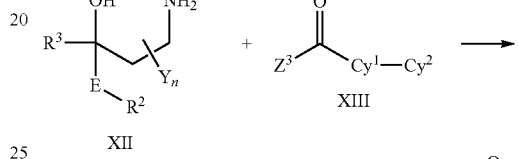

Intermediates of Formula II can also be prepared by reductive amination of β-hydroxyaldehydes of Formula Xa with amines of Formula VI. Methods for the reductive amination of aldehydes are described in Baxter, E. W. and Reitz, A. B. "Organic Reactions" Volume 59, Ed. Overman, L. E., Wiley Interscience, 2002.

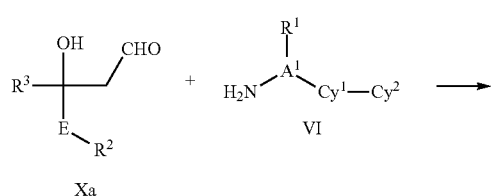

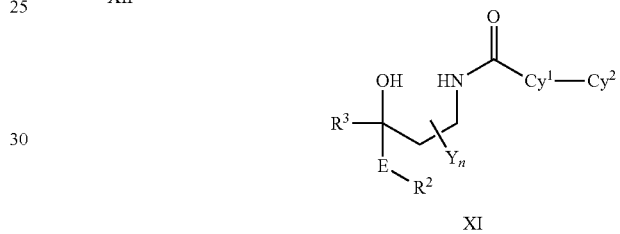

Amino-alcohol intermediates of Formula XII, wherein n=0, can be prepared by reaction of an epoxide of Formula XIV with cyanide ion followed by reduction of the resulting hydroxynitrile of Formula XV with hydrogen gas in the presence of a catalyst or with a hydride source such as LiAlH$_4$:

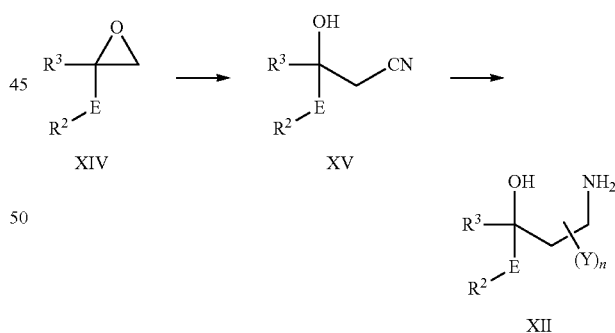

Aldehydes of Formula Xa can be prepared from homoallylic alcohols of Formula XXI by treatment with OsO$_4$ and NaIO$_4$.

Intermediates of Formula II, wherein $A^1$=CH$_2$ and $R^1$ is absent, can be prepared by reduction of amide intermediates of formula XI using a hydride reagent such as BH$_3$.THF solution, BH$_3$.Me$_2$S or LiAlH$_4$ in an inert solvent ethereal such as THF or DME at 20° C. to 100° C. for between 1 h and 48 h:

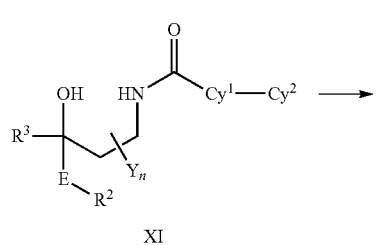

Epoxide compounds of formula XIV can, in turn, be prepared in a number of ways including, as described in Aube, J. "Epoxidation and Related Processes" Chapter 3.2 in Volume 1 of "Comprehensive Organic Synthesis" Edited by B. M. Trost, I. Fleming and Stuart L. Schreiber, Pergamon Press, New York, 1992.

Hydroxynitrile intermediates of Formula XV can be prepared by treatment of ketones of Formula XVI with acetonitrile anion, formed by treatment of acetonitrile with n-BuLi or LDA, in an inert, anhydrous solvent such as THF at low temperature:

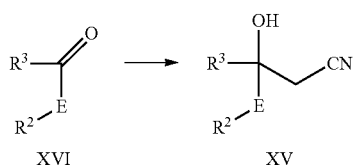

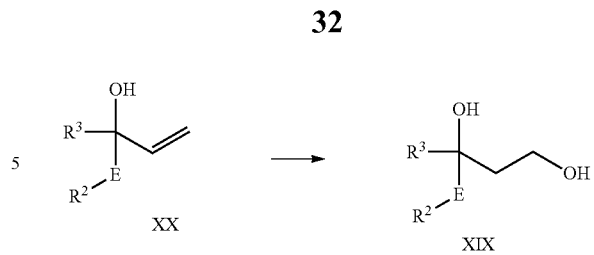

Amino-alcohol intermediates of Formula XII, wherein n is 0, can be prepared by treatment of sulfonate intermediates of Formula XVII, wherein $R^A$ is for example methyl, trifluoromethyl or p-methylphenyl, with ammonia:

Diol intermediates of Formula XIX can be prepared by ozonolysis and reduction of homoallyl alcohols of Formula XXI:

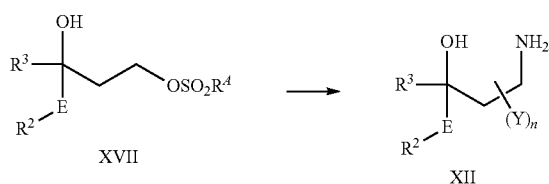

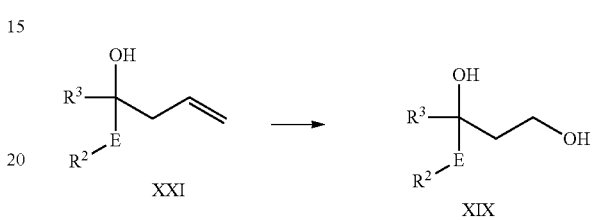

Amino-alcohol intermediates of Formula XII can be prepared by treatment of sulfonate intermediates of Formula XVII with sodium azide to give an azide intermediate of Formula XVIII, followed by catalytic hydrogenation or by Staudinger reduction with $PPh_3$ in wet THF:

Aminoalcohol intermediates of Formula II, wherein $A^1$ is a bond, $R^1$ is absent, and $Cy^1$ is a heteroaryl group or an aryl group bearing at least one strongly electron withdrawing group such as $CF_3$, can be prepared by reaction of an aminoalcohol intermediate of Formula XII with a compound of Formula XXII, wherein $Cy^1$ is a heteroaryl group or an aryl group bearing at least one strongly electron withdrawing group such as $CF_3$ and $R^B$ is a leaving group such a fluoro, chloro, bromo or iodo:

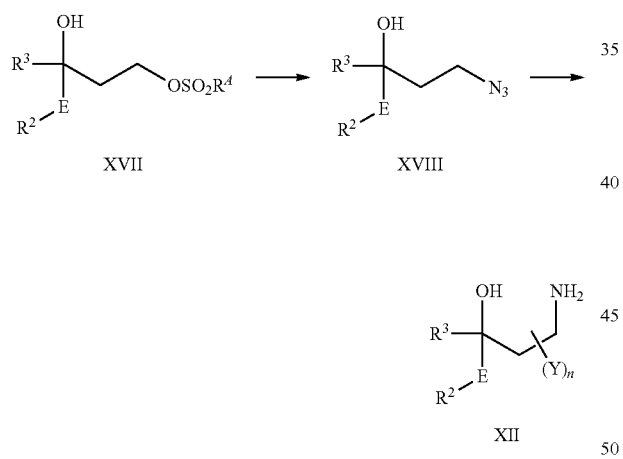

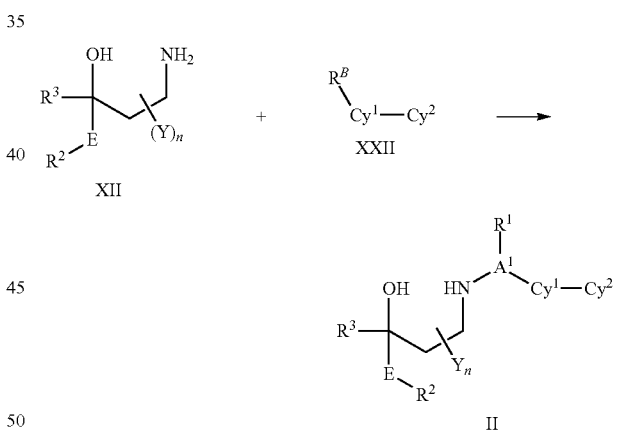

Sulfonate intermediates of Formula XVII can be prepared from diol intermediates of Formula XIX with a sulfonyl chloride $R^A SO_2Cl$:

Aminoalcohol intermediates of Formula II, wherein $A^1$ is $(C_1)$alkylene can be prepared by reaction of an aminoalcohol of Formula XII with an aldehyde or methyl ketone of Formula XII in the presence of a reducing agent such as $NaCNBH_3$ or $Na(OAc)_3BH$:

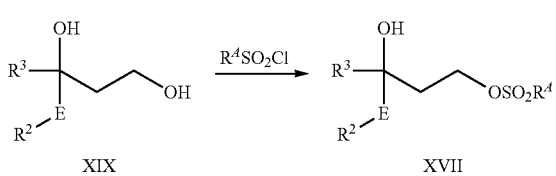

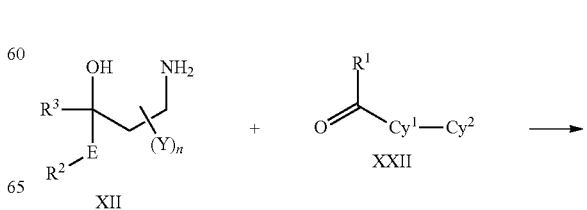

Diol intermediates of Formula XIX can be prepared by hydroboration of allyl alcohols of Formula XX:

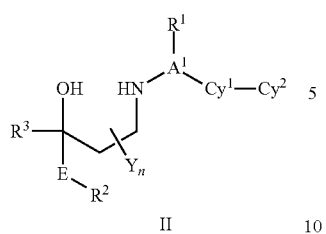

II

Methods for the reductive amination of aldehydes and ketones are described in Baxter, E. W. and Reitz, A. B. "Organic Reactions" Volume 59, Ed. Overman, L. E., Wiley Interscience, 2002.

In a second process a compound of Formula I* can be prepared by reaction of a ketocarbamate of Formula XXIV, wherein $R^D$ is alkyl or arylalkyl group such as methyl, t-butyl or benzyl, with an organometallic reagent of Formula XXV wherein M includes, but is not limited to, MgCl, MgBr, MgI or Li:

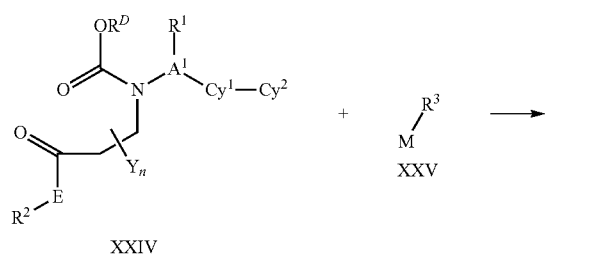

XXIV

I*

In specific examples, organometallic reagent XXV is allylmagnesium bromide, allylzinc(II) bromide, (2-methylallyl) magnesium chloride or (2-methoxy-2-oxoethyl)zinc(II) bromide. In certain cases when M is MgCl, MgBr or MgI, it is advantageous to add $CeCl_3$ to the reaction mixture.

Ketocarbamates of Formula XXIV can be prepared by reaction of aminoketones of Formula XXVI with intermediates of Formula XXVII wherein $R^E$ is a leaving group such as chloride, succinyloxy, imidazolyl or t-butoxycarboxycarbonyl:

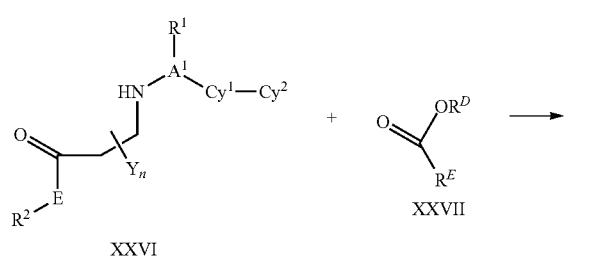

XXVI

XXVII

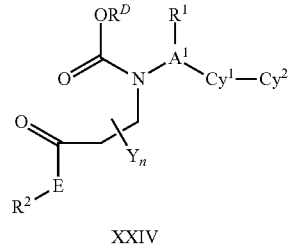

XXIV

Aminoketones of Formula XXVI, wherein n=0, can be prepared by reaction of α,β-unsaturated ketones of Formula XXVIII with amines of Formula VI:

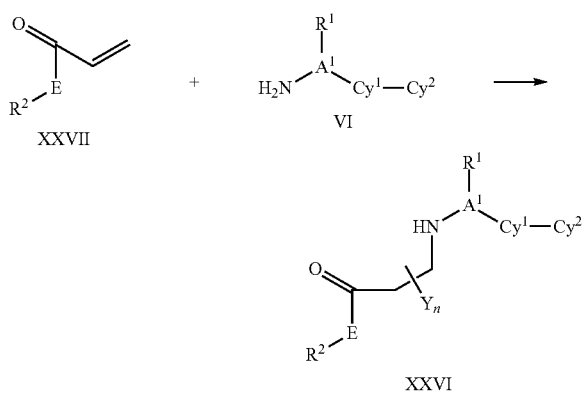

XXVII

VI

XXVI

Aminoketones of Formula XXVI, wherein n=0, can be prepared by reaction of β-dialkylaminoketones of Formula XXVIII, wherein $R^F$ is lower alkyl especially methyl, with amines of Formula VI:

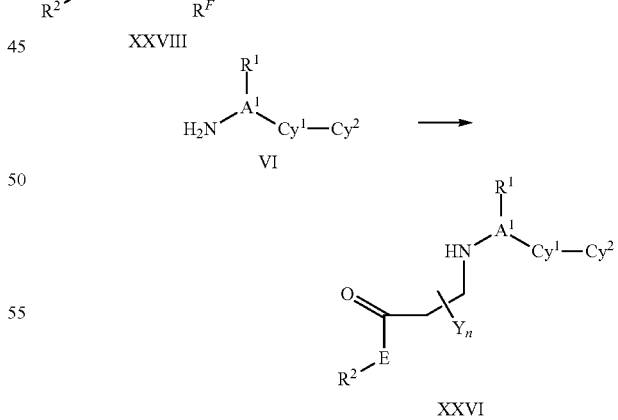

XXVIII

VI

XXVI

β-Dialkylaminoketones of Formula XXVIII are in turn derived from α,β-unsaturated ketones of Formula XXVII with dialkylamines of Formula $R^F NHR^F$.

In a third process a compound of Formula I* can be prepared by reaction of a compound of Formula XVII with an isocyanate of Formula XXIX in the presence of a base:

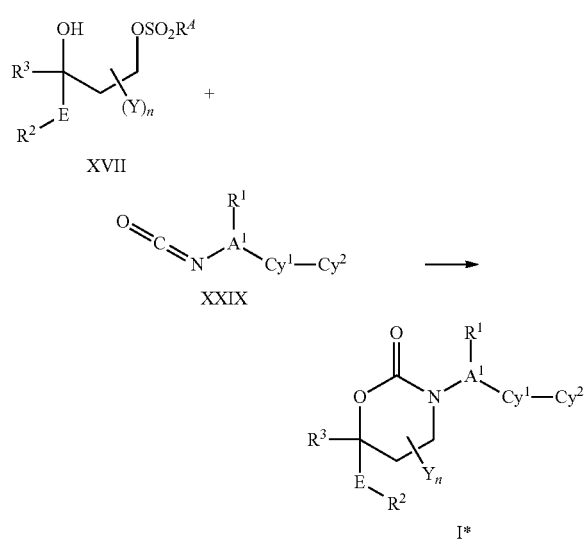

Isocyanates of Formula XXIX can be prepared from amines of Formula VI by treatment with phosgene, diphosgene or triphosgene. This third process is described in greater detail in U.S. Provisional Application Ser. No. 61/137,013, filed Jul. 25, 2008 entitled SYNTHESIS OF INHIBITORS OF 11β-HYDROXYSTEROID DEHYDROGENASE TYPE 1, the entire teachings of which are incorporated herein by reference.

In a fourth process a compound of Formula I* can be prepared by reaction of a halo compound of Formula, wherein Hal is chlorine or bromine, with an isocyanate of Formula XXIX in the presence of a base:

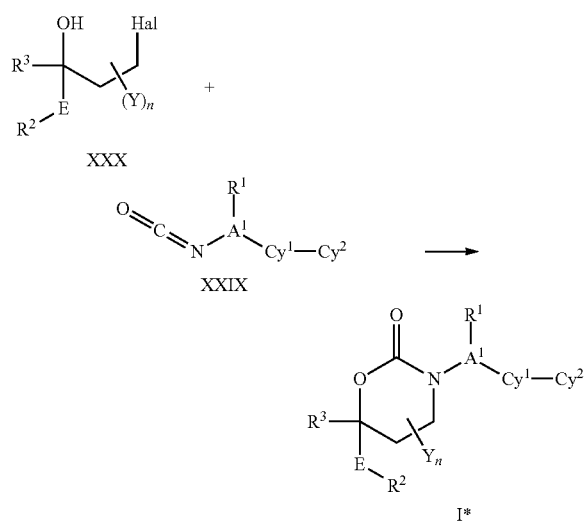

Halo compounds of Formula XXX can be prepared by reaction of β-haloketones of Formula XXXI with organometallic reagents of Formula XXV wherein M is a metal containing radical including MgCl, MgBr, MgI or Li. The reaction is optionally carried out in the presence of anhydrous cerium trichloride:

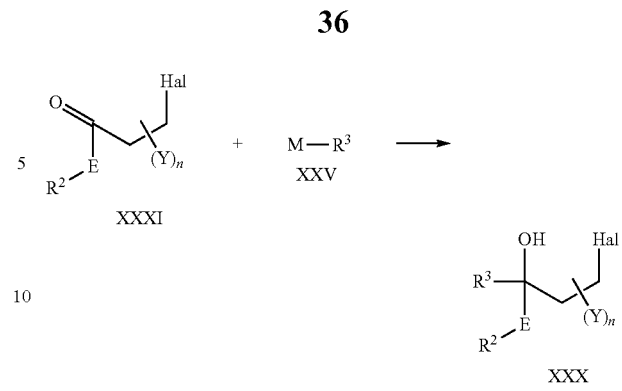

In a fifth process a compound of Formula I*, wherein $A^1$ is $CH_2$ or $CH_2CH_2$ and $R^1$ is absent, can be prepared by reaction of a compound of Formula XXXII, with a compound of Formula XXXIII, wherein $A^1$ is $CH_2$ or $CH_2CH_2$ and $R^G$ is a leaving group such as Br, I, $OSO_2Me$, $OSO_2CF_3$ or $OSO_2Ph$, in the presence of a base such as NaH or $K_2CO_3$:

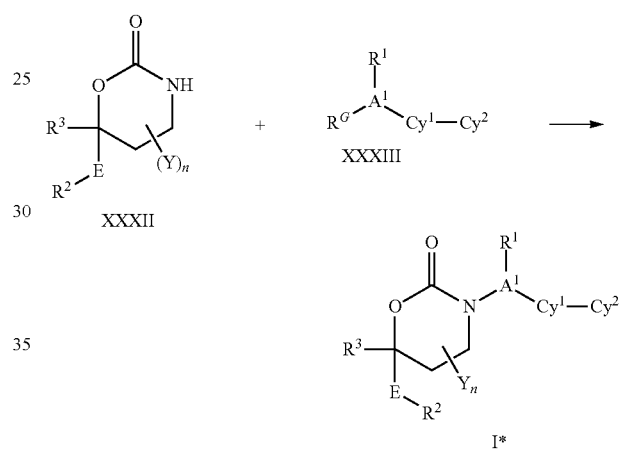

Compounds of Formula XXXII can be prepared by treatment of compounds of Formula XII with various reagents of Formula III, wherein $Z^1$ and $Z^2$ are leaving groups such as chloride, 1-imidazolyl or aryloxide in an inert solvent such as THF, $CH_2Cl_2$, toluene or MeCN, usually in the presence of an organic or inorganic base such as triethylamine or $NaHCO_3$ respectively, at $-10°$ C. to $120°$ C.:

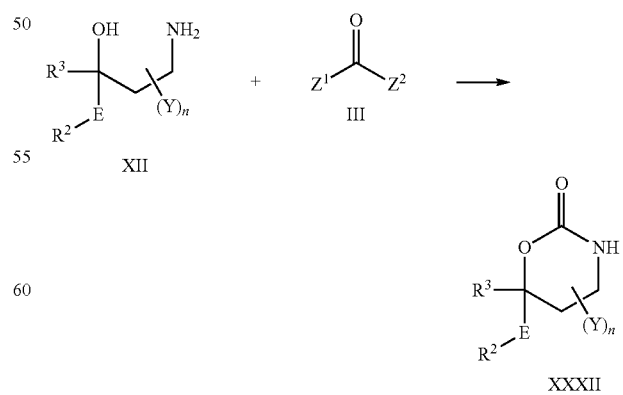

In a sixth process a compound of Formula I*, wherein $A^1$ is a bond and $R^1$ is absent, can be prepared by reaction of a compound of Formula XXXII, with a compound of Formula XXII, wherein $R^B$ is a leaving group such as chloro, bromo, iodo or $OSO_2CF_3$, in the presence of a base such as $K_2CO_3$ and a copper or palladium catalyst in an inert solvent such as dioxane, DMF or NMP at elevated temperature:

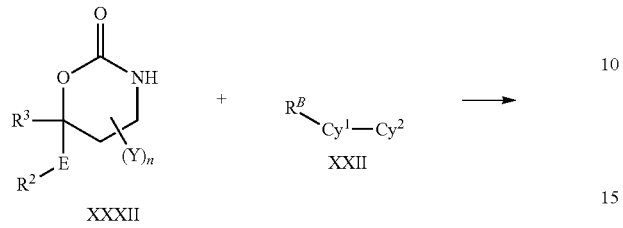

In a seventh process a compound of Formula I* can be prepared by Suzuki coupling of a compound of Formula XXXIV, wherein $Cy^1$ is aryl or heteroaryl and $R^X$ is bromo, iodo, or trifluoromethanesulfonyloxy, with a boronic acid ($R^Y$ is hydrogen) or a boronate ester of Formula XXXV ($R^Y$ is ($C_1$-$C_6$)alkyl and the two groups $R^Y$ taken together form a ($C_1$-$C_{12}$)alkylene group).

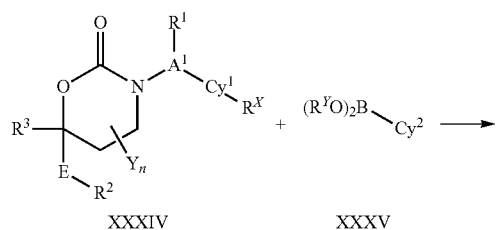

In an eighth process a compound of Formula XXXIV, wherein $Cy^1$ is aryl or heteroaryl and $R^X$ is bromo, iodo, or trifluoromethanesulfonyloxy, can be reacted with bis(pinacolato)diboron in the presence of a palladium catalyst to give a boronate ester of Formula XXXVI which can be further reacted with a heterocyclic compound of Formula XXXVII, wherein $R^X$ is bromo, iodo, or trifluoromethanesulfonyloxy, again in the presence of a palladium catalyst, to give a compound of Formula I*.

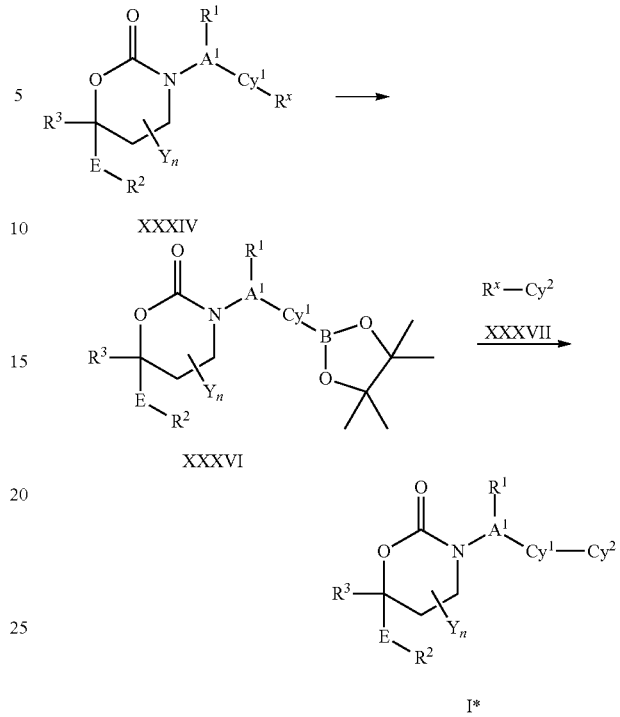

In a ninth process a compound of Formula I* can be prepared from another compound of Formula I*. For example:

(1) a compound of Formula I*, wherein $R^1$ or $R^3$ is ω-hydroxy($C_2$-$C_6$)alkyl, can be oxidized to a compound of Formula I*, wherein $R^1$ or $R^3$ is ω-carboxy($C_1$-$C_5$)alkyl, using Jones reagent.

(2) a compound of Formula I*, wherein $R^1$ or $R^3$ is ω-carboxy($C_1$-$C_6$)alkyl, can be coupled with ammonia or a ($C_1$-$C_6$)alkylamine using a standard peptide coupling reagent such as EDC to afford a compound of Formula I*, wherein $R^1$ or $R^3$ is ω-$H_2NC(=O)$($C_1$-$C_6$)alkyl or ω-{($C_1$-$C_6$)alkylNHC(=O)}($C_1$-$C_6$)alkyl.

(3) a compound of Formula I*, wherein $R^1$ or $R^3$ is ω-hydroxy($C_1$-$C_6$)alkyl, can be converted to its methanesulfonate or trifluoromethanesulfonate, treated with sodium azide and reduced to give a compound of Formula I*, wherein $R^1$ or $R^3$ is ω-amino($C_1$-$C_6$)alkyl.

(4) a compound of Formula I*, wherein $R^1$ or $R^3$ is amino($C_1$-$C_6$)alkyl, can be reacted with acetic anhydride or acetyl chloride to give a compound of Formula I*, wherein $R^1$ or $R^3$ is {acetylamino}($C_1$-$C_6$)alkyl.

(5) a compound of Formula I*, wherein $R^1$ or $R^3$ is amino($C_1$-$C_6$)alkyl, can be reacted with methanesulfonyl chloride to give a compound of Formula I*, wherein $R^1$ or $R^3$ is {methanesulfonylamino}($C_1$-$C_6$)alkyl.

(6) a compound of Formula I*, wherein $R^1$ is ($C_2$-$C_6$)alkenyl, is hydroborated to afford a compound of Formula I*, wherein $R^1$ is hydroxy($C_2$-$C_6$)alkyl.

(7) a compound of Formula I*, wherein $R^3$ is ($C_2$-$C_6$)alkenyl, is hydroborated to afford a compound of Formula I*, wherein $R^3$ is hydroxy($C_2$-$C_6$)alkyl.

(8) a compound of Formula I*, wherein $R^1$ is ($C_2$-$C_6$)alkenyl, can be reacted with osmium tetroxide and N-methylmorpholine-N-oxide to afford a compound of Formula I*, wherein $R^1$ is vicinal dihydroxy($C_2$-$C_6$)alkyl.

(9) a compound of Formula I*, wherein $R^3$ is ($C_2$-$C_6$)alkenyl, can be reacted with osmium tetroxide and N-methylmorpholine-N-oxide to afford a vicinal diol compound of Formula I*, wherein $R^3$ is vicinal dihydroxy($C_2$-$C_6$)alkyl.

(10) a compound of Formula I*, wherein $R^1$ is ($C_2$-$C_6$) alkenyl, can be reacted with ozone followed by $NaBH_4$ to give a compound of Formula I*, wherein $R^1$ is ω-hydroxy($C_1$-$C_5$) alkyl.

(11) a compound of Formula I*, wherein $R^3$ is ($C_2$-$C_6$) alkenyl, can be reacted with ozone followed by $NaBH_4$ to give a compound of Formula I*, wherein $R^3$ is ω-hydroxy($C_1$-$C_5$) alkyl.

(12) a compound of Formula I*, wherein $R^1$ or $R^3$ is amino ($C_1$-$C_6$)alkyl, can be reacted with an ($C_1$-$C_6$)alkyl isocyanate to give a compound of Formula I*, wherein $R^1$ or $R^3$ is ($C_1$-$C_6$)alkylaminocarbonylamino($C_1$-$C_6$)alkyl.

(13) a compound of Formula I*, wherein $R^1$ or $R^3$ is amino ($C_1$-$C_6$)alkyl, can be reacted with an ($C_1$-$C_6$)alkyl chloroformate to give a compound of Formula I*, wherein $R^1$ or $R^3$ is ($C_1$-$C_6$)alkoxycarbonylamino($C_1$-$C_6$)alkyl.

(14) a compound of Formula I*, wherein $R^1$ or $R^3$ is amino ($C_1$-$C_6$)alkyl, can be reacted with chlorosulfonyl isocyanate or sulfamide to give a compound of Formula I*, wherein $R^1$ or $R^3$ is aminosulfonylamino($C_1$-$C_6$)alkyl.

(15) a compound of Formula I*, wherein $R^1$ or $R^3$ is amino ($C_1$-$C_6$)alkyl, can be reacted with a ($C_1$-$C_6$)alkylsulfamoyl chloride to give a compound of Formula I*, wherein $R^1$ or $R^3$ is ($C_1$-$C_6$)alkylaminosulfonylamino($C_1$-$C_6$)alkyl.

(16) a compound of Formula I*, wherein $R^1$ or $R^3$ is hydroxy($C_1$-$C_6$)alkyl, can be reacted with chlorosulfonyl isocyanate to give a compound of Formula I*, wherein $R^1$ or $R^3$ is aminosulfonyloxy($C_1$-$C_6$)alkyl.

(17) a compound of Formula I*, wherein $R^1$ or $R^3$ is hydroxy($C_1$-$C_6$)alkyl, can be reacted with p-nitrophenyl chloroformate, pentafluorophenyl chloroformate or carbonyl diimidazole, followed by ammonia, a ($C_1$-$C_6$)alkylamine or a di($C_1$-$C_6$)alkylamine to give a compound of Formula I*, wherein $R^1$ or $R^3$ is aminocarboxy($C_1$-$C_6$)alkyl, ($C_1$-$C_6$)alkyl aminocarboxy($C_1$-$C_6$)alkyl or di($C_1$-$C_6$)alkyl aminocarboxy ($C_1$-$C_6$)alkyl.

(18) a compound of Formula I*, wherein $R^1$ or $R^3$ is hydroxy($C_1$-$C_6$)alkyl, can be reacted with $POCl_3$ to give a compound of Formula I*, wherein $R^1$ or $R^3$ is $(HO)_2P(=O)$ $O(C_1$-$C_6)$alkyl.

(19) a compound of Formula I*, wherein $R^3$ is allyl or homoallyl, can be reacted with oxygen in the presence of $PdCl_2$ and CuCl to afford a compound of Formula I*, wherein $R^3$ is 2-oxopropyl or 3-oxobutyl respectively.

(20) a compound of Formula I*, wherein $R^3$ is 2-oxopropyl or 3-oxobutyl, can be reacted with MeMgX, wherein X is Cl, Br or I, to give a compound of Formula I*, wherein $R^3$ is 2-hydroxy-2-methylpropyl or 3-hydroxy-3-methylpropyl respectively.

(21) a compound of Formula I*, wherein $R^3$ is —$CH_2CO_2Me$ can be treated with MeMgX, wherein X is Cl, Br or I, to give a compound of Formula I*, wherein $R^3$ is 2-hydroxy-2-methylpropyl.

(22) a compound of Formula I*, wherein $R^3$ is allyl or —$CH_2C(Me)=CH_2$, can be hydrocyanated with TsCN in the presence of triphenylsilane and various cobalt catalysts to afford compounds of Formula I*, wherein $R^3$ is —$CH_2CH$ (CN)Me or —$CH_2CMe_2CN$ respectively.

(23) a compound of Formula I*, wherein $R^3$ is $CH_2C(Me)_2$ CN, can be treated with acetamide in the presence of $PdCl_2$ to give a compound of Formula I*, wherein $R^3$ is $CH_2CMe_2CONH_2$.

(24) a compound of Formula I*, wherein $R^3$ is —$CH_2C$ (Me)=$CH_2$ can be treated with m-CPBA followed by lithium triethylborohydride to afford a compound of Formula I*, wherein $R^3$ is 2-hydroxy-2-methylpropyl.

In a tenth process, certain compounds of the invention of Formula I** are prepared as follows:

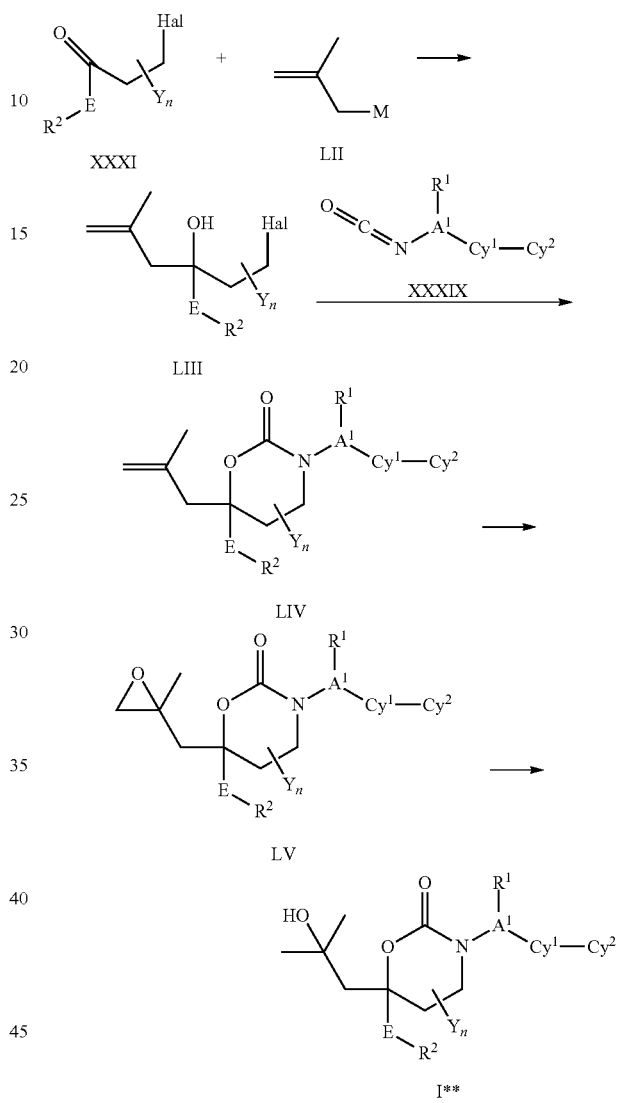

Halo compounds of Formula LIII can be formed by the treatment of β-haloketones of Formula XXXI with organometallic reagents of Formula LII, wherein M denotes MgCl, MgBr, MgI, ZnBr or ZnI and the reaction is optionally performed in the presence of anhydrous cerium trichloride in an inert anhydrous solvent, such as tetrahydrofuran, at about −25 to 0° C. for about 0.5 h.

Cyclic carbamates of Formula LIV can be prepared from the reaction between β-haloalcohols of Formula LIII where Hal is a chloride and isocyanates of Formula XXXIX in the presence of a base, such as but not limited to DBU (1,8-diazabicyclo[5.4.0]undec-7-ene), in a refluxing inert solvent, such as but not limited to tetrahydrofuran.

Tertiary alcohols of Formula LVII can be derived from trisubstituted alkenes of Formula LIV by first epoxidizing the alkene with an epoxidation reagent, such as m-CPBA (3-chloroperbenzoic acid), in an inert solvent, such as dichloromethane to produce the corresponding epoxides of Formula LV. The resulting epoxide is then reductively ring opened to provide the corresponding tertiary alcohol I* via treatment with a strong hydride reagent, such as lithium triethylborohydride, in an anhydrous inert solvent, such as tetrahydrofuran.

In a variation of the tenth process, a compound of the invention of Formula I*** is prepared by using a "Suzuki" coupling reaction of a boronate ester of Formula LIX with a haloheterocycle of Formula LX.

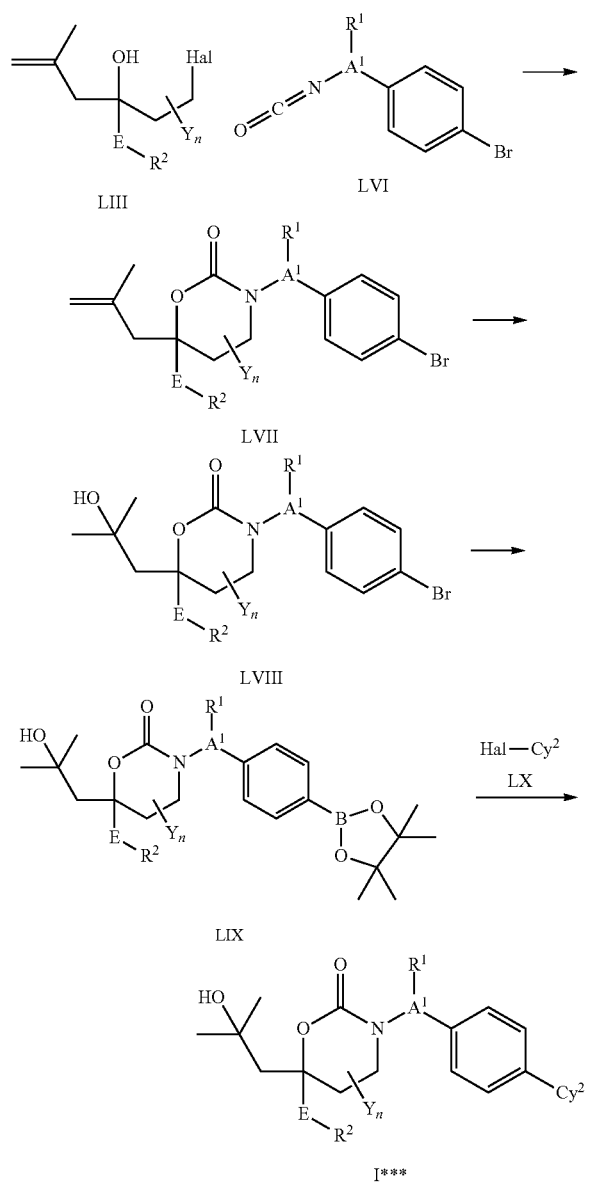

The boronate ester of Formula LIX is prepared by reaction of a bromide of Formula LVIII with bis(pinacolato)diboron. LVIII is prepared by epoxidation of alkene LVII, followed by reductive epoxide opening as described above, for 2-methyl-2-hydroxypropyl group is introduced via epoxidation and hydride ring opening as described above for conversion of LIV to I**.

This tenth process is described in greater detail in U.S. Provisional Application Ser. No. 61/137,013, filed Jul. 25, 2008 entitled SYNTHESIS OF INHIBITORS OF 11β-HYDROXYSTEROID DEHYDROGENASE TYPE 1, the entire teachings of which are incorporated herein by reference.

LC-MS Methods

Method 1 [LC-MS (3 min)]

Column: Chromolith SpeedRod, RP-18e, 50×4.6 mm; Mobil phase: A: 0.01% TFA/water, B: 0.01% TFA/CH$_3$CN; Flow rate: 1 mL/min; Gradient:

| Time (min) | A % | B % |
|---|---|---|
| 0.0 | 90 | 10 |
| 2.0 | 10 | 90 |
| 2.4 | 10 | 90 |
| 2.5 | 90 | 10 |
| 3.0 | 90 | 10 |

Method 2 (10-80)

| Column | YMC-PACK ODS-AQ, 50 × 2.0 mm 5 μm | |
|---|---|---|
| Mobile Phase | A: water (4 L) + TFA (1.5 mL)) | |
| | B: acetonitrile (4 L) + TFA (0.75 mL)) | |
| | TIME (min) | A % | B % |
| | 0 | 90 | 10 |
| | 2.2 | 20 | 80 |
| | 2.5 | 20 | 80 |
| Flow Rate | 1 mL/min | |
| Wavelength | UV 220 nm | |
| Oven Temp | 50° C. | |
| MS ionization | ESI | |

Method 3 (30-90)

| Column | YMC-PACK ODS-AQ, 50 × 2.0 mm 5 μm | |
|---|---|---|
| Mobile Phase | A: water (4 L) + TFA (1.5 mL)) | |
| | B: acetonitrile (4 L) + TFA (0.75 mL)) | |
| | TIME (min) | A % | B % |
| | 0 | 70 | 30 |
| | 2.2 | 10 | 90 |
| | 2.5 | 10 | 90 |
| Flow Rate | 1 mL/min | |
| Wavelength | UV220 | |
| Oven Temp | 50° C. | |
| MS ionization | ESI | |

Preparation 1

(S)-3-((S)-1-(4-bromophenyl)ethyl)-6-(2-hydroxy-2-methylpropyl)-6-phenyl-1,3-oxazinan-2-one Method 1

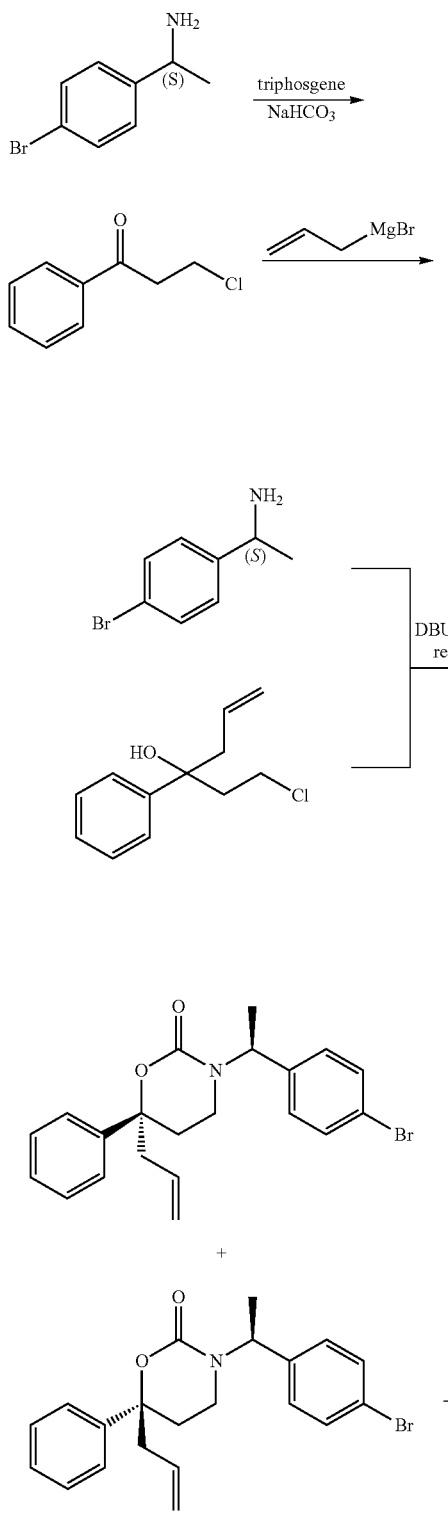

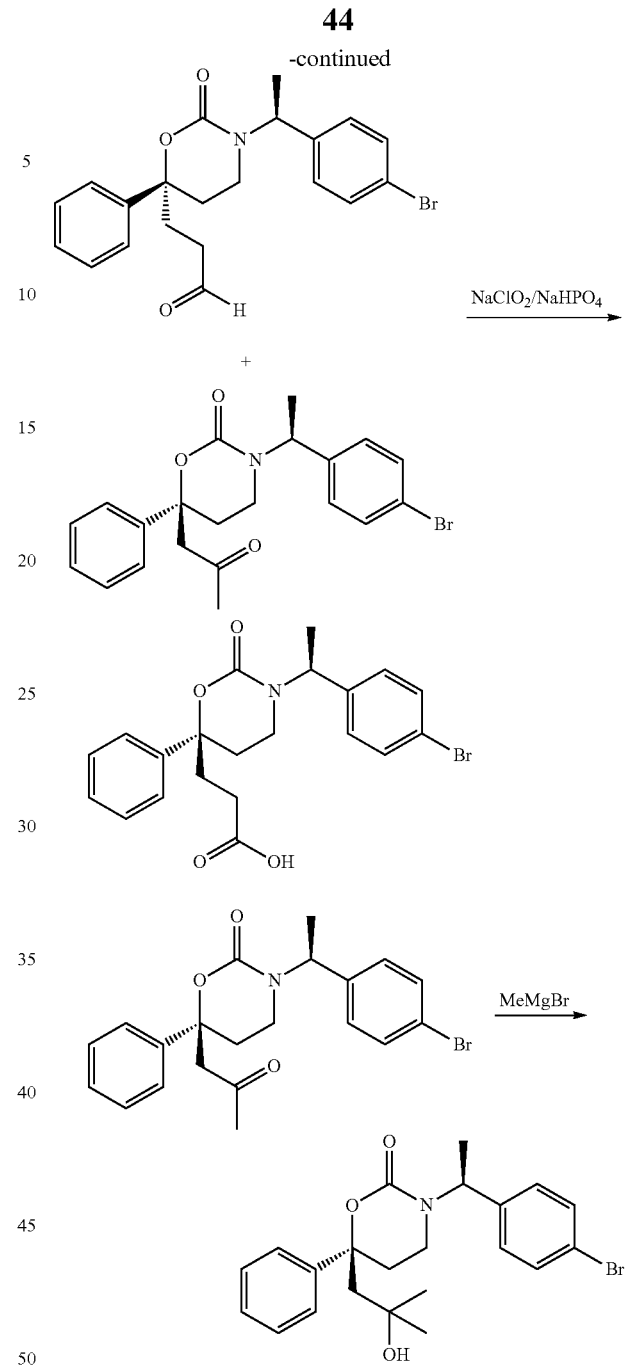

Step 1: (S)-1-bromo-4-(1-isocyanatoethyl)benzene

To a solution of (S)-1-(4-bromophenyl)ethanamine (240 g, 1.2 mol) in methylene chloride (3 L) and satd aq NaHCO₃ (3 L) solution was added triphosgene (118 g, 0.396 mol) at 0° C. The mixture was stirred for 15 min. The organic phase was separated, dried over Na₂SO₄ and concentrated to give 1-bromo-4-(1-isocyanato-ethyl)-benzene (170 g, 63%).

Step 2: 1-chloro-3-phenylhex-5-en-3-ol

To a solution of 3-chloro-1-phenylpropan-1-one (170 g, 1.01 mol) in anhydrous THF (1200 mL) was added allylmagnesium bromide (1.2 L, 1 mol/L) at −78° C. under nitrogen. The formed mixture was stirred for 30 min at −78° C. The reaction was quenched with aqueous NaHCO₃ solution. The organic phase was separated, dried over Na₂SO₄ and concentrated to give the crude product, which was purified by column chromatography (petroleum ether/EtOAc=100:1) to afford 1-chloro-3-phenylhex-5-en-3-ol (180 g, 86%). $^1$H NMR (CDCl₃): 2.27 (m, 2H), 2.51 (m, 1H), 2.74 (m, 1H), 3.22 (m, 1H), 3.58 (m, 1H), 5.16 (m, 2H), 5.53 (m, 1H), 7.23 (m, 1H), 7.39 (m, 4H).

Step 3: (R)-6-allyl-3-((S)-1-(4-bromophenyl)ethyl)-6-phenyl-1,3-oxazinan-2-one

A mixture of 1-chloro-3-phenyl-hex-5-en-3-ol (105 g, 0.050 mmol), (S)-(−)-1-(-bromophenyl)ethyl isocyanate (170 g, 0.752 mol), and DBU (228 g, 1.5 mol) in THF (1700 mL) was heated to reflux overnight. The mixture was diluted with EtOAc and washed with 1N aq HCl. The aqueous phase was extracted with EtOAc (3×). The combined organic phase was dried over Na₂SO₄. After the solvents were evaporated, the crude product was purified by column chromatography (petroleum ether/EtOAc=20:1 to 5:1) to give (R)-6-allyl-3-((S)-1-(4-bromophenyl)ethyl)-6-phenyl-1,3-oxazinan-2-one (100 g, 34%). $^1$H NMR (CDCl₃): 1.39 (d, 3H), 2.14 (m, 1H), 2.24 (m, 2H), 2.48-2.61 (m, 3H), 2.82 (m, 2H), 5.01 (m, 2H), 5.52 (q, 1H), 5.73 (m, 1H), 6.62 (d, 2H), 7.12 (m, 2H), 7.28 (m, 2H).

Step 4: (S)-3-((S)-1-(4-bromophenyl)ethyl)-6-(2-oxopropyl)-6-phenyl-1,3-oxazinan-2-one and 3-((R)-3-((S)-1-(4-bromophenyl)ethyl)-2-oxo-6-phenyl-1,3-oxazinan-6-yl)propanal To a solution of (R)-6-allyl-3-((S)-1-(4-bromophenyl)ethyl)-6-phenyl-1,3-oxazinan-2-one (31 g, 78 mmol) and CuCl (19.3 g, 195 mmol) in dry DMF (150 mL) was added H₂O (50 mL) and PdCl₂ (4.10 g, 23 mmol) at rt. After addition, the mixture was stirred overnight under oxygen. After TLC showed the starting material had disappeared, the solid was filtered off. Water (200 mL) and EtOAc (200 mL) was added, the organic layers were separated and the aqueous layer was extracted with EtOAc (3×40 mL). The combined organic layer was washed with brine, dried over Na₂SO₄, filtered and concentrated to give a residue which was purified by column chromatography (petroleum ether/EtOAc=5:1 to 1:1) to give a mixture of (S)-3-((S)-1-(4-bromophenyl)ethyl)-6-(2-oxopropyl)-6-phenyl-1,3-oxazinan-2-one and 3-((R)-3-((S)-1-(4-bromophenyl)ethyl)-2-oxo-6-phenyl-1,3-oxazinan-6-yl)propanal, (26 g, 81%).

Step 5: (S)-3-((S)-1-(4-bromophenyl)ethyl)-6-(2-oxopropyl)-6-phenyl-1,3-oxazinan-2-one To a mixture of (S)-3-((S)-1-(4-bromophenyl)ethyl)-6-(2-oxopropyl)-6-phenyl-1,3-oxazinan-2-one and 3-((R)-3-((S)-1-(4-bromophenyl)ethyl)-2-oxo-6-phenyl-1,3-oxazinan-6-yl)propanal (20 g, 48.2 mmol) in t-BuOH (250 mL) and 2-methyl-2-butene (50 mL) was added a solution of NaClO₂ (19.3 g, 0.213 mol) and NaH₂PO₄ (28 g, 0.179 mol) in H₂O (300 mL) at 0° C. The formed mixture was stirred for 1 h at 0° C. The mixture was treated with water (100 mL) and extracted with CH₂Cl₂. The combined organic layer was dried over Na₂SO₄, filtered and concentrated to leave a residue, which was purified by column chromatography (petroleum ether/EtOAc=5:1 to 2.5:1) to afford (S)-3-((S)-1-(4-bromophenyl)ethyl)-6-(2-oxopropyl)-6-phenyl-1,3-oxazinan-2-one (10.0 g, 83%). $^1$H NMR (CDCl₃): 1.49 (d, 3H), 2.12 (s, 3H), 2.33 (m, 2H), 2.63 (m, 1H), 2.86-3.08 (m, 3H), 5.57 (q, 1H), 6.66 (d, 2H), 7.19 (m, 2H), 7.33 (m, 5H).

Step 6: (S)-3-((S)-1-(4-bromophenyl)ethyl)-6-(2-hydroxy-2-methylpropyl)-6-phenyl-1,3-oxazinan-2-one To a solution of (S)-3-((S)-1-(4-bromophenyl)ethyl)-6-(2-oxopropyl)-6-phenyl-1,3-oxazinan-2-one (20 g, 46.4 mmol) in anhydrous THF (200 mL) was added dropwise methylmagnesium bromide (31 mL, 144 mmol) at −78° C. under nitrogen. Then the mixture was stirred at rt for 1 h. The reaction mixture was quenched with aq NaHCO₃ (50 mL) under ice water bath. The organic layers were separated. The aqueous layer was extracted with EtOAc (150 mL). The combined organic layers were washed with brine, dried over Na₂SO₄ and concentrated in vacuo to give the crude product, which was purified column chromatography (petroleum ether/EtOAc=5:1 to 2:1) to afford (S)-3-((S)-1-(4-bromophenyl)ethyl)-6-(2-hydroxy-2-methylpropyl)-6-phenyl-1,3-oxazinan-2-one (13 g, 65%). After re-crystallization from EtOH, 4 g of the pure compound was obtained. $^1$H NMR (CDCl₃): 1.06 (s, 3H), 1.12 (s, 3H), 1.44 (d, 3H), 2.14 (m, 3H), 2.21 (m, 1H), 2.33 (m, 1H), 2.76 (m, 1H), 5.54 (q, 1H), 6.74 (d, 2H), 7.16 (d, 2H), 7.28 (m, 5H).

Alternative Procedure for Method 1 Step 2

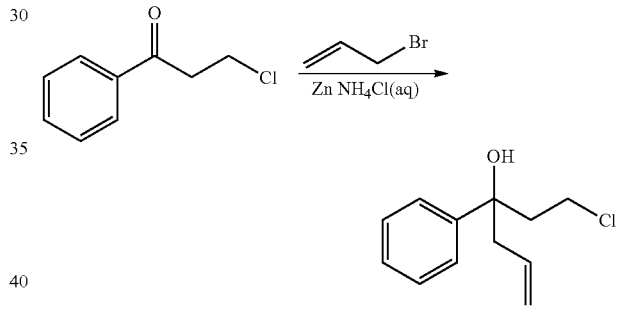

A solution of 3-chloro-1-phenylpropan-1-one (100 g, 0.595 mol) in THF (280 ml) was added dropwise to a well-stirred mixture of zinc powder (need not be activated) (40 g, 1.231 mol, satd aq NH₄Cl solution (1500 ml) and THF (400 ml). Allyl bromide (143 g, 1.19 mol) was dissolved in THF (200 ml) was slowly added to the reaction mixture. The reaction was mildly exothermic, and the mixture began to reflux spontaneously. After refluxing had ceased, the mixture was stirred for 1 h. The mixture was extracted with EtOAc, dried over anhydrous Na₂SO₄, and concentrated to give 1-chloro-3-phenylhex-5-en-3-ol (122 g, 97%). $^1$H NMR: (400 MHz, CDCl₃): δ=2.24 (s, 1H), 2.34 (m, 2H), 2.53 (m, 1H), 2.75 (m, 1H), 3.20 (m, 1H), 3.58 (m, 1H), 5.18 (t, 1H), 5.51 (m, 1H), 7.26 (m, 1H), 7.26-7.39 (m, 3H).

(R)-6-allyl-3-((S)-1-(4-bromophenyl)propyl)-6-phenyl-1,3-oxazinan-2-one was prepared from (S)-1-(4-bromophenyl)propan-1-amine following procedures analogous to those described in Preparation 1 Method 1 Steps 1 to 3 above.

(S)-3-((S)-1-(4-bromophenyl)ethyl)-6-(4-fluorophenyl)-6-(2-hydroxy-2-methylpropyl)-1,3-oxazinan-2-one was prepared from (R)-6-allyl-3-((S)-1-(4-bromophenyl)ethyl)-6-(4-fluorophenyl)-1,3-oxazinan-2-one following procedures analogous to those described in Preparation 1 Method 1 Steps 4 and 6.

Method 2

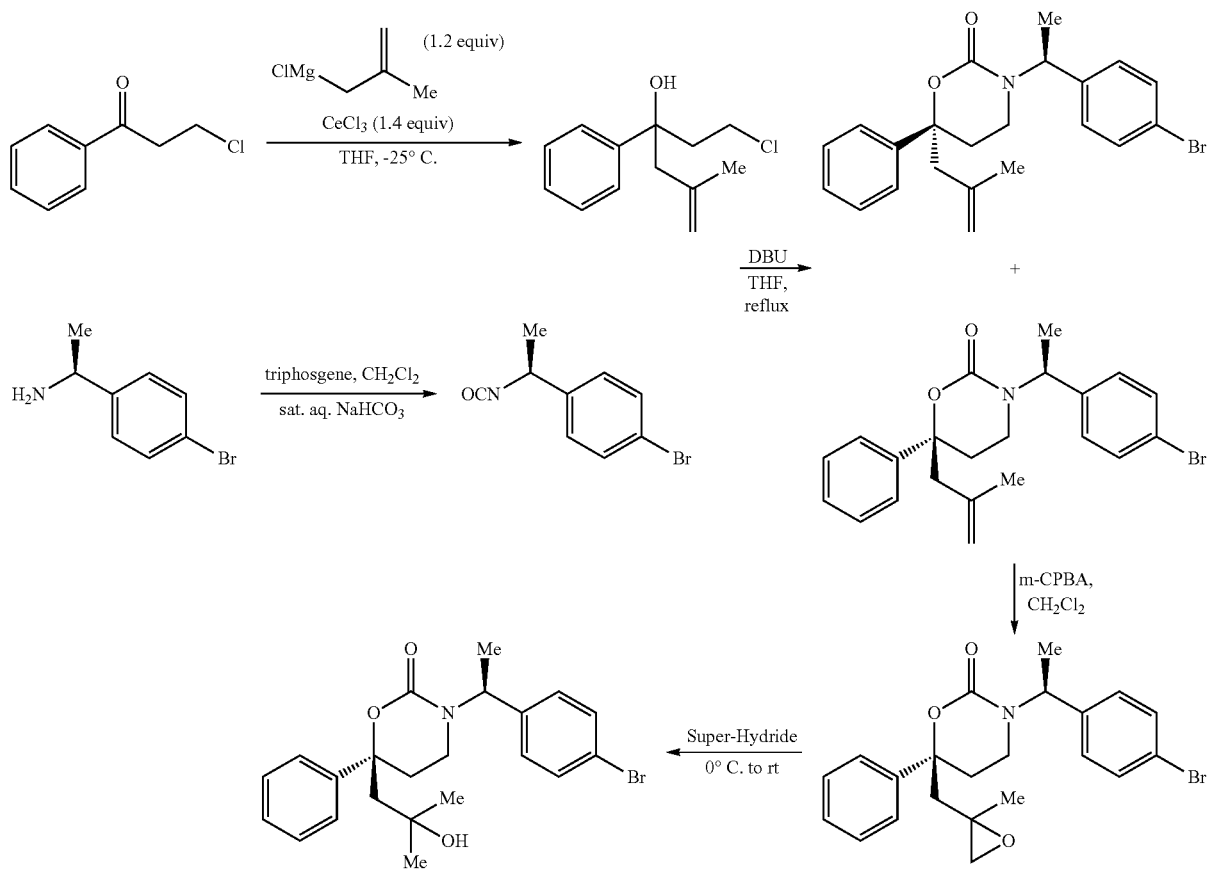

Step 1. 1-Chloro-5-methyl-3-phenyl-hex-5-en-3-ol

To a stirred suspension of magnesium turnings (46.7 g, 1.94 mol) in 1500 mL of THF ($H_2O$<100 ppm based on Karl Fischer titration) was charged 53.0 mL of 1 M DIBAL-H in hexane under nitrogen at rt. Then 3-chloro-2-methylprop-1-ene (160 g, 1.77 mol) was introduced while maintaining the internal temperature below 30° C. The resulting solution was agitated for 2 h at rt. The solution was titrated in the presence of 1,1'-bipyridine to indicate 0.8 M of the corresponding Grignard reagent. To a dry flask containing 307.0 g of anhydrous $CeCl_3$ (1.25 mol) at rt under nitrogen was added 1556.8 mL of the Grignard reagent (0.8 M, 1.25 mol). The resulting slurry was cooled to −10° C. and agitated for 0.5 h. To the slurry was added 200 g of 3-chloro-1-phenylpropan-1-one (1.19 mol) in 200 mL of THF while maintaining the internal temperature below 0° C. After the mixture was stirred for 0.5 h, 1200 mL of 1 M aq HCl was added to obtain a clear solution while maintaining the internal temperature below 30° C. After the phase cut, the aqueous layer was extracted with EtOAc (500 mL). The combined organic layers were washed with brine and dried over sodium sulfate. Removal of the solvent under vacuum produced crude 1-chloro-5-methyl-3-phenyl-hex-5-en-3-ol, which was chased with THF to achieve $H_2O$<500 ppm based on Karl Fischer titration. The crude product (306 g, 83 wt %, 95% yield) was used directly in Step 3. $^1$H-NMR spectroscopy (500 MHz, $CDCl_3$) δ 7.38-7.37 (d, J=7.8 Hz, 2H), 7.33 (t, J=7.9 Hz, 2H), 7.24 (t, J=7.4 Hz, 1H), 4.91 (s, 1H), 4.76 (s, 1H), 3.57 (ddd, J=5.6, 10.7, and 10.7, 1H), 3.13 (ddd, J=4.7, 10.7 and 10.7 Hz, 1H), 2.66 (d, J=13.3 Hz, 1H), 2.54 (d, J=11.3 Hz, 1H), 2.53 (s, 1H), 2.36 (ddd, J=5.4, 10.6 and 13.9 Hz, 1H), 2.29 (ddd, J=5.6, 11.3 and 13.3 Hz, 1H), 1.29 (s, 3H). $^{13}$C-NMR spectroscopy (125 MHz, $CDCl_3$) δ 144.3, 141.4, 128.0, 126.6, 124.8, 116.1, 74.2, 51.2, 46.0, 39.9, 23.9.

Step 2. 1-Bromo-4-((S)-1-isocyanato-ethyl)-benzene

To a 10 L jacketed reactor was charged 241 g of sodium bicarbonate (2.87 mol, 2.30 equiv) and 5 L of deionized water. The resulting solution was agitated for 10-20 min, until the solids dissolved (homogeneous). To the clear solution was charged 250 g (1.25 mol, 1.00 equiv) of (S)-(−)-1-(4-bromophenyl)ethylamine as a solution in 1.00 L of dichloromethane. An additional 4 L of dichloromethane was charged to the reactor. The biphasic solution was agitated and cooled to $T_{int}$=2-3° C. Triphosgene (126 g, 424 mmol, 0.340 equiv) was charged to the reactor in approximately two equal portions ~6 min apart. It should be noted that a slight exotherm was noted upon the addition of triphosgene. The resulting murky solution was agitated at $T_{int}$=2-5° C. for 30 min, at which point HPLC analysis indicates >99 A % conversion (220 nm). The dichloromethane layer was cut and dried with anhydrous sulfate. The resulting solution was passed through a celite plug and concentrated to ~1.5 L which fine particles of a white solid developed. The solution was filtered and concentrated to a thick oil via reduced pressure to produce 239 g of 1-bromo-4-((S)-1-isocyanato-ethyl)-benzene (93.7 wt %, 79.4% yield). $^1$H-NMR spectroscopy (400 MHz, CD$_2$Cl$_2$) δ 7.53 (d, J=11.4 Hz, 2H), 7.26 (d, J=8.2 Hz, 2H), 4.80 (q, J=6.7 Hz, 1H), 1.59 (d, J=6.7 Hz, 3H). The material was used in Step 3 without further purification.

Step 3. (R)-3-((S)-1-(4-bromophenyl)ethyl)-6-(2-methylallyl)-6-phenyl-1,3-oxazinan-2-one To a dried 10 L jacketed reactor under a nitrogen atmosphere was charged 1-chloro-5-methyl-3-phenyl-hex-5-en-3-ol (167 g, 81.7 wt %, 610 mmol, 1.00 equiv), 1-bromo-4-((S)-1-isocyanato-ethyl)-benzene (219 g, 93.7 wt %, 911 mmol, 1.50 equiv), anhydrous tetrahydrofuran (3.00 L), and then 1,8-diazabicyclo[5.4.0]undec-7-ene (DBU, 409 mL, 2.73 mol, 4.50 equiv). The resulting solution was agitated and refluxed (T$_{int}$=67-69° C., T$_{ext}$=75° C.) for 19 h, at which point HPLC analysis indicated ~1A % (220 nm) of the 1-chloro-5-methyl-3-phenyl-hex-5-en-3-ol remained. The dark solution was cooled to T$_{int}$=20-25° C. Two liters of tetrahydrofuran were removed by distillation under reduced pressure. The remaining dark solution was diluted with 4.0 L of ethyl acetate and 1.0 L of hexanes. The resulting solution was washed with 4.0 L of a 1.0 M aqueous solution of hydrogen chloride (note: the wash is slightly exothermic). The aqueous solution was cut and the remaining organic solution was dried with anhydrous sodium sulfate, filtered and then concentrated to an oil via reduced pressure. The resulting material was subjected to flash silica chromatography (5-30° A) ethyl acetate/hexanes, 1.74 kg of silica) to produce 137.8 g of material (59 wt %, 3.1:1 diastereomeric ratio favoring the desired diastereomer (R)-3-((S)-1-(4-bromophenyl)ethyl)-6-(2-methylallyl)-6-phenyl-1,3-oxazinan-2-one, 32.3% yield). The material was used in Step 4 without further purification.

Analytical data for (R)-3-((S)-1-(4-bromophenyl)ethyl)-6-(2-methylallyl)-6-phenyl-1,3-oxazinan-2-one: $^1$H-NMR spectroscopy (500 MHz, CD$_2$Cl$_2$) δ 7.42-7.35 (m, 3H), 7.33-7.31 (m, 2H), 7.25-7.23 (m, 2H), 6.80-6.74 (m, 2), 5.55 (q, J=7.1 Hz, 1H), 5.37-5.36 (m, 1H), 4.89 (s, 1H), 4.69 (s, 1H), 2.96-2.93 (m, 1H), 2.61 (dd, J=13.8 and 26.4 Hz, 2H), 2.37-2.25 (m, 3H), 1.68 (s, 3H), 1.50 (d, J=7.1 Hz, 3H). $^{13}$C-NMR spectroscopy (125 MHz, CD$_2$Cl$_2$) δ 152.5, 141.5, 140.1, 138.3, 130.6, 128.1, 128.0, 126.9, 124.4, 120.2, 115.3, 82.4, 52.1, 50.1, 35.6, 29.8, 23.4, 14.5.

Analytical data for (S)-3-((S)-1-(4-bromophenyl)ethyl)-6-(2-methylallyl)-6-phenyl-1,3-oxazinan-2-one: $^1$H-NMR spectroscopy (400 MHz, CD$_2$Cl$_2$) δ 7.50-7.48 (m, 2H), 7.43-7.39 (m, 2H), 7.35-7.32 (m, 3H), 7.20-7.18 (m, 2H), 5.60 (q, J=7.1 Hz, 1H), 4.85 (s, 1H), 4.66 (s, 1H), 2.73-2.67 (m, 2H), 2.60 (dd, J=13.9 and 19.4 Hz, 2H), 2.28 (dt, J=3.3 and 13.7 Hz, 1H), 2.14-2.05 (m, 1H), 1.66 (s, 3H), 1.24 (d, J=7.2 Hz, 3H). $^{13}$C-NMR spectroscopy (100 MHz, CD$_2$Cl$_2$) δ 153.4, 142.5, 141.0, 140.1, 131.8, 129.3, 128.9, 127.8, 125.3, 121.5, 116.3, 83.9, 53.2, 51.0, 36.6, 31.3, 24.3, 15.4.

Step 4. (6S)-3-((S)-1-(4-bromophenyl)ethyl)-6-((2-methyloxiran-2-yl)methyl)-6-phenyl-1,3-oxazinan-2-one To a 1.0 L 2-neck RBF was charged (R)-3-((S)-1-(4-bromophenyl)ethyl)-6-(2-methylallyl)-6-phenyl-1,3-oxazinan-2-one (135.8 g, 59 wt %, 3.1:1 dr, 193 mmol, 1.00 equiv), dichloromethane (700 mL), and then 3-chloroperbenzoic acid (m-CPBA, 70%, 95.3 g, 386 mmol, 2.0 equiv). The resulting solution was agitated at rt (T$_{int}$=20-25° C.) for 1 h, which HPLC analysis indicates >99 A % (220 nm) conversion. The resulting solution was diluted with 700 mL of methyl tert-butyl ether (MTBE) and washed with 1×500 mL of 30 wt % solution of sodium thiosulfate and 1×500 mL of saturated aqueous solution of sodium bicarbonate. The wash sequence was repeated until the peak on an HPLC trace of the organic solution that corresponds to a HPLC sample peak of m-CPBA is <2.5 A % (220 nm), which in this example the wash sequence was repeated 3 times. The resulting organic layer was dried with anhydrous sodium sulfate, filtered and then concentrated to an oil via reduced pressure. The resulting material was diluted with 200 mL of anhydrous tetrahydrofuran and then concentrated to a thick oil via reduced pressure to provide (6S)-3-((S)-1-(4-bromophenyl)ethyl)-6-((2-methyloxiran-2-yl)methyl)-6-phenyl-1,3-oxazinan-2-one which was used directly in Step 5.

Step 5. (S)-3-((S)-1-(4-bromophenyl)ethyl)-6-(2-hydroxy-2-methylpropyl)-6-phenyl-1,3-oxazinan-2-one To a 2.0 L 3-neck oven-dried RBF was charged the crude (6S)-3-((S)-1-(4-bromophenyl)ethyl)-6-((2-methyloxiran-2-yl)methyl)-6-phenyl-1,3-oxazinan-2-one and 750 mL of anhydrous THF. The resulting solution was agitated and cooled to T$_{int}$=2-3° C. To the agitated clear solution was charged 1.0 M lithium triethylborohydride in tetrahydrofuran (Super Hydride, 348 mL, 348 mmol, 1.8 equiv). The addition is exothermic and addition was controlled to maintain T$_{int}$=<8° C. The resulting solution was agitated at T$_{int}$=2-3° C. for 1.5 h and then allowed to warm to T$_{int}$=10-13° C. over a 2.5 h, which HPLC analysis indicates ~94 A % (220 nm) conversion. To the agitated solution was charged a solution of hydrogen peroxide (95.7 mL of a 35 wt % aqueous solution diluted with 400 mL of water, 1.08 mol, 5.60 equiv). The addition is highly exothermic and addition was controlled to maintain T$_{int}$=<25° C. The resulting solution was diluted with 1.00 L of methyl tert-butyl ether (MTBE) and washed with 1.00 L of water followed by 500 mL of a -30 wt % solution of sodium thiosulfate. The organic solution was dried with anhydrous sodium sulfate, filtered, and then concentrated via reduced pressure. The resulting material was subjected to flash silica chromatography (10-60% ethyl acetate, 600 g of silica) to produce 68 g of material consisting of both diastereomers (1.98:1 dr) and 41 g of the desired diastereomer, (>99:1 dr). The material consisting of the mixed fractions was recrystallized from 250 mL of isopropyl acetate (IPAC) and 200 mL of heptane (anti-solvent) to produce upon filtration 31.3 g of product (95.7 A % at 220 nm, 74:1 dr). The two samples were combined to produce 72.3 g of (S)-3-((S)-1-(4-bromophenyl)ethyl)-6-(2-hydroxy-2-methylpropyl)-6-phenyl-1,3-oxazinan-2-one (83.6% yield for the two step operation). $^1$H-NMR spectroscopy (400 MHz, CDCl$_3$) δ 7.37-7.29 (m, 5H), 7.25-7.21 (m, 2H), 6.82-6.79 (m, 2H), 5.61 (q, J=6.9 Hz, 1H), 2.83 (ddd, J=2.5, 5.4 and 11.6 Hz, 1H), 2.39 (ddd, J=5.7, 12.0 and 14.1 Hz, 1H), 2.27 (ddd, J=2.6, 4.8 and 14.0 Hz, 1H), 2.21-2.14 (m, 3H), 2.08 (s, 1H), 1.49 (d, J=7.0 Hz, 3H), 1.18 (s, 3H), 1.13 (s, 3H). $^{13}$C-NMR spectroscopy (100 MHz, CDCl$_3$) δ 153.2, 142.6, 138.5, 131.6, 129.13, 129.10, 128.0, 125.3, 121.6, 84.2, 71.4, 54.1, 53.3, 36.4, 33.6, 32.1, 30.8, 15.6.

Preparation 2

(S)-6-(2-hydroxy-2-methylpropyl)-6-phenyl-3-((S)-1-(4-(4,4,5,5-tetramethyl-1,3,2-dioxaborol-an-2-yl)phenyl)ethyl)-1,3-oxazinan-2-one

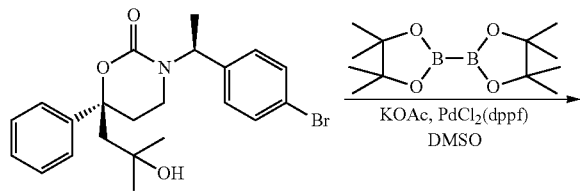

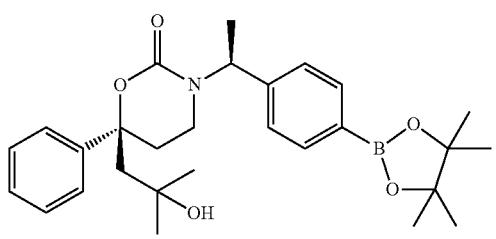

To a solution of (S)-3-((S)-1-(4-bromophenyl)ethyl)-6-(2-hydroxy-2-methylpropyl)-6-phenyl-1,3-oxazinan-2-one (6.6 g, 15.2 mmol) and 4,4,4',4',5,5,5',5'-octamethyl-2,2'-bi(1,3,2-dioxaborolane) (6.1 g, 24.3 mmol) in dry DMSO (20 mL) was added KOAc (4.8 g, 48.6 mmol) and Pd(dppf)cl$_2$ (372 mg, 0.46 mmol). After addition, the mixture was allowed to warm to 100° C. for 20 h. After TLC showed the starting material had disappeared, the solid was filtered off. Water (60 mL) and EtOAc (20 mL) were added. The layers were separated and the aqueous layer was extracted with EtOAc (3×15 mL). The combined organic layer was washed with brine, dried over Na$_2$SO$_4$, filtered and concentrated to give a residue, which was purified by column chromatography to give (S)-6-(2-hydroxy-2-methylpropyl)-6-phenyl-3-((S)-1-(4-(4,4,5,5-tetramethyl-1,3,2-dioxaborol-an-2-yl)phenyl)ethyl)-1,3-oxazinan-2-one (4.4 g, 60%).

(S)-6-(4-fluorophenyl)-6-(2-hydroxy-2-methylpropyl)-3-((S)-1-(4-(4,4,5,5-tetramethyl-1,3,2-dioxaborolan-2-yl)phenyl)ethyl)-1,3-oxazinan-2-one was prepared from (S)-3-((S)-1-(4-bromophenyl)ethyl)-6-(2-hydroxy-2-methylpropyl)-6-(4-fluorophenyl)-1,3-oxazinan-2-one following an analogous procedure.

(S)-6-(2-hydroxy-2-methylpropyl)-6-phenyl-3-((S)-1-(4-(4,4,5,5-tetramethyl-1,3,2-dioxaborolan-2-yl)phenyl)propyl)-1,3-oxazinan-2-one was prepared from (S)-3-((S)-1-(4-bromophenyl)propyl)-6-(2-hydroxy-2-methylpropyl)-6-phenyl-1,3-oxazinan-2-one following an analogous procedure.

(R)-6-Methoxymethyl-6-phenyl-3-{(S)-1-[4-(4,4,5,5-tetramethyl-[1,3,2]dioxaborolan-2-yl)-phenyl]ethyl}-[1,3]oxazinan-2-one was prepared from 3-[1-(4-bromo-phenyl)-ethyl]-6-methoxymethyl-6-phenyl-[1,3]oxazinan-2-one following an analogous procedure.

Preparation 3

3-((R)-3-((S)-1-(4-bromophenyl)ethyl)-2-oxo-6-phenyl-1,3-oxazinan-6-yl)-2,2-dimethylpropanenitrile

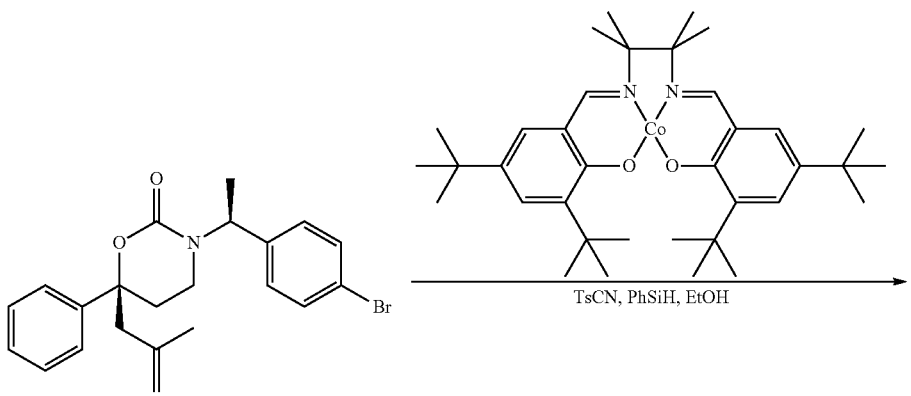

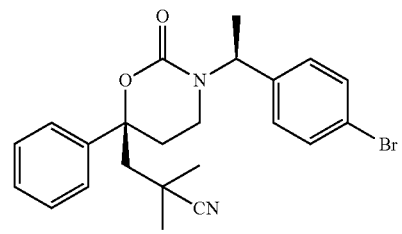

53

Preparation of Cobalt(II) Complex

A 50 mL flask was charged with N,N'-bis(3,5-di-tert-butylsalicylidene)-1,1,2,2-tetramethylethenediamine (0.430 g, 0.78 mmol, 1.0 equiv), EtOH (17 mL), and Co(OAc)$_2$ (0.139 g, 0.78 mmol, 1.0 equiv). The mixture was degassed and then heated to reflux under nitrogen for 3 h, cooled to room temperature. The precipitate was filtered and the purple solid was washed with EtOH (10 mL) and dried under high vacuum to give 0.353 g (75%) of the cobalt(II) complex.

A mixture of (R)-3-((S)-1-(4-bromophenyl)ethyl)-6-(2-methylallyl)-6-phenyl-1,3-oxazinan-2-one (490 mg, 1.18 mmol), the cobalt(II) complex whose preparation is described immediately above (8 mg, 0.01 equiv), TsCN (257 mg, 1.2 equiv), and PhSiH$_3$ (137 mg, 157 µL, 1.07 equiv) in ethanol (10 mL) was stirred 4 h at rt. After removing the solvent under reduced pressure, the residue was purified by chromatography on a 40 g silica gel column, eluted with a 25-80% EtOAc in hexanes gradient to afford 3-((R)-3-((S)-1-(4-bromophenyl)ethyl)-2-oxo-6-phenyl-1,3-oxazinan-6-yl)-2,2-dimethylpropanenitrile (267 mg, 51% yield). LC-MS (3 min. method) t$_R$=1.89 min., m/z 441, 443 (M+1)

Preparation 4

2,2-dimethyl-3-((R)-2-oxo-6-phenyl-3-((S)-1-(4-(4,4,5,5-tetramethyl-1,3,2-dioxaborolan-2-yl)phenyl)ethyl)-1,3-oxazinan-6-yl)propanenitrile

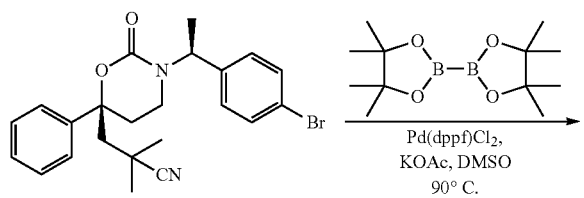

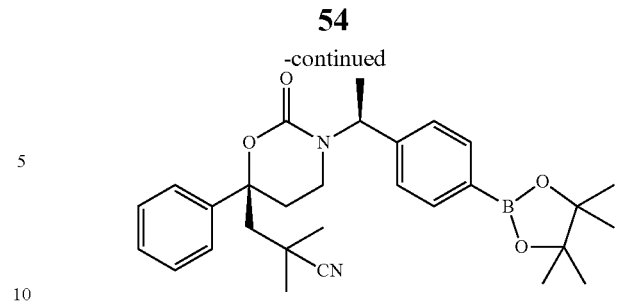

3-((R)-3-((S)-1-(4-bromophenyl)ethyl)-2-oxo-6-phenyl-1,3-oxazinan-6-yl)-2,2-dimethylpropanenitrile (467 mg, 1.06 mmol), 4,4,4',4',5,5,5',5'-octamethyl-2,2'-bi(1,3,2-dioxaborolane) (538 mg, 2 equiv), KOAc (333 mg, 3.2 equiv), PdCl$_2$(dppf)CH$_2$Cl$_2$ (27 mg, 0.033 equiv) were mixed with dry DMSO (6 mL). The mixture was degassed and refilled with N$_2$ gas 3 times. The mixture was then heated overnight at 90° C. under protection of N$_2$ gas. After being cooled to rt, the mixture was diluted with EtOAc (30 mL), washed with water (20 mL). The aqueous layer was extracted with EtOAc (2×15 mL). The combined organic layers were washed by water (15 mL), brine (2×10 mL) and dried over Na$_2$SO$_4$. After filtration and concentration, the residue was purified chromatography on a 40 g silica gel column, eluted with a 20-50% EtOAc in Hexanes gradient, to afford 2,2-dimethyl-3-((R)-2-oxo-6-phenyl-3-((S)-1-(4-(4,4,5,5-tetramethyl-1,3,2-dioxaborolan-2-yl)phenyl)ethyl)-1,3-oxazinan-6-yl)propanenitrile (393 mg, 76% yield).

Preparation 5

3-((R)-3-((S)-1-(4-bromophenyl)ethyl)-6-(4-fluorophenyl)-2-oxo-1,3-oxazinan-6-yl)-2-methylpropanenitrile Method 1

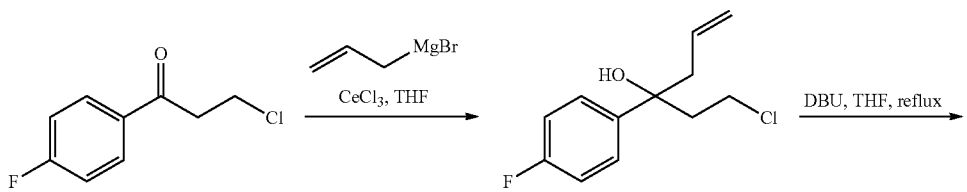

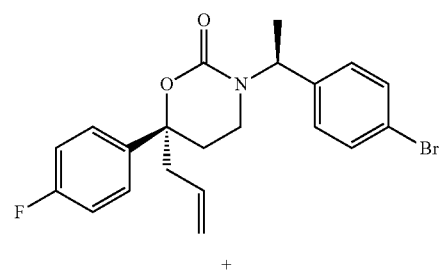

+

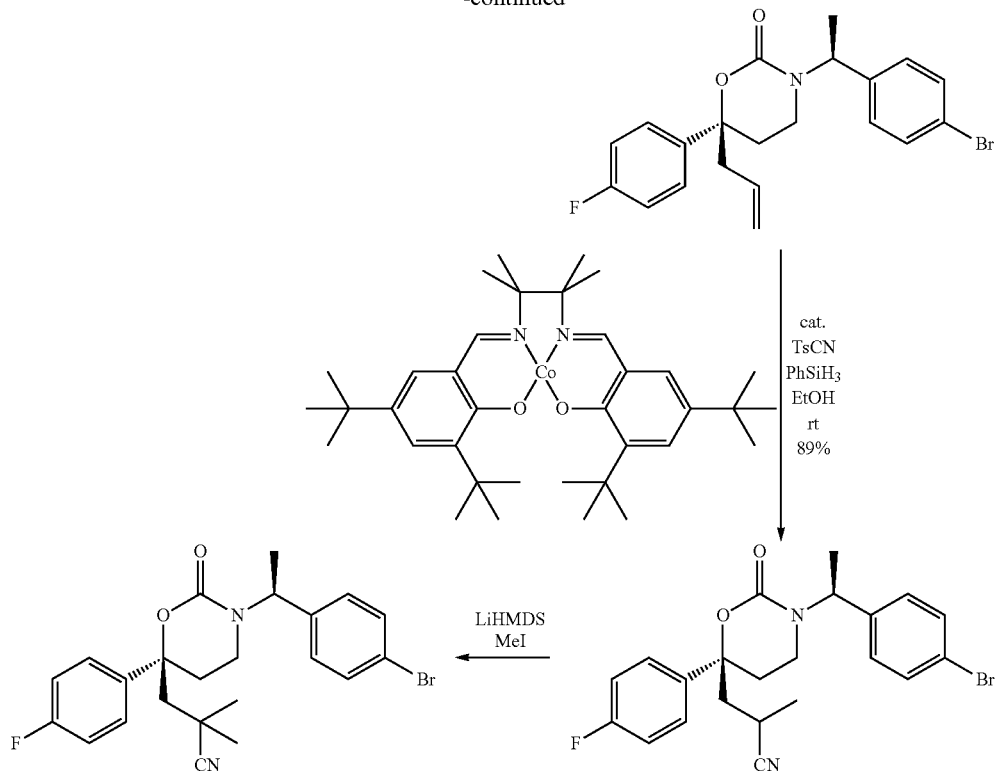

Step 1. 1-chloro-3-(4-fluorophenyl)hex-5-en-3-ol

A 250-mL flask was charged with anhydrous CeCl₃ (5.58 g, 22.6 mmol) and THF (40 mL). The mixture was vigorously stirred for 3.5 h at rt. The suspension was then cooled to −78° C. and a solution of allylmagnesium bromide (1.0 M in THF, 21 mL, 21.0 mmol) was added. After stirring for 2 h at −78° C., a solution of 3-chloro-1-(4-fluorophenyl)propan-1-one (2.522 g, 13.5 mmol) in THF (30 mL) was added via cannula. The reaction mixture was allowed to slowly warm to 8° C. while stirring overnight (18 h). The reaction was then quenched with satd aq NaHCO₃, extracted with EtOAc, and dried over Na₂SO₄. After the solvents were evaporated, the residue was purified by chromatography on silica gel eluted with hexanes/EtOAc to afford of 1-chloro-3-(4-fluorophenyl)hex-5-en-3-ol (3.0049 g, 97%) as an oil. LC-MS Method 1 $t_R$=1.79 min, m/z 213, 211 (M-OH)⁺; ¹H NMR (400 MHz, CDCl₃) δ 7.37-7.32 (m, 2H), 7.07-7.02 (m, 2H), 5.57-5.47 (m, 1H), 5.20-5.19 (m, 1H), 5.16 (m, 1H), 3.59-3.52 (m, 1H), 3.24-3.18 (m, 1H), 2.70 (dd, J=13.8, 5.9 Hz, 1H), 2.50 (dd, J=13.8, 8.5 Hz, 1H), 2.29 (t, J=7.9 Hz, 2H), 2.22 (s, 1H); ¹⁹F NMR (376 MHz, CDCl₃) δ −116.52 (m).

Step 2. (R)-6-allyl-3-((S)-1-(4-bromophenyl)ethyl)-6-(4-fluorophenyl)-1,3-oxazinan-2-one and (S)-6-allyl-3-((S)-1-(4-bromophenyl)ethyl)-6-(4-fluorophenyl)-1,3-oxazinan-2-one A mixture of 1-chloro-3-(4-fluorophenyl)hex-5-en-3-ol (0.4129 g, 1.8 mmol, 1.0 equiv), (S)-(−)-1-(4-bromophenyl)ethyl isocyanate (0.5005 g, 2.2 mmol, 1.2 equiv), and DBU (0.7375 g, 4.8 mmol, 2.7 equiv) in THF (10 mL) was heated to reflux for 25 h. The mixture was diluted with EtOAc and washed with 1 N aq HCl. The aqueous phase was extracted with EtOAc (2×). The combined organic phase was dried over Na₂SO₄. After the solvents were evaporated, the crude product was directly used in the next step without further purification.

An analytical sample was purified by chromatography on silica gel eluted with hexanes/EtOAc to afford the two diastereomers of 6-allyl-3-((S)-1-(4-bromo-phenyl)ethyl)-6-(4-fluorophenyl)-1,3-oxazinan-2-one.

Isomer 1: (S)-6-allyl-3-((S)-1-(4-bromophenyl)ethyl)-6-(4-fluorophenyl)-1,3-oxazinan-2-one. LC-MS Method 1 $t_R$=2.03 min, m/z 420, 418 (MH⁺); ¹H NMR (400 MHz, CDCl₃) δ 7.46 (d, J=8.2 Hz, 2H), 7.31-7.28 (m, 2H), 7.17 (d, J=8.2 Hz, 2H), 7.07 (t, J=8.5 Hz, 2H), 5.76-5.66 (m, 2H), 5.10-4.99 (m, 2H), 2.75-2.52 (m, 4H), 2.23-2.19 (m, 1H), 2.08-2.00 (m, 1H), 1.24 (d, J=7.0 Hz, 3H); ¹⁹F NMR (376 MHz, CDCl₃) δ −115.07 (m).

Isomer 2: (R)-6-allyl-3-((S)-1-(4-bromophenyl)ethyl)-6-(4-fluorophenyl)-1,3-oxazinan-2-one. LC-MS Method 1 $t_R$=1.98 min, m/z 420, 418 (MH⁺); ¹H NMR (400 MHz, CDCl₃) δ 7.25-7.20 (m, 4H), 7.05-7.01 (m, 2H), 6.71 (d, J=8.5 Hz, 2H), 5.74-5.64 (m, 1H), 5.58 (q, J=7.0 Hz, 1H), 5.09-4.99 (m, 2H), 2.92-2.87 (m, 1H), 2.63-2.50 (m, 2H), 2.33-2.16 (m, 3H), 1.47 (d, J=7.0 Hz, 3H); ¹⁹F NMR (376 MHz, CDCl₃) δ −114.91 (m).

Step 3

A mixture of (R)-6-allyl-3-((S)-1-(4-bromophenyl)ethyl)-6-(4-fluorophenyl)-1,3-oxazinan-2-one (1.067 g, 2.55 mmol, 1.0 equiv), the cobalt(II) catalyst described in Preparation 3 (0.016 g, 0.0264 mmol, 0.010 equiv), TsCN (0.555 g, 3.06 mmol, 1.2 equiv), and PhSiH₃ (0.294 g, 2.72 mmol, 1.07 equiv) in EtOH (5 mL) was stirred at room temperature for 4 h. After the solvent was removed under reduced pressure, the residue was purified by chromatography on silica gel eluted with hexanes/ethyl acetate to afford 1.0130 g (89%) of 3-((R)-3-((S)-1-(4-bromophenyl)ethyl)-6-(4-fluorophenyl)-2-oxo-1,3-oxazinan-6-yl)-2-methylpropanenitrile as a solid. LC-MS $t_R$=1.83, 1.86 min in 3 min chromatography, m/z 445, 447 (MH$^+$); $^1$H NMR (400 MHz, CDCl$_3$) δ 7.32-7.22 (m, 4H), 7.13-7.05 (m, 2H), 6.80-6.73 (m, 2H), 5.60-5.56 (m, 1H), 3.00-1.94 (m, 7H), 1.51-1.49 (m, 3H), 1.35-1.32 (m, 1.5H), 1.27-1.24 (m, 1.5H); $^{19}$F NMR (376 MHz, CDCl$_3$) δ −113.08 (m), −113.69 (m).

Step 4

To a solution of 3-((R)-3-((S)-1-(4-bromophenyl)ethyl)-6-(4-fluorophenyl)-2-oxo-1,3-oxazinan-6-yl)-2-methylpropanenitrile (0.332 g, 0.746 mmol) and MeI (1.40 g, 13 equiv) in THF (12 mL) at −78° C. was added 2.4 mL (2.4 mmol, 3.2 equiv) of a 1.0 M LiHMDS solution in THF. The resulting mixture was stirred overnight, with the temperature slowly rising to ambient. The reaction mixture was quenched with brine (1 mL), diluted with CH$_2$Cl$_2$, and dried over Na$_2$SO$_4$. After the solvents were evaporated, the residue was purified by reversed-phase HPLC (SunFire™ Prep C$_{18}$ OBD™ 5 μm 19×50 mm column, 10%→90% CH$_3$CN/H$_2$O, 0.1% CF$_3$COOH over 8 min and then 90% CH$_3$CN/H$_2$O, 0.1% CF$_3$COOH over 2 min, flow rate 20 mL/min) to afford 0.255 g (74%) of 3-((R)-3-((S)-1-(4-bromophenyl)ethyl)-6-(4-fluorophenyl)-2-oxo-1,3-oxazinan-6-yl)-2,2-dimethylpropanenitrile. LC-MS Method 1 $t_R$=1.89 min, m/z 459, 461 (MH$^+$); $^1$H NMR (400 MHz, CD$_3$OD) δ 7.31-7.27 (m, 2H), 7.22-7.18 (m, 2H), 7.04-6.99 (m, 2H), 6.83 (d, J=8.2 Hz, 2H), 5.41 (q, J=7.0 Hz, 1H), 3.02-2.97 (m, 1H), 2.42-2.36 (m, 1H), 2.29-2.08 (m, 4H), 1.42 (d, J=7.0 Hz, 3H), 1.30 (s, 3H), 1.22 (s, 3H); $^{19}$F NMR (376 MHz, CD$_3$OD) δ −116.50 (m).

Method 2

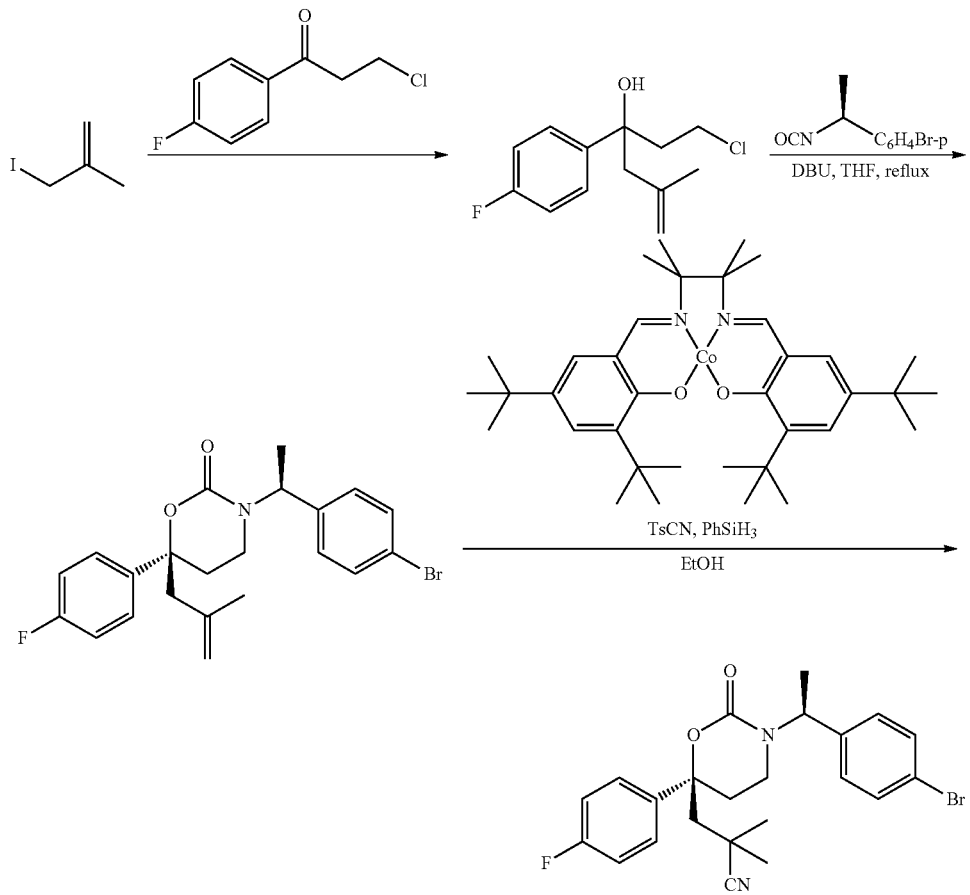

Step 1

A solution of 3-chloro-1-(4-fluorophenyl)-propan-1-one (18.6 g, 0.1 mol) in THF (50 mL) was added to a well-stirred suspension of zinc power (13 g, 0.2 mol) in a mixture of aqueous saturated NH$_4$Cl solution (260 mL) and THF (65 mL). A solution of 3-iodo-2-methylprop-1-ene (36.4 g, 0.2 mol) in THF (50 mL) was added dropwise. The reaction mixture was mildly exothermic, and began to reflux spontaneously. After the refluxing had ceased, the mixture was stirred for 1 h. TLC showed the 3-chloro-1-(4-fluorophenyl)propan-1-one not reacted completely. A solution of 3-iodo-2-methylprop-1-ene (18.2 g, 0.1 mol) in THF (30 mL) was added, and the mixture was stirred at rt overnight. The mixture was extracted with EtOAc (2×500 mL). The combined organic layer was dried and concentrated. The residue was purified by column chromatography on silica gel eluted with petroleum ether/EtOAc 50:1→30:1→5:1, to give 1-chloro-3-(4-fluorophenyl)-5-methylhex-5-en-3-ol (17 g, yield 76%) as an oil.

Step 2

A mixture of 1-chloro-3-(4-fluorophenyl)-5-methylhex-5-en-3-ol (3.15 g, 13 mmol), (S)-(−)-1-(-bromophenyl)ethyl isocyanate (3.5 g, 16 mmol), and DBU (8 g, 33 mmol) in THF (80 mL) was heated to reflux for 25 h. The mixture was diluted with EtOAc and washed with 1N aq HCl. The aqueous phase was extracted with EtOAc (3 x). The combined organic phase was dried over Na₂SO₄. After the solvents were evaporated, the crude product was purified by column to give (R)-3-((S)-1-(4-bromophenyl)-ethyl)-6-(4-fluorophenyl)-6-(2-methylallyl)-1,3-oxazinan-2-one (2.13 g, yield: 38%).

Step 3

A mixture of (R)-3-((S)-1-(4-bromophenyl)ethyl)-6-(4-fluorophenyl)-6-(2-methylallyl)-1,3-oxazinan-2-one (2.13 g, 4.9 mmol), the cobalt(II) catalyst described in Preparation 3 (0.032 g, 0.053 mmol), TsCN (1.11 g, 6.12 mmol), and PhSiH₃ (0.6 g, 5.54 mmol) in EtOH (10 mL) was stirred at room temperature for 8 h. After the solvent was removed under reduced pressure, the residue was purified by column chromatography to give 3-((R)-3-((S)-1-(4-bromophenyl)ethyl)-6-(4-fluorophenyl)-2-oxo-1,3-oxazinan-6-yl)-2,2-dimethylpropanenitrile (1.84 g, 81.1%).

Preparation 6

3-((R)-6-(4-fluorophenyl)-2-oxo-3-((S)-1-(4-(4,4,5,5-tetramethyl-1,3,2-dioxaborolan-2-yl)phenyl)ethyl)-1,3-oxazinan-6-yl)-2,2-dimethylpropanenitrile

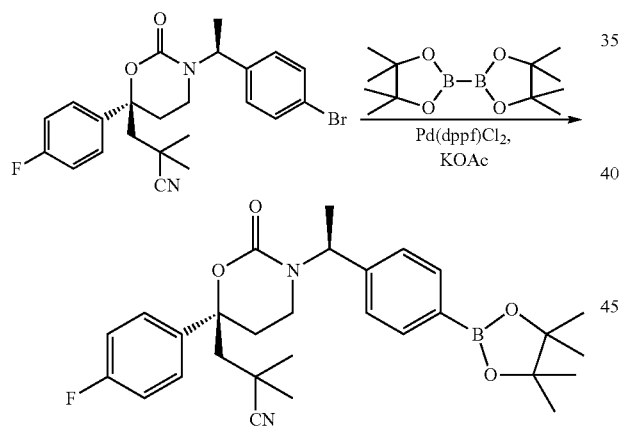

To a solution of 3-((R)-3-((S)-1-(4-bromophenyl)ethyl)-6-(4-fluorophenyl)-2-oxo-1,3-oxazinan-6-yl)-2,2-dimethyl-propanenitrile (730 mg, 1.59 mmol) in DMSO (8 mL) was added bis(pinacolato)diboron (480 mg, 1.89 mmol), KOAc (480 mg, 4.89 mmol) and Pd(dppf)Cl₂ (45 mg, 0.042 mmol) under nitrogen atmosphere. The formed mixture was stirred at 90° C. for 20 h. The reaction was quenched with water and extracted with EtOAc. The combined organic phase was dried over anhydrous Na₂SO₄ and concentrated to give the crude product, which was purified by column chromatography to give 3-((R)-6-(4-fluorophenyl)-2-oxo-3-((S)-1-(4-(4,4,5,5-tetramethyl-1,3,2-dioxaborolan-2-yl)phenyl)ethyl)-1,3-oxazinan-6-yl)-2,2-dimethylpropanenitrile (191 mg, 23.7%).

Preparation 7

(R)-6-allyl-6-(4-fluorophenyl)-3-((S)-1-(4-(4,4,5,5-tetramethyl-1,3,2-dioxaborolan-2-yl)phenyl)ethyl)-1,3-oxazinan-2-one

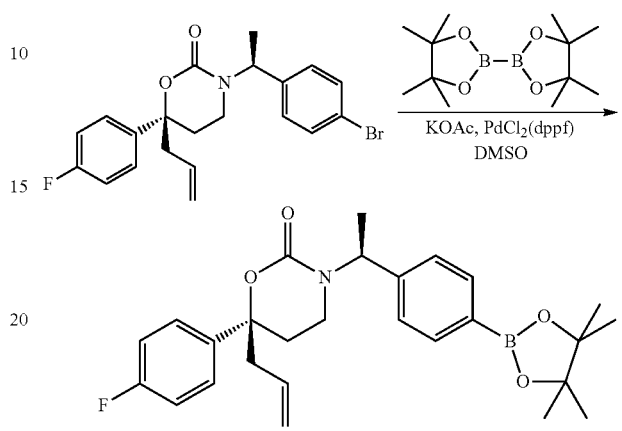

A mixture of (R)-6-allyl-3-((S)-1-(4-bromophenyl)ethyl)-6-(4-fluorophenyl)-1,3-oxazinan-2-one (0.4910 g, 1.17 mmol, 1.0 equiv), bis(pinacolato)diboron (0.3925 g, 1.55 mmol, 1.3 equiv), KOAc (0.3696 g, 3.76 mmol, 3.2 equiv), and PdCl₂(dppf).CH₂Cl₂ (0.0316 g, 0.0386 mmol, 0.033 equiv) in DMSO (6 mL) was heated at 90° C. under N₂ for 20 h. After cooling, the reaction mixture was partitioned between EtOAc and water. The organic phase was washed with brine, and dried over Na₂SO₄. After the solvents were evaporated, the residue was purified by chromatography on silica gel eluted with hexanes/ethyl acetate to give 0.4776 g (87%) of (R)-6-allyl-6-(4-fluorophenyl)-3-((S)-1-(4-(4,4,5,5-tetramethyl-1,3,2-dioxaborolan-2-yl)phenyl)ethyl)-1,3-oxazinan-2-one as a white solid.

Preparation 8

(R)-3-((S)-1-(4-bromophenyl)ethyl)-6-(3-hydroxypropyl)-6-phenyl-1,3-oxazinan-2-one

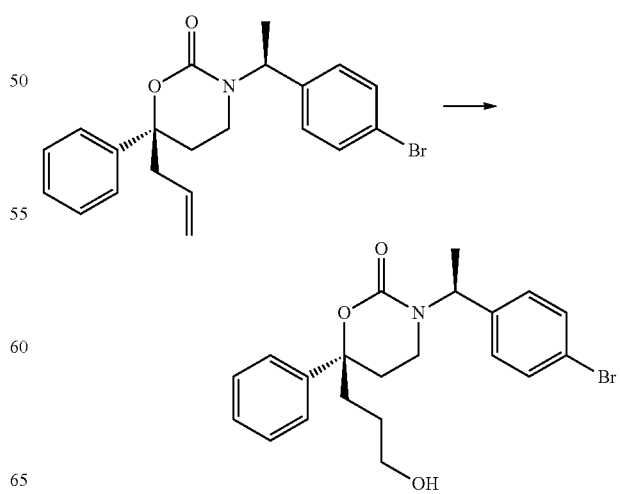

To a solution of (R)-6-allyl-3-((S)-1-(4-bromophenyl)ethyl)-6-phenyl-1,3-oxazinan-2-one (5 g, 12.5 mmol) in tetrahydrofuran (60 mL) was added BH₃·THF (25 mL, 1 mol/L, 25 mmol) at 0° C. under nitrogen atmosphere. The formed mixture was stirred for 2 h. The reaction was quenched with water. Then NaOH (3 mol/L, 10 mL) and H₂O₂ (15 mL) were added to the above mixture. When the reaction was over, the mixture was extracted with EtOAc. The combined organic phase was concentrated to give the crude product, which was purified by column chromatography to give (R)-3-((S)-1-(4-bromophenyl)ethyl)-6-(3-hydroxypropyl)-6-phenyl-1,3-oxazinan-2-one (2.5 g, 40%). $^1$H NMR: (400 MHz, CDCl₃): δ=1.48 (t, 3H), 1.53 (m, 1H), 1.73 (m, 1H), 1.93-1.98 (m, 2H), 2.17-2.28 (m, 3H), 3.57 (t, 2H), 5.59 (m, 1H), 6.72 (m, 2H), 7.20 (m, 2H), 7.25-7.37 (m, 5H).

(R)-3-((S)-1-(4-bromophenyl)ethyl)-6-(4-fluorophenyl)-6-(3-hydroxypropyl)-1,3-oxazinan-2-one was prepared from (R)-6-allyl-3-((S)-1-(4-bromophenyl)ethyl)-6-(4-fluorophenyl)-1,3-oxazinan-2-one following an analogous procedure.

(R)-3-((S)-1-(4-bromophenyl)propyl)-6-(3-hydroxypropyl)-6-phenyl-1,3-oxazinan-2-one was prepared from (R)-6-allyl-3-((S)-1-(4-bromophenyl)propyl)-6-phenyl-1,3-oxazinan-2-one following an analogous procedure.

Preparation 9

(R)-6-(3-hydroxypropyl)-6-phenyl-3-((S)-1-(4-(4,4,5,5-tetramethyl-1,3,2-dioxaborolan-2-yl)phenyl)ethyl)-1,3-oxazinan-2-one

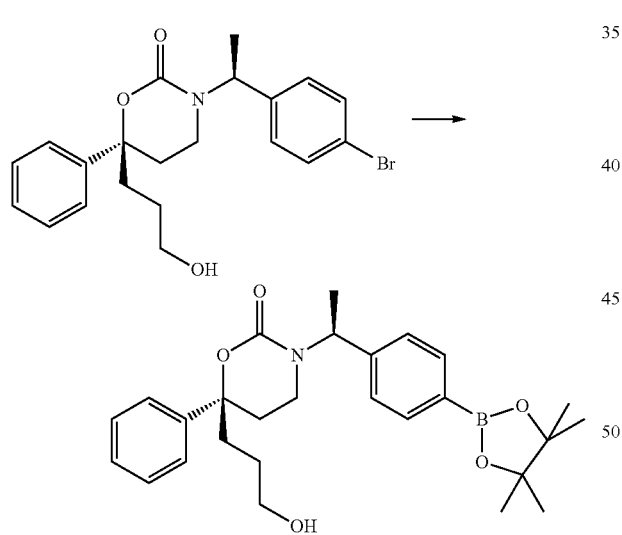

To a solution of ((R)-3-((S)-1-(4-bromophenyl)ethyl)-6-(3-hydroxypropyl)-6-phenyl-1,3-oxazinan-2-one (2 g, 4.8 mmol) in DMSO (30 mL) were added bis(pinacolato)diboron (1.58 g, 6.3 mmol), KOAc (1.51 g, 15.4 mmol) and PdCl₂ (130 mg, 0.16 mmol) under nitrogen atmosphere. The formed mixture was stirred at 90° C. for 20 h. The reaction was quenched with water and extracted with EtOAc. The combined organic phase was concentrated to give the crude product, which was purified by column chromatography to give (R)-6-(3-hydroxypropyl)-6-phenyl-3-((S)-1-(4-(4,4,5,5-tetramethyl-1,3,2-dioxaborolan-2-yl)phenyl)ethyl)-1,3-oxazinan-2-one (1.7 g, 77%). $^1$H NMR: (400 MHz, CDCl₃): δ=1.18 (t, 1H), 1.33 (S, 11H), 1.43 (m, 2H), 1.48 (m, 3H), 1.71 (m, 1H), 1.88 (m, 2H), 2.1-2.3 (t, 3H), 2.7 (m, 1H), 3.5 (m, 2H), 5.5 (m, 1H), 6.72 (m, 2H), 7.25-7.37 (m, 5H), 7.48 (m, 2H).

(R)-6-(4-fluorophenyl)-6-(3-hydroxypropyl)-3-((S)-1-(4-(4,4,5,5-tetramethyl-1,3,2-dioxaborolan-2-yl)phenyl)ethyl)-1,3-oxazinan-2-one was prepared from (R)-3-((S)-1-(4-bromophenyl)ethyl)-6-(4-fluorophenyl)-6-(3-hydroxypropyl)-1,3-oxazinan-2-one following an analogous procedure.

(R)-6-(3-hydroxypropyl)-6-phenyl-3-((S)-1-(4-(4,4,5,5-tetramethyl-1,3,2-dioxaborolan-2-yl)phenyl)propyl)-1,3-oxazinan-2-one was prepared from (R)-3-((S)-1-(4-bromophenyl)propyl)-6-(3-hydroxypropyl)-6-phenyl-1,3-oxazinan-2-one following an analogous procedure.

(R)-6-(3-hydroxypropyl)-6-phenyl-3-((S)-1-(4-(4,4,5,5-tetramethyl-1,3,2-dioxaborolan-2-yl)phenyl)propyl)-1,3-oxazinan-2-one was prepared from (R)-3-((S)-1-(4-bromophenyl)propyl)-6-(3-hydroxypropyl)-6-phenyl-1,3-oxazinan-2-one following an analogous procedure.

Preparation 10

(R)-3-((S)-1-(4-bromophenyl)ethyl)-6-(methoxymethyl)-6-phenyl-1,3-oxazinan-2-one

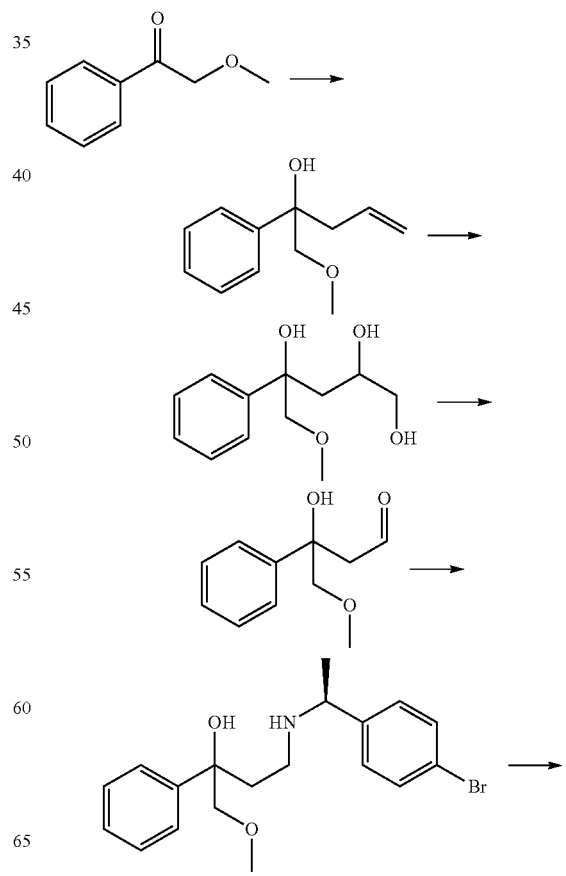

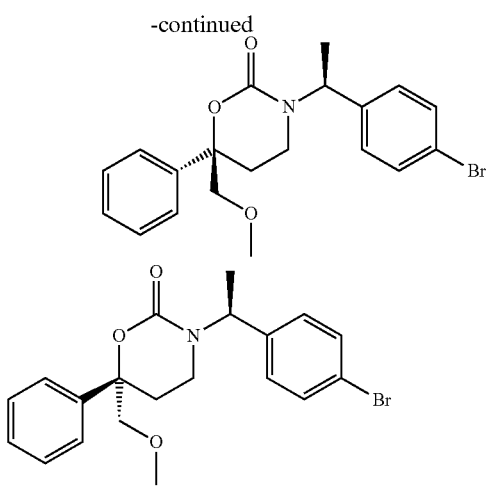

Step 1. 1-Methoxy-2-phenyl-pent-4-en-2-ol

2-Methoxy-1-phenyl-ethanone (5.00 g) dissolved in tetrahydrofuran (50 mL) was added to 2 M allylmagnesium chloride in tetrahydrofuran (21 mL) at room temperature. The solution was stirred at room temperature for 3 h and then 10% aqueous NH$_4$Cl solution (50 mL) was added. The resulting mixture was extracted with tert-butyl methyl ether (3×50 mL) and the combined extracts were washed with water (50 mL) and brine (50 mL). The solvent was evaporated to afford the title compound as a colorless oil.

Yield: 6.40 g (quantitative). Mass spectrum (ESI$^+$): m/z=175 [M+H—H$_2$O]$^+$

Step 2. 5-Methoxy-4-phenyl-pentane-1,2,4-triol

OsO$_4$ (4% in water, 2 mL; alternatively, K$_2$OsO$_4$ may be used) followed by N-methyl-morpholine-N-oxide (5.20 g) was added to a solution of 1-methoxy-2-phenyl-pent-4-en-2-ol (1.10 g) in tetrahydrofuran (10 mL) chilled in an ice bath. The cooling bath was removed and the solution was stirred at room temperature overnight. Then, 10% aqueous Na$_2$S$_2$O$_5$ solution (10 mL) was added and the resulting mixture was stirred at room temperature for another 1.5 h. After removal of the organic solvent under reduced pressure, the remaining mixture was extracted with ethyl acetate. The combined extracts were washed with brine and dried (MgSO$_4$). The solvent was evaporated to afford the title compound in good purity (ca. 95%). Yield: 1.20 g (96% of theory). Mass spectrum (ESI): m/z=225 [M−H]$^-$

Step 3. 3-Hydroxy-4-methoxy-3-phenyl-butyraldehyde

NaIO$_4$ (5.20 g) was added to a mixture of 5-methoxy-4-phenyl-pentane-1,2,4-triol (1.10 g), dichloromethane (10 mL), and water (5 mL) chilled in an ice bath. The mixture was stirred vigorously while warming to ambient temperature in the cooling bath and further stirred at this temperature overnight. Then, water (20 mL) and dichloromethane (50 mL) were added, the organic layer was separated, and the aqueous layer was extracted with dichloromethane (2×25 mL). The combined organic phases were washed with water and dried (MgSO$_4$). After removal of the solvent, the title compound was yielded which was directly submitted to the next reaction step (glycol cleavage).

Yield: 0.94 g (quantitative)

Step 4. 4-[(S)-1-(4-Bromo-phenyl)-ethylamino]-1-methoxy-2-phenyl-butan-2-ol (S)-1-(4-Bromo-phenyl)-ethylamine (0.93 g), NaB(OAc)$_3$ (0.98 g), and acetic acid (0.27 mL) were added in the given order to a solution of 3-hydroxy-4-methoxy-3-phenyl-butyraldehyde (0.90 g) in tetrahydrofuran (20 mL) at ca. 10-15° C. The cooling bath was removed and the mixture was stirred at room temperature for 2 h. Then, water (50 mL) and 1 M aqueous NaOH solution (20 mL) were added and the resulting mixture was stirred for another 30 min. The mixture was extracted with ethyl acetate and the combined extracts were washed with water and brine. After drying (MgSO$_4$), the solvent was removed to give the title compound which was submitted to the subsequent reaction step without further purification. Yield: 1.80 g (quantitative). Mass spectrum (ESI$^+$): m/z=378/380 (Br) [M+H]$^+$

Step 5. 3-[(S)-1-(4-Bromo-phenyl)-ethyl]-(R)-6-methoxymethyl-6-phenyl-[1,3]oxazinan-2-one and 3-[(S)-1-(4-Bromo-phenyl)-ethyl]-(S)-6-methoxymethyl-6-phenyl-[1,3]oxazinan-2-one Triphosgene (157 mg) was added to an ice-cold solution of 4-[(S)-1-(4-bromo-phenyl)-ethylamino]-1-methoxy-2-phenyl-butan-2-ol (1:1 diastereomeric mixture, 200 mg) and EtNiPr$_2$ (91 µL) in dichloromethane (5 mL). The resulting solution was stirred with cooling for 2 h and at room temperature overnight. Then, the solution was concentrated under reduced pressure and the residue was purified by HPLC on reversed phase (MeCN/H$_2$O/NH$_3$) to afford the title compounds in separate fractions.

Isomer 1: 3-[(S)-1-(4-Bromo-phenyl)-ethyl]-(R)-6-methoxymethyl-6-phenyl-[1,3]oxazinan-2-one. Yield: 45 mg (21% of theory). Mass spectrum (ESI$^+$): m/z=404 [M+H]$^+$ $^1$H NMR (400 MHz, DMSO-d$_6$) δ 1.41 (d, J=7.1 Hz, 3H), 2.19 (td, J=11.2, 5.2 Hz, 1H), 2.24-2.34 (m, 1H), 2.34-2.41 (m, 1H), 3.02-3.09 (m, 1H), 3.27 (s, 3H), 3.49 (d, B part of an AB signal, J=10.6 Hz, 1H), 3.53 (d, A part of an AB signal, J=10.6 Hz, 1H), 5.34 (q, J=7.0 Hz, 1H), 6.80 (dm, J=8.4 Hz, 2H), 7.27 (dm, J=8.4 Hz, 2H), 7.32-7.42 (m, 5H).

Isomer 2: 3-[(S)-1-(4-Bromo-phenyl)-ethyl]-(S)-6-methoxymethyl-6-phenyl-[1,3]oxazinan-2-one. Yield: 45 mg (21% of theory). Mass spectrum (ESI$^+$): m/z=404 [M+H]$^+$ $^1$H NMR (400 MHz, DMSO-d$_6$) δ 1.20 (d, J=7.2 Hz, 3H), 2.13-2.23 (m, 1H), 2.32-2.40 (m, 1H), 2.63-2.72 (m, 1H), 2.73-2.81 (m, 1H), 3.26 (s, 3H), 3.48 (d, B part of an AB signal, J=10.6 Hz, 1H), 3.55 (d, A part of an AB signal, J=10.6 Hz, 1H), 5.35 (q, J=7.2 Hz, 1H), 7.19 (dm, J=8.4 Hz, 2H), 7.32-7.45 (m, 5H), 7.53 (dm, J=8.4 Hz, 2H).

Preparation 11

N-(3-((R)-3-((S)-1-(4-bromophenyl)ethyl)-2-oxo-6-phenyl-1,3-oxazinan-6-yl)propyl)-N-methylacetamide

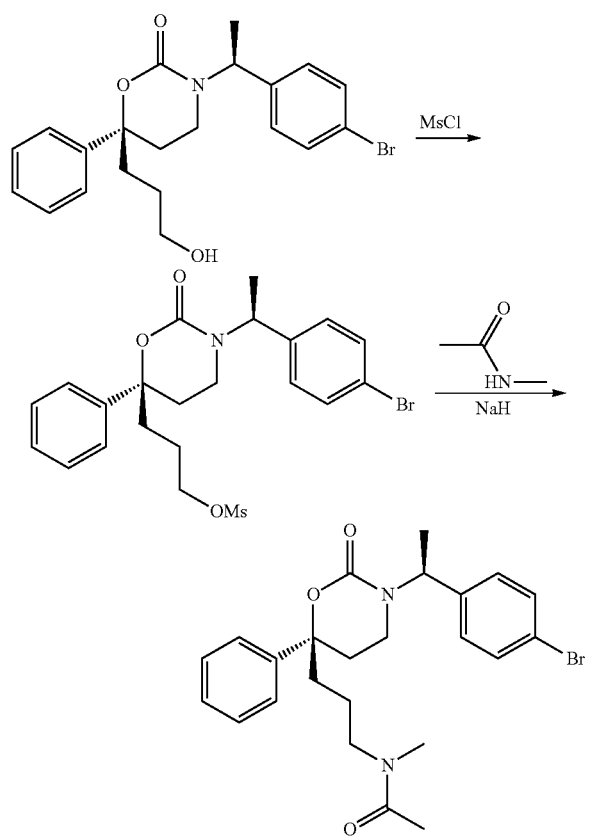

Step 1

To a solution of (R)-3-((S)-1-(4-bromophenyl)ethyl)-6-(3-hydroxypropyl)-6-phenyl-1,3-oxazinan-2-one (200 mg, 0.48 mmol) in CH$_2$Cl$_2$ (5 mL) was added Et$_3$N (240 mg, 2.4 mmol) and methanesulfonyl chloride (164 mg, 1.4 mmol) at 0° C. The reaction solution was stirred at rt for 1 h. The reaction was quenched with H$_2$O and the mixture was extracted with CH$_2$Cl$_2$. The organic phase was concentrated to give 3-((R)-3-((S)-1-(4-bromophenyl)ethyl)-2-oxo-6-phenyl-1,3-oxazinan-6-yl)propyl methanesulfonate (234 mg, 98%), which was used for the next step without further purification.

Step 2

To a solution of 3-((R)-3-((S)-1-(4-bromophenyl)ethyl)-2-oxo-6-phenyl-1,3-oxazinan-6-yl)propyl methanesulfonate (234 mg, 0.24 mmol) in CH$_2$Cl$_2$ (3 mL) was added NaH (82 mg, 3.4 mmol) at 0° C. The mixture was stirred at rt for 30 min. Then N-methylacetamide (204 mg, 2.8 mmol) was added the above mixture. The formed mixture was stirred at 80° C. for 5 h. After the reaction was over, the reaction was quenched with water and the mixture was extracted with EtOAc. The combined organic phase was concentrated to give the crude product, which was purified by preparative TLC to give N-(3-((R)-3-((S)-1-(4-bromophenyl)ethyl)-2-oxo-6-phenyl-1,3-oxazinan-6-yl)propyl)-N-methylacetamide (150 mg, 68%). LC-MS Method 2 t$_R$=1.50 min, m/z=497, 495, 475, 473. $^1$H NMR (400 MHz, CDCl$_3$): δ=1.41 (m, 1H), 1.48 (t, 3H), 1.73 (m, 1H), 1.83-1.95 (m, 2H), 2.01 (m, 3H), 2.1-2.3 (m, 3H), 2.71 (m, 1H), 2.81 (s, 3H), 3.1 (m, 1H), 3.2 (m, 1H), 5.5 (m, 1H), 6.72 (m, 2H), 7.10 (m, 2H), 7.20 (m, 2H), 7.37 (m, 3H).

(R)-3-((S)-1-(4-bromophenyl)ethyl)-6-(3-(2-oxopyrrolidin-1-yl)propyl)-6-phenyl-1,3-oxazinan-2-one was prepared from (R)-3-((S)-1-(4-bromophenyl)ethyl)-6-(3-hydroxypropyl)-6-phenyl-1,3-oxazinan-2-one following an analogous procedure using pyrrolidin-2-one in Step 2.

Preparation 12

(S)-3-((S)-1-(4-bromophenyl)ethyl)-6-(2-(1,-dioxoisothiazolidin-2-yl)ethyl)-6-phenyl-1,3-oxazinan-2-one

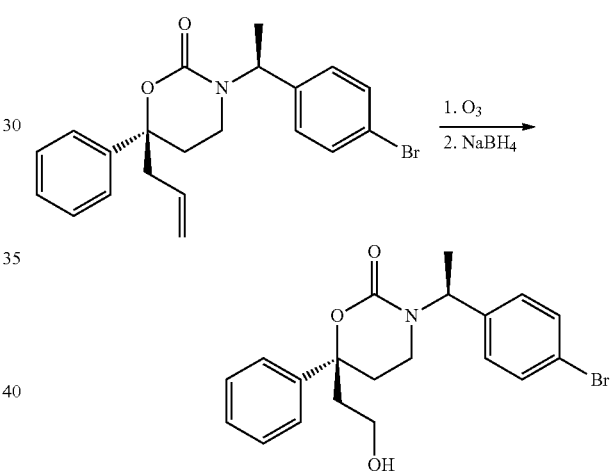

To a solution of (R)-6-allyl-3-((S)-1-(4-bromophenyl)ethyl)-6-phenyl-1,3-oxazinan-2-one (3 g, 7.5 mmol) in CH$_2$Cl$_2$ (50 mL) was treated with O$_3$ at −78° C. till the mixture turned blue. Then NaBH$_4$ (285 mg, 75 mmol) was added to the solution at 0° C., and the reaction solution was stirred at room temperature for 3 hours. The reaction was quenched by H$_2$O, and the mixture was extracted with EtOAc. The combined organic phase was concentrated to give the crude product, which was purified by preparative TLC to give (S)-3-((S)-1-(4-bromo-phenyl)ethyl)-6-(2-hydroxyethyl)-6-phenyl-1,3-oxazinan-2-one (2.5 g, 84%). $^1$H NMR (CDCl$_3$): 1.48 (t, 3H), 2.05-2.41 (m, 4H), 2.71-2.92 (m, 2H), 3.51 (m, 1H), 3.71 (m, 1H), 5.58 (m, 1H), 6.73 (d, 2H), 7.12 (m, 2H), 7.23-7.45 (m, 6H).

(S)-3-((S)-1-(4-bromophenyl)propyl)-6-(2-hydroxyethyl)-6-phenyl-1,3-oxazinan-2-one was prepared from (R)-6-allyl-3-((S)-1-(4-bromophenyl)propyl)-6-phenyl-1,3-oxazinan-2-one following a procedure analogous to that described immediately above.

Preparation 13

(S)-3-((S)-1-(4-bromophenyl)ethyl)-6-(2-(1,1-dioxo-isothiazolidin-2-yl)ethyl)-6-phenyl-1,3-oxazinan-2-one

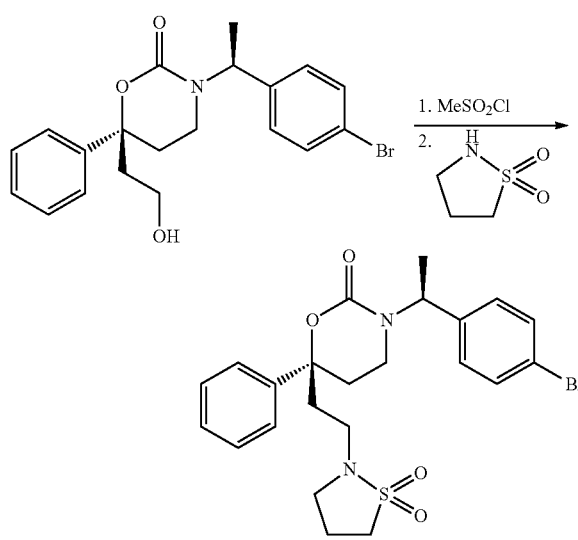

Step 1

To a solution of (S)-3-((S)-1-(4-bromophenyl)ethyl)-6-(2-hydroxyethyl)-6-phenyl-1,3-oxazinan-2-one (300 mg, 0.75 mmol) in dichloromethane (20 mL) were added Et$_3$N (390 mg, 3.75 mmol) and methanesulfonyl chloride (256 mg, 2.25 mmol) at 0° C. The reaction solution was stirred at rt for 1 h. The reaction was quenched with H$_2$O and the mixture was extracted with dichloromethane. The organic phase was concentrated to give 2-((S)-3-((S)-1-(4-bromophenyl)ethyl)-2-oxo-6-phenyl-1,3-oxazinan-6-yl)ethyl-methane sulfonate (352.8 mg, 98%), which was used for the next step without further purification.

Step 2

To a solution of 2-((S)-3-((S)-1-(4-bromophenyl)ethyl)-2-oxo-6-phenyl-1,3-oxazinan-6-yl)ethyl-methanesulfonate (360 mg, 0.75 mmol) and K$_2$CO$_3$ (207 mg, 1.5 mmol) in acetonitrile (10 mL) was added isothiazolidine 1,1-dioxide (121 mg, 4.6 mmol), and the mixture was refluxed overnight. The mixture was filtered and the filtrate was concentrated to give the crude product, which was purified by preparative HPLC to afford compound (S)-3-((S)-1-(4-bromophenyl)ethyl)-6-(2-(1,1-dioxo-isothiazolidin-2-yl)ethyl)-6-phenyl-1,3-oxazinan-2-one (2.43 mg, 1%). LC-MS Method 2 t$_R$=1.37 min, m/z=509, 507. $^1$H NMR (CDCl$_3$): 1.48 (t, 3H), 2.05-2.41 (m, 7H), 2.71-2.92 (m, 2H), 3.11 (m, 3H), 3.21 (m, 2H), 5.58 (m, 1H), 6.73 (d, 2H), 7.18 (m, 1H), 7.23 (m, 3H); 7.35 (m, 3H).

(R)-3-((S)-1-(4-bromophenyl)ethyl)-6-(3-(1,1-dioxo-isothiazolidin-2-yl)propyl)-6-phenyl-1,3-oxazinan-2-one was prepared from (R)-3-((S)-1-(4-bromophenyl)ethyl)-6-(3-hydroxypropyl)-6-phenyl-1,3-oxazinan-2-one following an analogous procedure.

Preparation 14

(S)-3-((S)-1-(4-bromophenyl)ethyl)-6-(4-fluorophenyl)-6-((1-hydroxycyclopropyl)methyl)-1,3-oxazinan-2-one

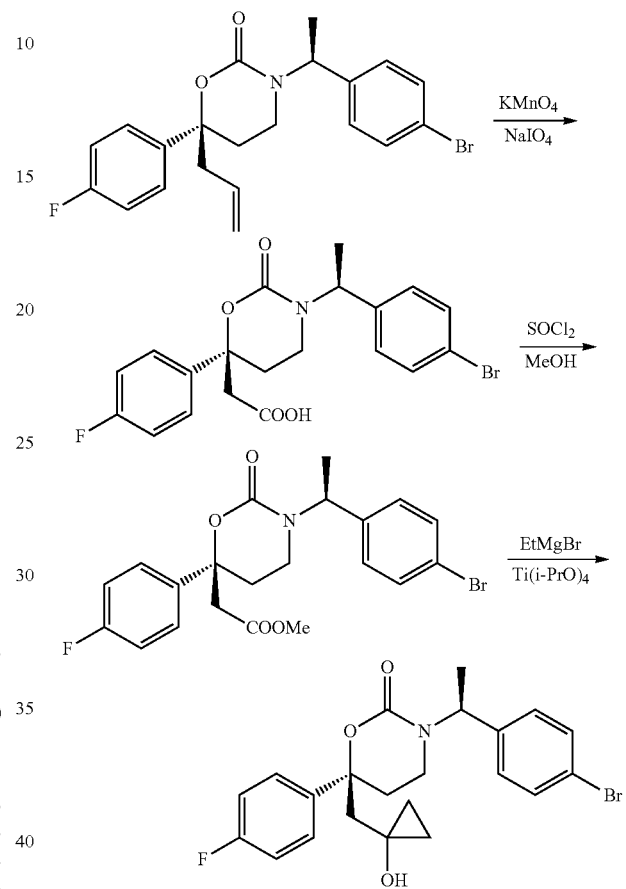

Step 1

To a solution of (R)-6-allyl-3-((S)-1-(4-bromophenyl)ethyl)-6-(4-fluorophenyl)-1,3-oxazinan-2-one (450 mg, 1.01 mmol) in acetone (10 mL) was added a solution of KMnO$_4$ (190 mg, 1.2 mmol) and NaIO$_4$ (1.5 g, 7.2 mmol) in water (10 mL). The mixture was stirred for 2 h at 0° C. The mixture was filtered and the filtrate was adjusted to pH 5-6 with aqueous 1 N aq HCl solution. The mixture was extracted with EtOAc. The organic phase washed with brine, dried over anhydrous Na$_2$SO$_4$ and concentrated to give 2-((S)-3-((S)-1-(4-bromophen-yl)ethyl)-6-(4-fluorophenyl)-2-oxo-1,3-oxazinan-6-yl)acetic acid (540 mg, crude), which was used for the next step without purification.

Step 2

To a solution of 2-((S)-3-((S)-1-(4-bromophen-yl)ethyl)-6-(4-fluorophenyl)-2-oxo-1,3-oxazinan-6-yl)acetic acid (540 mg, 1.24 mol) in MeOH (20 mL) was added SOCl$_2$ (5 mL) at 0° C., and the reaction mixture was stirred at rt for 2 h. The reaction mixture was concentrated and the residue was purified by preparative TLC to give methyl 2-((S)-6-(4-fluorophenyl)-3-((S)-1-(4-(1-methyl-6-oxo-1,6-dihydropyridin-3-yl)phenyl)-ethyl)-2-oxo-1,3-oxazinan-6-yl)acetate (150 mg, 27%). $^1$H NMR (CDCl$_3$): δ=1.49 (d, 3H), 2.19 (m, 1H), 2.44 (m, 1H), 2.60 (m, 1H), 2.77-3.08 (m, 3H), 3.51 (s, 3H), 5.52 (m, 2H), 6.62 (d, 2H), 6.98 (t, 2H), 7.23 (t, 2H), 7.28 (m, 2H).

Step 3

To a solution of methyl 2-((S)-6-(4-fluorophenyl)-3-((S)-1-(4-(1-methyl-6-oxo-1,6-dihydropyridin-3-yl)phenyl)-ethyl)-2-oxo-1,3-oxazinan-6-yl)acetate (150 mg, 0.33 mmol), and tetraisopropoxytitanium (189 mg, 0.66 mmol) in THF (20 mL) was added 3.0 M ethylmagnesium bromide (4 mL, 12 mmol) at rt under nitrogen. Then the mixture was stirred for 2 h. The reaction was quenched with aqueous NH$_4$Cl solution, and the mixture was filtered. The filtrate was extracted with EtOAc. The combined organic phase was washed with brine, dried over anhydrous Na$_2$SO$_4$, and concentrated to give the crude product, which was purified by preparative HPLC to give (S)-3-((S)-1-(4-bromophenyl)ethyl)-6-(4-fluorophenyl)-6-((1-hydroxycyclopropyl)methyl)-1,3-oxazinan-2-one (2.51 mg, 2%). $^1$H NMR (CDCl$_3$): 0.03 (m, 1H), 0.18 (m, 1H), 0.49 (m, 1H), 0.60 (m, 1H), 1.43 (m, 3H), 2.08 (s, 2H), 2.26 (m, 1H), 2.37 (m, 2H), 2.88 (m, 1H), 5.53 (m, 1H), 6.66 (d, 2H), 6.97 (t, 2H), 7.16 (m, 2H), 7.26 (m, 2H).

Preparation 15

N-(3-((R)-3-((S)-1-(4-bromophenyl)ethyl)-2-oxo-6-phenyl-1,3-oxazinan-6-yl)propyl)-N-methylmethane-sulfonamide

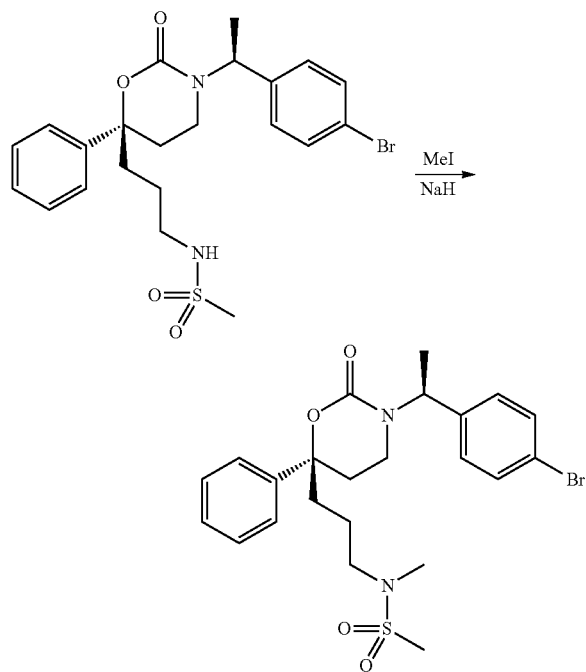

To a solution of 3-((R)-3-((S)-1-(4-bromophenyl)ethyl)-2-oxo-6-phenyl-1,3-oxazinan-6-yl) propyl methanesulfonate (180 mg, 0.36 mmol) in DMF (5 mL) was added NaH (14.6 mg, 0.36 mmol) at 0° C. The mixture was stirred at rt for 30 min. Then iodomethane (153 mg, 1.1 mmol) was added to the above mixture. The formed mixture was stirred at 40° C. for 3 h. After the reaction was over, the reaction was quenched with NH$_4$Cl solution and the mixture was extracted with EtOAc. The combined organic phase was concentrated to give the crude product, which was purified by preparative TLC to give N-(3-((R)-3-((S)-1-(4-bromophenyl)ethyl)-2-oxo-6-phenyl-1,3-oxazinan-6-yl)propyl)-N-methylmethane-sulfonamide (100 mg, 55%). LC-MS Method 2 t$_R$=1.41 min, m/z=511, 509. $^1$H NMR (400 MHz, CDCl$_3$): δ=1.45 (m, 1H), 1.48 (t, 3H), 1.83-1.97 (m, 3H), 2.1-2.2 (m, 3H), 2.61 (s, 3H), 2.71 (s, 3H), 2.91 (m, 1H), 3.0 (m, 2H), 5.5 (m, 1H), 6.72 (m, 2H), 7.10 (m, 2H), 7.20 (m, 2H), 7.37 (m, 3H).

Example 1

(S)-6-(2-hydroxy-2-methylpropyl)-3-((S)-1-(4-(6-oxo-1,6-dihydropyridin-3-yl)phenyl)ethyl)-6-phenyl-1,3-oxazinan-2-one

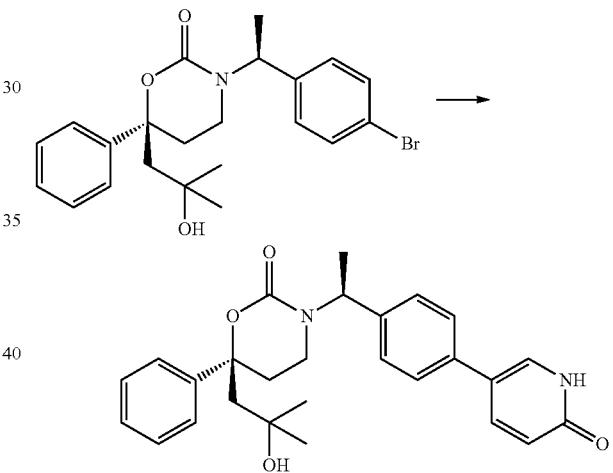

To a solution of (S)-3-((S)-1-(4-bromophenyl)ethyl)-6-(2-hydroxy-2-methylpropyl)-6-phenyl-1,3-oxazinan-2-one (112 mg, 0.259 mmol) in 1,4-dioxane (3 mL) was added 6-oxo-1,6-dihydropyridin-3-ylboronic acid (55 mg, 0.40 mmol), followed by Pd(dppf)Cl$_2$ (11 mg, 0.015 mmol), and an aq solution of Cs$_2$CO$_3$ (0.48 mL, 2M in H$_2$O). A reflux condenser was attached and the apparatus was degassed and flushed with N$_2$ three times. The reaction was heated to 90° C. for 24 h. After cooling to rt the mixture was diluted with water and extracted three times with EtOAc. The organic layers were washed with brine, dried over Na$_2$SO$_4$, filtered and concentrated. The residue was purified by prep HPLC to afford the title compounds (21.6 mg) as an oil. LC-MS Method 1 t$_R$=1.25 min, m/z=447, 389; $^1$H NMR (CD$_3$OD) 0.96 (s, 3H), 1.28 (s, 3H), 1.57 (d, 3H), 2.16 (s, 2H), 2.21 (m, 1H), 2.46 (m, 2H), 3.03 (m, 1H), 5.57 (q, 1H), 6.66 (d, 1H), 7.02 (d, 2H), 7.25-7.40 (7H), 7.66 (s, 1H), 7.90 (d, 1H).

Example 2

(S)-6-(2-hydroxy-2-methylpropyl)-3-((S)-1-(4-(2-oxo-1,2-dihydropyridin-4-yl)phenyl)ethyl)-6-phenyl-1,3-oxazinan-2-one

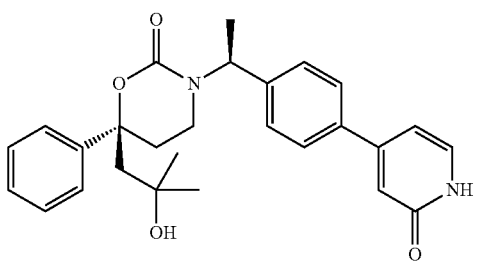

The title compound was prepared from (S)-6-(2-hydroxy-2-methylpropyl)-6-phenyl-3-((S)-1-(4-(4,4,5,5-tetramethyl-1,3,2-dioxaborol-an-2-yl)phenyl)ethyl)-1,3-oxazinan-2-one and 4-iodopyridin-2(1H)-one following a procedure analogous to that described in Example 1. LC-MS Method 1 $t_R$=1.23 min, m/z=389, 447 (M+1); $^1$H NMR (CD$_3$OD) 7.40 (d, J=6.7 Hz, 1H), 7.31 (d, J=8.2 Hz, 2H), 7.29-7.20 (m, 5H), 6.96 (d, J=8.2 Hz, 2H), 6.57-6.52 (m, 2H), 5.49 (q, J=7.0 Hz, 1H), 2.98-2.93 (m, 1H), 2.47-2.34 (m, 2H), 2.16-2.09 (m, 1H), 2.07 (s, 2H), 1.45 (d, J=7.0 Hz, 3H), 1.19 (s, 3H), 0.87 (s, 3H).

Example 3

(S)-3-((S)-1-(4-(1-cyclopropyl-6-oxo-1,6-dihydropyridin-3-yl)phenyl)ethyl)-6-(2-hydroxy-2-methylpropyl)-6-phenyl-1,3-oxazinan-2-one Na$_2$CO$_3$ (1.110 g, 10.47 mmol, 2.20 equiv) in dichloroethane (30 mL) was stirred at 70° C. for 22 h under air. The reaction mixture was quenched with satd aq NH$_4$Cl, diluted with CH$_2$Cl$_2$, dried over Na$_2$SO$_4$. After the solvent was removed under reduced pressure, the residue was purified by chromatography on silica gel eluted with hexanes/EtOAc to afford 0.585 g (58%) of 5-bromo-1-cyclopropylpyridin-2(1H)-one. LC-MS Method 1 $t_R$=1.05 min, m/z 214, 216 (MH$^+$); $^1$H NMR (400 MHz, CDCl$_3$) δ 7.41 (d, J=2.7 Hz, 1H), 7.31 (dd, J=9.7, 2.9 Hz, 1H), 6.47 (d, J=9.9 Hz, 1H), 3.33-3.27 (m, 1H), 1.17-1.12 (m, 2H), 0.89-0.84 (m, 2H); $^{13}$C NMR (100 MHz, CDCl$_3$) δ 162.58, 142.29, 137.00, 121.77, 97.92, 32.83, 6.93.

Step 2. (S)-3-((S)-1-(4-(1-cyclopropyl-6-oxo-1,6-dihydropyridin-3-yl)phenyl)ethyl)-6-(2-hydroxy-2-methylpropyl)-6-phenyl-1,3-oxazinan-2-one To a solution of (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one (0.729 g, 1.52 mmol) in 1,4-dioxane (16 mL) were added 5-bromo-1-cyclopropylpyridin-2(1H)-one (0.323 g, 1.51 mmol), 2 M aq Cs$_2$CO$_3$ (4 mL), and PdCl$_2$(dppf).CH$_2$Cl$_2$ (0.079 g, 0.0964 mmol). The mixture was degassed and heated, under a nitrogen atmosphere, at 120° C. for 16 h. The mixture was diluted with CH$_2$Cl$_2$, dried over Na$_2$SO$_4$. After the solvents were evaporated, the residue was purified by chromatography on silica gel eluted with MeOH/CH$_2$Cl$_2$ to afford 0.543 g (74%) of (S)-3-((S)-1-(4-(1-cyclopropyl-6-oxo-1,6-dihydropyridin-3-yl)phenyl)ethyl)-6-(2-hydroxy-2-methylpropyl)-6-phenyl-1,3-oxazinan-2-one. LC-MS Method 1 $t_R$=1.41 min, m/z 487 (MH$^+$); $^1$H NMR (400 MHz, CD$_3$OD) δ 7.66-7.64 (m, 2H), 7.30-7.19 (m, 7H), 6.94 (d, J=8.2 Hz, 2H), 6.52 (d, J=10 Hz, 1H), 5.48 (q, J=7.0 Hz, 1H), 3.32-3.26 (m, 1H), 2.97-2.92 (m,

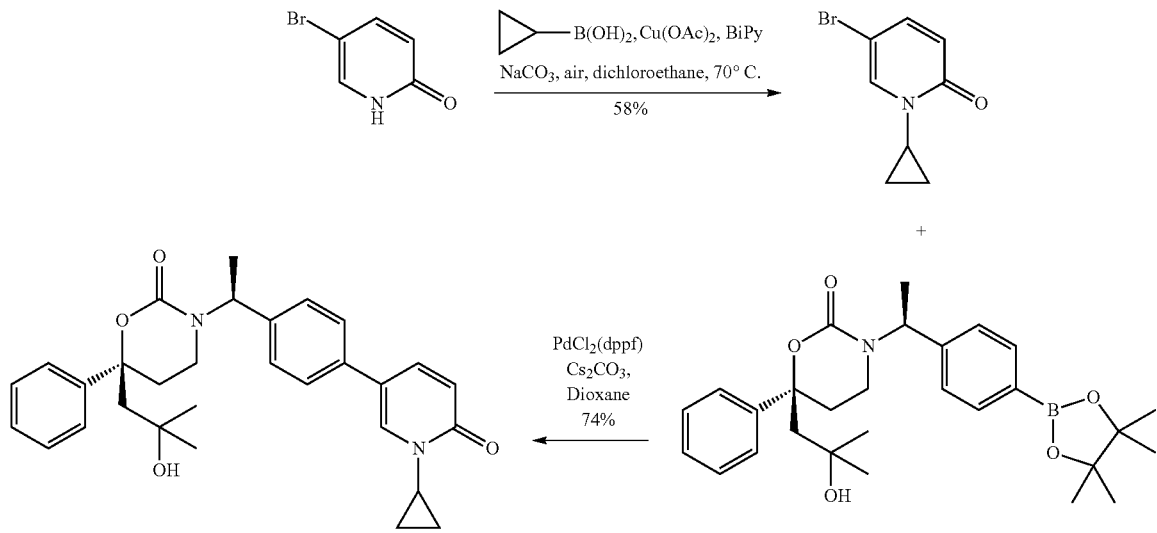

Step 1. 5-bromo-1-cyclopropylpyridin-2(1H)-one

A mixture of 5-bromo-2-hydroxypyridine (0.8300 g, 4.77 mmol, 1.0 equiv), Cu(OAc)$_2$ (0.902 g, 4.96 mmol, 1.04 equiv), bipyridine (0.785 g, 5.03 mmol, 1.05 equiv), cyclopropylboronic acid (0.846 g, 9.85 mmol, 2.06 equiv) and 1H), 2.46-2.32 (m, 2H), 2.16-2.09 (m, 1H), 2.08 (s, 2H), 1.45 (d, J=7.0 Hz, 3H), 1.19 (s, 3H), 1.10-1.05 (m, 2H), 0.90-0.86 (m, 5H); $^{13}$C NMR (100 MHz, CD$_3$OD) δ 165.59, 155.82, 144.08, 141.05, 139.60, 136.60, 136.30, 129.77, 128.86, 128.64, 126.83, 126.15, 121.93, 120.53, 85.33, 71.67, 55.18, 54.78, 37.46, 34.10, 33.04, 31.79, 30.00, 15.60, 7.49, 7.47.

Example 4

(S)-3-((S)-1-(4-(1-(difluoromethyl)-6-oxo-1,6-dihydropyridin-3-yl)phenyl)ethyl)-6-(2-hydroxy-2-methylpropyl)-6-phenyl-1,3-oxazinan-2-one

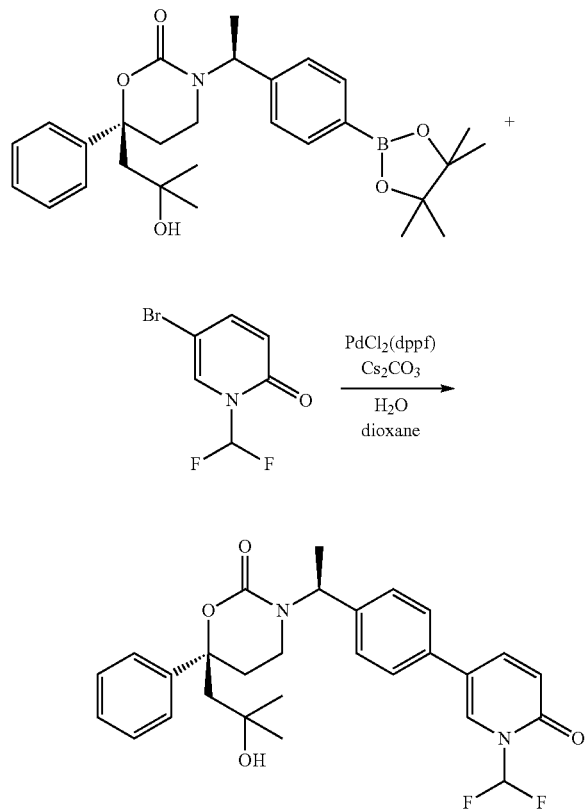

A microwave vial equipped with a flea stirbar was charged with (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one (20 mg, 0.047 mmol), 5-bromo-1-(difluoromethyl)pyridin-2(1H)-one (25 mg, 0.113 mmol), $Cs_2CO_3$ (27 mg, 0.083 mmol), $H_2O$ (0.1 mL) and dry dioxane (1 mL). The mixture was sparged with $N_2$ for 10 min and heated at 110° C. in the microwave for 0.5 h. The mixture was diluted with glacial HOAc (0.1 mL) and MeOH (0.5 mL) and filtered. The filtrate was directly purified by prep HPLC to afford (S)-3-((S)-1-(4-(1-(difluoromethyl)-6-oxo-1,6-dihydropyridin-3-yl)phenyl)ethyl)-6-(2-hydroxy-2-methylpropyl)-6-phenyl-1,3-oxazinan-2-one (11.8 mg, 57%) as an oil. LC-MS Method 1 $t_R$=1.55 min, m/z=497, 248; $^1$H NMR ($CDCl_3$) 1.13 (s, 3H), 1.19 (s, 3H), 1.56 (d, 3H), 2.15-2.35 (s, 4H), 2.42 (m, 2H), 2.88 (m, 1H), 5.71 (q, 1H), 6.64 (d, 1H), 7.04 (d, 2H), 7.18 (d, 2H), 7.30-7.40 (5H), 7.52 (1H), 7.60 (m, 1H), 7.75 (t, 1H).

5-bromo-1-(difluoromethyl)pyridin-2(1H)-one was prepared as described in Ando, M.; Wada, T.; Sato, N. *Org. Lett.* 2006, 8, 3805-3808.

Example 5

(S)-3-((S)-1-(4-(1-(difluoromethyl)-2-oxo-1,2-dihydropyridin-4-yl)phenyl)ethyl)-6-(2-hydroxy-2-methylpropyl)-6-phenyl-1,3-oxazinan-2-one

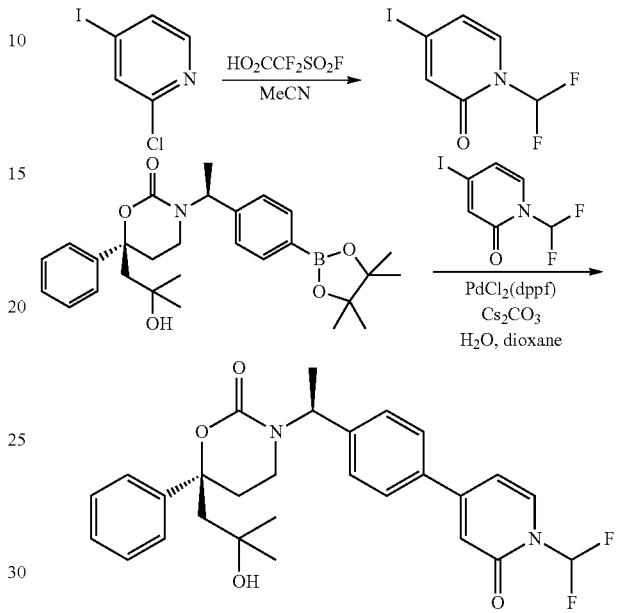

Step 1

A stirred mixture of 2-chloro-4-iodopyridine (1.33 g, 5.6 mmol) and powdered $NaHCO_3$ (935 mg, 11.2 mmol) in MeCN (2 mL) was warmed to 40° C. in an oil bath and a solution of 2,2-difluoro-2-(fluorosulfonyl)acetic acid (0.57 mL, 5.6 mmol) in MeCN (10 mL) was added dropwise over 10 min. The mixture was stirred at 40° C. for 2 h. LC-MS showed partial conversion to desired product. Powdered $NaHCO_3$ (935 mg, 11.2 mmol) was added followed by a solution of 2,2-difluoro-2-(fluorosulfonyl)acetic acid (0.57 mL, 5.6 mmol) in MeCN (10 mL) dropwise over 10 min. The mixture was stirred at 40° C. for 2 h. The mixture was diluted with satd aq $NaHCO_3$ (25 mL) and concentrated under reduced pressure. The aqueous residue was extracted with EtOAc (90 mL). The organic extract was washed with brine (20 mL), dried over $Na_2SO_4$ and concentrated to afforded an amber oil (1.14 g). Chromatography on a 40-g silica gel cartridge, eluted with a 0-40% EtOAc in hexanes gradient, afforded 1-(difluoromethyl)-4-iodopyridin-2(1H)-one (255 mg, yield 16%, estimated purity 45%) as yellow oil. LC-MS Method 1 $t_R$=1.23 min, m/z=272. The material was used without further purification.

Step 2

A microwave vial equipped with a flea stir bar was charged with (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one (52 mg, 0.11 mmol), 1-(difluoromethyl)-4-iodopyridin-2(1H)-one (29 mg, 0.11 mmol), $Cs_2CO_3$ (71 mg, 0.22 mmol), $H_2O$ (0.1 mL) and dry dioxane (1 mL). The mixture was sparged with $N_2$ for 5 min and $PdCl_2$(dppf) (5 mg, 0.007 mmol) was added. The mixture was sparged with $N_2$ for 5 min and heated at 110° C. in the microwave for 1 h. The mixture was diluted with 5% aq HCl (0.2 mL) and MeOH (2 mL) and filtered. The filtrate was directly purified by prep HPLC to afford a brown oil (16.2 mg) which was applied to a 2-g silica SPE cartridge which was eluted sequentially with 25 and 50% EtOAc in hexanes (15 mL of each) and EtOAc (3×15 mL) to afford five fractions. Fractions 3 and 4 were pooled and concentrated to afford (S)-3-((S)-1-(4-(1-(difluoromethyl)-2-oxo-1,2-dihydropyridin-4-yl)phenyl)ethyl)-6-(2-hydroxy-2-methylpropyl)-6-phenyl-1,3-oxazinan-2-one (13.4 mg, 25%) as a colorless oil. LC-MS Method 1 $t_R$=1.57 min, m/z=497, 439; $^1$H NMR (CD$_3$OD) 0.96 (5, 3H), 1.27 (s, 3H), 1.56 (d, 3H), 2.15 (s, 2H), 2.21 (m, 1H), 2.40-2.60 (2H), 3.08 (m, 1H), 5.59 (q, 1H), 6.66 (s, 1H), 6.74 (d, 1H), 7.07 (d, 2H), 7.30-7.40 (5H), 7.45 (d, 2H), 7.77 (1H), 7.79 (t, 1H).

Example 6

2,2-dimethyl-3-((R)-3-((S)-1-(4-(1-methyl-6-oxo-1,6-dihydropyridin-3-yl)phenyl)ethyl)-2-oxo-6-phenyl-1,3-oxazinan-6-yl)propanamide

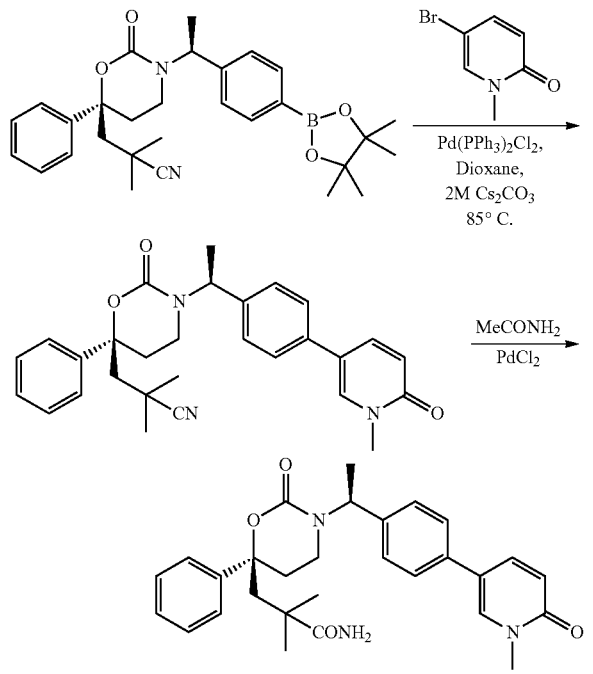

Step 1

A mixture of 2,2-dimethyl-3-((R)-2-oxo-6-phenyl-3-((S)-1-(4-(4,4,5,5-tetramethyl-1,3,2-dioxaborolan-2-yl)phenyl)ethyl)-1,3-oxazinan-6-yl)propanenitrile (392 mg, 0.775 mmol), 5-bromo-1-methylpyridin-2(1H)-one (220 mg, 1.5 equiv), 2M aq Cs$_2$CO$_3$ solution (900 µL), Pd(PPh$_3$)$_2$Cl$_2$ (40 mg, 7 mol %) and anhydrous 1,4-dioxane (8.5 mL) was degassed and refilled with N$_2$ gas 3 times. The mixture was then heated overnight at 85° C. under protection of N$_2$ gas. After being cooled to rt, the mixture was diluted with EtOAc (20 mL), washed by water (20 mL). The aqueous layer was extracted with EtOAc (2×10 mL). The combined organic layers were washed by water (10 mL), brine (2×10 mL) and dried over Na$_2$SO$_4$. After filtration and concentration, the residue was purified by Gilson to afford 34 mg product (9% yield). LC-MS (3 min. method) $t_R$=1.44 min., m/z 470 (M+1). $^1$H NMR (CDCl$_3$) δ 7.68 (dd, 1H), 7.52 (d, 1H), 7.31 (q, 2H), 7.16 (d, 2H), 7.07 (t, 2H), 6.97 (d, 2H), 6.91 (d, 1H), 5.66 (q, 1H), 3.71 (s, 3H), 2.99 (dt, 1H), 2.47 (dd, 2H), 2.27 (m, 1H), 2.13 (s, 2H), 1.55 (d, 3H), 1.44 (s, 3H), 1.24 (s, 3H).

Step 2

A THF:H$_2$O (2 mL, 3:1) solution of 2,2-dimethyl-3-((R)-3-((S)-1-(4-(1-methyl-6-oxo-1,6-dihydropyridin-3-yl)phenyl)ethyl)-2-oxo-6-phenyl-1,3-oxazinan-6-yl)propanenitrile (55 mg, 0.12 mmol), acetamide (177 mg, 3 mmol) and PdCl$_2$ (21 mg, 0.12 mmol) was stirred overnight. The solvent was removed and the crude material redissolved in CH$_3$CN. The crude product was purified via prep HPLC to afford 2,2-dimethyl-3-((R)-3-((S)-1-(4-(1-methyl-6-oxo-1,6-dihydropyridin-3-yl)phenyl)ethyl)-2-oxo-6-phenyl-1,3-oxazinan-6-yl)propanamide (28 mg). LC-MS Method 1 $t_R$=1.25 min, m/z=488 (M+1); $^1$H NMR (CDCl$_3$) 7.55 (dd, 1H, J=9 Hz, 3 Hz), 7.42 (d, 1H, J=3 Hz), 7.32 (d, 1H, J=4 Hz), 7.29 (m, 4H), 7.14 (d, 2H, 8 Hz), 7.00 (d, 2H, J=8 Hz), 6.79 (d, 1H, J=9 Hz), 5.66 (q, 1H, J=8 Hz), 3.62 (s, 3H), 2.95-2.89 (m, 1H), 2.5 (d, 1H, J=15 Hz), 2.26-2.1 (m, 3H), 2.2 (d, 1H, J=15 Hz), 2.5 (d, 1H, J=15 Hz), 2.26-2.10 (m, 3H), 2.2 (d, 1H, J=15 Hz), 1.53 (d, 3H, J=7 Hz), 1.22 (s, 3H), 1.20 (s, 3H)

Example 7

(S)-6-(2-amino-2-methylpropyl)-3-((S)-1-(4-(1-methyl-6-oxo-1,6-dihydropyridin-3-yl)phenyl)ethyl)-6-phenyl-1,3-oxazinan-2-one

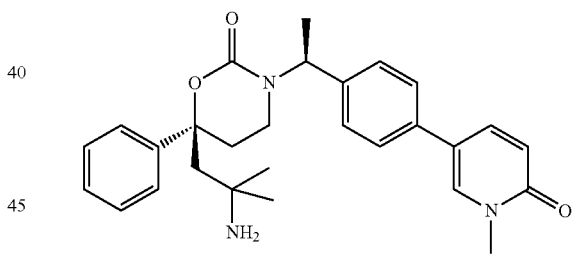

A foil covered flask charged with 2,2-dimethyl-3-((R)-3-((S)-1-(4-(1-methyl-6-oxo-1,6-dihydropyridin-3-yl)phenyl)ethyl)-2-oxo-6-phenyl-1,3-oxazinan-6-yl)propanamide (20 mg, 0.04 mmol) in 1:1 CH$_3$CN/H$_2$O (1 mL) was treated with PhI(O$_2$CCF$_3$)$_2$ (31 mg, 0.07 mmol). The reaction was complete after 24 h. The solvent was removed and the crude material purified by prep HPLC to afford (S)-6-(2-amino-2-methylpropyl)-3-((S)-1-(4-(1-methyl-6-oxo-1,6-dihydropyridin-3-yl)phenyl)ethyl)-6-phenyl-1,3-oxazinan-2-one (16 mg). LC/MS ES+=460 (M+1). LC-MS Method 1 $t_R$=1.06 min, m/z=460 (M+1); $^1$H NMR (CDCl$_3$) 7.60 (dd, 1H, J=9 Hz, 2 Hz), 7.46 (d, 1H, J=3 Hz), 7.39-7.27 (m, 5H), 7.20 (d, 2H, J=7 Hz), 7.1 (d, 2H, J=8 Hz), 6.78 (d, 1H, J=9 Hz, 5.61 (q, 1H, J=7 Hz), 3.65 (s, 3H), 2.87 (m, 1H), 2.80 (d, 1H, J=16 Hz), 2.23 (d, 1H, J=16 Hz), 2.19-2.08 (m, 3H), 1.54 (d, 3H, J=7 Hz), 1.41 (s, 3H), 0.96 (s, 3H).

Example 8

N-(2-methyl-1-((S)-3-((S)-1-(4-(1-methyl-6-oxo-1,6-dihydropyridin-3-yl)phenyl)ethyl)-2-oxo-6-phenyl-1,3-oxazinan-6-yl)propan-2-yl)acetamide

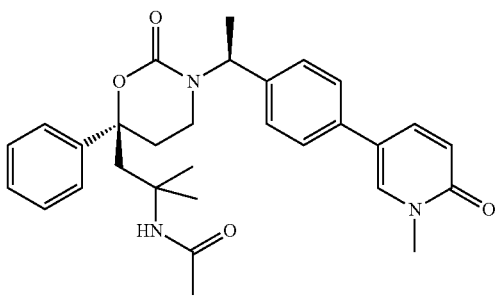

A CH$_2$Cl$_2$ (1 mL) solution of (S)-6-(2-amino-2-methylpropyl)-3-((S)-1-(4-(1-methyl-6-oxo-1,6-dihydropyridin-3-yl)phenyl)ethyl)-6-phenyl-1,3-oxazinan-2-one (5 mg, 0.009 mmol) was treated with DMAP (5 mg, 0.04 mmol), i-Pr$_2$NEt (10 drops), and acetic anhydride (20 drops). The reaction was stirred overnight. The reaction solution was washed with water. The organic layer was evaporated and the crude material purified by prep HPLC affording N-(2-methyl-1-((S)-3-((S)-1-(4-(1-methyl-6-oxo-1,6-dihydropyridin-3-yl)phenyl)ethyl)-2-oxo-6-phenyl-1,3-oxazinan-6-yl)propan-2-yl)acetamide (0.88 mg). LC-MS Method 1 $t_R$=1.3 min, m/z=502 (M+1).

Example 9

Methyl 2-methyl-1-((S)-3-((S)-1-(4-(1-methyl-6-oxo-1,6-dihydropyridin-3-yl)phenyl)ethyl)-2-oxo-6-phenyl-1,3-oxazinan-6-yl)propan-2-ylcarbamate

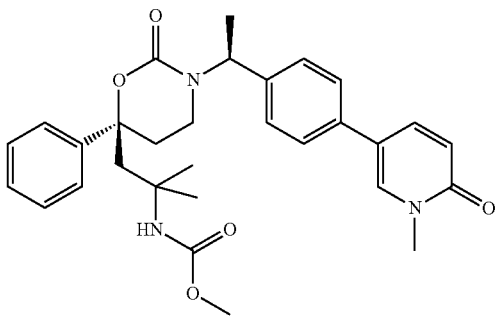

A CH$_2$Cl$_2$ (1 mL) solution of (S)-6-(2-amino-2-methylpropyl)-3-((S)-1-(4-(1-methyl-6-oxo-1,6-dihydropyridin-3-yl)phenyl)ethyl)-6-phenyl-1,3-oxazinan-2-one (5 mg, 0.009 mmol) was treated with DMAP (5 mg, 0.04 mmol), i-Pr$_2$NEt (10 drops), and methyl chloroformate (20 drops). The reaction was stirred overnight. The reaction solution was by prep HPLC affording methyl 2-methyl-1-((S)-3-((S)-1-(4-(1-methyl-6-oxo-1,6-dihydropyridin-3-yl)phenyl)ethyl)-2-oxo-6-phenyl-1,3-oxazinan-6-yl)propan-2-ylcarbamate (2.58 mg). LC-MS Method 1 $t_R$=1.45 min, m/z=518 (M+1); $^1$H NMR (CDCl$_3$) 7.66 (dd, 1H, J=9 Hz, 2 Hz), 7.48 (d, 1H, J=3 Hz), 7.35-7.27 (m, 5H), 7.15 (d, 2H, J=8 Hz), 7.01 (d, 2H, J=8 Hz), 6.87 (d, 1H, J=9 Hz), 5.67 (q, 1H, J=7 Hz), 3.69 (s, 3H), 2.2 (s, 3H), 1.54 (d, 3H, J=7 Hz), 1.46-1.36 (m, 2H), 1.30 (s, 3H), 1.20 (s, 3H).

Example 10

N-(2-methyl-1-((S)-2-oxo-3-((S)-1-(4-(6-oxo-1,6-dihydropyridin-3-yl)phenyl)ethyl)-6-phenyl-1,3-oxazinan-6-yl)propan-2-yl)methanesulfonamide

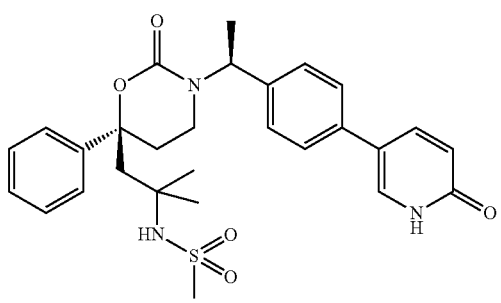

The title compound was prepared from N-(1-((S)-3-((S)-1-(4-bromophenyl)ethyl)-2-oxo-6-phenyl-1,3-oxazinan-6-yl)-2-methylpropan-2-yl)methanesulfonamide and 2-oxo-1,2-dihydropyridin-5-ylboronic acid following a procedure analogous to that described in Example 4. LC-MS Method 1 $t_R$=1.3 min, m/z=524 (M+1); $^1$H NMR (CDCl$_3$) 7.81 (d, 1H, J=9 Hz), 7.63 (br s, 1H), 7.39-7.31 (m, 5H), 7.18 (d, 2H, J=8 Hz), 7.03 (d, 2H, J=7 Hz), 6.79 (d, 1H, J=9 Hz), 5.67 (q, 1H, J=6 Hz), 2.93 (s, 3H), 2.90 (m, 1H), 2.49 (d, 1H, J=15 Hz), 2.32 (d, 1H, J=15 Hz), 2.28-2.18 (m, 3H), 1.54 (d, 3H, J=7 Hz), 1.36 (s, 3H), 1.25 (s, 3H).

N-(1-((S)-3-((S)-1-(4-bromophenyl)ethyl)-2-oxo-6-phenyl-1,3-oxazinan-6-yl)-2-methylpropan-2-yl)methanesulfonamide was prepared from 3-((R)-3-((S)-1-(4-bromophenyl)ethyl)-2-oxo-6-phenyl-1,3-oxazinan-6-yl)-2,2-dimethylpropanenitrile by sequential application of procedures analogous to those described in Examples 6 Step 2, Example 7 and Example 11.

Example 11

N-(2-methyl-1-((S)-3-((S)-1-(4-(1-methyl-6-oxo-1,6-dihydropyridin-3-yl)phenyl)ethyl)-2-oxo-6-phenyl-1,3-oxazinan-6-yl)propan-2-yl)methanesulfonamide

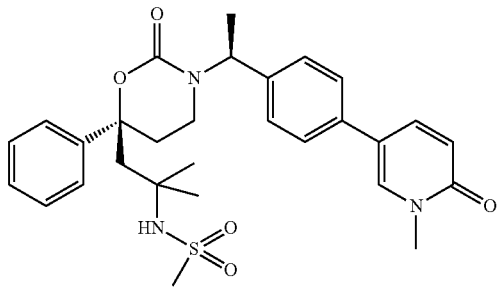

A CH$_2$Cl$_2$ (1 mL) solution of (S)-6-(2-amino-2-methylpropyl)-3-((S)-1-(4-(1-methyl-6-oxo-1,6-dihydropyridin-3-yl)phenyl)ethyl)-6-phenyl-1,3-oxazinan-2-one (5 mg, 0.009 mmol) was treated with DMAP (5 mg, 0.04 mmol), i-Pr₂NEt (10 drops), and MsCl (20 drops). The reaction was stirred overnight. The reaction solution was washed with water. The organic layer was evaporated and the crude material purified by prep HPLC affording N-(2-methyl-1-((S)-3-((S)-1-(4-(1-methyl-6-oxo-1,6-dihydropyridin-3-yl)phenyl)ethyl)-2-oxo-6-phenyl-1,3-oxazinan-6-yl)propan-2-yl)methanesulfonamide (3.30 mg). LC-MS Method 1 t$_R$=1.39 min, m/z=538 (M+1); ¹H NMR (CDCl₃) 7.61 (dd, 1H, J=9 Hz, 3 Hz), 7.46 (d, 1H, J=2 Hz), 7.40-7.27 (m, 5H), 7.17 (d, 2H, J=8 Hz), 7.04 (d, 2H, J=8 Hz), 6.79 (d, 1H, J=9 Hz), 5.67 (q, 1H, J=7 Hz), 3.66 (s, 3H), 2.93 (s, 3H), 2.31-2.22 (m, 2H), 1.55 (d, 3H, J=7 Hz), 1.48-1.36 (m, 2H), 1.33 (s, 3H), 1.24 (s, 3H).

Example 12

N-methyl-N-(2-methyl-1-((S)-3-((S)-1-(4-(1-methyl-6-oxo-1,6-dihydropyridin-3-yl)phenyl)ethyl)-2-oxo-6-phenyl-1,3-oxazinan-6-yl)propan-2-yl)methanesulfonamide

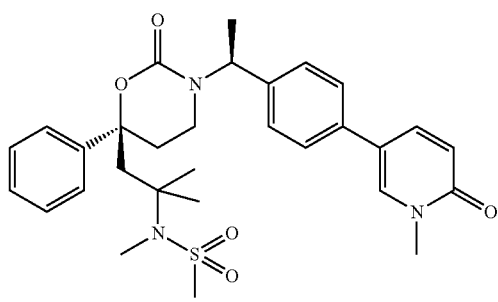

To a rt solution of N-(2-methyl-1-((S)-2-oxo-3-((S)-1-(4-(6-oxo-1,6-dihydropyridin-3-yl)phenyl)ethyl)-6-phenyl-1,3-oxazinan-6-yl)propan-2-yl)methanesulfonamide (7 mg, 0.013 mmol) in THF, NaH (10 mg, 0.20 mmol) was added followed by methyl iodide (30 uL, 0.080 mmol). The reaction was heated to 60° C. for 5 h. The flask was cooled to rt then to 0° C. before quenching with satd aq NH₄Cl. The mixture was extracted with EtOAc (3×) and the combined organic layers were dried over Na₂SO₄, filtered, evaporated and purified by prep HPLC to afford N-methyl-N-(2-methyl-1-((S)-3-((S)-1-(4-(1-methyl-6-oxo-1,6-dihydropyridin-3-yl)phenyl)ethyl)-2-oxo-6-phenyl-1,3-oxazinan-6-yl)propan-2-yl)methanesulfonamide (4.63 mg). LC-MS Method 1 t$_R$=1.45 min, m/z=552 (M+1); ¹H NMR (CDCl₃) 7.55 (dd, 1H, J=9 Hz, 3 Hz), 7.41 (d, 1H, J=3 Hz), 7.35-7.27 (m, 5H), 7.13 (d, 2H, J=8 Hz), 6.98 (d, 2H, J=8 Hz), 6.79 (d, 1H, J=9 Hz), 6.55 (q, 1H, J=7 Hz), 3.62 (s, 3H), 2.91-2.86 (m, 1H), 2.86 (s, 3H), 2.73 (d, 1H, J=15 Hz), 2.74 (s, 3H), 2.46 (d, 1H, J=15 Hz), 2.39-2.36 (m, 2H), 2.25-21.6 (m, 1H), 1.53 (d, 3H, J=7 Hz), 1.53 (s, 3H), 1.22 (s, 3H).

Example 13

N-(2-methyl-1-((S)-3-((S)-1-(4-(1-methyl-2-oxo-1,2-dihydropyridin-4-yl)phenyl)ethyl)-2-oxo-6-phenyl-1,3-oxazinan-6-yl)propan-2-yl)methanesulfonamide

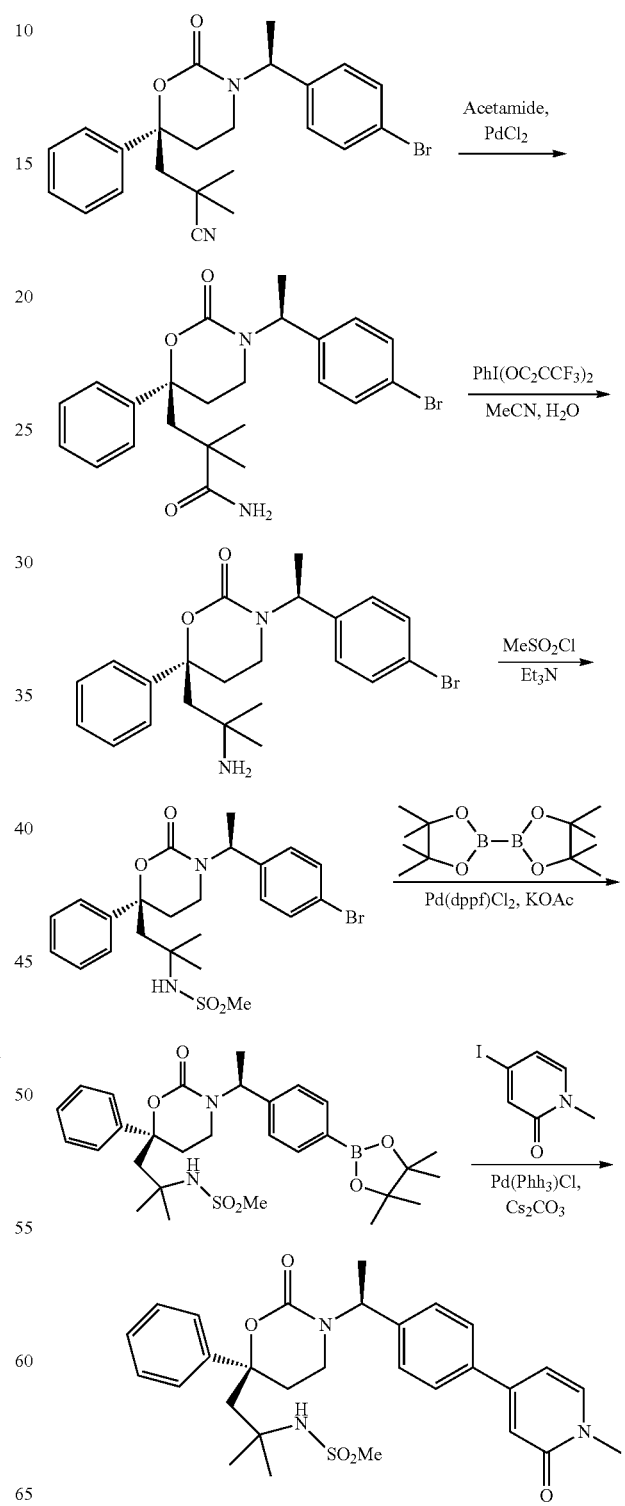

Step 1

To a solution of 3-(R-3-S-1-(4-bromophenyl)-ethyl)-2-oxo-6-phenyl-1,3-oxazinan-6-yl)-2,2-dimethylpropanenitrile (1 g, 2.27 mmol) in a mixture of THF/H$_2$O (3:1, 10 mL) was added acetamide (3.35 g, 56.75 mmol) and PdCl$_2$ (0.402 g, 2.27 mmol). The reaction was stirred overnight. The solvent was removed, and the residue was purified by TLC to afford 3-(R-3-S-1-(4-bromophenyl)-ethyl)-2-oxo-6-phenyl-1,3-oxazinan-6-yl)-2,2-dimethylpropanamide (0.745 g, 71.6%).

Step 2

To a solution of 3-(R-3-S-1-(4-bromophenyl)-ethyl)-2-oxo-6-phenyl-1,3-oxazinan-6-yl)-2,2-dimethylpropanamide (0.74 g, 1.612 mmol) in a mixture of CH$_3$CN/H$_2$O (20 mL, 1:1) was added PhI(OC$_2$CCF$_3$)$_2$ (1.178 g, 2.74 mmol). The mixture reaction was stirred overnight. The mixture was extracted with EtOAc (30 mL). The organic layer was washed with brine, and concentrated to afford S-6-(2-amino-2-methylpropyl)-3-S-1-(4-bromophenyl)-ethyl)-6-phenyl-1,3-oxazinan-2-one (0.6 g, 87%).

Step 3

To a solution of S-6-(2-amino-2-methylpropyl)-3-S-1-(4-bromophenyl)-ethyl)-6-phenyl-1,3-oxazinan-2-one (0.6 g, 1.39 mmol) in CH$_2$Cl$_2$ (10 mL) was added Et$_3$N (0.84 g, 8.34 mmol). The mixture was cooled at 0° C., MsCl (0.48 g, 4.17 mmol) was added. The reaction was stirred at rt for 1 h. The mixture was evaporated to afford the crude product. The residue was purified by column to afford N-1-S-3-S-1-(4-bromophenyl)-ethyl)-2-oxo-6-phenyl-1,3-oxazinan-6-yl)-2-methylpropan-2-yl)-methyl-sulfonamide (0.5 g, 70.4%).

Step 4

To a solution of N-1-S-3-S-1-(4-bromophenyl)ethyl)-2-oxo-6-phenyl-1,3-oxazinan-6-yl)-2-methylpropan-2-yl)-methyl-sulfonamide (0.5 g, 0.98 mmol) and 4,4,4',4',5,5,5',5'-octamethyl-2,2'-bi-(1,3,2-dioxaborolane) (0.399 g, 1.57 mmol) in dry DMSO (15 mL) was added KOAc (0.31 g, 3.14 mmol) and Pd(dppf)Cl$_2$ (0.025 g, 0.03 mmol) under N$_2$ atmosphere. After addition, the mixture was stirred at 90° C. overnight. After TLC showed the starting material had disappeared, the solid was filtered off. Water (30 mL) and EtOAc (50 mL) was added, the mixture was extracted with EtOAc (3×30 mL). The combined organic layer was washed with brine (50 mL), dried over Na$_2$SO$_4$, filtered, and concentrated to dryness. The residue was purified by column chromatography to afford N-(2-methyl-1-S-2-oxo-6-phenyl-3-S-1-(4-(4,4,5,5-tetramethyl-1,3,2-dioxaborolan-2-yl)phenyl)ethyl)-1,3-oxazinan-6-yl)propan-2-yl)-methyl-sulfonamide (0.2 g, yield: 37%).

Step 5

To a solution of N-(2-methyl-1-S-2-oxo-6-phenyl-3-S-1-4-4,4,5,5-tetramethyl-1,3,2-dioxaborolan-2-yl)phenyl)ethyl)-1,3-oxazinan-6-yl)propan-2-yl)-methyl sulfonamide (150 mg, 0.27 mmol) and 4-iodo-1-methylpyridin-2(1H)-one in dry 1,4-dioxane (5 mL) was added Cs$_2$CO$_3$ (0.3 mL, 6 mmol) and Pd(PPh$_3$)Cl$_2$ (20 mg). After addition, the mixture was warmed at 110° C. for 2 min. After TLC showed the starting material had disappeared, the solid was filtered off. Water (20 mL) and EtOAc (30 mL) were added. The organic layer was separated, and the aqueous layer was extracted with EtOAc (3×30 mL). The combined organic layer was washed with brine, dried over Na$_2$SO$_4$, filtered, and concentrated to give the crude product, which was purified by preparative HPLC to provide N-2-methyl-1-S-3-S-1-4-(1-methyl-2-oxo-1,2-dihydropyridin-4-yl)-phenyl)-ethyl)-2-oxo-6-phenyl-1,3-oxazinan-6-yl)propan-2-yl)methyl sulfonamide (20 mg, 14%). LC-MS Method 2 t$_R$=1.154 min, m/z=538.1; $^1$H NMR (CDCl$_3$): δ1.25 (s, 3H), 1.32 (s, 3H), 1.55 (d, 3H), 2.50 (d, 2H), 2.91 (s, 3H), 3.63 (s, 3H), 4.54 (b, 1H), 5.67 (m, 1H), 6.53 (d, 1H), 6.92 (s, 1H), 7.06 (d, 2H), 7.30-7.50 (m, 8H).

Example 14

2,2-dimethyl-3-((R)-2-oxo-3-((S)-1-(4-(2-oxo-1,2-dihydropyridin-4-yl)phenyl)ethyl)-6-phenyl-1,3-oxazinan-6-yl)propanenitrile

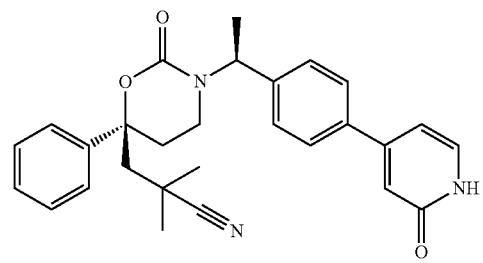

The title compound was prepared from 2,2-dimethyl-3-((R)-2-oxo-6-phenyl-3-((S)-1-(4-(4,4,5,5-tetramethyl-1,3,2-dioxaborolan-2-yl)phenyl)ethyl)-1,3-oxazinan-6-yl)propanenitrile and 4-iodopyridin-2(1H)-one following a procedure analogous to that described in Example 4. LC-MS Method 1 t$_R$=1.36 min, m/z=456 (M+1); $^1$H NMR (CDCl$_3$) 7.77 (d, 1H), 7.43-7.32 (m, 7H), 7.01 (t, 4H), 5.67 (q, 1H), 2.99 (dd, 1H), 2.57-2.43 (m, 2H), 2.32 (m, 1H), 2.17 (s, 2H), 1.57 (d, 3H), 1.40 (s, 3H), 1.33 (s, 3H).

Example 15

3-((R)-6-(4-fluorophenyl)-2-oxo-3-((S)-1-(4-(6-oxo-1,6-dihydropyridin-3-yl)phenyl)ethyl)-1,3-oxazinan-6-yl)-2,2-dimethylpropanenitrile

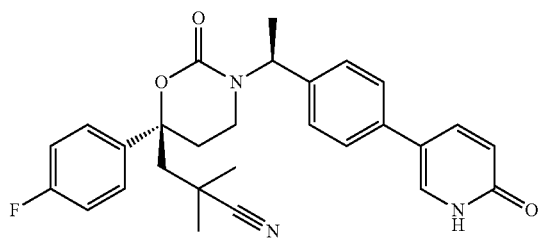

The title compound was prepared from 3-((R)-3-((S)-1-(4-bromophenyl)ethyl)-6-(4-fluorophenyl)-2-oxo-1,3-oxazinan-6-yl)-2,2-dimethylpropanenitrile and 2-oxo-1,2-dihydropyridin-5-ylboronic acid following a procedure analogous to that described in Example 4. LC-MS Method 1 t$_R$=1.37 min, m/z=474 (M+1); $^1$H NMR (CDCl$_3$) 7.97, (dd, 1H), 7.73 (s, 1H), 7.33 (m, 2H), 7.20 (d, 2H), 7.17 (t, 2H), 6.98 (m, 3H), 5.67 (q, 1H), 3.00 (dt, 1H), 2.49 (m, 2H), 2.30 (m, 1H), 2.13 (s, 2H), 1.55 (d, 3H), 1.45 (s, 3H), 1.34 (s, 3H).

Example 16

3-((R)-6-(4-fluorophenyl)-3-((S)-1-(4-(1-methyl-2-oxo-1,2-dihydropyridin-4-yl)phenyl)ethyl)-2-oxo-1,3-oxazinan-6-yl)-2,2-dimethylpropanenitrile

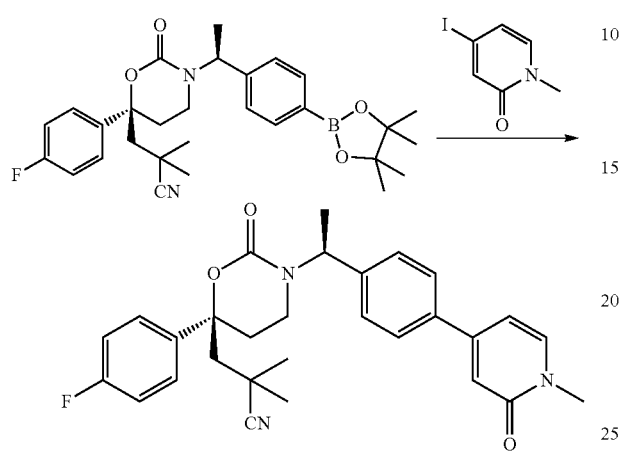

A mixture of 3-((R)-6-(4-fluorophenyl)-2-oxo-3-((S)-1-(4-(4,4,5,5-tetramethyl-1,3,2-dioxaborolan-2-yl)phenyl)ethyl)-1,3-oxazinan-6-yl)-2,2-dimethylpropanenitrile (100 mg, 0.21 mmol) and 4-iodo-1-methyl-1H-pyridin-2-one (40 mg, 0.17 mmol), Pd(PPh$_3$)$_2$Cl$_2$ (20 mg), and aq. Cs$_2$CO$_3$ solution (2.0 mL, 2M) in 1,4-dioxane (5 mL) was stirred at reflux for 2 h. The organic phase was separated and concentrated to give the crude product, which was purified by preparative TLC to give 3-((R)-6-(4-fluorophenyl)-3-((S)-1-(4-(1-methyl-2-oxo-1,2-dihydropyridin-4-yl)phenyl)ethyl)-2-oxo-1,3-oxazinan-6-yl)-2,2-dimethylpropanenitrile (55 mg, 66%). LC-MS Method 2 $t_R$=1.096 min, m/z=488.3; $^1$H NMR (CDCl$_3$): δ 1.27 (s, 3H), 1.40 (s, 3H), 1.48 (d, 3H), 2.06 (s, 2H), 2.23 (m, 1H), 2.41 (m, 2H), 2.90 (m, 1H), 3.51 (s, 3H), 5.60 (m, 1H), 6.27 (m, 1H), 6.65 (d, 1H), 6.89 (d, 2H), 6.99 (t, 2H), 7.26 (m, 5H).

Example 17

6-(2-hydroxy-2-methylpropyl)-6-isopropyl-3-((S)-1-(4-(1-methyl-2-oxo-1,2-dihydropyridin-4-yl)phenyl)ethyl)-1,3-oxazinan-2-one

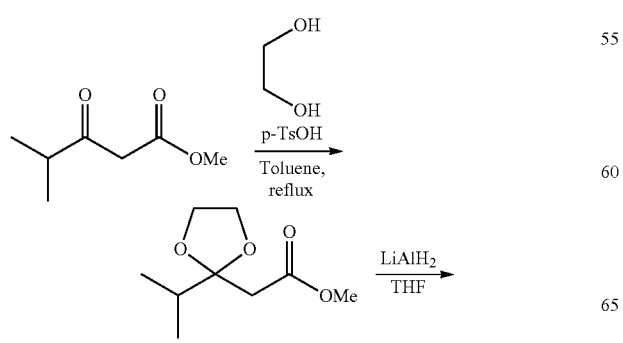

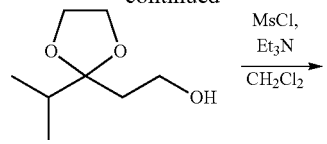

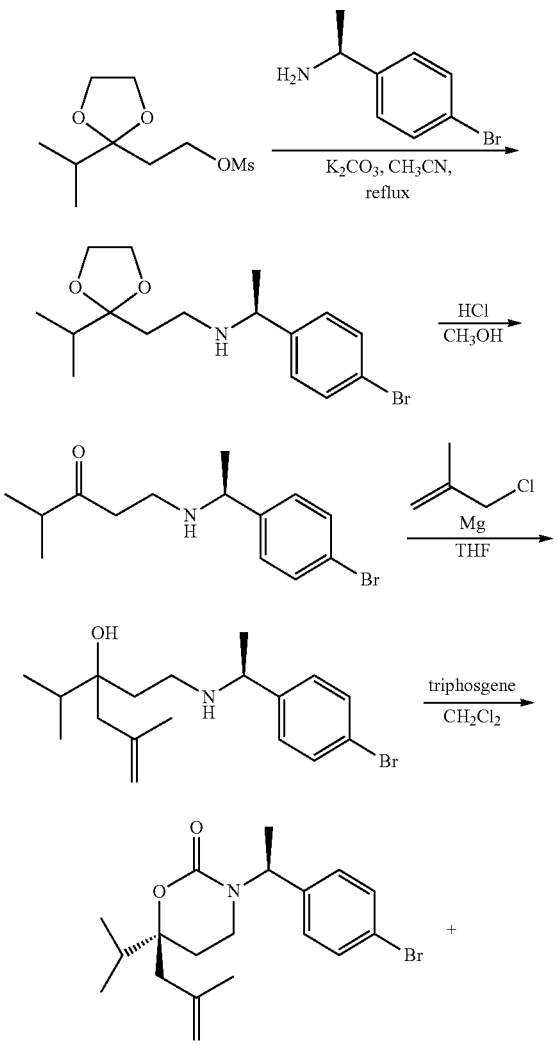

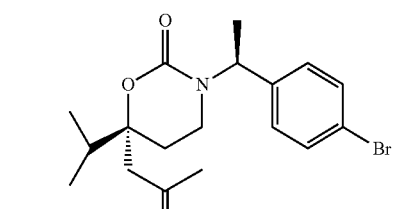

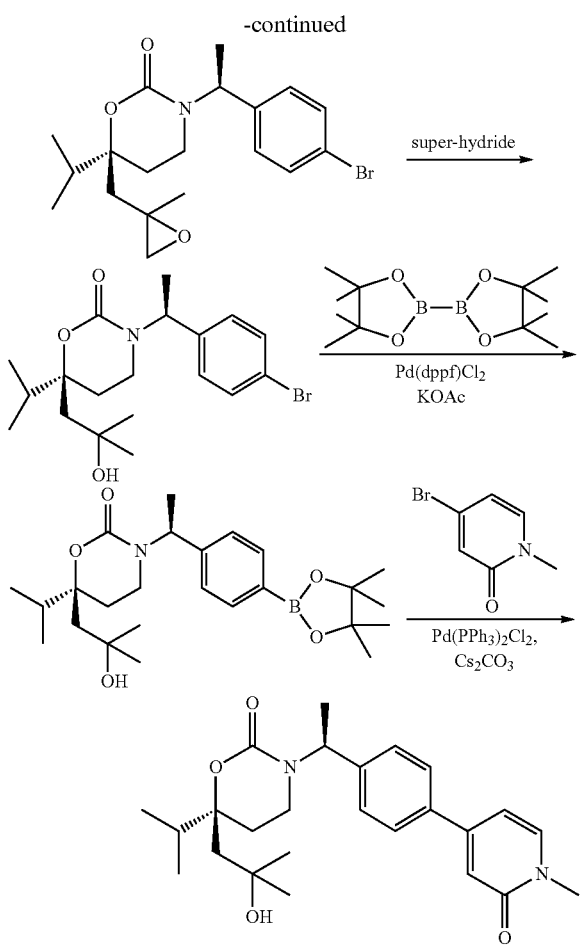

Step 1

To a solution of methyl 4-methyl-3-oxopentanoate (72 g, 0.5 mol), and ethylene glycol (56 g, 1 mol) in toluene (500 mL) was added 4-methylbenzenesulfonic acid (1.9 g, 0.01 mol). The mixture was stirred at reflux with a Dean-Stark trap to remove water. The reaction mixture was washed with a small amount of water and brine, dried over anhydrous $Na_2SO_4$, and concentrated in vacuum to give the crude methyl 2-(2-isopropyl-1,3-dioxolan-2-yl)-acetate (67 g 71% yield), which was used for the next step without further purification.

Step 2

In a flame-dried three neck flask equipped with an addition funnel, magnetic stirring bar, rubber septum, and a nitrogen inlet, was placed $LiAlH_4$ (3.12 g, 82.1 mmol) and THF (700 mL). After being cooled at 0° C., a solution of methyl 2-(2-isopropyl-1,3-dioxolan-2-yl)acetate (12 g, 63.8 mmol) in THF (160 mL) was added dropwise with stirring. The mixture was warmed to rt, and stirred for 24 hours. The reaction was quenched by adding water (5 mL), 15% aqueous NaOH (10 mL), and water (5 mL) slowly. The organic layer was separated, and the residue was extracted with EtOAc (3×100 mL). The combined organic phase was dried over $Na_2SO_4$, and concentrated to afford the crude product, which was purified by column chromatography to give 2-(2-isopropyl-1,3-dioxolan-2-yl)-ethanol (6.8 g, 67%). $^1$H NMR ($CDCl_3$): δ 0.90 (d, J=6.8 Hz, 6H), 1.87-1.96 (m, 3H), 2.81 (br, 1H), 3.69-3.72 (m, 2H), 3.92-4.01 (m, 4H).

Step 3

To a solution of 2-(2-isopropyl-1,3-dioxolan-2-yl)-ethanol (8.0 g, 50 mmol) and triethylamine (23.5 mL, 170 mmol) in anhydrous $CH_2Cl_2$ (120 mL) was added methanesulfonyl chloride (11.6 mL, 150 mmol) at 0° C., and the reaction mixture was stirred at rt till the reaction was finished. The reaction mixture was washed with water and brine, dried over $Na_2SO_4$, filtered, and concentrated to give the crude 2-(2-isopropyl-1,3-dioxolan-2-yl)ethyl methanesulfonate (12 g, crude), which was used for the next step without further purification.

Step 4

To a solution of 2-(2-isopropyl-1,3-dioxolan-2-yl)ethyl methanesulfonate (12 g, 50 mmol) and (S)-1-(4-methoxyphenyl)-ethyl amine (19.9 g, 100 mmol) in $CH_3CN$ (250 mL) was added $K_2CO_3$ (8 g, 58 mmol), and the mixture was refluxed for 10 h. The solution was filtered, and the filtrate was concentrated to afford the crude product, which was purified by column chromatography to give (S)-1-(4-bromophenyl)-N-(2-(2-isopropyl-1,3-dioxolan-2-yl)ethyl)ethanamine (6.5 g, 38% yield).

Step 5

To a solution of (S)-1-(4-bromophenyl)-N-(2-(2-isopropyl-1,3-dioxolan-2-yl)ethyl)ethanamine (6.5 g, 19 mmol) in MeOH (60 mL) was added conc HCl (60 mL). The mixture was stirred at 65° C. till the reaction was finished. The mixture was cooled to 0° C., and the pH of the mixture was adjusted to 7 by adding the satd aq $NaHCO_3$. The mixture was concentrated, and the residue was extracted with EtOAc (3×100 mL). The organic layer was washed with brine, dried over $Na_2SO_4$, and concentrated to give (S)-1-(1-(4-bromophenyl)ethylamino)-4-methylpentan-3-one (5.5 g, 97% yield), which was used for the next step without further purification. $^1$H NMR ($CDCl_3$): δ 1.07 (d, J=6.8 Hz, 6H), 1.29 (d, J=6.4 Hz, 3H), 1.89 (br, 1H), 2.54-2.62 (m, 4H), 2.66-2.69 (m, 1H), 3.68-3.72 (m, 1H), 7.18-7.20 (m, 2H), 7.41-7.44 (m, 2H).

Step 6

To a suspension of Mg (11 g, 458 mmol) and $I_2$ (0.5 g) in anhydrous THF (50 mL) was added 3-chloro-2-methylprop-1-ene (1 mL) to initiate the reaction. THF (300 mL) was added, more solution of 3-chloro-2-methylprop-1-ene (15 mL) in THF (20 mL) was dropped into the reaction at 0° C. under $N_2$ over 30 min. A solution of (S)-1-(1-(4-bromophenyl)-ethylamino)-4-methylpentan-3-one (5 g) in THF (50 mL) was added dropwise at −78° C. over 45 min. The reaction was stirred at rt for 2 h, cautiously quenched with satd aq $NH_4Cl$, and filtered. The filtrate was extracted with EtOAc (3×100 mL), washed with brine, dried over anhydrous $Na_2SO_4$, and concentrated in vacuo to give 1-(S-1-(4-bromophenylamino)-3-isopropyl-5-methylhex-5-en-3-ol (6.4 g, 90% yield), which was used for the next step without further purification.

Step 7

To a solution of 1-(S-1-(4-bromophenylamino)-3-isopropyl-5-methylhex-5-en-3-ol (6.4 g, 16.8 mmol) and triethylamine (5.34 g, 52 mmol) in $CH_2Cl_2$ (260 mL) was added triphosgene (2.52 g, 8.5 mmol) at 0° C. under $N_2$, and the mixture was stirred at rt overnight. The reaction mixture was quenched with water, and extracted with $CH_2Cl_2$ (3×50 mL). The combined organic layer was washed with brine, dried over $Na_2SO_4$, filtered, and concentrated to afford the crude product, which was purified by column chromatography to give two isomers of 3-((S)-1-(4-bromophenyl)ethyl)-6-isopropyl-6-(2-methylallyl)-1,3-oxazinan-2-one.

Isomer 1: (1.85 g, 27% yield) $^1$H NMR ($CDCl_3$): δ0.83 (d, J=7.2 Hz, 3H), 0.89 (d, J=7.2 Hz, 3H), 1.45 (d, J=6.8 Hz, 3H), 1.64-1.70 (m, 2H), 1.79 (s, 3H), 1.88-1.95 (m, 1H), 2.20-2.34 (m, 2H), 2.59-2.65 (m, 1H), 3.01-3.08 (m, 1H), 4.70 (s, 1H), 4.87 (s, 1H), 5.68-5.77 (m, 1H), 7.14 (d, J=8.4 Hz, 2H), 7.41 (d, J=8.4 Hz, 2H).

Isomer 2: (1.25 g, 18% yield) ¹H NMR (CDCl₃): δ0.87 (d, J=6.8 Hz, 3H), 0.92 (d, J=6.8 Hz, 3H), 1.50 (d, J=7.2 Hz, 3H), 1.60-1.66 (m, 1H), 1.78 (s, 3H), 1.73-1.79 (m, 1H), 1.78-2.05 (m, 1H), 2.08 (d, J=14.0 Hz, 1H), 2.30 (d, J=14.0 Hz, 1H), 2.62-2.68 (m, 1H), 2.98-3.05 (m, 1H), 4.64 (s, 1H), 4.84 (s, 1H), 5.70-5.75 (m, 1H), 7.13 (d, J=8.4 Hz, 2H), 7.40 (d, J=8.4 Hz, 2H).

Step 8

To a solution of 3-((S)-1-(4-bromophenyl)ethyl)-6-isopropyl-6-(2-methylallyl)-1,3-oxazinan-2-one. isomer 1 (500 mg, 1.32 mmol) in dry CH₂Cl₂ (64 mL) was added m-CPBA (455 g, 2.64 mmol) at rt. The reaction mixture was stirred until the starting material was consumed (monitored by TLC). The mixture was diluted with (CH₃)₃COCH₃ (70 mL), washed with 30% Na₂S₂O₃, and aq NaHCO₃ (3×), dried over Na₂SO₄, filtered, and concentrated to give 3-((S)-1-(4-bromophenyl)ethyl)-6-isopropyl-6-((2-methyloxiran-2-yl)methyl)-1,3-oxazinan-2-one isomer 1 (520 mg, 99%), which was used directly for the next step without further purification.

Step 9

To a solution of 3-((S)-1-(4-bromophenyl)ethyl)-6-isopropyl-6-((2-methyloxiran-2-yl)methyl)-1,3-oxazinan-2-one isomer 1 (520 mg, 1.32 mmol) in THF (32 mL) was added dropwise LiEt₃BH (Super-Hydride, 13.6 mL, 13.6 mmol) at 0° C. under N₂ over 30 min., the resulting solution was stirred at 10-13° C. for 21.5 h. To the mixture was added H₂O₂ (40 mL). The resulting solution was diluted with (CH₃)₃COCH₃ (380 mL), and washed with water, 30% aq Na₂S₂O₃, and brine. The organic phase was dried over Na₂SO₄, and filtered. The filtrate was concentrated to give the crude product, which was purified by column chromatography to afford 3-((S)-1-(4-bromophenyl)ethyl)-6-(2-hydroxy-2-methylpropyl)-6-isopropyl-1,3-oxazinan-2-one isomer 1 (320 mg, 61%). ¹H NMR (CDCl₃): δ0.82 (d, J=6.8 Hz, 3H), 0.95 (d, J=6.8 Hz, 3H), 1.31 (s, 3H), 1.34 (s, 3H), 1.51 (d, J=10.0 Hz, 3H), 1.61 (d, J=15.2 Hz, 1H), 1.78-1.84 (m, 1H), 1.91 (d, J=15.2 Hz, 1H), 2.02-2.15 (m, 2H), 2.36 (br, 1H), 2.62-2.68 (m, 1H), 3.03-3.09 (m, 1H), 5.73 (t, J=7.2 Hz, 1H), 7.17-7.19 (m, 2H), 7.44-7.48 (m, 2H).

Step 10

To a solution of 3-((S)-1-(4-bromophenyl)ethyl)-6-(2-hydroxy-2-methylpropyl)-6-isopropyl-1,3-oxazinan-2-one isomer 1 (315 mg, 0.793 mmol) in DMSO (10 mL) was added 4,4,5,5-tetramethyl-1,3,2-dioxaborolan-2-yl)-1,3,2-dioxaborolane (602 mg, 2.38 mmol), CH₃CO₂K (770 mg, 79.3 mmol), Pd(dppf)₂Cl₂ (50 mg, 0.06 mmol) under N₂, the reaction was stirred at 90° C. for 4 h. The mixture was quenched with NH₄Cl, and extracted with EtOAc, washed with water and brine. The organic phase was dried over Na₂SO₄ and filtered. The filtrate was concentrated to give the crude product, which was purified by preparative TLC to give 6-(2-hydroxy-2-methylpropyl)-6-isopropyl-3-((S)-1-(4-(4,4,5,5-tetramethyl-1,3,2-dioxaborolan-2-yl)phenyl)ethyl)-1,3-oxazinan-2-one isomer 1 (250 mg, 71%).

Step 11

To a solution of 6-(2-hydroxy-2-methylpropyl)-6-isopropyl-3-((S)-1-(4-(4,4,5,5-tetramethyl-1,3,2-dioxaborolan-2-yl)phenyl)ethyl)-1,3-oxazinan-2-one isomer 1 (250 mg, 0.39 mmol), 4-bromo-1-methylpyridin-2(1H)-one (127 mg, 0.68 mmol), Cs₂CO₃ (2N, 4 mL) in 1,4-dioxane (20 mL) was added Pd(PPh₃)₂Cl₂ (54 mg, 0.056 mmol) under N₂. The reaction mixture was refluxed for 2 h, quenched with water, and extracted with EtOAc. The organic phase was washed with H₂O and brine, dried over Na₂SO₄, and filtered. The filtrate was concentrated to give the crude product, which was purified by preparative TLC and preparative HPLC to afford 6-(2-hydroxy-2-methylpropyl)-6-isopropyl-3-((S)-1-(4-(1-methyl-2-oxo-1,2-dihydropyridin-4-yl)phenyl)ethyl)-1,3-oxazinan-2-one isomer 1 (79 mg, 47% yield). LC-MS Method 2 t_R=1.023 min, m/z=427.6; ¹H NMR (CDCl₃) 0.85 (d, 3H), 0.96 (d, 3H), 1.26 (s, 3H), 1.28 (s, 3H), 1.54 (m, 4H), 1.84-1.88 (m, 2H), 2.04 (br, 1H), 2.01-2.18 (m, 2H), 2.75 (m, 1H), 3.10 (m, 1H), 3.52 (s, 3H), 5.80 (t, 1H), 6.37 (m, 1H), 6.74 (m, 1H), 7.28 (m, 1H), 7.25-7.37 (m, 2H), 7.50 (m, 2H).

6-(2-hydroxy-2-methylpropyl)-6-isopropyl-3-((S)-1-(4-(1-methyl-2-oxo-1,2-dihydropyridin-4-yl)phenyl)ethyl)-1,3-oxazinan-2-one isomer 2 was prepared from 3-((S)-1-(4-bromophenyl)ethyl)-6-isopropyl-6-(2-methylallyl)-1,3-oxazinan-2-one isomer 2 following procedures analogous to those described in Steps 8-11 above. LC-MS Method 2 t_R=1.023 min, m/z=427.6; ¹H NMR (CDCl₃) 0.79 (d, 3H), 0.92 (d, 3H), 1.27 (s, 3H), 1.30 (s, 3H), 1.51 (d, 3H), 1.58 (d, 1H), 1.73-1.81 (m, 1H), 1.88 (d, 1H), 2.0 (br, 1H), 2.04-2.08 (m, 2H), 2.65-2.68 (m, 1H), 3.04-3.07 (m, 1H), 3.52 (s, 3H), 5.75 (t, 1H), 6.37 (m, 1H), 6.74 (m, 1H), 7.21-7.35 (m, 3H), 7.51 (m, 2H).

Example 18

6-cyclopropyl-6-(2-hydroxy-2-methylpropyl)-3-((S)-1-(4-(1-methyl-2-oxo-1,2-dihydropyridin-4-yl)phenyl)ethyl)-1,3-oxazinan-2-one

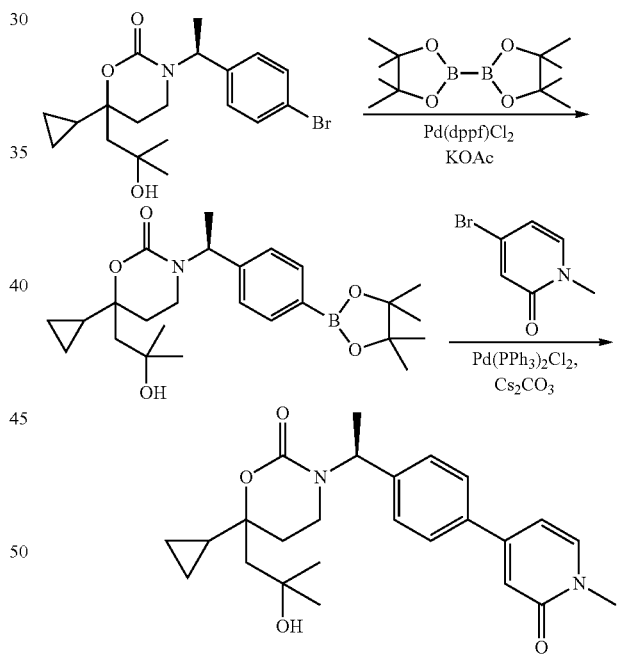

The two diastereomers of 3-((S)-1-(4-bromophenyl)ethyl)-6-cyclopropyl-6-(2-hydroxy-2-methylpropyl)-1,3-oxazinan-2-one were prepared from methyl 3-cyclopropyl-3-oxopropanoate following procedures analogous to those described in Example 17 Steps 1-7. The title compound was prepared as follows.

Step 1

To a solution of 3-((S)-1-(4-bromophenyl)ethyl)-6-cyclopropyl-6-(2-hydroxy-2-methylpropyl)-1,3-oxazinan-2-one isomer 1 (230 mg, 0.58 mmol) in DMSO (15 mL) was added 4,4,5,5-tetramethyl-1,3,2-dioxaborolan-2-yl)-1,3,2-dioxaborolane (450 mg, 1.77 mmol), CH₃CO₂K (800 mg, 8.16 mmol), Pd(pddf)₂Cl₂ (50 mg, 0.06 mmol) under N₂. The reaction was stirred at 90° C. for 34 h, quenched with NH₄Cl, and extracted with EtOAc. The organic phase was washed with water and brine, dried over Na₂SO₄, and filtered. The filtrate was concentrated to give the crude product, which was purified by preparative TLC to give 6-cyclopropyl-6-(2-hydroxy-2-methylpropyl)-3-((S)-1-(4-(4,4,5,5-tetramethyl-1,3,2-dioxaborolan-2-yl)phenyl)ethyl)-1,3-oxazinan-2-one isomer 1 (140 mg, 54.3%).

Step 2

To a solution of 6-cyclopropyl-6-(2-hydroxy-2-methylpropyl)-3-((S)-1-(4-(4,4,5,5-tetramethyl-1,3,2-dioxaborolan-2-yl)phenyl)ethyl)-1,3-oxazinan-2-one isomer 1 (140 mg, 0.316 mmol), 4-bromo-1-methylpyridin-2(1H)-one (74.3 mg, 0.316 mmol), 2 M aq Cs₂CO₃ (3 mL) in 1,4-dioxane (20 mL) was added Pd(dppf)₂Cl₂ (30 mg, 0.043 mmol) under N₂. The reaction mixture was refluxed for 2 h, quenched with water, and extracted with EtOAc. The organic phase was washed with H₂O and brine, dried over Na₂SO₄, and filtered. The filtrate was concentrated to give the crude product, which was purified by preparative TLC and preparative HPLC to afford 6-cyclopropyl-6-(2-hydroxy-2-methylpropyl)-3-((S)-1-(4-(1-methyl-2-oxo-1,2-dihydropyridin-4-yl)phenyl)ethyl)-1,3-oxazinan-2-one isomer 1 (49.5 mg, 37.7%). LC-MS Method 2 $t_R$=1.016 min, m/z=367.2; ¹H NMR (CDCl₃) 0.50 (m, 2H), 0.62 (m, 2H), 0.97 (m, 1H), 1.32 (m, 6H), 1.58 (d, 3H), 1.97 (m, 3H), 2.28 (m, 1H), 2.78 (m, 1H), 3.40 (m, 1H), 3.58 (s, 3H), 5.85 (m, 1H), 6.41 (d, 1H), 6.79 (s, 1H), 7.33 (d, 1H), 7.41 (d, 1H), 7.56 (d, 1H)

6-cyclopropyl-6-(2-hydroxy-2-methylpropyl)-3-((S)-1-(4-(1-methyl-2-oxo-1,2-dihydropyridin-4-yl)phenyl)ethyl)-1,3-oxazinan-2-one isomer 2 was prepared from 3-((S)-1-(4-bromophenyl)ethyl)-6-cyclopropyl-6-(2-hydroxy-2-methylpropyl)-1,3-oxazinan-2-one isomer 2 following procedures analogous to those described in Steps 1 and 2 immediately above. LC-MS Method 2 $t_R$=0.99 min, m/z=367.1; ¹H NMR (CDCl₃) 0.02 (m, 3H), 0.23 (m, 1H), 0.51 (m, 1H), 0.96 (s, 6H), 1.17 (d, 3H), 1.40-1.60 (m, 4H), 1.94 (m, 1H), 2.55 (m, 1H), 2.73 (m, 1H), 3.20 (s, 3H), 5.41 (m, 1H), 6.03 (d, 1H), 6.40 (s, 1H), 6.98 (m, 1H), 7.03 (m, 2H), 7.18 (m, 2H)

Example 19

(R)-6-(2-(5-methyl-1,3,4-oxadiazol-2-yl)ethyl)-3-((S)-1-(4-(1-methyl-2-oxo-1,2-dihydropyridin-4-yl)phenyl)ethyl)-6-phenyl-1,3-oxazinan-2-one

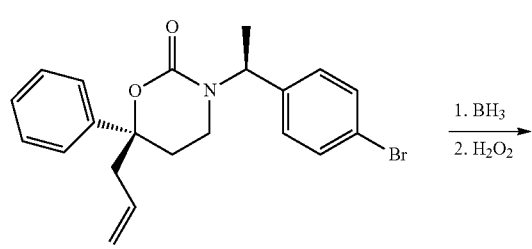

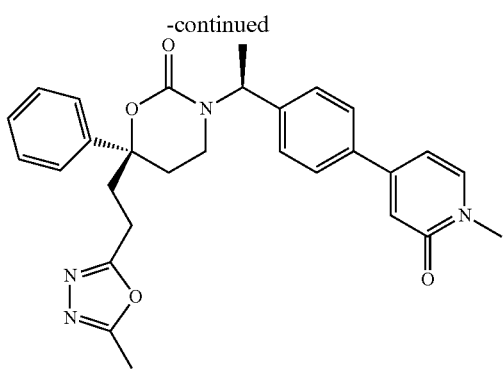

Step 4

To a solution of N'-acetyl-3-((R)-3-((S)-1-(4-bromophenyl)ethyl)-2-oxo-6-phenyl-1,3-oxazinan-6-yl)propanehydrazide (0.1 g, 0.21 mmol) in THF (2 mL) was added Burgess Reagent (75 mg, 0.315 mmol). The sealed vial was irradiated in the microwave at 100° C. for 15 min. The mixture was extracted with EtOAc (3×30 mL). The combined organic layer was washed with brine (50 mL), dried over $Na_2SO_4$, filtered, and concentrated. The residue was purified by preparative TLC to afford (R)-3-(S)-1-(4-bromophenyl)ethyl)-6-(2-(5-methyl-1,3,4-oxadiazol-2-yl)ethyl)-6-phenyl-1,3-oxazinan-2-one (58 mg, yield: 59%). $^1$H NMR ($CDCl_3$): δ1.49-1.51 (m, 3H), 2.23-2.26 (m, 2H), 2.30-2.33 (m, 2H), 2.42 (s, 3H), 2.43-2.45 (m, 1H), 2.49-2.54 (m, 1H), 2.87-2.91 (m, 1H), 3.06-3.09 (m, 1H), 5.61-5.63 (m, 1H), 6.76-6.78 (d, 2H), 7.20-7.22 (m, 2H), 7.26-7.33 (m, 2H), 7.35-7.37 (m, 3H).

Step 5

To a solution of (R)-3-((S)-1-(4-bromophenyl)ethyl)-6-(2-(5-methyl-1,3,4-oxadiazol-2-yl)ethyl)-6-phenyl-1,3-oxazinan-2-one (490 mg, 1.04 mmol), and 4,4,4',4',5,5,5',5'-octamethyl-2,2'-bi(1,3,2-dioxaborolane) (424 mg, 1.67 mmol) in dry DMSO (20 mL) was added KOAc (326 mg, 3.33 mmol) and $Pd(dppf)Cl_2$ (25.3 mg, 0.031 mmol) under $N_2$ atmosphere. The mixture was warmed at 100° C. for 3 h. After TLC showed the starting material had disappeared, the solid was filtered off, water (50 mL) and EtOAc (50 mL) were added, and the mixture was extracted with EtOAc (3×50 mL). The combined organic layer was washed with brine (50 mL), dried over $Na_2SO_4$, filtered, and concentrated. The residue was purified by prep TLC to afford (R)-6-(2-(5-methyl-1,3,4-oxadiazol-2-yl)ethyl)-6-phenyl-3-((S)-1-(4-(4,4,5,5-tetramethyl-1,3,2-dioxaborolan-2-yl)phenyl)ethyl)-1,3-oxazinan-2-one (0.395 g, yield: 73.6%).

Step 6

To a solution of (R)-6-(2-(5-methyl-1,3,4-oxadiazol-2-yl)ethyl)-6-phenyl-3-((S)-1-(4-(4,4,5,5-tetramethyl-1,3,2-dioxaborolan-2-yl)phenyl)ethyl)-1,3-oxazinan-2-one (60 mg, 0.12 mmol) and 4-iodo-1-methylpyridin-2(1H)-one (33 mg, 0.14 mmol) in dry 1,4-dioxane (15 mL) were added $Cs_2CO_3$ (2M, 1 mL) and $Pd(PPh_3)Cl_2$ (7.7 mg, 0.01 mmol). The mixture was heated at reflux for 2 h under $N_2$ atmosphere, the solid was filtered off, and the mixture was diluted with water (30 mL) and EtOAc (30 mL). The combined organic layers was washed with brine (50 mL), dried over $Na_2SO_4$, filtered, and concentrated. The residue was purified by prep TLC to afford (R)-6-(2-(5-methyl-1,3,4-oxadiazol-2-yl)ethyl)-3-((S)-1-(4-(1-methyl-2-oxo-1,2-dihydropyridin-4-yl)phenyl)ethyl)-6-phenyl-1,3-oxazinan-2-one (25 mg, yield: 41.8%). LC-MS Method 2 $t_R$=0.984 min, m/z=499.1; $^1$H NMR ($CDCl_3$): δ1.48-1.50 (m, 3H), 2.16-2.20 (m, 1H), 2.23-2.26 (m, 1H), 2.27-2.32 (m, 2H), 2.39 (s, 3H), 2.40-2.47 (m, 1H), 2.49-2.54 (m, 1H), 2.87-2.90 (m, 1H), 2.98-3.01 (m, 1H), 3.58 (s, 3H), 5.62-5.64 (m, 1H), 6.45-6.48 (m, 1H), 6.87 (s, 1H), 6.92-6.94 (d, 2H), 7.20-7.24 (m, 4H), 7.25-7.35 (m, 4H).

Example 20

(S)-6-(2-hydroxy-2-methylpropyl)-3-((S)-1-(4-(1-(2-hydroxyethyl)-2-oxo-1,2-dihydropyridin-4-yl)phenyl)ethyl)-6-phenyl-1,3-oxazinan-2-one

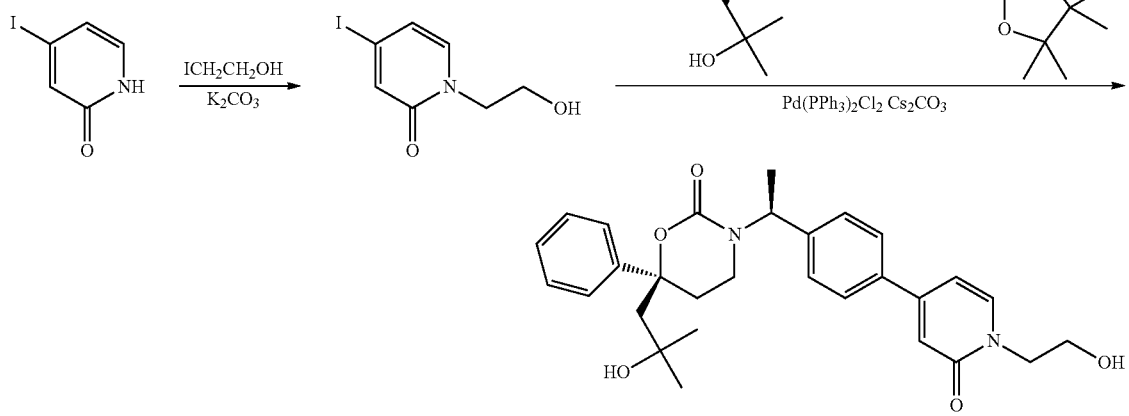

Step 1

To the mixture of 4-iodopyridin-2(1H)-one (50 mg, 0.213 mmol) in DMF (3 mL) was added 2-iodoethanol (73 mg, 0.426 mmol), $K_2CO_3$ (88 mg, 0.638 mmol) at rt. The mixture was stirred for 2 h at rt. After the reaction was finished, the mixture was washed with water and extracted with EtOAc. The organic phase was washed with brine, dried over Na₂SO₄, filtered, and concentrated to give the crude product, which was purified by TLC to provide 1-(2-hydroxyethyl)-4-iodopyridin-2(1H)-one (60 mg 100%).

Step 2

A mixture of compounds (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one (72 mg 0.150 mmol), 1-(2-hydroxyethyl)-4-iodopyridin-2(1H)-one (48 mg 0.181 mmol), Pd(PPh₃)₂Cl₂ (14 mg, 0.020 mmol), and Cs₂CO₃ (2 mL) in 1,4-dioxane (8 mL) was stirred at reflux for 2 h. After the reaction was finished, the mixture was washed with water, and extracted with EtOAC. The organic phase was washed with brine, dried over Na₂SO₄, filtered, and concentrated to get the crude product, which was purified by TLC to provide compound (S)-6-(2-hydroxy-2-methylpropyl)-3-((S)-1-(4-(1-(2-hydroxyethyl)-2-oxo-1,2-dihydropyridin-4-yl)phenyl)ethyl)-6-phenyl-1,3-oxazinan-2-one (19.7 mg, 28%). LC-MS Method 2 $t_R$=1.065 min, m/z=491.2; ¹HNMR (CDCl₃): δ 1.10 (d, 6H), 1.50 (d, 3H), 2.20 (m, 5H), 2.35 (m, 1H), 3.50 (m, 1H), 3.90 (m, 2H), 4.10 (m, 2H), 5.60 (m, 1H), 6.40 (m, 1H), 6.70 (s, 1H), 6.95 (d, 2H), 7.35 (m, 8H).

Example 21

(6S)-6-(2,3-dihydroxy-2-methylpropyl)-3-((S)-1-(4-(1-methyl-2-oxo-1,2-dihydropyridin-4-yl)phenyl)ethyl)-6-phenyl-1,3-oxazinan-2-one

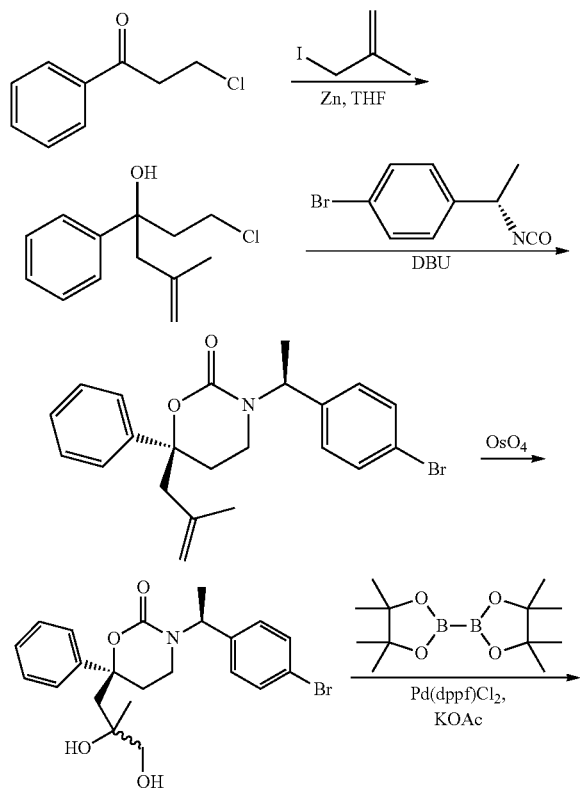

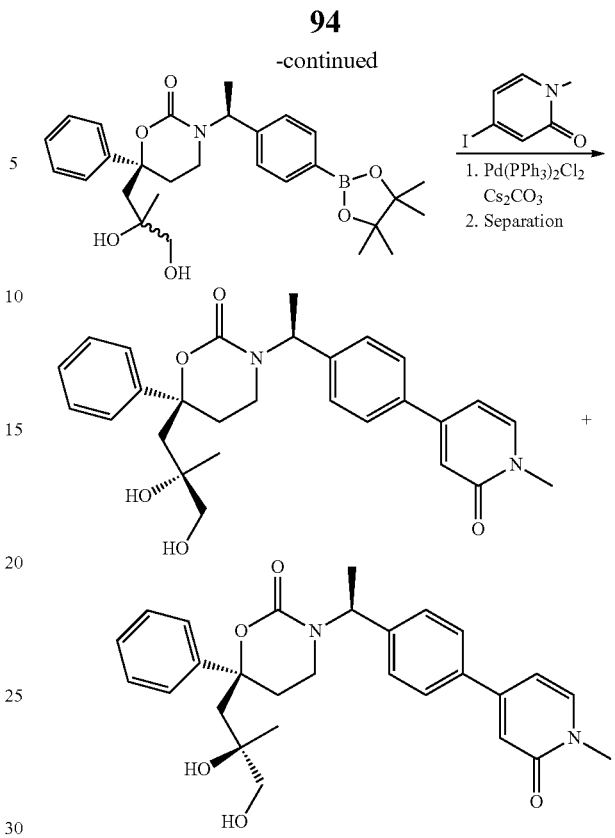

Step 1

A solution of 3-chloro-1-phenylpropan-1-one (16.8 g, 0.1 mol) in THF (50 mL) was added to a well-stirred suspension of zinc powder (13 g, 0.2 mol) in a mixture of satd aq NH₄Cl solution (260 mL) and THF (65 mL). A solution of 3-iodo-2-methylprop-1-ene (36.4 g, 0.2 mol) in THF (50 mL) was added dropwise. The reaction was mildly exothermic, and the mixture began to reflux spontaneously. After refluxing had ceased, the mixture was stirred for 1 h. TLC showed the 3-chloro-1-phenylpropan-1-one had not reacted completely. A solution of 3-iodo-2-methylprop-1-ene (18.2 g, 0.1 mol) in THF (30 mL) was added, and the mixture was stirred at rt overnight. The mixture was extracted with EtOAc (2×500 mL). The combined organic layer was dried and concentrated. The residue was purified by column chromatography on silica gel eluted with petroleum ether/EtOAc 50:1→30:1→5:1, to give 1-chloro-5-methyl-3-phenylhex-5-en-3-ol (17 g, yield 76%) as an oil. ¹H NMR (CDCl₃): δ1.28 (s, 3H), 2.31 (m, 2H), 2.54 (m, 2H), 2.68 (d, 1H), 3.15 (m, 1H), 3.58 (m, 1H), 4.78 (m, 1H), 4.93 (m, 1H), 7.27 (t, 1H), 7.38 (m, 4H).

Step 2

A mixture of 1-chloro-5-methyl-3-phenylhex-5-en-3-ol (2.9 g, 13 mmol), (S)-1-bromo-4-(1-isocyanatoethyl)benzene (3.5 g, 16 mmol), and DBU (8 g, 33 mmol) in THF (80 mL) was heated at reflux overnight. The mixture was diluted with EtOAc, and washed with 1N aq HCl. The aqueous phase was extracted with EtOAc (3×), and the combined organic phase was dried over Na₂SO₄. After the solvents were evaporated, the crude product was purified by column chromatography to give (R)-3-((S)-1-(4-bromophenyl)-ethyl)-6-(2-methylallyl)-6-phenyl-1,3-oxazinan-2-one (1.62 g, yield 30%).

Step 3

To a solution of (R)-3-((S)-1-(4-bromophenyl)ethyl)-6-(2-methylallyl)-6-phenyl-1,3-oxazinan-2-one (300 mg, 0.726 mmol), 4-methylmorpholine 4-oxide (195 mg, 1.44 mmol) in a mixture of H₂O (6 mL), THF (30 mL) and t-BuOH (12 mL) was added osmium (VIII) oxide (4%, 0.231 mL) at 0° C. The mixture was stirred at rt overnight. The mixture was quenched with 3% NaHSO₃ (15 mLx3) and extracted with EtOAc. The organic layer was dried over Na₂SO4 and concentrated to give the crude product (S)-3-((S)-1-(4-bromophenyl)-ethyl)-6-(2,3-dihydroxy-2-methylpropyl)-6-phenyl-1,3-oxazinan-2-one (242 mg, 74.5%).

Step 4

To a solution of (S)-3-((S)-1-(4-bromophenyl)-ethyl)-6-(2, 3-dihydroxy-2-methylpropyl)-6-phenyl-1,3-oxazinan-2-one (235 mg, 0.524 mmol) in DMSO (5 mL) were added KOAc (771.6 mg, 7.86 mmol), Pd(dppf)Cl2 (40 mg) under N2. The mixture was stirred at 90° C. for 3 h. The reaction mixture was quenched with water and extracted with EtOAc. The organic layer was dried over Na₂SO₄ and concentrated to give the crude product, which was purified by preparative TLC to afford (S)-6-(2,3-dihydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one (121 mg, 46.6%).

Step 5

A mixture of (S)-6-(2,3-dihydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one (105 mg, 211.9 mmol), 4-iodo-1-methylpyridin-2(1H)-one (65 mg, 275.5 mmol), Pd(PPh₃)₂Cl₂ (20 mg) in aq. Cs₂CO₃ solution (3 mL) was stirred at reflux for 2 h. After the reaction was finished, the mixture was washed with water and extracted with EtOAc. The organic layer was dried over Na₂SO₄ and concentrated to give the crude product, which was purified by preparative HPLC to afford two isomers of (6S)-6-(2,3-dihydroxy-2-methylpropyl)-3-((S)-1-(4-(1-methyl-2-oxo-1,2-dihydropyridin-4-yl)phenyl)ethyl)-6-phenyl-1,3-oxazinan-2-one Isomer 1 (6.11 mg, 6%): LC-MS Method 2 t$_R$=0.84 min, m/z=477.4; ¹H NMR (CDCl₃): δ 0.97 (s, 3H), 1.55 (d, 3H), 2.27 (m, 3H), 2.38 (m, 3H), 2.91 (m, 1H), 3.34 (d, 1H), 3.58 (s, 3H), 5.68 (m, 1H), 6.35 (d, 1H), 6.71 (s, 1H), 7.02 (d, 2H), 7.36 (m, 8H).

Isomer 2 (6.78 mg, 6.7%): LC-MS Method 2 t$_R$=0.832 min, m/z=477; ¹H NMR (CDCl₃): δ 1.14 (s, 3H), 1.48 (d, 3H), 2.09 (m, 1H), 2.14 (m, 2H), 2.31 (m, 2H), 2.81 (m, 1H), 3.24 (d, 1H), 3.27 (d, 1H), 3.50 (s, 3H), 5.62 (m, 1H), 6.28 (d, 1H), 6.63 (s, 1H), 6.98 (d, 2H), 7.27 (m, 8H).

Example 22

(6S)-6-(2-hydroxy-3-methoxy-2-methylpropyl)-3-((S)-1-(4-(1-methyl-2-oxo-1,2-dihydropyridin-4-yl)phenyl)ethyl)-6-phenyl-1,3-oxazinan-2-one

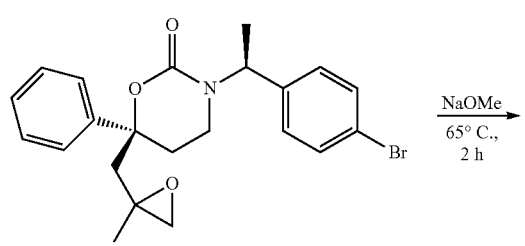

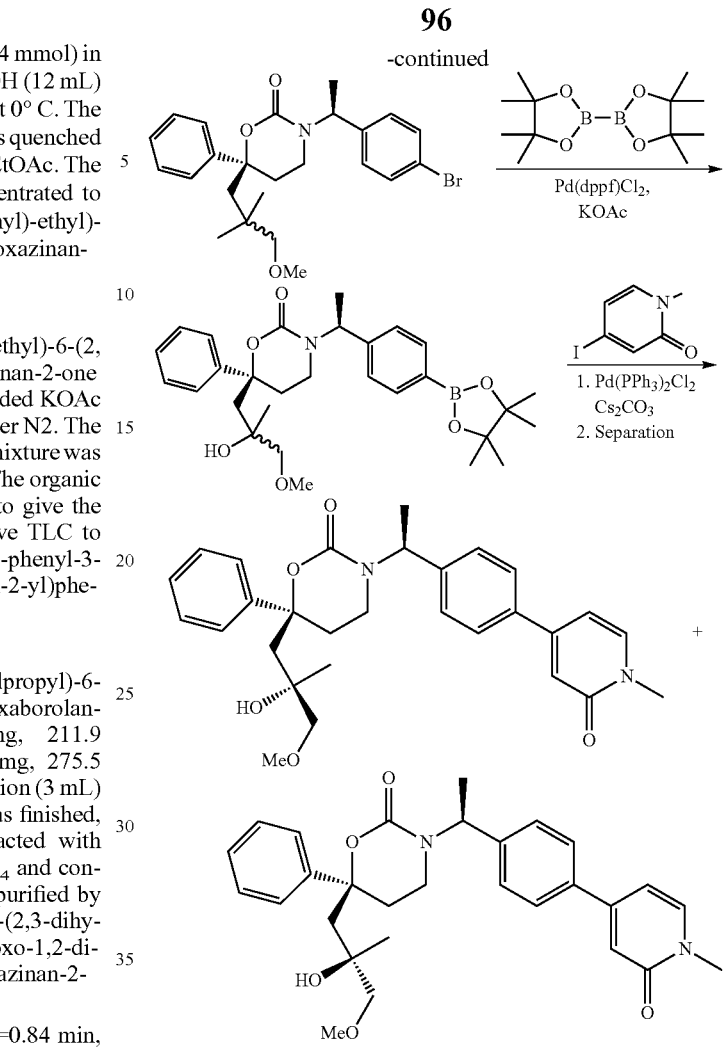

Step 1

Sodium (90 mg) was added to MeOH (5 mL). When sodium had disappeared, a solution of 6(S)-3-(S-1-(4-bromophenyl)ethyl)-6-((2-methyloxiran-2-yl)-methyl)-6-phenyl-1,3-oxa zinan-2-one (500 mg, 1.16 mmol) was added to the mixture. The mixture was stirred at 65° C. for 5 h. The mixture was added H₂O and concentrated. The residue was extracted with EtOAc, the organic layer was dried over Na₂SO₄ and concentrated to give the crude product, which was purified by preparative TLC (2:1 PE/EtOAc) to afford (S)-3-(S-1-(4-bromophenyl)ethyl)-6-(2-hydroxy-3-methoxy-2-methylpropyl)-6-phenyl-1,3-oxazinan-2-one (227 mg, 42.3%).

Step 2

To a solution of (S)-3-(S-1-(4-bromophenyl)ethyl)-6-(2-hydroxy-3-methoxy-2-methylpropyl)-6-phenyl-1,3-oxazinan-2-one (205 mg, 0.443 mmol) in DMSO (5 mL) was added KOAc (435.13 mg, 4.43 mmol), Pd(dppf)Cl₂ (45 mg) under N₂. The mixture was stirred at 90° C. for 3 hours. The reaction mixture was quenched by water and extracted with EtOAc. The organic layer was dried over Na₂SO₄ and concentrated to give the crude product, which was purified by preparative TLC (PE:EA=1:2) to afford (S)-6-(2-hydroxy-3-methoxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one (113 mg, 50%).

Step 3

A mixture of (S)-6-(2-hydroxy-3-methoxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one (100 mg, 196.29 mmol), 4-iodo-1-methylpyridin-2(1H)-one (60.49 mg, 255.2 mmol), Pd(PPh$_3$)$_2$Cl$_2$ (20 mg), and aq Cs$_2$CO$_3$ solution (2 mol/L, 3 mL) in 1,4-dioxane (4 mL) was stirred at reflux for 2 hours. After the reaction was finished, the mixture was washed with water and extracted with EtOAc. The organic layer was dried over Na$_2$SO$_4$ and concentrated to give the crude product, which was purified by preparative HPLC to afford two isomers of (6S)-6-(2-hydroxy-3-methoxy-2-methylpropyl)-3-((S)-1-(4-(1-methyl-2-oxo-1,2-dihydropyridin-4-yl)phenyl)ethyl)-6-phenyl-1,3-oxazinan-2-one.

Isomer 1 (5.25 mg, 5.6%): LC-MS Method 2 t$_R$=0.921 min, m/z=403.2; $^1$H NMR (CDCl$_3$): δ 0.94 (s, 3H), 1.47 (d, 3H), 2.28 (m, 4H), 2.35 (m, 1H), 2.82 (m, 1H), 3.11 (d, 1H), 3.16 (s, 3H), 3.25 (d, 1H), 3.50 (s, 3H), 5.62 (m, 1H), 6.27 (d, 1H), 6.63 (s, 1H), 6.92 (d, 2H), 7.25 (m, 8H).

Isomer 2 (5.40 mg, 5.8%): LC-MS Method 2 t$_R$=0.923 min, m/z=513.1; $^1$H NMR (CDCl$_3$): δ 1.18 (s, 3H), 1.47 (d, 3H), 2.11 (m, 2H), 2.23 (m, 2H), 2.45 (m, 1H), 2.81 (d, 2H), 2.96 (d, 1H), 3.15 (s, 3H), 3.50 (s, 3H), 5.62 (m, 1H), 6.27 (d, 1H), 6.65 (s, 1H), 6.90 (d, 2H), 7.26 (m, 8H).

Example 23

(S)-6-(2-fluorophenyl)-6-(2-hydroxy-2-methylpropyl)-3-((S)-1-(4-(1-methyl-6-oxo-1,6-dihydropyridin-3-yl)phenyl)ethyl)-1,3-oxazinan-2-one

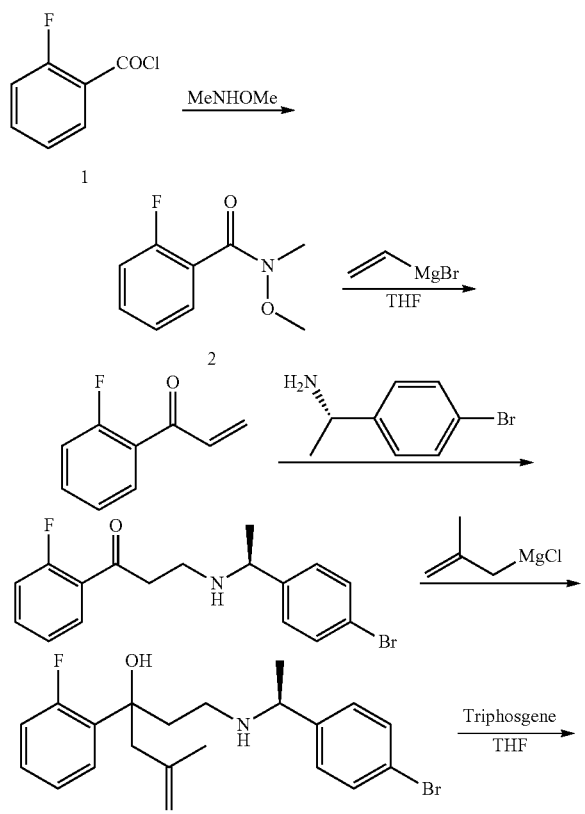

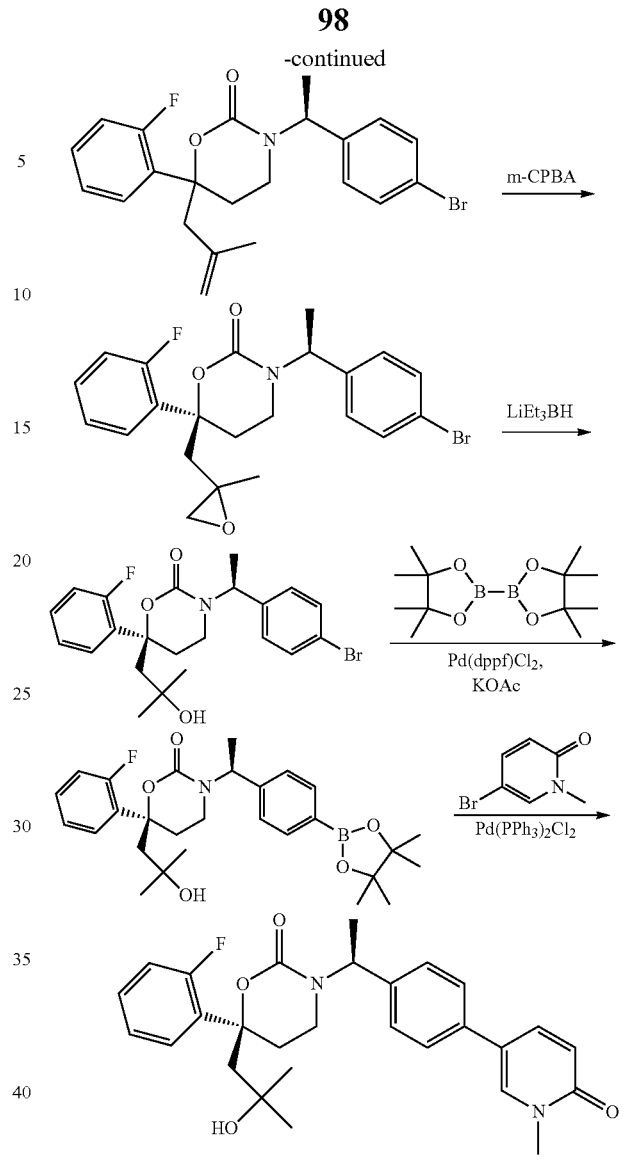

Step 1

To a solution of 2-fluorobenzoyl chloride (50 g, 0.31 mol) in CH$_2$Cl$_2$ (200 mL) was added N,O-dimethylhydroxylamine (46 g, 0.47 mol), and a solution of triethylamine (127 g, 1.26 mol) in CH$_2$Cl$_2$ (100 mL) at 0° C. The reaction mixture was warmed slowly to rt, and stirred for 3 h. The mixture was quenched with iced water and extracted with CH$_2$Cl$_2$ (200 mL). The organic layer was dried over Na$_2$SO$_4$, filtered, and concentrated to afford 2-fluoro-N-methoxy-N-methylbenzamide (48 g, yield: 84.6%).

Step 2

A solution of 2-fluoro-N-methoxy-N-methylbenzamide (16 g, 87.4 mmol) in THF (150 mL) was cooled to −78° C. Vinylmagnesium bromide (120 mL, 120 mmol) was slowly added, and the mixture stirred at −78° C. for 10 min, slowly warmed to rt, and stirred for another 3 h. The reaction mixture was quenched with 1 N aq HCl (100 mL) at 0° C. The aqueous layer was extracted with EtOAc (100 mL). The combined organic phase was washed with brine (50 mL), dried over Na$_2$SO$_4$, and concentrated. The residue was purified by column chromatography to afford 1-(2-fluorophenyl)-prop-2-en-1-one (7.6 g, yield: 58.4%) as a colorless oil.

Step 3

To a solution of 1-(2-fluorophenyl)-prop-2-en-1-one (5.6 g, 37.3 mmol) in CH₃CN (50 mL) was added (S)-1-(4-bromophenyl)-ethylamine (7.4 g, 37 mmol), and the mixture was stirred for 12 h at 40° C. The solution was concentrated to afford the crude product, which was purified by column chromatography to give (S)-3-(1-(4-bromophenyl)-ethylamino)-1-(2-fluorophenyl)-propan-1-one (4 g, yield: 30.7%) as a yellow liquid.

Step 4

To a suspension of Mg (2.5 g, 104 mmol), I₂ (0.1 g) in anhydrous THF (15 mL) was added 3-chloro-2-methylprop-1-ene (0.6 mL, 6 mmol). After a solution of 3-chloro-2-methylprop-1-ene (9 mL, 90 mmol) in THF (120 mL) was dropped at 0° C. under N₂ in 30 min. (S)-3-(1-(4-bromophenyl)-ethylamino)-1-(2-fluorophenyl)-propan-1-one (3 g, 8.6 mmol) in THF (50 mL) was added dropwise at −78° C. over 45 min. The reaction mixture was stirred at rt for 2 h and cautiously quenched by addition of satd aq NH₄Cl. The mixture was extracted with EtOAc, and the organic layer was washed with brine, dried over anhydrous Na₂SO₄, and concentrated in vacuo to give 1-(S-1-(4-bromophenyl)-ethylamino)-3-(2-fluorophenyl)-5-methylhex-5-en-3-ol (3.3 g, yield: 94.5%), which was used for the next step without further purification.

Step 5

A mixture of 1-(S-1-(4-bromophenyl)ethylamino)-3-(2-fluorophenyl)-5-methylhex-5-en-3-ol (2 g, 5 mmol) in a solution of triethylamine (1.5 g, 15 mmol) in 1,2-dichloroethane (100 mL) was added triphosgene (1.46 g, 5 mmol) at 0° C. under N₂, and the mixture was heated at 100° C. for 4 h. The reaction mixture was quenched with water, and extracted with CH₂Cl₂ (100 mL). The combined organic layer was washed with brine, dried over Na₂SO₄, filtered, and concentrated to afford the crude product (2.1 g, yield: 99%), which was used for the next step without further purification.

Step 6

To a solution of (S)-3-(1-(4-bromophenyl)ethyl)-6-(2-fluorophenyl)-6-(2-methylallyl)-1,3-oxazinan-2-one (3.2 g, 7.4 mmol) in dry CH₂Cl₂ (100 mL) was added m-CPBA (2.6 g, 14.8 mmol) at rt and the mixture was stirred overnight. The mixture was diluted with (CH₃)₃COCH₃ (100 mL), washed with 30% aq Na₂S₂O₃ and aq NaHCO₃, dried over Na₂SO₄, filtered, and concentrated to give 3-(S-1-(4-bromophenyl)-ethyl)-6-(2-fluorophenyl)-6-(2-methyloxiran-2-yl-methyl)-1,3-oxazinan-2-one (2.8 g, yield: 84.3%), which was used directly for the next step without further purification.

Step 7

To a solution of 3-(S-1-(4-bromophenyl)-ethyl)-6-(2-fluorophenyl)-6-(2-methyloxiran-2-yl)-methyl)-1,3-oxazinan-2-one (2.2 g, 4.92 mmol) in THF (100 mL) was added dropwise LiEt₃BH (Super-hydride, 50 mL, 50 mmol) at 0° C. under N₂ for 30 min., and the resulting mixture was stirred at 2-3° C. for 1.5 h, and stirred for 2.5 h at 10-13° C. H₂O₂ (20 mL) was added dropwise and the reaction mixture was diluted with (CH₃)₃COCH₃ (280 mL). The mixture was washed with water, 30% aq Na₂S₂O₃ and brine. The organic phase was dried over Na₂SO₄ and filtered. The filtrate was concentrated to give the crude product, which was purified by column chromatography to afford (S)-3-(S-1-(4-bromophenyl)-ethyl)-6-(2-fluorophenyl)-6-(2-hydroxy-2-methylpropyl)-1,3-oxazinan-2-one (550 mg, 23.9%) as a white solid. ¹H NMR (CDCl₃): δ 1.03 (s, 3H), 1.14 (s, 3H), 1.43 (d, J=6.8 Hz, 3H), 2.08-2.13 (m, 1H), 2.17 (d, J=2.8 Hz, 1H), 2.21-2.22 (m, 1H), 2.31 (dd, J=0.8, 15.2 Hz, 1H), 2.77-2.81 (m, 1H), 5.56 (q, J=2.8 Hz, 2H), 6.82-6.83 (m, 2H), 6.85-6.94 (m, 1H), 7.08-7.13 (m, 1H), 7.18-7.25 (m, 1H), 7.26-7.40 (m, 2H), 7.42-7.44 (m, 1H).

Step 8

To a solution of (S)-3-(S-1-(4-bromophenyl)-ethyl)-6-(2-fluorophenyl)-6-(2-hydroxy-2-methylpropyl)-1,3-oxazinan-2-one (540 mg, 1.2 mmol) in DMSO (15 mL) was added 4,4,5,5-tetramethyl-1,3,2-dioxaborolan-2-yl)-1,3,2-dioxaborolane (900 mg, 3.3 mmol), CH₃CO₂K (1.5 g, 16 mmol), Pd(dppf)Cl₂ (108 mg, 0.13 mmol) under N₂, and the reaction was stirred at 90° C. for 2.5 h. The mixture was quenched with water, and extracted with EtOAc (90 mL). The organic layer was washed with water and brine, dried over Na₂SO₄, and filtered. The filtrate was concentrated to give the crude product, which was purified by preparative TLC to afford (S)-6-(2-fluorophenyl)-6-(2-hydroxy-2-methylpropyl)-3-((S)-1-(4-(4,4,5,5-tetramethyl-1,3,2-dioxa borolan-2-yl)phenyl)ethyl)-1,3-oxazinan-2-one (360 mg, 62%) as a yellow liquid.

Step 9

To a solution of (S)-6-(2-fluorophenyl)-6-(2-hydroxy-2-methylpropyl)-3-((S)-1-(4-(4,4,5,5-tetramethyl-1,3,2-dioxaborolan-2-yl)phenyl)ethyl)-1,3-oxazinan-2-one (120 mg, 0.24 mmol), 5-bromo-1-methylpyridin-2-(1H)-one (54 mg, 0.28 mmo), 2N aq Cs₂CO₃ (2 mL) in dioxane (8 mL) was added Pd(PPh₃)₂Cl₂ (17 mg, 0.024 mmol) under N₂. The reaction mixture was refluxed for 2 h and quenched by addition of water. The mixture was extracted with EtOAc (30 mL), and the organic layer was washed with H₂O and brine, dried over Na₂SO₄, and filtered. The filtrate was concentrated to give the crude product, which was purified by preparative TLC and preparative HPLC to afford (S)-6-(2-fluorophenyl)-6-(2-hydroxy-2-methylpropyl)-3-((S)-1-(4-(1-methyl-6-oxo-1,6-dihydropyridin-3-yl)phenyl)ethyl)-1,3-oxazinan-2-one (14 mg, yield: 10%). LC-MS Method 2 t_R=1.2 min, m/z=473.9; ¹H NMR (CDCl₃): δ1.21 (s, 3H), 1.30 (s, 3H), 1.48 (d, J=7.2 Hz, 3H), 2.15-2.26 (m, 3H), 2.33 (dd, J=11.2, 26.4 Hz, 1H), 2.43-2.46 (m, 1H), 2.79-2.85 (m, 1H), 3.63 (s, 3H), 5.62 (q, J=6.8 Hz, 1H), 6.58-6.60 (m, 1H), 6.89-6.94 (m, 1H), 7.00-7.02 (m, 2H), 7.10-7.24 (m, 3H), 7.34-7.39 (m, 1H), 7.40-7.45 (m, 1H), 7.48-7.70 (m, 2H).

Example 24

(S)-6-(3-fluorophenyl)-6-(2-hydroxy-2-methylpropyl)-3-((S)-1-(4-(1-methyl-6-oxo-1,6-dihydropyridin-3-yl)phenyl)ethyl)-1,3-oxazinan-2-one

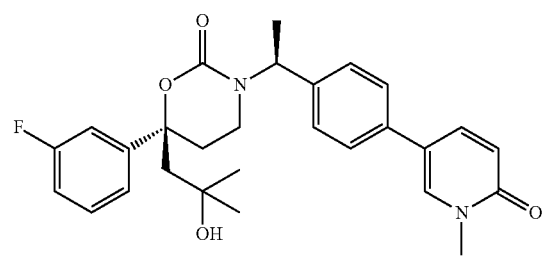

The title compound was prepared from (S)-3-(1-(4-bromophenyl)ethylamino)-1-(3-fluorophenyl)propan-1-one following procedures analogous to those described in Steps 4-9 in Example 23. LC-MS Method 2 t_R=1.416 min, m/z=500.9; ¹H NMR (CDCl₃) 1.18 (s, 3H), 1.29 (s, 3H), 1.47 (d, 3H), 2.05-2.28 (m, 4H), 2.31-2.39 (m, 1H), 2.82-2.87 (m, 1H), 3.58 (s, 3H), 5.64 (q, 1H), 6.57-6.59 (m, 1H), 6.88-7.19 (m, 5H), 7.21-7.25 (m, 2H), 7.28 (m, 1H), 7.36 (m, 1H), 7.40-7.45 (m, 1H), 7.45-7.48 (m, 1H)

(S)-3-(1-(4-bromophenyl)ethylamino)-1-(3-fluorophenyl)propan-1-one was prepared as shown below.

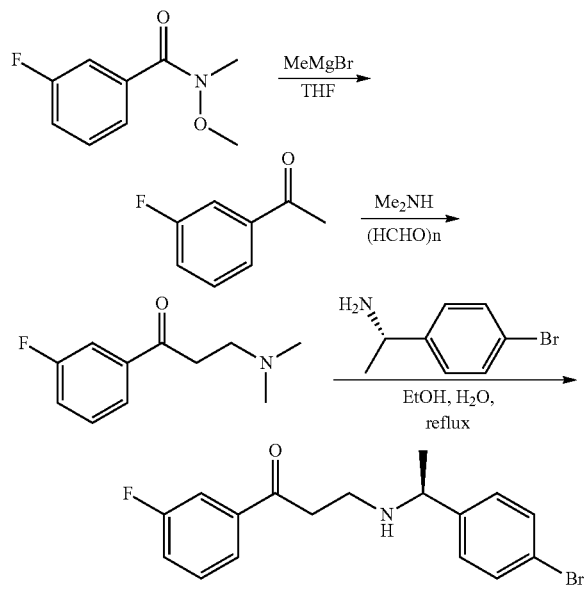

Step 1

A solution of 3-fluoro-N-methoxy-N-methylbenzamide (16 g, 87.4 mmol) in THF (150 mL) was cooled to −78° C. Vinylmagnesium bromide (120 mL, 120 mmol) was added slowly. The mixture was stirred at −78° C. for 10 min, at rt for 3 h, and quenched by addition of 1 N aq HCl (100 mL) at 0° C. The aqueous layer was extracted with EtOAc (100 mL). The combined organic phase was washed with brine (50 mL), dried over $Na_2SO_4$, and concentrated. The residue was purified by column chromatography to afford 1-(3-fluorophenyl)ethanone (9.7 g, yield: 75%) as a colorless oil.

Step 2

1-(3-Fluorophenyl)ethanone (17 g, 0.123 mol), dimethylamine (13.7 g, 0.172 mol), and paraformaldephyde (5.5 g, 0.185 mol) were suspended in ethanol (50 mL), and conc HCl solution (0.3 mL) was added. The mixture was heated at reflux overnight. The solvent was removed under vacuum, and the residue was washed with EtOAc (3×) to give 3-(dimethylamino)-1-(3-fluorophenyl)propan-1-one (20.7 g, 88%), which was used for the next step without purification.

Step 3

A solution of 3-dimethylamino-1-(3-fluoro-phenyl)-propan-1-one (17 g, 0.087 mol) and (S)-1-(4-bromophenyl)-ethanamine (17 g, 0.087 mol) in a mixture of EtOH (50 mL) and $H_2O$ (50 mL) was refluxed at 80° C. overnight. The solvent was removed under vacuum, and the residue was purified by column chromatography to afford (S)-3-(1-(4-bromophenyl)-ethylamino)-1-(3-fluorophenyl)-propan-1-one (6.2 g, 20%).

Example 25

(S)-3-((S)-1-(4-(1-(2-fluoroethyl)-2-oxo-1,2-dihydropyridin-4-yl)phenyl)ethyl)-6-(2-hydroxy-2-methylpropyl)-6-phenyl-1,3-oxazinan-2-one

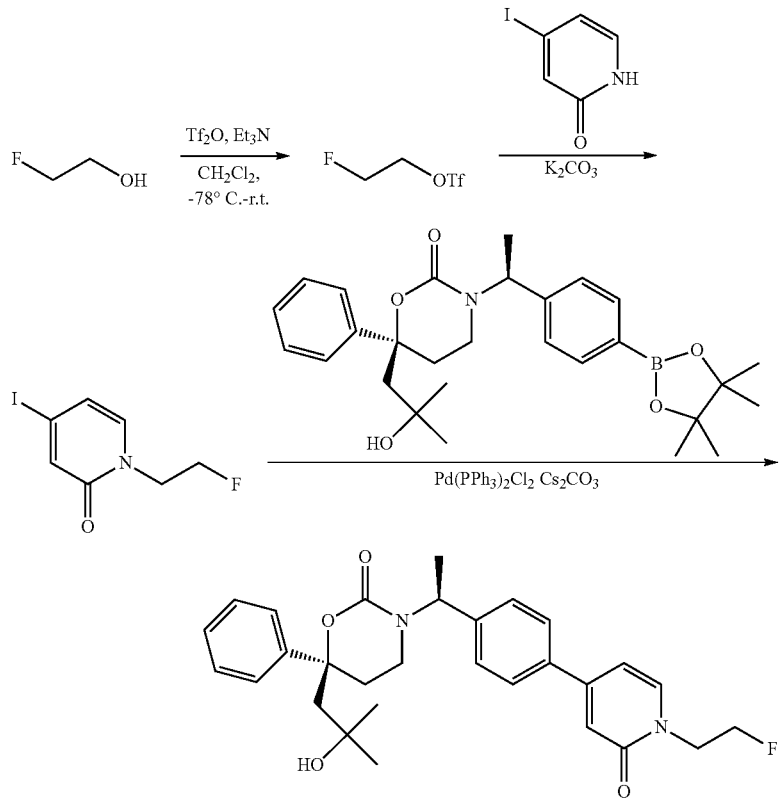

1-(2-fluoroethyl)-4-iodopyridin-2(1H)-one was prepared from 4-iodopyridin-2(1H)-one and 2-fluoroethyl trifluoromethanesulfonate following a procedure analogous to that described in Example 20 Step 1.

The title compound was prepared from (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one and 1-(2-fluoroethyl)-4-iodopyridin-2(1H)-one following a procedure analogous to that described in Example 6 Step 1. LC-MS Method 2 $t_R$=1.09 min, m/z=515, 493, 475, 435.

Example 26

(S)-6-(2-fluorophenyl)-6-(2-hydroxy-2-methylpropyl)-3-((S)-1-(4-(1-methyl-2-oxo-1,2-dihydropyridin-4-yl)phenyl)ethyl)-1,3-oxazinan-2-one

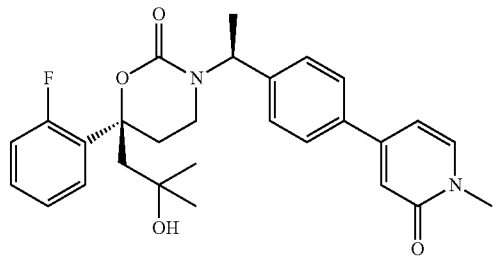

The title compound was prepared from (S)-6-(2-fluorophenyl)-6-(2-hydroxy-2-methylpropyl)-3-((S)-1-(4-(4,4,5,5-tetramethyl-1,3,2-dioxaborolan-2-yl)phenyl)ethyl)-1,3-oxazinan-2-one and 4-iodo-1-methylpyridin-2(1H)-one following a procedure analogous to that described in Example 23 Step 9. LC-MS Method 2 $t_R$=1.58 min, m/z=501, 479, 421.

Example 27

(S)-6-(3-fluorophenyl)-6-(2-hydroxy-2-methylpropyl)-3-((S)-1-(4-(1-methyl-2-oxo-1,2-dihydropyridin-4-yl)phenyl)ethyl)-1,3-oxazinan-2-one

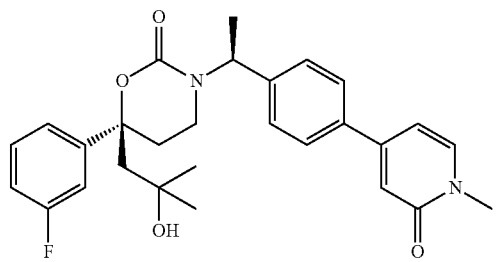

The title compound was prepared from (S)-6-(3-fluorophenyl)-6-(2-hydroxy-2-methylpropyl)-3-((S)-1-(4-(4,4,5,5-tetramethyl-1,3,2-dioxaborolan-2-yl)phenyl)ethyl)-1,3-oxazinan-2-one and 4-iodo-1-methylpyridin-2(1H)-one following a procedure analogous to that described in Example 23 Step 9. LC-MS Method 2 $t_R$=1.57 min, m/z=501, 479, 421.

Example 28

6-(3-hydroxypropyl)-6-isopropyl-3-((S)-1-(4-(1-methyl-2-oxo-1,2-dihydropyridin-4-yl)phenyl)ethyl)-1,3-oxazinan-2-one

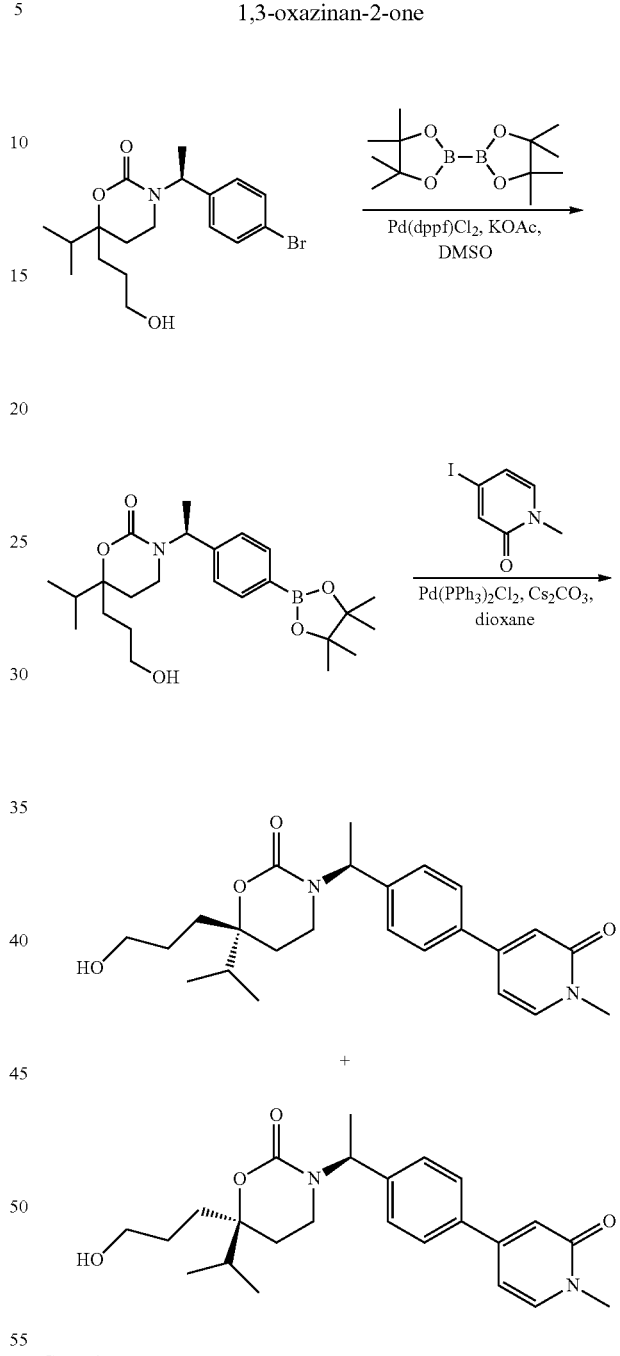

Step 1

To a mixture of 3-((S)-1-(4-bromophenyl)ethyl)-6-(3-hydroxypropyl)-6-isopropyl-1,3-oxazinan-2-one (100 mg, 0.26 mmol), 4,4,4',4',5,5,5',5'-octamethyl-2,2'-bi(1,3,2-dioxaborolane) (198 mg, 0.783 mmol), potassium acetate (256 mg, 2.61 mmol) in DMSO (5 mL) was added Pd(dppf)Cl$_2$ (21 mg, 0.0261 mmol) under N$_2$. The mixture was stirred at 85° C. for 3 h, treated with EtOAc (50 mL) and water (50 mL). The organic layer was washed with water (2×50 mL) and brine (50 mL), dried, and concentrated to give the crude product. The crude product was purified by preparative TLC to give 6-(3-hydroxypropyl)-6-isopropyl-3-((S)-1-(4-(4,4,5,5-tetramethyl-1,3,2-dioxaborolan-2-yl)phenyl)ethyl)-1,3-oxazinan-2-one (40 mg, 35%), Step 2

A mixture of 6-(3-hydroxypropyl)-6-isopropyl-3-((S)-1-(4-(4,4,5,5-tetramethyl-1,3,2-dioxaborolan-2-yl)phenyl)ethyl)-1,3-oxazinan-2-one (40 mg, 0.092 mmol), 4-iodo-1-methylpyridin-2(1'-O-one (20 mg, 0.085 mmol), Pd(PPh$_3$)$_2$Cl$_2$ (6 mg, 0.0085 mmol), and Cs$_2$CO$_3$ (2 N, 0.425 mL, 0.85 mmol) in 1,4-dioxane (2 mL) was refluxed for 3 h under N$_2$. The reaction mixture was treated with EtOAc (20 mL) and water (20 mL), and the organic layer was dried and concentrated in vacuo. The residue was purified by preparative HPLC to give two isomers.

Isomer 1: (2.20 mg, 6%). LC-MS Method 2 t$_R$=1.06 min, m/z=413; m/z=$^1$H NMR (CD$_3$OD): δ 1.00 (m, 6H), 1.62 (m, 7H), 1.82 (m, 1H), 2.10 (m, 2H), 2.85 (m, 1H), 3.29 (m, 1H), 3.54 (t, 2H), 3.63 (s, 3H), 5.71 (q, 1H), 6.78 (dd, 1H), 6.83 (d, 1H), 7.51 (d, 2H), 7.75 (m, 3H), Isomer 2: (2.10 mg, 6%) LC-MS Method 2 t$_R$=1.03 min, m/z=413; $^1$H NMR (CD$_3$OD): δ 0.86 (m, 6H), 1.53 (m, 5H), 1.71 (m, 4H), 1.92 (m, 1H), 2.82 (m, 1H), 3.25 (m, 1H), 3.49 (t, 2H), 3.52 (s, 3H), 5.59 (q, 1H), 6.67 (dd, 1H), 6.72 (d, 1H), 7.39 (d, 2H), 7.63 (m, 3H).

Example 29

4108.1002-007 Example 221

(R)-6-(3-hydroxypropyl)-3-((S)-1-(4-(6-oxo-1,6-dihydropyridin-3-yl)phenyl)ethyl)-6-phenyl-1,3-oxazinan-2-one

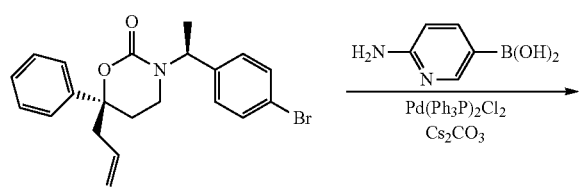

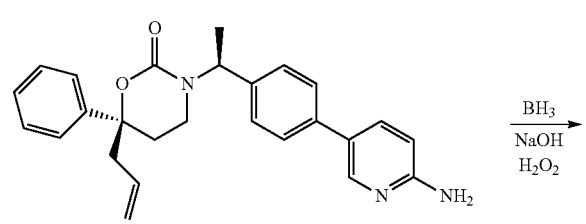

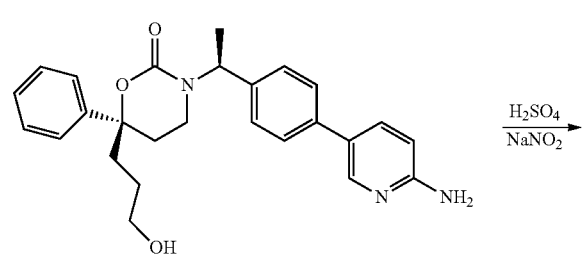

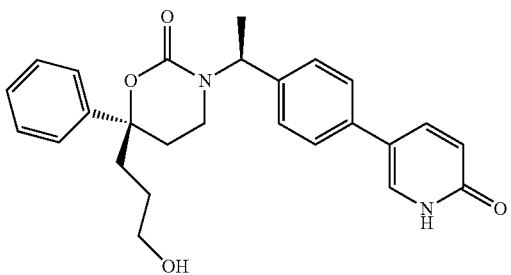

Step 1

A mixture of (R)-6-allyl-3-((S)-1-(4-bromophenyl)ethyl)-6-phenyl-1,3-oxazinan-2-one (150 mg, 0.375 mmol) and 6-aminopyridin-3-ylboronic acid (56 mg, 0.45 mmol), Pd(Ph$_3$P)$_2$Cl$_2$ (15 mg), and aqueous Cs$_2$CO$_3$ solution (0.5 mL, 2 M) in 1,4-dioxane (10 mL) was stirred and heated to reflux for 2 h. The organic phase was separated, and concentrated to give the crude product, which was purified by preparative HPLC to give (R)-6-allyl-3-((S)-1-(4-(6-aminopyridin-3-yl)phenyl)ethyl)-6-phenyl-1,3-oxazinan-2-one (90 mg, 60%).

Step 2

To a solution of (R)-6-allyl-3-((S)-1-(4-(6-aminopyridin-3-yl)phenyl)ethyl)-6-phenyl-1,3-oxazinan-2-one (90 mg, 0.23 mmol) in tetrahydrofuran (10 mL) was added BH$_3$ THF (3.0 mL, 1 mol/L, 4 mmol) at 0° C. under nitrogen atmosphere. The formed mixture was stirred for 2 h. The reaction was quenched by water. Then NaOH (2 mL, 3 mol/L) and H$_2$O$_2$ (1 mL) was added to the above mixture. When the reaction was over, the mixture was extracted with EtOAc. The combined organic phase was concentrated to give the crude product, which was purified by preparative HPLC to give (R)-3-((S)-1-(4-(6-aminopyridin-3-yl)phenyl)ethyl)-6-3-hydroxypropyl)-6-phenyl-1,3-oxa zinan-2-one (40 mg, 41%).

Step 3

(R)-3-((S)-1-(4-(6-aminopyridin-3-yl)phenyl)ethyl)-6-(3-hydroxypropyl)-6-phenyl-1,3-oxazinan-2-one (40 mg, 0.09 mmol.) was dissolved in 3.5 M H$_2$SO$_4$ (10 mL), and 2 M NaNO$_2$ (10 mL) was added at 0° C. The reaction mixture was stirred at rt for 2 h and treated with NaOH solution. The mixture was extracted with EtOAc. The combined organic layer was washed with brine, dried over anhydrous Na$_2$SO$_4$, and concentrated to afford the residue, which was purified by preparative HPLC to give (R)-6-(3-hydroxypropyl)-3-((S)-1-(4-(6-oxo-1,6-dihydropyridin-3-yl)phenyl)ethyl)-6-phenyl-1,3-oxazinan-2-one (10 mg, 20%). LC-MS Method 2 t$_R$=1.66, min, m/z=433, 455; $^1$H NMR (CDCl$_3$): 1.36 (m, 2H), 1.50 (m, 3H), 1.68 (m, 2H), 1.92 (m, 2H), 2.10-2.30 (m, 3H), 2.84 (m, 1H), 3.50 (m, 2H), 5.12 (m, 1H), 6.62 (m, 1H), 6.86 (m, 2H), 7.08 (m, 2H), 7.18-7.32 (m, 5H), 7.46 (m, 1H), 7.62 (m, 1H).

Example 30

4108.1002-007 Example 313

(R)-6-(3-hydroxypropyl)-3-((S)-1-(4-(1-methyl-6-oxo-1,6-dihydropyridin-3-yl)phenyl)ethyl)-6-phenyl-1,3-oxazinan-2-one

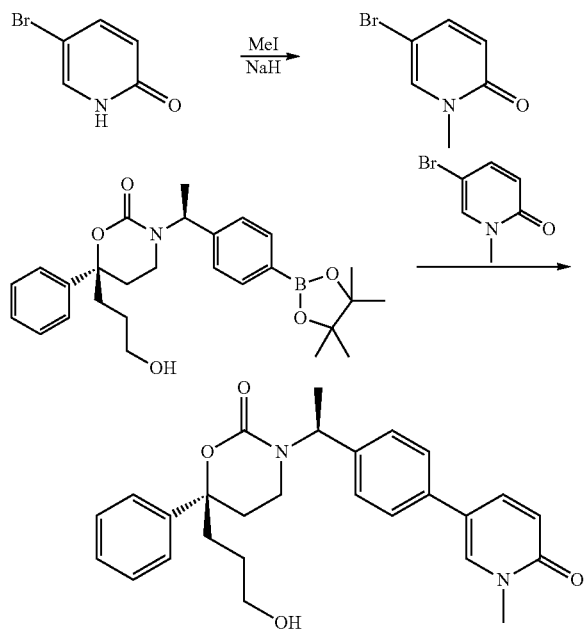

Step 1

To a suspension of NaH (4.8 g, 0.2 mol) in THF (10 mL) was added a solution of 5-bromopyridin-2(1H)-one (8.6 g, 0.05 mol) in THF (120 mL) at 0° C. The resulting mixture was stirred for 1 h and CH$_3$I (35.5 g, 0.25 mol) was added. The mixture was stirred for 3 h. The reaction was quenched with aqueous NH$_4$Cl solution. The organic phase was concentrated to give the crude product, which was purified by column chromatography to give 5-bromo-1-methylpyridin-2(1H)-one (8.9 g, 96.78%). $^1$H NMR (CDCl$_3$): δ=3.5 (S, 3H), 6.52 (m, 1H), 7.32 (m, 1H), 7.45 (m, 1H).

Step 2

A mixture of (R)-6-(3-hydroxypropyl)-6-phenyl-3-((S)-1-(4-(4,4,5,5-tetramethyl-1,3,2-dioxaborolan-2-yl)phenyl)ethyl)-1,3-oxazinan-2-one (1.7 g, 3.7 mmol) and 5-bromo-1-methylpyridin-2(1H)-one (816 mg, 4.4 mmol), Pd(Ph$_3$P)$_2$Cl$_2$ (200 mg), and aq Cs$_2$CO$_3$ solution (4 mL, 2M) in 1,4-dioxane (30 mL) was stirred and heated to reflux for 2 h. When the reaction was over, the mixture was washed with water and extracted with EtOAc, and the organic phase was washed with brine, dried over Na$_2$SO$_4$, filtered and concentrated to give crude product, which was purified by preparative TLC to give (R)-6-(3-hydroxypropyl)-3-((S)-1-(4-(1-methyl-6-oxo-1,6-dihydropyridin-3-yl)phenyl)ethyl)-6-phenyl-1,3-oxazinan-2-one (614 mg, 37%). LC-MS Method 2 t$_R$=1.075 min, m/z=447.1; $^1$H NMR (CDCl$_3$): δ=1.38 (m, 1H), 1.47 (d, 3H), 1.73 (m, 2H), 1.98 (m, 2H), 2.20 (m, 1H), 2.31 (m, 2H), 2.94 (m, 1H), 3.51 (m, 2H), 3.56 (s, 3H), 5.63 (m, 1H), 6.67 (m, 1H), 6.87 (m, 2H), 7.05 (m, 2H), 7.31-7.41 (m, 6H), 7.48 (m, 1H).

Example 31

4108.1002-007 Example 458

(S)-6-(4-fluorophenyl)-6-(2-hydroxyethyl)-3-((S)-1-(4-(1-methyl-6-oxo-1,6-dihydropyridin-3-yl)phenyl)ethyl)-1,3-oxazinan-2-one

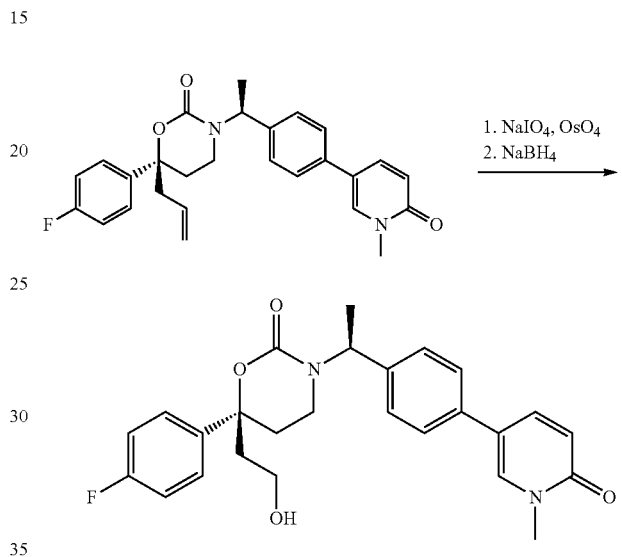

To a solution of (R)-6-allyl-6-(4-fluorophenyl)-3-((S)-1-(4-(1-methyl-6-oxo-1,6-dihydropyridin-3-yl)phenyl)ethyl)-1,3-oxazinan-2-one (0.064 g, 0.144 mmol, 1.0 equiv) in THF-H$_2$O (1:1, 6 mL) were added NaIO$_4$ (0.145 g, 0.678 mmol, 4.7 equiv) and OsO$_4$ (2.5 wt. % solution in t-BuOH, 0.048 g, 0.0047 mmol, 0.033 equiv), and the mixture was stirred at rt for 1 h. The mixture was diluted with EtOAc, dried over Na$_2$SO$_4$, and concentrated under reduced pressure. The residue was dissolved in MeOH (3 mL) and NaBH$_4$ (0.100 g) was added. After the mixture was stirred for 0.5 h at rt, acetone was added. The solvents were removed in vacuo, the residue was treated with saturated brine, extracted with CH$_2$Cl$_2$, and dried over Na$_2$SO$_4$. After the solvent was evaporated, the residue was purified by reversed-phase HPLC (SunFire™ Prep C$_{18}$ OBD™ 5 µm 19×50 mm column, 10%→90% CH$_3$CN/H$_2$O, 0.1% CF$_3$COOH over 8 min and then 90% CH$_3$CN/H$_2$O, 0.1% CF$_3$COOH over 2 min, flow rate 20 mL/min) to afford (S)-6-(4-fluorophenyl)-6-(2-hydroxyethyl)-3-((S)-1-(4-(1-methyl-6-oxo-1,6-dihydropyridin-3-yl)phenyl)ethyl)-1,3-oxazinan-2-one. LC-MS Method 1 t$_R$=1.21 min, m/z=451 (M+1); $^1$H NMR (400 MHz, CD$_3$OD) δ 7.80 (m, 1H), 7.69 (d, J=9.4 Hz, 1H), 7.22-7.19 (m, 4H), 7.00-6.92 (m, 4H), 6.52 (d, J=9.4 Hz, 1H), 5.45 (q, J=7.0 Hz, 1H), 3.60-3.52 (m, 1H), 3.52 (s, 3H), 3.24-3.18 (m, 1H), 3.02-2.98 (m, 1H), 2.39-2.35 (m, 1H), 2.23-2.12 (m, 2H), 2.01 (t, J=7.3 Hz, 2H), 1.43 (d, J=7.0 Hz, 3H); $^{19}$F NMR (376 MHz, CD$_3$OD) δ −117.19 (m).

Example 32
4108.1002-007 Example 459
(S)-6-(4-fluorophenyl)-6-(2-hydroxy-2-methylpropyl)-3-((S)-1-(4-(1-methyl-6-oxo-1,6-dihydropyridin-3-yl)phenyl)ethyl)-1,3-oxazinan-2-one
Method 1
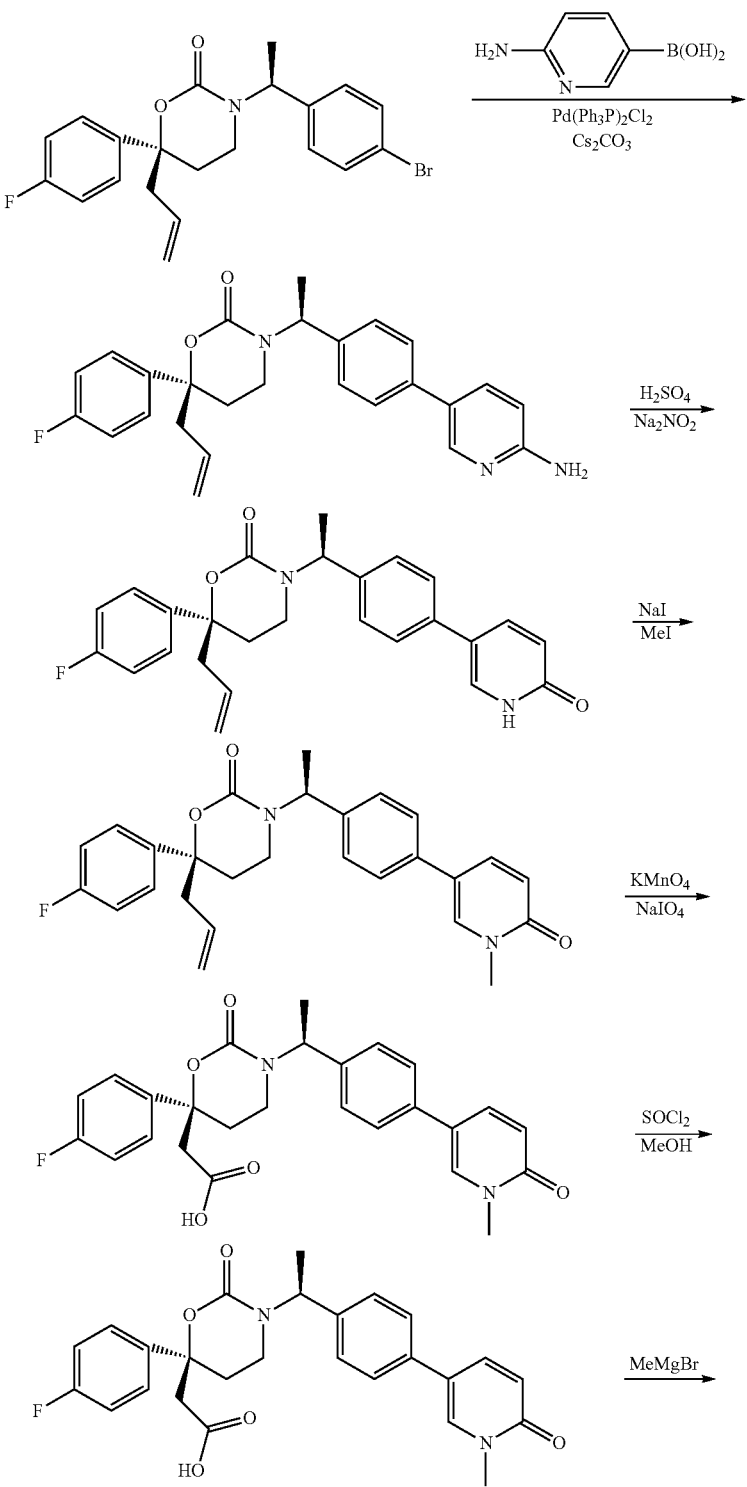

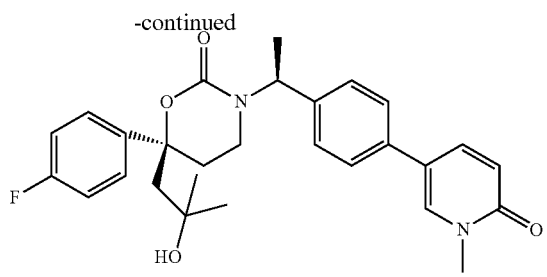

Step 1

A mixture of (R)-6-allyl-3-((S)-1-(4-bromophenyl)ethyl)-6-(4-fluorophenyl)-1,3-oxa zinan-2-one (1.6 g, 3.84 mmol) and 6-aminopyridin-3-ylboronic acid (1.0 g, 4.61 mmol), Pd(Ph$_3$P)$_2$Cl$_2$ (150 mg), and aq Cs$_2$CO$_3$ solution (3.84 mL, 2 M) in 1,4-dioxane (150 mL) was stirred and heated to reflux for 2 h. The mixture was filtered and the filtrate was extracted with EtOAc. The combined organic phase was washed with brine, dried over anhydrous Na$_2$SO$_4$, and concentrated to give (R)-6-allyl-3-((S)-1-(4-(6-aminopyridin-3-yl)phenyl)ethyl)-6-(4-fluorophenyl)-1,3-oxazinan-2-one (1.5 g, 90%), which was used for the next step without purification. $^1$H NMR (CDCl$_3$): δ=1.51 (d, 3H), 2.17-2.31 (m, 3H), 2.54-2.60 (m, 2H), 2.90 (m, 1H), 4.46 (s, 2H), 4.99-5.09 (m, 2H), 5.65-5.71 (m, 2H), 6.54 (m, 2H), 6.88 (d, 2H), 7.03 (t, 2H), 7.21-7.27 (m, 3H), 7.58 (d, 1H), 8.22 (d, 1H).

Step 2

To a solution of (R)-6-allyl-3-((S)-1-(4-(6-aminopyridin-3-yl)phenyl)ethyl)-6-(4-fluorophenyl)-1,3-oxazinan-2-one (1.5 g, 3.47 mmol.) in 3.5 M H$_2$SO$_4$ (25 mL) was added 2 M NaNO$_2$ (15 mL) at 0° C. The reaction mixture was stirred at rt overnight. The reaction was treated with aqueous NaOH solution (8%), and the mixture was extracted with CH$_2$Cl$_2$. The combined organic layer was washed with brine, dried over anhydrous Na$_2$SO$_4$ and concentrated to give crude product, which was purified by preparative TLC to give (R)-6-allyl-6-(4-fluorophenyl)-3-((S)-1-(4-(6-oxo-1,6-dihydropyridin-3-yl)phenyl)ethyl)-1,3-oxazinan-2-one (891 mg, 59%). $^1$H NMR (CDCl$_3$): δ=1.52 (d, 3H), 2.15-2.38 (m, 3H), 2.51-2.60 (m, 2H), 2.94 (m, 1H), 4.99-5.11 (m, 2H), 5.65-5.74 (m, 2H), 6.67 (m, 1H), 6.89 (d, 2H), 7.00 (t, 2H), 7.13-7.20 (m, 2H), 7.20-7.27 (d, 2H), 7.33 (m, 1H), 7.46 (m, 1H), 7.77 (m, 1H).

Step 3

To a suspension of NaH (330 mg, 8.24 mmol) in THF (20 mL) was added a solution of (R)-6-allyl-6-(4-fluorophenyl)-3-((S)-1-(4-(6-oxo-1,6-dihydropyridin-3-yl)phenyl)ethyl)-1,3-oxazinan-2-one (891 mg, 0.174 mmol) in THF (30 mL) at 0° C., and the resulting mixture was stirred for 1 h. CH$_3$I (2 ml) was added and the mixture was stirred overnight. The reaction was quenched by aqueous NH$_4$Cl solution. The organic phase was separated, and concentrated to give the crude product, which was purified by preparative TLC to give (R)-6-allyl-6-(4-fluorophenyl)-3-((S)-1-(4-(1-methyl-6-oxo-1,6-dihydropyridin-3-yl)phenyl)ethyl)-1,3-oxazinan-2-one (634 mg, 69%). $^1$H NMR (CDCl$_3$): δ=1.52 (d, 3H), 2.16-2.35 (m, 3H), 2.52-2.64 (m, 2H), 2.94 (m, 1H), 3.61 (s, 3H), 5.00-5.11 (m, 2H), 5.66-5.74 (m, 2H), 6.64 (d, 1H), 6.90 (d, 2H), 7.02 (t, 2H), 7.11-7.14 (d, 2H), 7.25-7.28 (m, 2H), 7.41 (m, 1H), 7.53 (m, 1H).

Step 4

To a solution of (R)-6-allyl-6-(4-fluorophenyl)-3-((S)-1-(4-(1-methyl-6-oxo-1,6-dihydropyridin-3-yl)phenyl)ethyl)-1,3-oxazinan-2-one (320 mg, 0.717 mmol) in acetone (20 mL) was added aqueous KMnO$_4$ and NaIO$_4$ solution (15 mL). Then the formed mixture was stirred for 30 min at 0° C. The mixture was filtered, and the filtrate was adjusted to pH=5-6 with 1 N aq HCl solution. The mixture was extracted with EtOAc, and the combined organic phase was washed with brine, dried over anhydrous Na$_2$SO$_4$ and concentrated to give 2-((S)-6-(4-fluorophenyl)-3-((S)-1-(4-(1-methyl-6-oxo-1,6-dihydropyridin-3-yl)phenyl)ethyl)-2-oxo-1,3-oxazinan-6-yl)acetic acid.

Step 5

To a solution of 2-((S)-6-(4-fluorophenyl)-3-((S)-1-(4-(1-methyl-6-oxo-1,6-dihydropyridin-3-yl)phenyl)ethyl)-2-oxo-1,3-oxazinan-6-yl)acetic acid (290 mg, 0.625 mol) in MeOH (20 mL) was added SOCl$_2$ (2 mL) at 0° C., and the reaction mixture was stirred at rt for 2 h. The reaction mixture was concentrated to give the residue, which was purified by preparative TLC to give methyl 2-((S)-6-(4-fluorophenyl)-3-((S)-1-(4-(1-methyl-6-oxo-1,6-dihydropyridin-3-yl)phenyl)ethyl)-2-oxo-1,3-oxazinan-6-yl)acetate (130 mg, 43.5%). $^1$H NMR (CDCl$_3$): δ=1.52 (d, 3H), 2.36-2.55 (m, 3H), 2.67-2.71 (m, 2H), 2.90-3.04 (m, 3H), 3.68 (s, 3H), 3.71 (s, 3H), 5.66 (m, 2H), 6.66 (d, 1H), 6.90 (d, 2H), 7.03 (t, 2H), 7.13-7.15 (d, 2H), 7.23-7.29 (m, 2H), 7.42 (m, 1H), 7.56 (m, 1H).

Step 6

To a solution of methyl 2-((S)-6-(4-fluorophenyl)-3-((S)-1-(4-(1-methyl-6-oxo-1,6-dihydropyridin-3-yl)phenyl)ethyl)-2-oxo-1,3-oxazinan-6-yl)acetate (130 mg, 0.22 mmol) in dry THF (20 mL) was added MeMgBr (2 mL) at −78° C., and the mixture was stirred under N$_2$ at rt overnight. The reaction was quenched with water, and the mixture was extracted with EtOAc. The combined organic phase was dried over Na$_2$SO$_4$, and concentrated to give the residue, which was purified by preparative HPLC to give (S)-6-(4-fluorophenyl)-6-(2-hydroxy-2-methylpropyl)-3-((S)-1-(4-(1-methyl-6-oxo-1,6-dihydropyridin-3-yl)phenyl)ethyl)-1,3-oxazinan-2-one (24 mg, 30%). LC-MS Method 2 $t_R$=1.116 min, m/z=479.1; $^1$H NMR (CDCl$_3$): 1.1 (m, 6H), 1.18 (m, 1H), 1.48 (d, 3H), 1.58 (m, 1H), 1.80-2.00 (m, 2H), 2.21 (m, 3H), 2.86 (m, 1H), 5.55 (m, 1H), 7.72 (m, 2H), 7.00 (m, 2H), 7.18 (m, 4H).

Method 2

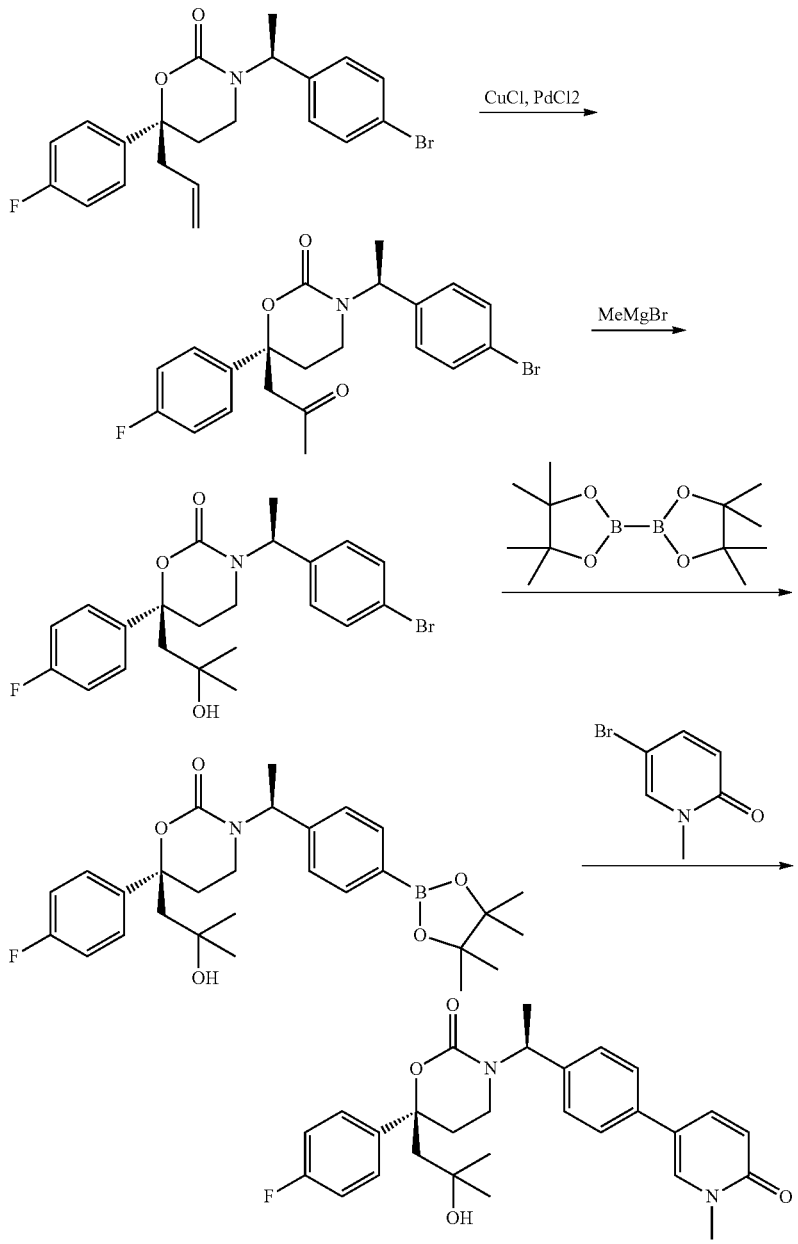

Step 1

To a solution of (R)-6-allyl-3-((S)-1-(4-bromophenyl)ethyl)-6-(4-fluorophenyl)-1,3-oxazinan-2-one (5 g, 12 mmol) and CuCl (2.75 g, 27.8 mmol) in dry DMF (50 mL) was added H$_2$O (20 mL) and PdCl$_2$ (950 mg, 3.2 mmol) at room temperature. The mixture was vigorously stirred under a balloon of oxygen for 24 h. After TLC showed the starting material had disappeared, the solid was filtered off. Water (200 mL) and EtOAc (50 mL) was added, the layers were separated and the aqueous layer was extracted with EtOAc (3×40 mL). The combined organic layer was washed with brine, dried over Na$_2$SO$_4$, filtered and concentrated to give (S)-3-((S)-1-(4-bromophenyl)ethyl)-6-(4-fluorophenyl)-6-(2-oxopropyl)-1,3-oxazinan-2-one (5.25 g, 92%), which was purified by column chromatography. $^1$H NMR (CDCl$_3$): 1.47 (s, 3H), 2.06 (s, 3H), 2.10-2.36 (m, 3H), 2.58 (m, 1H), 2.90 (m, 2H), 5.58 (m, 1H), 6.69 (m, 1H), 6.79 (m, 1H), 7.02 (m, 2H), 7.19-7.33 (m, 4H).

Step 2

To a solution of (S)-3-((S)-1-(4-bromophenyl)ethyl)-6-(4-fluorophenyl)-6-(2-oxopropyl)-1,3-oxazinan-2-one (5.25 g, 12.1 mmol) in anhydrous THF (100 mL) was added dropwise methylmagnesium bromide (20 mL, 60 mmol) at −78° C. under nitrogen. Then the mixture was stirred at rt for 2 h. The reaction mixture was cooled in an ice bath and quenched with aqueous NH$_4$Cl. The layers were separated. The aqueous layer was extracted with EtOAc (15 mL), washed with a brine (30 mL), dried over Na$_2$SO$_4$ and concentrated in vacuo to give the crude product, which was purified by preparative HPLC and chiral HPLC to afford (S)-3-((S)-1-(4-bromophenyl)

ethyl)-6-(4-fluorophenyl)-6-(2-hydroxy-2-methylpropyl)-1,3-oxazinan-2-one (2.5 mg, 46%). ¹H NMR (CDCl₃): 1.08 (s, 3H), 1.12 (s, 3H), 1.48 (m, 3H), 1.99 (m, 1H), 2.10-2.24 (m, 4H), 2.35 (m, 1H), 2.85 (m, 1H), 5.61 (m, 1H), 6.80 (m, 2H), 6.99 (m, 2H), 7.15-7.28 (m, 5H).

Step 3

A mixture of (S)-3-((S)-1-(4-bromophenyl)ethyl)-6-(4-fluorophenyl)-6-(2-hydroxy-2-methylpropyl)-1,3-oxazinan-2-one (640 mg, 1.42 mmol), 4,4,4',4',5,5,5',5'-octamethyl-2,2'-bi(1,3,2-dioxaborolane) (470 mg, 1.85 mmol), PdCl₂dppf (40 mg, 0.047 mmol, KOAc (490 mg, 4.97 mmol) in DMSO (8 mL) was heated at 90° C. for 20 h. The mixture was diluted with EtOAc, and washed with water. The organic phase was separated, and concentrated to give the crude product, which was purified by preparative TLC to afford (S)-6-(4-fluorophenyl)-6-(2-hydroxy-2-methylpropyl)-3-((S)-1-(4-(4,4,5,5-tetramethyl-1,3,2-dioxaborolan-2-yl)phenyl)ethyl)-1,3-oxazinan-2-one (700 mg, 99%). ¹H NMR (CDCl₃): δ=1.08 (s, 3H), 1.13 (s, 3H), 1.32 (s, 12H), 1.51 (t, 3H), 1.94 (m, 2H), 2.16 (m, 5H), 2.33 (m, 1H), 2.83 (m, 1H), 5.69 (m, 1H), 6.99 (m, 4H), 7.25 (m, 2H), 7.61 (m, 2H).

Step 4

A mixture of (S)-6-(4-fluorophenyl)-6-(2-hydroxy-2-methylpropyl)-3-((S)-1-(4-(4,4,5,5-tetramethyl-1,3,2-dioxaborolan-2-yl)phenyl)ethyl)-1,3-oxazinan-2-one (700 mg, 1.41 mmol), 5-bromo-1-methylpyridin-2(1H)-one (398 mg, 2.12 mmol), PdCl₂(Ph₃P)₂ (70 mg), Cs₂CO₃ (1.5 mL, 3.0 mmol) in 1,4-dioxane (15 mL) was heated under reflux for 2 h. The mixture was diluted with EtOAc, and washed with water. The organic phase was separated, and concentrated to give the crude product, which was purified by preparative TLC to afford (S)-6-(4-fluorophenyl)-6-(2-hydroxy-2-methylpropyl)-3-((S)-1-(4-(1-methyl-6-oxo-1,6-dihydropyridin-3-yl)phenyl)ethyl)-1,3-oxazinan-2-one (150 mg, 22%). ¹H NMR (CDCl₃): δ=1.12 (s, 3H), 1.13 (s, 3H), 1.51 (t, 3H), 2.16 (m, 2H), 2.21 (m, 2H), 2.41 (m, 1H), 2.92 (m, 1H), 3.63 (s, 3H), 5.69 (q, 1H), 6.69 (m, 1H), 6.99 (m, 4H), 7.18 (m, 2H) δ7.27 (m, 2H) δ 7.42 (m, 1H), 7.52 (m, 1H).

Example 33

4108.1002-007 Example 460

(R)-6-(4-fluorophenyl)-6-(3-hydroxypropyl)-3-((S)-1-(4-(1-methyl-6-oxo-1,6-dihydropyridin-3-yl)phenyl)ethyl)-1,3-oxazinan-2-one

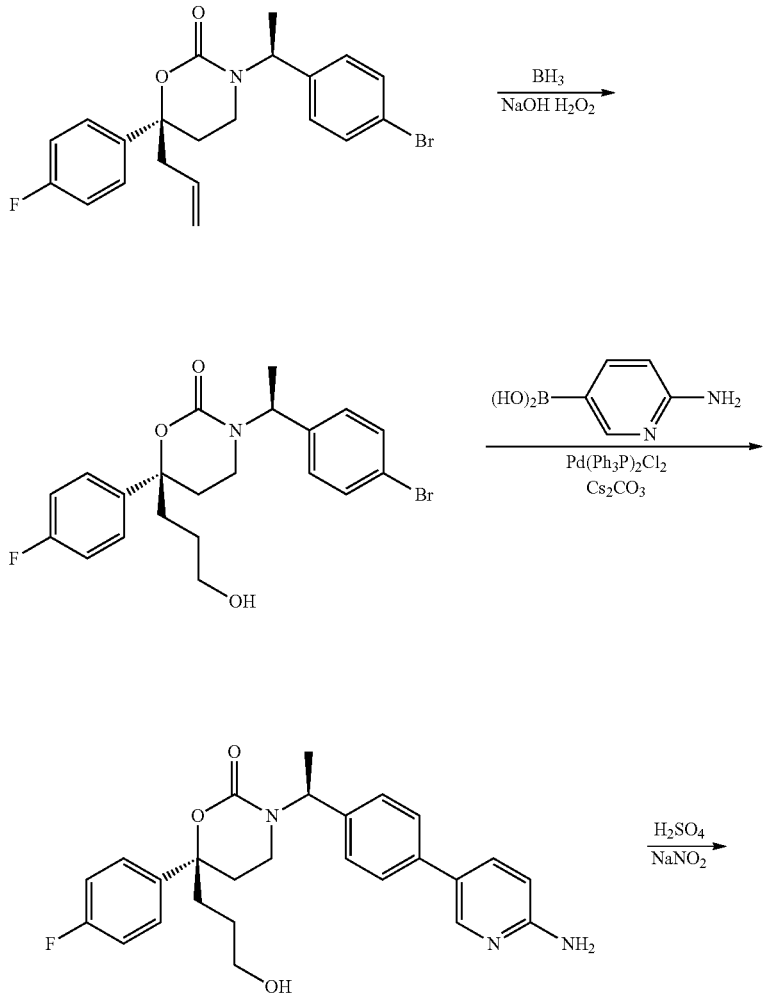

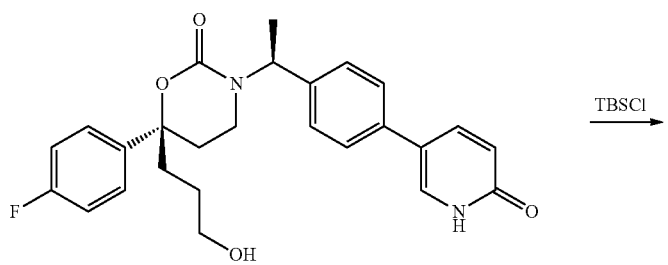

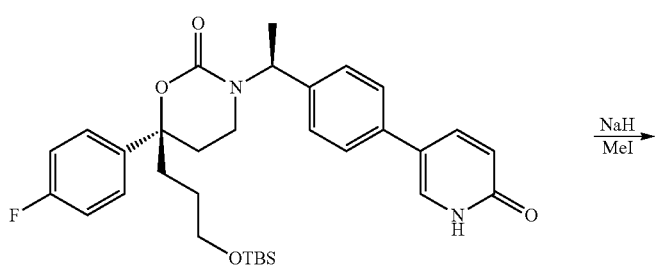

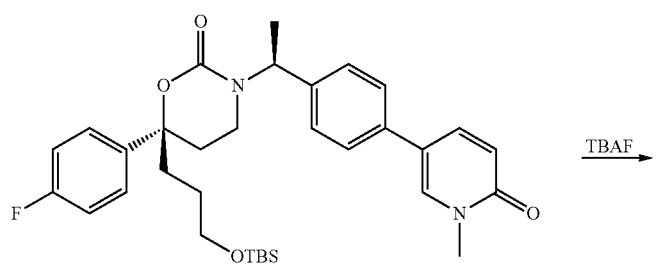

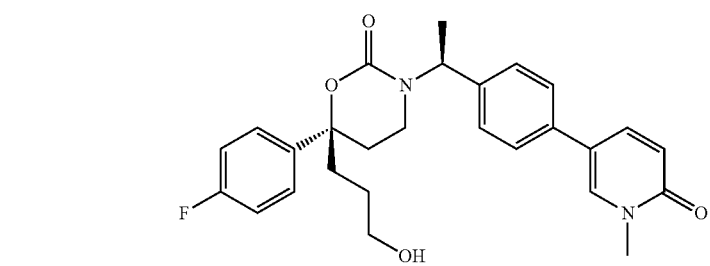

Step 1

To a solution of (R)-6-allyl-3-((S)-1-(4-bromophenyl)ethyl)-6-(4-fluorophenyl)-1,3-oxazinan-2-one (1.19 g, 2.8 mmol) in THF (30 mL) was added BH₃ THF (8.5 mL, 1 mol/L, 8.5 mmol) at 0° C. under nitrogen atmosphere. The formed mixture was stirred for 2 h. The reaction was quenched with water. Then NaOH (1 mol/L, 6 mL) and H₂O₂ (5 mL) were added to the above mixture. When the reaction was over, the mixture was extracted with EtOAc. The combined organic phase was concentrated to give the crude product, which was purified by preparative TLC to give (R)-3-((S)-1-(4-bromophenyl)ethyl)-6-(4-fluorophenyl)-6-(3-hydroxypropyl)-1,3-oxazinan-2-one (1.13 g, 92%).

Step 2

A mixture of (R)-3-((S)-1-(4-bromophenyl)ethyl)-6-(4-fluorophenyl)-6-(3-hydroxypropyl)-1,3-oxazinan-2-one (520 mg, 1.2 mmol) and 6-aminopyridin-3-ylboronic acid (280 mg, 1.44 mmol), Pd(Ph₃P)₂Cl₂ (100 mg), and aq Cs₂CO₃ solution (3 mL, 2M) in 1,4-dioxane (20 mL) was stirred and heated to reflux for 2 h. The organic phase was separated, and concentrated to give crude product, which was purified by preparative TLC to give (R)-3-((S)-1-(4-(6-aminopyridin-3-yl)phenyl)ethyl)-6-(4-fluoophenyl)-6-(3-hydroxy propyl)-1,3-oxazinan-2-one. (400 mg, 74%).
Step 3
(R)-3-((S)-1-(4-(6-aminopyridin-3-yl)phenyl)ethyl)-6-(4-fluorophenyl)-6-(3-hydroxypropyl)-1,3-oxazinan-2-one (400 mg, 0.88 mmol.) was dissolved in 3.5 M $H_2SO_4$ (10 mL), and 2 M $NaNO_2$ (6 mL) was added at 0° C. The reaction mixture was stirred at rt for 20 min. The reaction mixture was then treated with aqueous NaOH solution (8%), and extracted with $CH_2Cl_2$. The combined organic layer was washed with brine, dried over anhydrous $Na_2SO_4$, and concentrated to give crude product, which was purified by preparative TLC to give (R)-6-(4-fluorophenyl)-6-(3-hydroxypropyl)-3-((S)-1-(4-(6-oxo-1,6-dihydropyridin-3-yl)phenyl)ethyl)-1,3-oxazinan-2-one (350 mg, 0.78 mmol). $^1$H NMR (CDCl$_3$): δ=1.10-1.25 (m, 8H), 1.37 (m, 1H), 1.42-1.55 (m, 2H), 1.78-1.93 (m, 2H), 2.10-2.38 (m, 2H), 2.87 (m, 2H), 3.52-3.58 (m, 1H), 3.31-3.97 (m, 1H), 4.12-4.19 (m, 1H), 5.53-5.63 (m, 1H), 6.85-7.15 (m, 3H), 7.35-7.55 (m, 1H), 7.75-7.89 (m, 1H), 8.10-8.12 (m, 1H).
Step 4
A mixture of (R)-6-(4-fluorophenyl)-6-(3-hydroxypropyl)-3-((S)-1-(4-(6-oxo-1,6-dihydropyridin-3-yl)phenyl)ethyl)-1,3-oxazinan-2-one (100 mg, 0.78 mmol), imidazole (142.8 mg, 2.1 mmol), and tert-butylchlorodimethylsilane (350 mg, 2.34 mmol) in $CH_2Cl_2$ (20 mL) was stirred overnight. The mixture was washed with water and extracted with EtOAc. The combined organic phase was washed with brine, dried over $Na_2SO_4$, filtered and concentrated to give crude (R)-6-(3-(tert-butyldimethylsilyloxy)propyl)-6-(4-fluorophenyl)-3-((S)-1-(4-(6-oxo-1,6-dihydropyridin-3-yl)phenyl)ethyl)-1,3-oxazinan-2-one (120 mg), which was used for the next step without further purification.
Step 5
To a suspension of NaH (18 mg, 0.72 mmol) in THF (0.5 mL) was added a solution of (R)-6-(3-(tert-butyldimethylsilyloxy)propyl)-6-(4-fluorophenyl)-3-((S)-1-(4-(6-oxo-1,6-dihydropyridin-3-yl)phenyl)ethyl)-1,3-oxazinan-2-one (100 mg, 0.18 mmol) in THF (10 mL) at 0° C. The resulting mixture was stirred for 1 h. Then CH$_3$I (613 mg, 43.2 mmol) was added, and the mixture was stirred for 3 h. The reaction was quenched with aq NH$_4$Cl solution. The organic phase was separated, and concentrated to give (R)-6-(3-(tert-butyldimethylsilyloxy)propyl)-6-(4-fluorophenyl)-3-((S)-1-(4-(1-methyl-6-oxo-1,6-dihydropyridin-3-yl)phenyl)ethyl)-1,3-oxazinan-2-one (104 mg, 100%), which was used for the next step without further purification.
Step 6
A mixture of (R)-6-(3-(tert-butyldimethylsilyloxy)propyl)-6-(4-fluorophenyl)-3-((S)-1-(4-(1-methyl-6-oxo-1,6-dihydropyridin-3-yl)phenyl)ethyl)-1,3-oxazinan-2-one (200 mg, 0.35 mmol) and TBAF (182 mg, 0.7 mmol) in CH$_3$CN was stirred and heated to reflux for 15 min. When the reaction was over, the mixture was washed with water and extracted with EtOAc. The combined organic phase was washed with brine, dried over Na$_2$SO$_4$, filtered and concentrated to give crude product, which was purified by preparative HPLC to give (R)-6-(4-fluorophenyl)-6-(3-hydroxypropyl)-3-((S)-1-(4-(1-methyl-6-oxo-1,6-dihydropyridin-3-yl)phenyl)ethyl)-1,3-oxazinan-2-one (5.01 mg, 4%). LC-MS Method 2 $t_R$=1.065 min, m/z=464.21; $^1$H NMR (CDCl$_3$): δ=1.38 (m, 1H), 1.47 (d, 3H), 1.63 (m, 2H), 1.91 (m, 2H), 2.10-2.30 (m, 3H), 2.87 (m, 1H), 2.84 (m, 1H), 3.51 (m, 2H), 3.56 (s, 3H), 5.63 (m, 1H), 6.67 (m, 1H), 6.87-6.98 (m, 4H), 7.15 (m, 2H), 7.27 (m, 1H), 7.29 (m, 1H), 7.32 (m, 1H), 7.55 (m, 1H).

Example 34

4108.1002-007 Example 461

N-(3-((R)-6-(4-fluorophenyl)-3-((S)-1-(4-(1-methyl-6-oxo-1,6-dihydropyridin-3-yl)phenyl)ethyl)-2-oxo-1,3-oxazinan-6-yl)propyl)methanesulfonamide

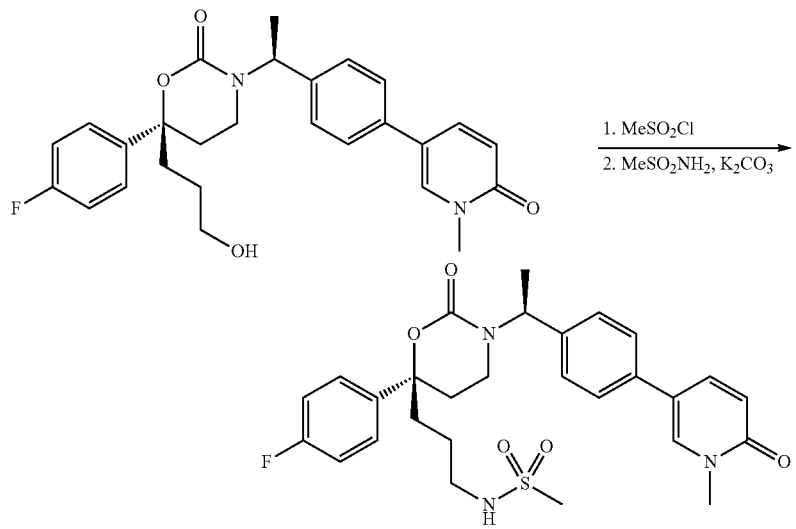

The title compound was prepared from (R)-6-(4-fluorophenyl)-6-(3-hydroxypropyl)-3-((S)-1-(4-(1-methyl-6-oxo-1,6-dihydropyridin-3-yl)phenyl)ethyl)-1,3-oxazinan-2-one by treatment with (i) MeSO$_2$Cl and (ii) MeSO$_2$NH$_2$. LC-MS Method 2 $t_R$=1.02 min, m/z=542.3; $^1$H NMR (CDCl$_3$) 1.35 (m, 1H), 1.53 (d, 3H), 1.69 (m, 1H), 1.89 (m, 1H), 2.00 (m, 1H), 2.17-2.33 (m, 3H), 2.89 (s, 3H), 2.97 (m, 1H), 3.06 (m, 2H), 3.66 (s, 3H), 4.38 (s, 1H), 5.67 (m, 1H), 6.82 (d, 1H), 6.99 (m, 4H), 7.15 (m, 2H), 7.22 (m, 2H), 7.47 (s, 1H), 7.63 (d, 1H).

Example 35

4108.1002-007 Example 484

3-((R)-2-oxo-3-((S)-1-(4-(6-oxo-1,6-dihydropyridin-3-yl)phenyl)ethyl)-6-phenyl-1,3-oxazinan-6-yl)propanamide

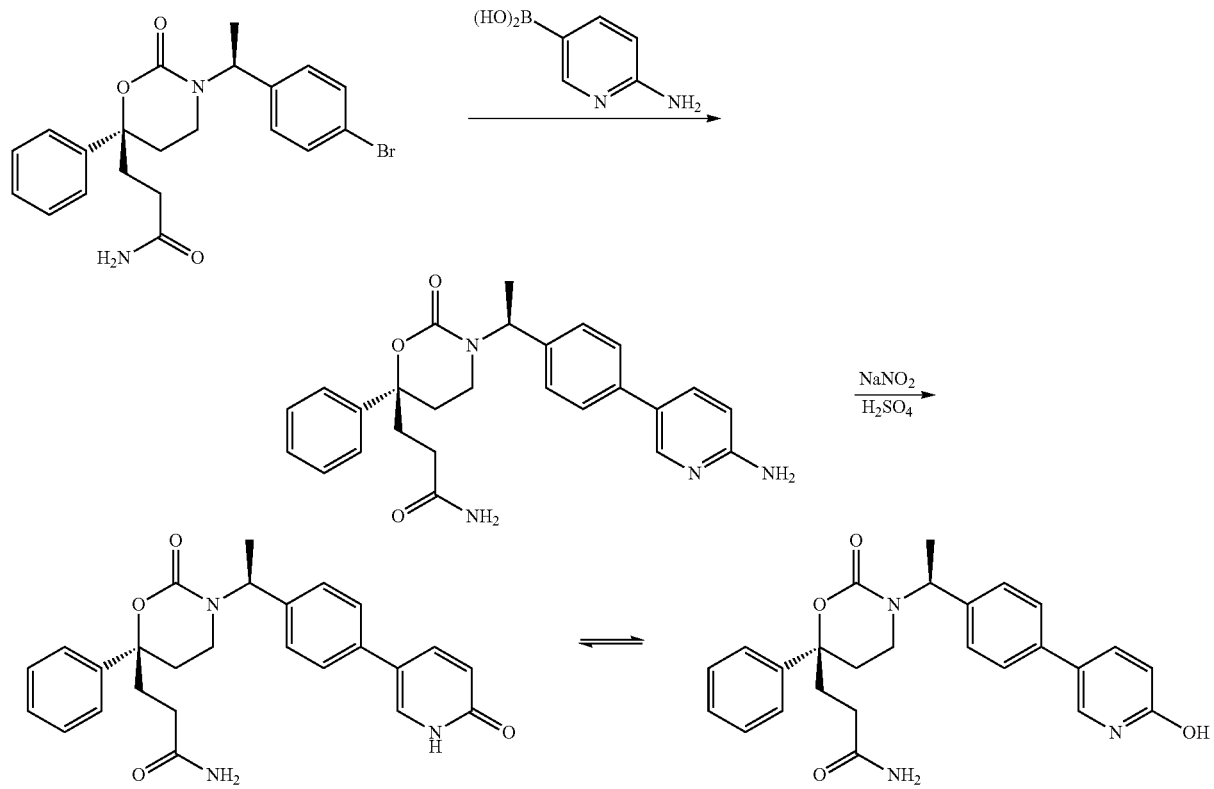

The title compound was prepared from 3-((R)-3-((S)-1-(4-bromophenyl)ethyl)-2-oxo-6-phenyl-1,3-oxazinan-6-yl)propanamide following procedures analogous to those described in Example 33 Steps 2 and 3. LC-MS Method 2 $t_R$=0.999 min, m/z=446.1; $^1$H NMR (CD$_3$OD) 1.53 (d, 3H), 1.91-2.01 (m, 1H), 2.18-2.34 (m, 4H), 2.35-2.51 (m, 2H), 3.03-3.12 (m, 1H), 5.56 (m, 1H), 6.62 (d, 2H), 7.03 (d, 2H), 7.24-7.44 (m, 7H), 7.59 (m, 1H), 7.87 (m, 1H).

Example 36

4108.1002-007 Example 485

(S)-6-(2-hydroxyethyl)-3-((S)-1-(4-(1-methyl-6-oxo-1,6-dihydropyridin-3-yl)phenyl)ethyl)-6-phenyl-1,3-oxazinan-2-one

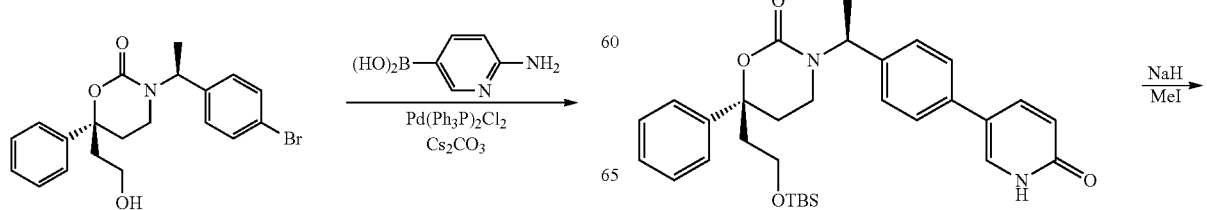

-continued

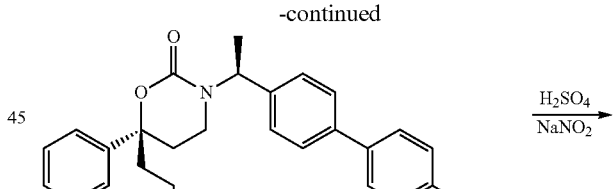

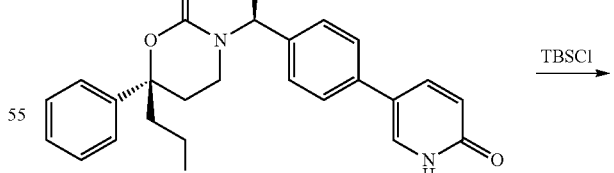

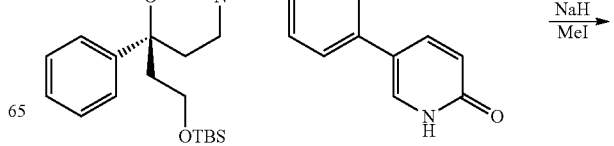

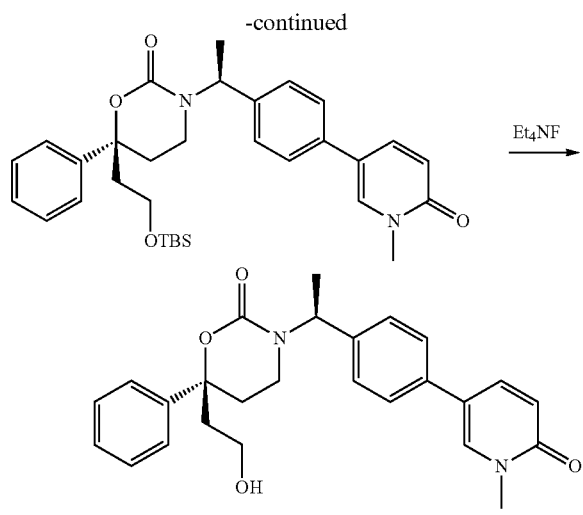

The title compound was prepared from (S)-3-((S)-1-(4-bromophenyl)ethyl)-6-(2-hydroxyethyl)-6-phenyl-1,3-oxazinan-2-one using a procedure analogous to that described in Example 33 Steps 2 to 6. LC-MS Method 2 $t_R$=1.038 min, m/z=433.1; $^1$H NMR (CDCl$_3$) 1.48 (d, 3H), 2.06-2.19 (m, 2H), 2.11-2.31 (m, 3H), 2.84 (m, 1H), 3.50 (m, 1H), 3.54 (s, 3H), 3.72 (m, 1H), 5.62 (m, 1H), 6.60 (d, 1H), 6.86 (d, 2H), 7.06 (d, 2H), 7.26 (m, 3H), 7.32 (m, 3H), 7.47 (d, 1H).

Example 37

4108.1002-007 Example 486

(S)-6-(2-hydroxy-2-methylpropyl)-3-((S)-1-(4-(1-methyl-6-oxo-1,6-dihydropyridin-3-yl)phenyl)ethyl)-6-phenyl-1,3-oxazinan-2-one Method 1

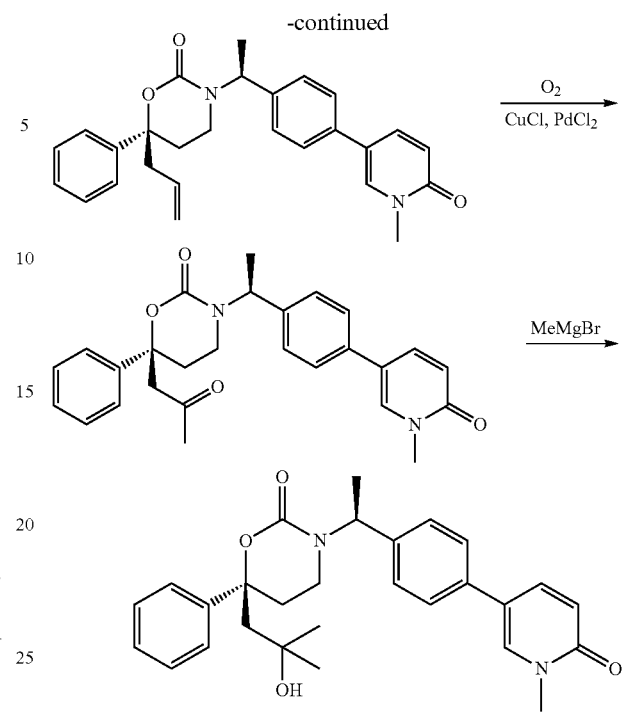

The title compound was prepared from (R)-6-allyl-3-((S)-1-(4-bromophenyl)ethyl)-6-phenyl-1,3-oxazinan-2-one using procedures analogous to those described in Example 33 Steps 2, 3 and 5, followed by procedures analogous to those described in Preparation 1 Method 1 Steps 4 and 6. LC-MS Method 2 $t_R$=1.116 min, m/z=461.1; $^1$H NMR (CDCl$_3$) 1.09 (s, 3H), 1.16 (s, 3H), 1.51 (m, 3H), 2.05-2.20 (4H), 2.40 (m, 1H), 2.84 (m, 1H), 3.59 (s, 3H), 5.64 (m, 1H), 6.62 (m, 1H), 6.96 (m, 2H), 7.14 (m, 2H), 7.28-7.39 (m, 5H), 7.48 (m, 1H), 7.50 (m, 1H).

Method 2

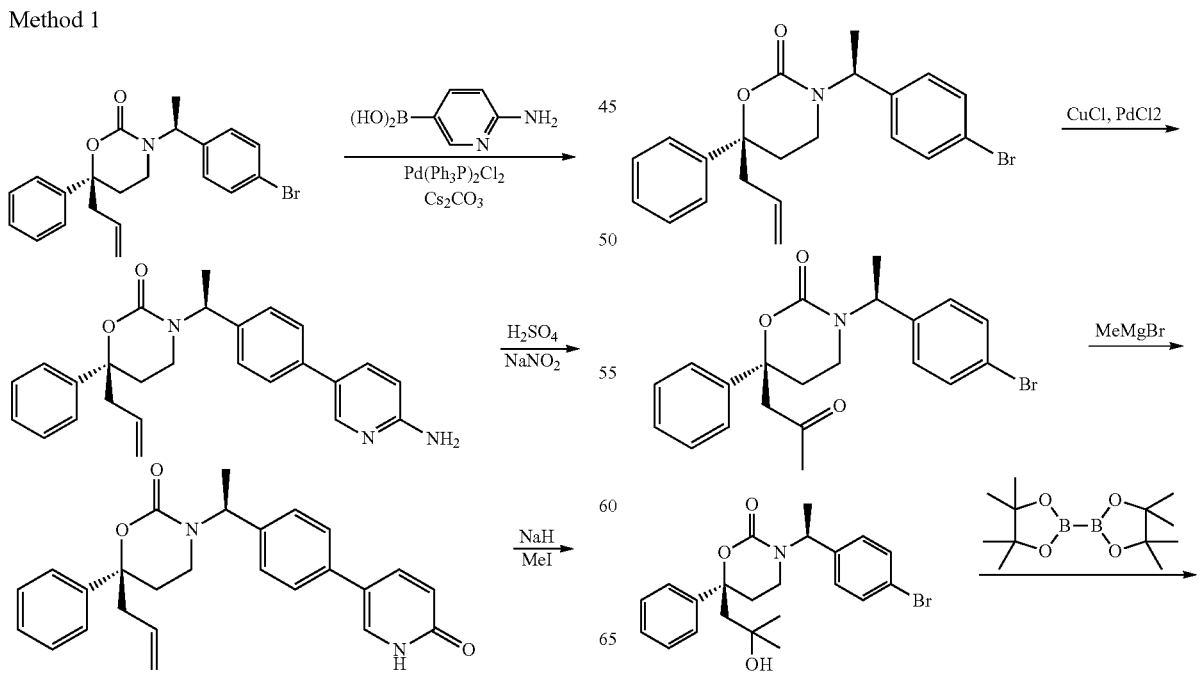

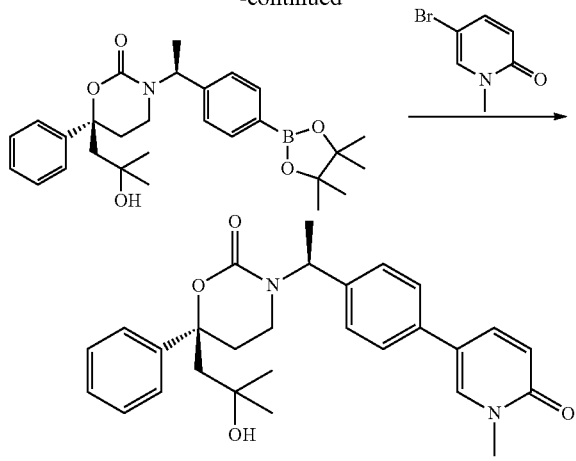

Step 1

To a solution of (R)-6-allyl-3-((S)-1-(4-bromophenyl)ethyl)-6-phenyl-1,3-oxazinan-2-one (20 g, 50 mmol) and CuCl (12.4 g, 125 mmol) in dry DMF (50 mL) was added H₂O (12 mL) and PdCl₂ (2.66 g, 15 mmol) at 0~-1-5° C. After addition, the mixture was allowed to warm to rt gradually for 48 h under O₂. After TLC showing the stating material had disappeared, the solid was filtered off. Water (200 mL) and EtOAc (50 mL) were added. The layers were separated and the aqueous layer was extracted with EtOAc (3×40 mL). The combined organic layer was washed with brine, dried over Na₂SO₄, filtered and concentrated to give a residue, which was purified by column chromatography to give (S)-3-((S)-1-(4-bromo-phenyl)ethyl)-6-(2-oxopropyl)-6-phenyl-1,3-oxazinan-2-one (12 g, 58%).

Step 2

To a solution of (S)-3-((S)-1-(4-bromophenyl)ethyl)-6-(2-oxopropyl)-6-phenyl-1,3-oxazinan-2-one (12 g, 28.8 mmol) in anhydrous THF (100 mL) was added dropwise methylmagnesium bromide (48 mL, 144 mmol) at −78° C. under nitrogen. The mixture was stirred at rt for 1 h. The reaction mixture was quenched with aqueous NH₄Cl solution (50 mL) in ice water bath. The layers were separated and the aqueous layer was extracted with EtOAc (150 mL). The combined organic phases were washed with brine (30 mL), dried over Na₂SO₄ and concentrated in vacuo to give the crude product, which was purified by preparative HPLC and chiral HPLC to afford (S)-3-((S)-1-(4-bromophenyl)ethyl)-6-(2-hydroxy-2-methylpropyl)-6-phenyl-1,3-oxazinan-2-one (6.6 g, 53%).

Step 3

To a solution of (S)-3-((S)-1-(4-bromophenyl)ethyl)-6-(2-hydroxy-2-methylpropyl)-6-phenyl-1,3-oxazinan-2-one (6.6 g, 15.2 mmol) and 4,4,4',4',5,5,5',5'-octamethyl-2,2'-bi(1,3,2-dioxaborolane) (6.1 g, 24.3 mmol) in dry DMSO (20 mL) was added KOAc (4.8 g, 48.6 mmol) and Pd(dppf)cl₂ (372 mg, 0.46 mmol). After addition, the mixture was allowed to warm to 100° C. for 20 h. After TLC showed the starting material had disappeared, the solid was filtered off. Water (60 mL) and EtOAc (20 mL) were added. The layers were separated and the aqueous layer was extracted with EtOAc (3×15 mL). The combined organic layer was washed with brine, dried over Na₂SO₄, filtered and concentrated to give a residue, which was purified by column chromatography to give (S)-6-(2-hydroxy-2-methylpropyl)-6-phenyl-3-((S)-1-(4-(4,4,5,5-tetramethyl-1,3,2-dioxaborol-an-2-yl)phenyl)ethyl)-1,3-oxazinan-2-one (4.4 g, 60%).

Step 4

To a solution of (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one (2.2 g, 4.58 mmol) and 5-bromo-1-methylpyridin-2(1H)-one (1.37 g, 7.33 mmol) in dry 1,4-dioxane (4 mL) was added aqueous CsCO₃ solution (10 mL, 10 mmol) and Pd(PPh₃)₂Cl₂ (967 mg, 1.38 mmol). After addition, the mixture was heated at 110° C. for 30 min in a microwave. After TLC showed the stating material had disappeared, the solid was filtered off. Water (20 mL) and EtOAc (10 mL) were added. The layers were separated and the aqueous layer was extracted with EtOAc (3×10 mL). The combined organic layer was washed with brine, dried over Na₂SO₄, filtered and concentrated to give a residue, which was purified by preparative HPLC to give (S)-6-(2-hydroxy-2-methylpropyl)-3-((S)-1-(4-(1-methyl-6-oxo-1,6-dihydropyridin-3-yl)phenyl)ethyl)-6-phenyl-1,3-oxazinan-2-one (730 mg, 35%). ¹H NMR (CDCl₃): 1.09 (s, 3H), 1.16 (s, 3H), 1.51 (m, 3H), 2.05-2.20 (4H), 2.40 (m, 1H), 2.84 (m, 1H), 3.59 (s, 3H), 5.64 (m, 1H), 6.62 (m, 1H), 6.96 (m, 2H), 7.14 (m, 2H), 7.28-7.39 (m, 5H), 7.48 (m, 1H), 7.50 (m, 1H). The compound was recrystallized by two methods.

Recrystallization Method A

A mixture of (S)-6-(2-hydroxy-2-methylpropyl)-3-((S)-1-(4-(1-methyl-6-oxo-1,6-dihydropyridin-3-yl)phenyl)ethyl)-6-phenyl-1,3-oxazinan-2-one (ca. 2.94 g) and isopropyl acetate (160 mL) was vigorously stirred at room temperature or warmed at 50° C. until most of the solid was dissolved. The resulting mixture was filtered through an HPLC filter and then the filtrate was slowly stirred at room temperature overnight. The solids were filtered, washed with isopropyl acetate and dried at rt under high vacuum to afford 1.43 g (49%) of a crystalline solid. M.p. 95-101° C. This form was determined to be a hydrate which released 3.6% water by weight on heating.

Recrystallization Method B

A mixture of (S)-6-(2-hydroxy-2-methylpropyl)-3-((S)-1-(4-(1-methyl-6-oxo-1,6-dihydropyridin-3-yl)phenyl)ethyl)-6-phenyl-1,3-oxazinan-2-one (ca. 10.03 g) and isopropyl acetate (600 mL) was heated to reflux in a 130° C. oil bath until the solid was completely dissolved to form a homogeneous solution. Heating was stopped and the resulting solution was slowly stirred while slowly cooling to room temperature in the oil bath overnight. The solids were filtered, washed with isopropyl acetate and dried at rt under high vacuum to afford 7.30 g (73%) of crystalline solid. M.p. 180-181° C. This form was determined to be anhydrous.

Example 38

4108.1002-007 Example 487

3-((R)-3-((S)-1-(4-(1-methyl-6-oxo-1,6-dihydropyridin-3-yl)phenyl)ethyl)-2-oxo-6-phenyl-1,3-oxazinan-6-yl)propanamide

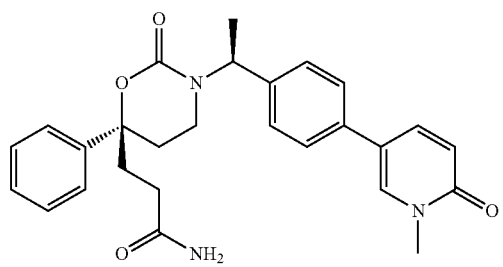

The title compound was prepared from (R)-6-allyl-3-((S)-1-(4-(1-methyl-6-oxo-1,6-dihydropyridin-3-yl)phenyl)ethyl)-6-phenyl-1,3-oxazinan-2-one using a procedure analogous to that described in Example 29 Step 2 followed by treatment with (i) Jones reagent and (ii) NH$_3$, EDC, HOBt. LC-MS Method 2 t$_R$=1.028 min, m/z=460.2; $^1$H NMR (CDCl$_3$) 1.53 (d, 3H), 1.91-2.01 (m, 1H), 2.11-2.42 (m, 5H), 2.46-2.54 (m, 1H), 2.88-2.96 (m, 1H), 3.60 (s, 3H), 5.26 (s, 1H), 5.42 (s, 1H), 5.66 (m, 1H), 6.69 (d, 1H), 6.95-7.03 (d, 2H), 7.12-7.20 (m, 2H), 7.24-7.41 (m, 5H), 7.52 (m, 1H).

Example 39

4108.1002-007 Example 488

N-(3-((R)-3-((S)-1-(4-(1-methyl-6-oxo-1,6-dihydropyridin-3-yl)phenyl)ethyl)-2-oxo-6-phenyl-1,3-oxazinan-6-yl)propyl)methanesulfonamide

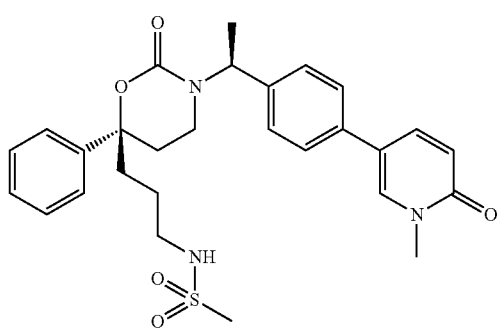

The title compound was prepared from (R)-6-(3-hydroxypropyl)-3-((S)-1-(4-(1-methyl-6-oxo-1,6-dihydropyridin-3-yl)phenyl)ethyl)-6-phenyl-1,3-oxazinan-2-one by treatment with (i) MeSO$_2$Cl and (ii) MeSO$_2$NH$_2$, K$_2$CO$_3$. LC-MS Method 2 t$_R$=1.095 min, m/z=524.1; $^1$H NMR (CDCl$_3$) 1.30-1.41 (m, 1H), 1.52 (d, 3H), 1.71 (m, 1H), 1.87-2.07 (m, 3H), 2.09-2.20 (m, 3H), 2.22-2.32 (m, 2H), 2.88 (s, 3H), 3.06 (m, 2H), 3.60 (s, 3H), 4.32 (s, 1H), 5.65 (m, 1H), 6.67 (d, 1H), 6.94 (m, 2H), 7.11 (d, 2H), 7.25 (m, 1H), 7.27-7.40 (m, 4H), 7.53 (dd, 1H).

Example 40

4108.1002-007 Example 499

(S)-6-(2-hydroxyethyl)-3-((S)-1-(4-(1-methyl-6-oxo-1,6-dihydropyridin-3-yl)phenyl)propyl)-6-phenyl-1,3-oxazinan-2-one

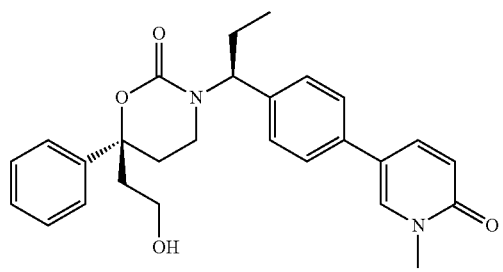

The title compound was prepared from (S)-3-((S)-1-(4-bromophenyl)propyl)-6-(2-hydroxyethyl)-6-phenyl-1,3-oxazinan-2-one following a procedure analogous to that described in Example 18 using 5-bromo-1-methylpyridin-2(1H)-one in Step 2. LC-MS Method 2 t$_R$=1.627 min, m/z=447.1; $^1$H NMR (CDCl$_3$) 1.06 (m, 3H), 1.87-2.06 (m, 2H), 2.11-2.28 (m, 2H), 2.33 (m, 3H), 2.96 (m, 1H), 3.53 (m, 1H), 3.62 (s, 3H), 3.78 (m, 1H), 5.48 (m, 1H), 6.69 (m, 1H), 7.03 (m, 2H), 7.14 (m, 2H), 7.21-7.38 (m, 4H), 7.41 (s, 1H), 7.56 (m, 1H).

Example 41

4108.1002-007 Example 501

(R)-6-(4-fluorophenyl)-6-(3-hydroxypropyl)-3-((S)-1-(4-(2-oxo-1,2-dihydropyridin-3-yl)phenyl)ethyl)-1,3-oxazinan-2-one

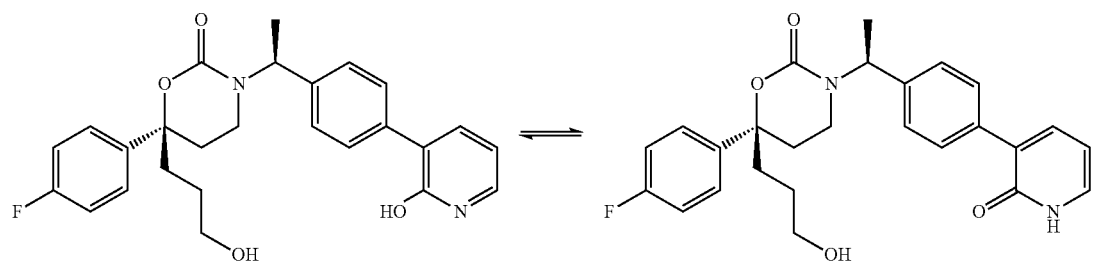

The title compound was prepared from (R)-6-allyl-6-(4-fluorophenyl)-3-((S)-1-(4-(4,4,5,5-tetramethyl-1,3,2-dioxaborolan-2-yl)phenyl)ethyl)-1,3-oxazinan-2-one and 3-bromo-2-hydroxypyridine using a procedure analogous to that described in Example 3 Step 2, followed by a procedure analogous to that described in Example 29 Step 2. LC-MS Method 1 $t_R$=1.24, m/z=452 (M+1); $^1$H NMR (CDCl$_3$) 7.76 (d, 1H), 7.52 (d, 1H), 7.42 (dd, 2H), 7.24 (m, 2H), 7.08-7.00 (m, 4H), 6.75 (t, 1H), 5.70 (m, 1H), 3.58 (t, 1H), 2.94 (m, 1H), 1.54 (d, 3H).

Example 42

4108.1002-007 Example 538

(R)-6-(4-fluorophenyl)-6-(3-hydroxypropyl)-3-((S)-1-(4-(1-methyl-2-oxo-1,2-dihydropyridin-3-yl)phenyl)ethyl)-1,3-oxazinan-2-one

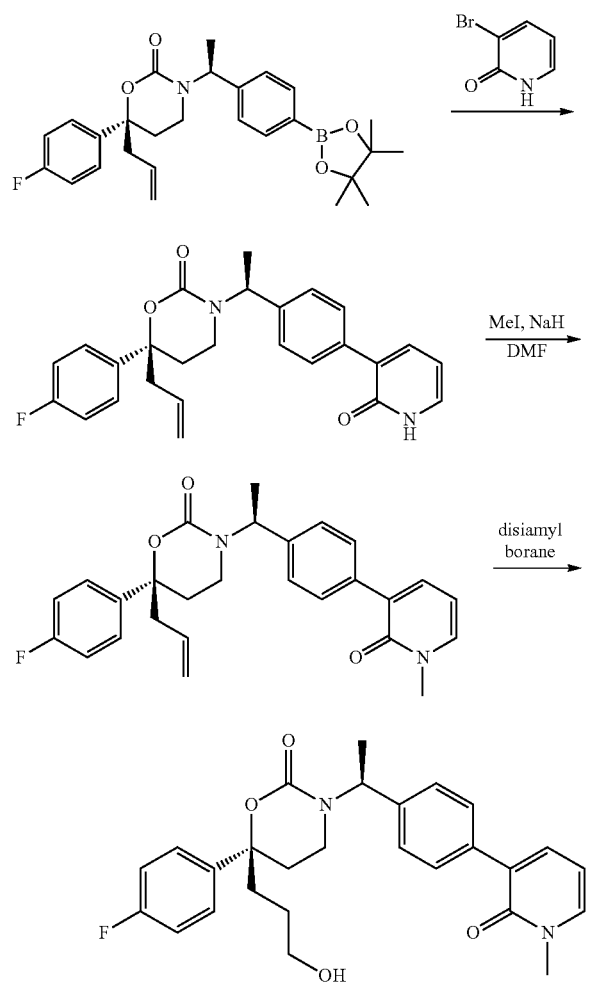

Step 1

(R)-6-allyl-6-(4-fluorophenyl)-3-((S)-1-(4-(4,4,5,5-tetramethyl-1,3,2-dioxaborolan-2-yl)phenyl)ethyl)-1,3-oxazinan-2-one (18 mg, 0.039 mmol), 3-bromo-2-hydroxypyridine (14 mg, 2 equiv), Pd(dppf)Cl$_2$ (3 mg, 10% mol), 2M aq Na$_2$CO$_3$ solution (800 µL) and 1,4-dioxane (1.5 mL) were mixed. The mixture was evacuated and refilled with N$_2$ gas (3×) before being heated overnight at 85° C. After being cooled to rt, the mixture was filtered and acidified with 5% aq HCl solution before being purified by prep HPLC to afford (R)-6-allyl-6-(4-fluorophenyl)-3-((S)-1-(4-(2-oxo-1,2-dihydropyridin-3-yl)phenyl)ethyl)-1,3-oxazinan-2-one (7.2 mg, 43% yield). LC-MS Method 1 $t_R$=1.57 min, m/z 433 (M+1).

Step 2

A solution of (R)-6-allyl-6-(4-fluorophenyl)-3-((S)-1-(4-(2-oxo-1,2-dihydropyridin-3-yl)phenyl)ethyl)-1,3-oxazinan-2-one (15.5 mg, 0.036 mmol) in dry DMF (1 mL) was cooled to 0° C. Sodium hydride (60% in mineral oil, 3 mg, 2 equiv) was added. After 20 min, iodomethane (4.5 µL, 2 equiv) was added. The mixture was stirred another 20 min before being warmed to it slowly and stirred for 2 h. LC-MS found the reaction completed. The mixture was quenched with satd aq NH$_4$Cl (1 mL) and purified by prep HPLC to afford (R)-6-allyl-6-(4-fluorophenyl)-3-((S)-1-(4-(1-methyl-2-oxo-1,2-dihydropyridin-3-yl)phenyl)ethyl)-1,3-oxazinan-2-one (13.3 mg, 83% yield). LC-MS Method 1 $t_R$=1.63 min, m/z 447 (M+1).

Step 3

A solution of (R)-6-allyl-6-(4-fluorophenyl)-3-((S)-1-(4-(1-methyl-2-oxo-1,2-dihydropyridin-3-yl)phenyl)ethyl)-1,3-oxazinan-2-one (13.3 mg, 0.030 mmol) in dry THF (1.5 mL) was cooled to 0° C. Disiamyl borane (0.5M in THF, 500 µL, excess) was added. After 10 min, the mixture was warmed to it and stirred for 1 h. The mixture was cooled to 0° C. again, quenched with water (1 mL) and NaBO$_3$ (10 mg). The mixture was concentrated and purified by prep HPLC to afford (R)-6-(4-fluorophenyl)-6-(3-hydroxypropyl)-3-((S)-1-(4-(1-methyl-2-oxo-1,2-dihydropyridin-3-yl)phenyl)ethyl)-1,3-oxazinan-2-one (4.2 mg, 30% yield). LC-MS Method 1 $t_R$=1.33 min, m/z=487 (M+1); $^1$H NMR (CD$_3$Cl) δ 7.47 (dd, 1H), 7.38 (m, 3H), 7.24 (m, 2H), 7.07 (t, 2H), 6.96 (d, 2H), 6.39 (t, 1H), 5.65 (m, 1H), 4.26 (t, 1H), 3.66 (s, 3H), 2.91 (m, 1H), 2.40-2.14 (m, 3H), 1.54 (d, 3H).

Example 43

4108.1002-007 Example 540

(R)-3-((S)-1-(4-(1-ethyl-6-oxo-1,6-dihydropyridin-3-yl)phenyl)ethyl)-6-(3-hydroxypropyl)-6-phenyl-1,3-oxazinan-2-one

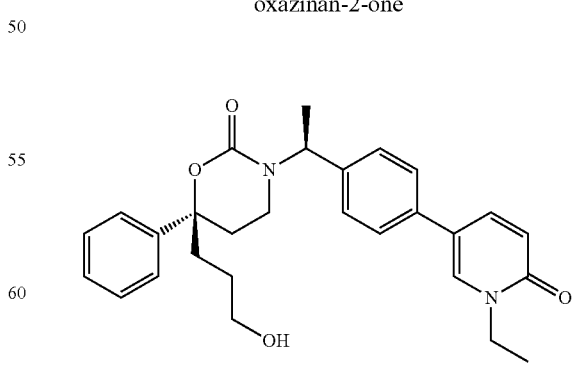

The title compound was prepared following procedures analogous to those described in Example 30 using ethyl iodide in Step 1, to afford 5-bromo-1-ethylpyridin-2(1H)-one which was used in Step 2. LC-MS Method 2 $t_R$=1.297 min, m/z=461.1; $^1$H NMR (CDCl$_3$) 1.31 (m, 1H), 1.36 (t, 3H), 1.51 (d, 3H), 1.68 (m, 1H), 1.86-2.01 (m, 2H), 2.18 (m, 1H), 2.27 (m, 2H), 2.91 (m, 1H), 3.52 (m, 2H), 4.18 (m, 2H), 5.13 (m, 1H), 5.62 (m, 1H), 6.91 (m, 3H), 7.08 (m, 2H), 7.18-7.33 (m, 5H), 7.41 (s, 1H), 7.61 (d, 1H).

Example 44

4108.1002-007 Example 541

(R)-6-(3-hydroxypropyl)-3-((S)-1-(4-(1-methyl-6-oxo-1,6-dihydropyridin-3-yl)phenyl)propyl)-6-phenyl-1,3-oxazinan-2-one

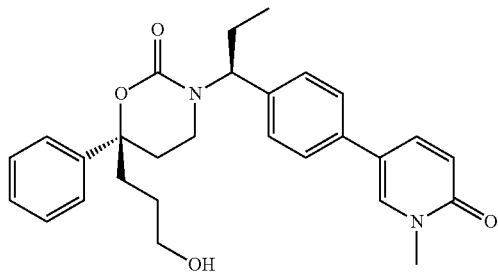

The title compound was prepared from (R)-6-(3-hydroxypropyl)-6-phenyl-3-((S)-1-(4-(4,4,5,5-tetramethyl-1,3,2-dioxaborolan-2-yl)phenyl)propyl)-1,3-oxazinan-2-one following procedures analogous to those described in Example 30 Step 2. LC-MS Method 2 $t_R$=1.113 min, m/z=461.1; $^1$H NMR (CDCl$_3$) 0.95 (t, 3H), 1.30 (m, 1H), 1.68 (m, 1H), 1.81-1.99 (m, 2H), 2.11-2.32 (m, 3H), 2.88 (m, 1H), 3.50 (m, 2H), 3.58 (m, 2H), 5.43 (m, 1H), 6.49 (d, 1H), 6.98 (d, 2H), 7.08 (d, 2H), 7.19 (m, 1H), 7.25 (m, 4H), 7.32 (s, 1H), 7.47 (m, 1H).

Example 45

4108.1002-007 Example 560

(R)-6-(3-hydroxypropyl)-3-((S)-1-(4-(2-hydroxypyridin-4-yl)phenyl)ethyl)-6-phenyl-1,3-oxazinan-2-one

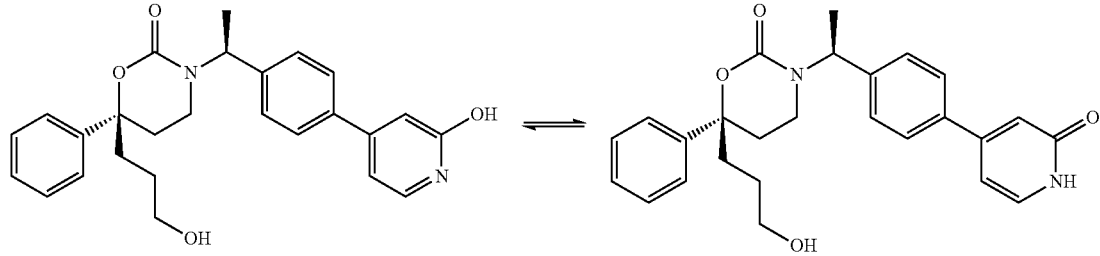

The title compound was prepared from (R)-6-(3-hydroxypropyl)-6-phenyl-3-((S)-1-(4-(4,4,5,5-tetramethyl-1,3,2-dioxaborolan-2-yl)phenyl)ethyl)-1,3-oxazinan-2-one and 4-bromo-2-hydroxypyridine following a procedure analogous to that described in Example 30 Step 2. LC-MS Method 2 $t_R$=1.019 min, m/z=865.4; $^1$H NMR (CDCl$_3$) 1.29-1.40 (m, 1H), 1.49 (d, 3H), 1.60-1.72 (m, 1H), 1.83-2.01 (m, 3H), 2.18 (m, 1H), 2.21-2.37 (m, 2H), 2.88 (m, 1H), 3.51 (m, 2H), 5.63 (m, 1H), 6.41 (d, 1H), 6.68 (s, 1H), 6.90 (d, 2H), 7.21-7.33 (m, 7H), 7.39 (d, 1H).

Example 46

4108.1002-007 Example 565

(R)-6-(3-hydroxypropyl)-3-((S)-1-(4-(1-methyl-6-oxo-1,6-dihydropyridin-2-yl)phenyl)ethyl)-6-phenyl-1,3-oxazinan-2-one

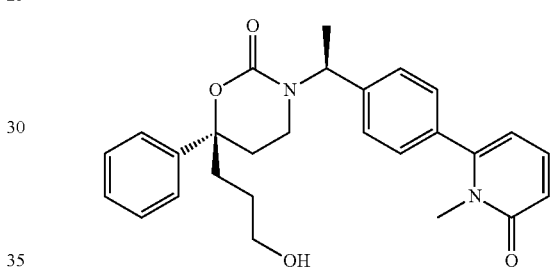

The title compound was prepared from (R)-6-(3-hydroxypropyl)-6-phenyl-3-((S)-1-(4-(4,4,5,5-tetramethyl-1,3,2-dioxaborolan-2-yl)phenyl)ethyl)-1,3-oxazinan-2-one and 6-bromo-1-methylpyridin-2(1H)-one following a procedure analogous to that described in Example 30 Step 2. LC-MS Method 2 $t_R$=1.088 min, m/z=447; $^1$H NMR (CDCl$_3$) 1.38 (m, 1H), 1.56 (d, 3H), 1.70 (m, 1H), 1.95-2.08 (m, 2H), 2.23 (m, 1H), 2.37 (s, 2H), 3.05 (m, 1H), 3.33 (s, 3H), 3.58 (m, 2H), 5.73 (m, 1H), 6.29 (d, 1H), 6.89 (d, 1H), 7.01-7.09 (m, 4H), 7.21-7.39 (m, 5H), 7.53 (t, 1H).

6-Bromo-1-methylpyridin-2(1H)-one was prepared from 6-bromopyridin-2(1H-one following a procedure analogous to that described in Example 59 Step 1.

Example 47

4108.1002-007 Example 566

(R)-6-(3-hydroxypropyl)-3-((S)-1-(4-(1-methyl-2-oxo-1,2-dihydropyridin-4-yl)phenyl)ethyl)-6-phenyl-1,3-oxazinan-2-one

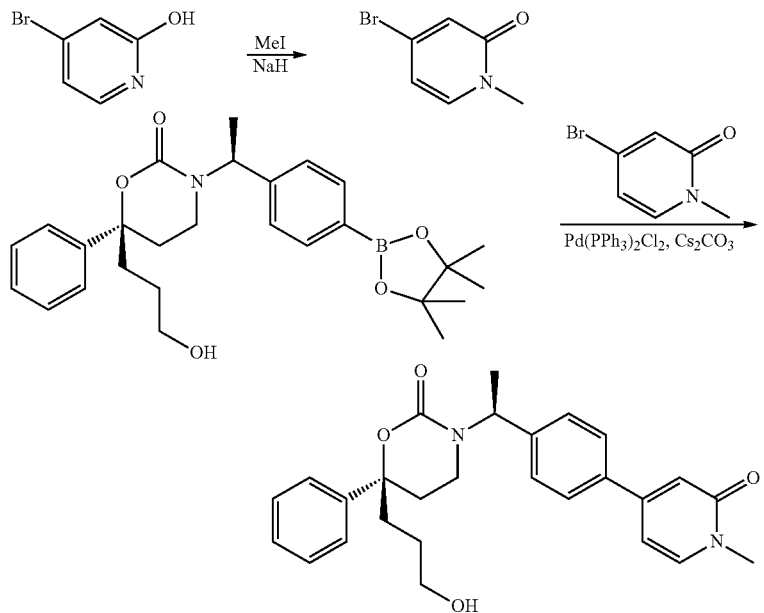

Step 1

To a suspension of NaH (80 mg, 2 mmol) in THF (10 mL) was added 4-bromopyridin-2-ol (80 mg, 0.46 mmol) at 0° C. The resulting mixture was stirred for 1 h. Then CH₃I (355 mg, 2.5 mmol) was added to the above mixture, and the mixture was stirred overnight. The reaction was quenched with aqueous NH₄Cl solution. The organic phase was concentrated to give the crude product, which was purified by column to give 4-bromo-1-methylpyridin-2(1H)-one (42.3 mg, 50%).

Step 2

A mixture of (R)-6-(3-hydroxypropyl)-6-phenyl-3-((S)-1-(4-(4,4,5,5-tetramethyl-1,3,2-dioxaborolan-2-yl)phenyl)ethyl)-1,3-oxazinan-2-one (50 mg, 0.11 mmol) and 4-bromo-1-methylpyridin-2(1H)-one (30 mg, 0.16 mmol), Pd(Ph₃P)₂Cl₂ (10 mg), and aq. Cs₂CO₃ solution (4 mL, 2 M) in 1,4-dioxane (10 mL) was stirred and heated to reflux for 2 h. When the reaction was over, the mixture was washed with water and extracted with EtOAc. The organic phase was washed with brine, dried over Na₂SO₄, filtered and concentrated to give the crude product, which was purified by preparative TLC to give (R)-6-(3-hydroxypropyl)-3-((S)-1-(4-(1-methyl-2-oxo-1,2-dihydropyridin-4-yl)phenyl)ethyl)-6-phenyl-1,3-oxazinan-2-one (25 mg, 51%). $^1$H NMR (CDCl₃): δ=1.35 (m, 1H), 1.47 (d, 3H), 1.63 (m, 2H), 1.94 (m, 2H), 2.18 (m, 1H), 2.39 (m, 2H), 2.86 (m, 1H), 3.51 (m, 5H), 5.63 (m, 1H), 6.31 (m, 1H), 6.70 (m, 1H), 6.91 (m, 2H), 7.20-7.32 (m, 8H).

Example 48

4108.1002-007 Example 588

(S)-6-(2-hydroxy-2-methylpropyl)-3-((S)-1-(4-(1-methyl-2-oxo-1,2-dihydropyridin-4-yl)phenyl)ethyl)-6-phenyl-1,3-oxazinan-2-one Method 1

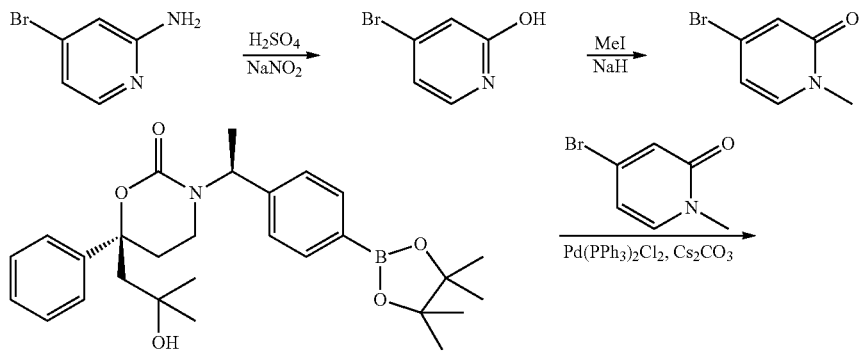

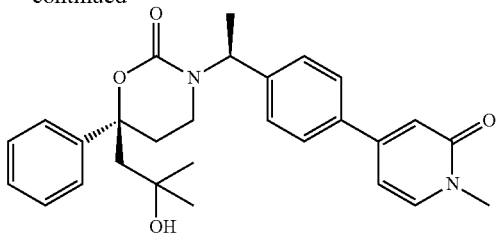

Step 1

A solution of 4-bromopyridin-2-amine (600 mg, 3.5 mmol) in a mixture of 2 M H₂SO₄ (20 mL) and 2 M Na₂NO₂ (10 mL) was stirred at 0-5° C. for 2 h. The reaction mixture was extracted with CH₂Cl₂, and the organic layer was washed with a saturated NaCl solution, dried over anhydrous Na₂SO₄ and concentrated. The residue was purified by preparative TLC to give 4-bromopyridin-2-ol (303 mg, 50%).

Step 2

To a suspension of NaH (300 mg, 7.5 mmol) in THF (10 mL) was added 4-bromopyridin-2-ol (303 mg, 1.73 mmol) at 0° C. After the resulting mixture was stirred for 1 h, CH₃I (491 mg, 3.46 mmol) was added, and the mixture was stirred overnight. The reaction was quenched with aqueous NH₄Cl solution. The organic phase was concentrated to give the crude product, which was purified by column to give 4-bromo-1-methylpyridin-2(1H)-one (161 mg, 50%).

Step 3

A mixture of (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one (200 mg, 0.42 mmol), 4-bromo-1-methylpyridin-2(1H)-one (118 mg, 0.63 mmol), Pd(Ph₃P)₂Cl₂ (20 mg), and 2 M aq Cs₂CO₃ solution (5 mL, 10 mmol) in 1,4-dioxane (20 mL) was stirred and heated to reflux for 2 h. When the reaction was finished, the mixture was washed with water and extracted with EtOAc. The organic phase was washed with brine, dried over Na₂SO₄, filtered, and concentrated to give the crude product, which was purified by preparative TLC to give (S)-6-(2-hydroxy-2-methylpropyl)-3-((S)-1-(4-(1-methyl-2-oxo-1,2-dihydropyridin-4-yl)phenyl)ethyl)-6-phenyl-1,3-oxazinan-2-one (83 mg, 43%). LC-MS Method 2 $t_R$=1.16 min, m/z=921.5; ¹H NMR (CDCl₃) 1.11 (s, 3H), 1.18 (s, 3H), 1.22 (t, 1H), 1.52 (m, 3H), 2.21 (s, 2H), 2.22-2.34 (m, 2H), 2.34-2.46 (m, 1H), 2.85 (m, 1H), 3.57 (s, 3H), 5.59 (m, 1H), 6.33 (d, 1H), 6.68 (s, 1H), 7.01 (d, 2H), 7.29-7.41 (m, 8H); ¹H NMR (CD₃OD) 0.98 (s, 3H), 1.29 (s, 3H), 1.58 (d, 3H), 2.17 (s, 2H), 2.22 (m, 1H), 2.50 (m, 2H), 3.08 (m, 1H), 3.59 (s, 3H), 5.59 (m, 1H), 6.61 (d, 1H), 6.66 (s, 1H), 7.08 (m, 2H), 7.30-7.40 (5H), 7.42 (d, 2H), 7.70 (d, 1H).

Method 2

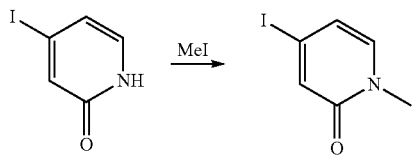

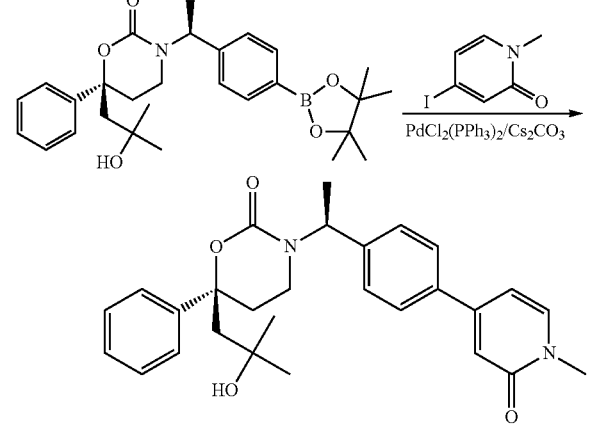

Step 1

To a solution of 4-iodopyridin-2(1H)-one (3 g, 0.013 mol) and K₂CO₃ (3.55 g, 0.026 mol) in DMF (30 mL) was added iodomethane (4.7 g, 0.033 mmol). The mixture was stirred at room temperature overnight. Water and EtOAc were added. The organic phase was dried over Na₂SO₄ and concentrated to give 4-iodo-1-methylpyridin-2(1H)-one (1.6 g, 53%).

Step 2

A mixture of 4-iodo-1-methylpyridin-2(1H)-one (0.909 g, 3.76 mmol), (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one (1.5 g, 3.13 mmol), 2 M aq Cs₂CO₃ (3 mL, 6 mmol), and PdCl₂(PPh₃)₂ (0.201 g, 0.282 mmol) in 1,4-dioxane (15 mL) was refluxed under N₂ for 2 hours. The reaction mixture was filtered, and the filtrate was extracted with EtOAc. The combined organic layer was washed with brine, dried over Na₂SO₄ and concentrated to obtain the crude compound, which was purified by preparative HPLC and chiral HPLC to obtain (S)-6-(2-hydroxy-2-methylpropyl)-3-((S)-1-(4-(1-methyl-2-oxo-1,2-dihydropyridin-4-yl)phenyl)ethyl)-6-phenyl-1,3-oxazinan-2-one (399 mg, 28%). LC-MS and ¹H NMR (CD₃OD) were the same as those of product made by Method 1. The compound was recrystallized using below methods.

The compound was obtained as a crystalline monohydrate by dropwise addition of 60 mL of water to a solution of 7.6 g of compound in 15 mL of methanol. After stirring for 1 h, the solid is filtered by suction, washed with water and diethylether and dried in an exsiccator over conc. sulphuric acid/potassium hydroxide. The compound was also recrystallized from water/ethanol (80:20) to also yield the monohydrate. Melting point: 118-122° C.

The compound was recrystallized from isopropyl acetate following a procedure analogous to that described for Example 37 in Recrystallization Method B to give a crystalline solid with mp 106-116° C. The compound was also recrystallized by this method from EtOAc (mp 90-93° C., mp 102-122° C.) from isobutyl acetate (mp 108-126° C.), from EtOH/TBME (mp 108-126° C.) and from 2-butanone.
Method 3

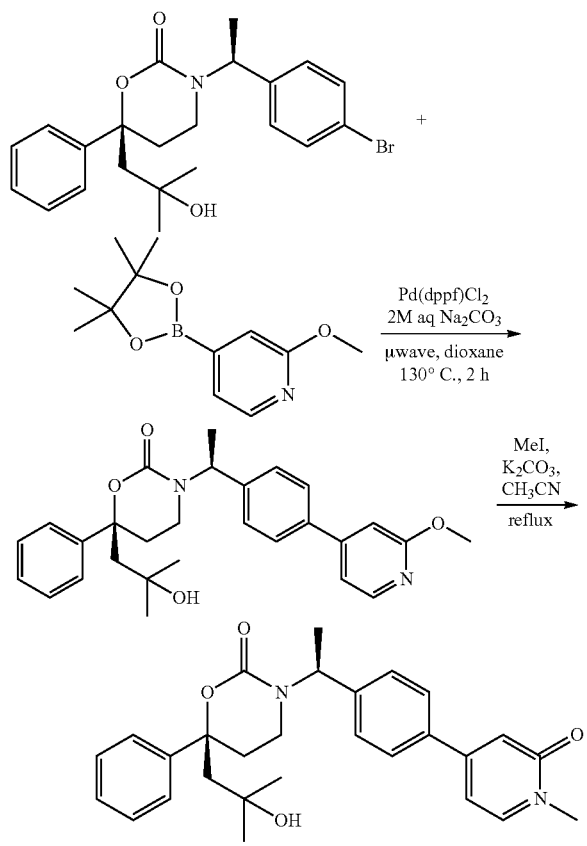

Step 1
A mixture of (S)-3-((S)-1-(4-bromophenyl)ethyl)-6-(2-hydroxy-2-methylpropyl)-6-phenyl-1,3-oxazinan-2-one (100 mg, 0.23 mmol), 2-methoxy-4-(4,4,5,5-tetramethyl-1,3,2-dioxaborolan-2-yl)pyridine (68 mg, 1.25 equiv), Pd(dppf) Cl$_2$.CH$_2$Cl$_2$ (19 mg, 10% mol), 2M aq Na$_2$CO$_3$ (1 mL), 1,4-dioxane (3 mL) was degassed, refilled with N$_2$ gas for 3 times before being put into microwave oven for 2 h at 130° C. LC-MS found the reaction was completed. The mixture was diluted with EtOAc (50 mL), washed with water (10 mL) and brine (8 mL), and dried over Na$_2$SO$_4$. After filtration and concentration, the residue was purified by chromatography on a 12-g silica gel column, eluted with a 0 to 10% MeOH in CH$_2$Cl$_2$ gradient to afford (S)-6-(2-hydroxy-2-methylpropyl)-3-((S)-1-(4-(2-methoxypyridin-4-yl)phenyl)ethyl)-6-phenyl-1,3-oxazinan-2-one (112 mg, quant yield). LC-MS Method 1 t$_R$=1.66 min, m/z=461 (M+1).
Step 2
(S)-6-(2-hydroxy-2-methylpropyl)-3-((S)-1-(4-(2-methoxypyridin-4-yl)phenyl)ethyl)-6-phenyl-1,3-oxazinan-2-one (28 mg, 0.061 mmol), potassium carbonate (17 mg, 2 equiv), and Iodomethane (40 µL, 10 equiv) were mixed with acetonitrile (2.5 mL) and heated at reflux for 4 h. After being cooled to rt, the mixture was acidified with 5% aq HCl and purified by prep HPLC to afford (S)-6-(2-hydroxy-2-methylpropyl)-3-((S)-1-(4-(1-methyl-2-oxo-1,2-dihydropyridin-4-yl)phenyl)ethyl)-6-phenyl-1,3-oxazinan-2-one (14.4 mg, 52%). LC-MS and $^1$H NMR (CD$_3$OD) were the same as those of product made by Method 1.

Example 49

4108.1002-007 Example 593

2,2-dimethyl-3-((R)-3-((S)-1-(4-(1-methyl-6-oxo-1,6-dihydropyridin-3-yl)phenyl)ethyl)-2-oxo-6-phenyl-1,3-oxazinan-6-yl)propanenitrile

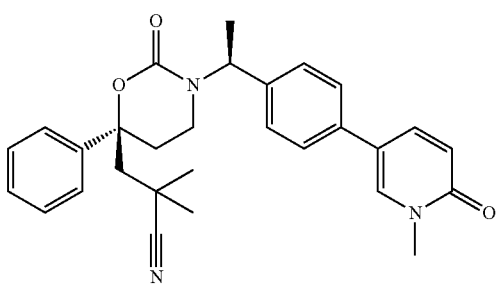

Method 1
The title compound was prepared from 2,2-dimethyl-3-((R)-2-oxo-6-phenyl-3-((S)-1-(4-(4,4,5,5-tetramethyl-1,3,2-dioxaborolan-2-yl)phenyl)ethyl)-1,3-oxazinan-6-yl)propanenitrile and 5-bromo-1-methylpyridin-2(1H)-one following a procedure analogous to that described in Example 6 Step 1. LC-MS Method 2 t$_R$=1.231 min, m/z=470.1; $^1$H NMR (CDCl$_3$) 1.28 (s, 3H), 1.40 (s, 3H), 1.47 (d, 3H), 2.09 (s, 2H), 2.21 (m, 1H), 2.41 (m, 2H), 2.83 (m, 1H), 3.52 (s, 3H), 5.56 (m, 1H), 6.58 (d, 1H), 6.82 (d, 2H), 7.02 (d, 2H), 7.30 (m, 6H), 7.43 (m, 1H).
Method 2

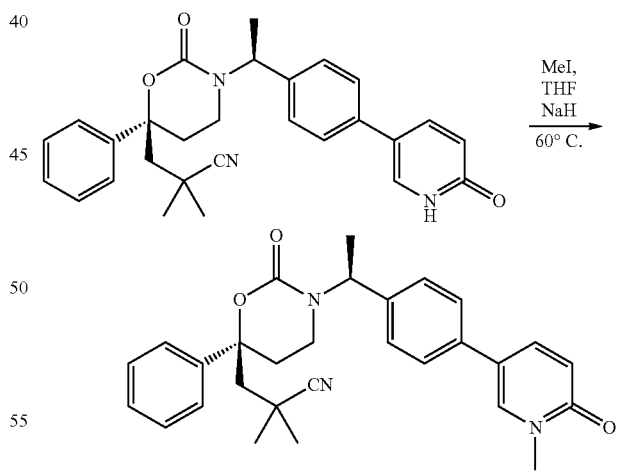

A solution of 2,2-dimethyl-3-((R)-2-oxo-3-((S)-1-(4-(6-oxo-1,6-dihydropyridin-3-yl)phenyl)ethyl)-6-phenyl-1,3-oxazinan-6-yl)propanenitrile (202 mg, 0.444 mmol) and MeI (110 µL, 4 equiv) in dry THF (5 mL) was cooled to 0° C. NaH (60% in mineral oil, 36 mg, 2 equiv) was added. After 10 min, the mixture was warmed to rt slowly and stirred for 3 h. LC-MS showed about 50% conversion. The mixture was heated for 1 h at 60° C. LC-MS found the reaction completed. After cooling to rt, the mixture was cooled to 0° C. and quenched with satd aq NH₄Cl (3 mL). The mixture was then diluted with CH₂Cl₂ (20 mL), washed with 1% aq HCl (5 mL) and brine (4 mL), and dried over Na₂SO₄. After filtration and concentration, the residue was purified by prep HPLC to afford 2,2-dimethyl-3-((R)-3-((S)-1-(4-(1-methyl-6-oxo-1,6-dihydropyridin-3-yl)phenyl)ethyl)-2-oxo-6-phenyl-1,3-oxazinan-6-yl)propanenitrile (177.4 mg, 85% yield) product as a light brown oil.

Method 3

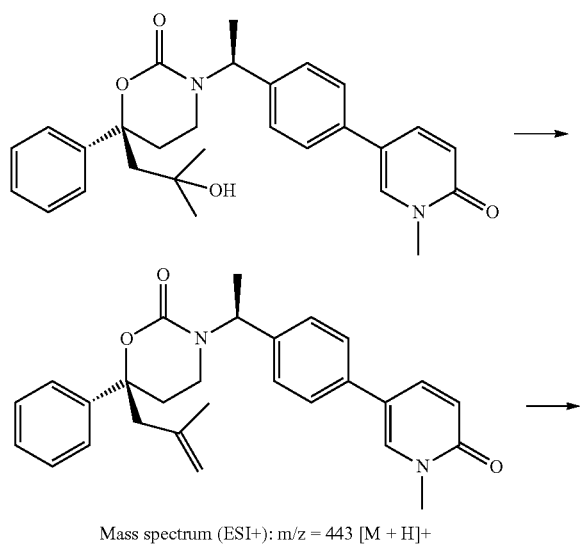

Mass spectrum (ESI+): m/z = 443 [M + H]+

Mass spectrum (ESI+): m/z = 470 [M + H]+

2,2-Dimethyl-3-(3-{(S)-1-[4-(1-methyl-6-oxo-1,6-dihydro-pyridin-3-yl)-phenyl]-ethyl}-2-oxo-(S)-6-phenyl-[1,3]oxazinan-6-yl)-propionitrile was prepared from (S)-6-(2-hydroxy-2-methylpropyl)-3-((S)-1-(4-(1-methyl-6-oxo-1,6-dihydropyridin-3-yl)phenyl)ethyl)-6-phenyl-1,3-oxazinan-2-one following procedures analogous to those described Example 71 Method 2 to prepare 3-((R)-3-((S)-1-(4-bromophenyl)ethyl)-2-oxo-6-phenyl-1,3-oxazinan-6-yl)-2,2-dimethylpropanenitrile. (S)-6-(2-hydroxy-2-methyl-propyl)-3-{(S)-1-[4-(1-methyl-6-oxo-1,6-dihydro-pyridin-3-yl)-phenyl]ethyl}-6-phenyl-[1,3]oxazinan-2-one, is obtained from coupling (S)-6-(2-hydroxy-2-methylpropyl)-6-phenyl-3-[(S)-1-(4-(4,4,5,5-tetramethyl-1,3,2-dioxaborolan-2-yl)phenyl)ethyl]-1,3-oxazinan-2-one with 5-iodo-1-methyl-1H-pyridin-2-one by the action of Pd(PPh₃)₄ and 2 M aqueous Na₂CO₃ solution in a mixture of methanol and dioxane (1:3) at 80° C. The compound that had been obtained as a foam was dissolved in a small amount of ethyl acetate and stirred overnight at rt. The solid was filtered by suction, washed with a small amount of diethylether and dried. Melting point: 143-145° C.

Example 50

4108.1002-007 Example 594

2,2-dimethyl-3-((R)-3-((S)-1-(4-(1-methyl-2-oxo-1,2-dihydropyridin-4-yl)phenyl)ethyl)-2-oxo-6-phenyl-1,3-oxazinan-6-yl)propanenitrile

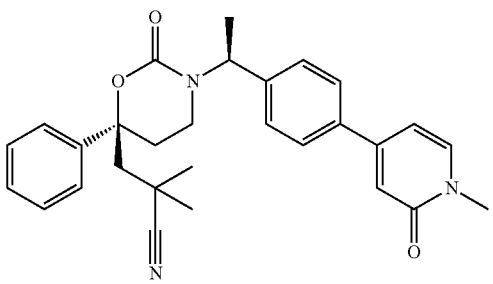

Method 1

The title compound was prepared from 2,2-dimethyl-3-((R)-2-oxo-6-phenyl-3-((S)-1-(4-(4,4,5,5-tetramethyl-1,3,2-dioxaborolan-2-yl)phenyl)ethyl)-1,3-oxazinan-6-yl)propanenitrile and 4-bromo-1-methylpyridin-2(1H)-one following a procedure analogous to that described in Example 6 Step 1. LC-MS Method 2 $t_R$=1.103, m/z=470.4; ¹H NMR (CDCl₃) 1.26 (s, 3H), 1.41 (s, 3H), 1.49 (d, 3H), 2.09 (s, 2H), 2.24 (m, 1H), 2.53 (m, 2H), 2.88 (m, 1H), 3.56 (s, 3H), 5.59 (m, 1H), 6.38 (d, 1H), 6.78 (s, 1H), 6.84 (d, 2H), 7.19 (m, 2H), 7.31 (m, 6H).

Method 2

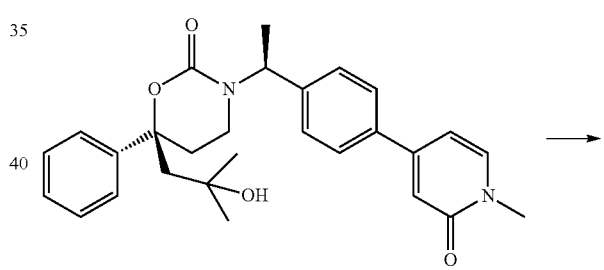

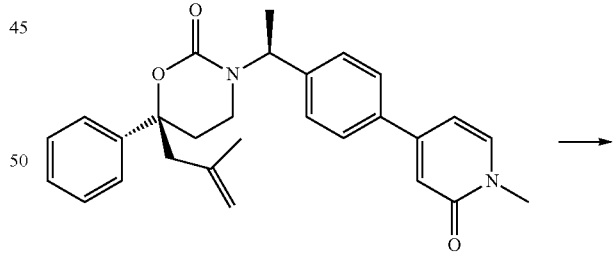

Mass spectrum (ESI+): m/z = 443 [M + H]+

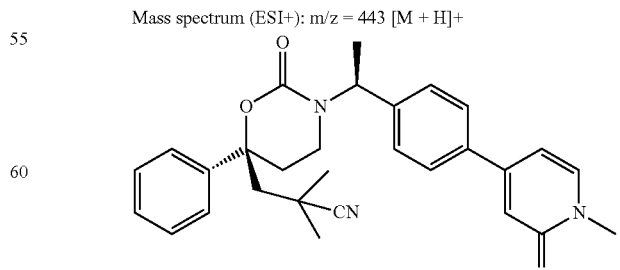

Mass spectrum (ESI+): m/z = 470 [M + H]+

(S)-2,2-Dimethyl-3-(3-{1-[(S)-4-(1-methyl-2-oxo-1,2-dihydro-pyridin-4-yl)-phenyl]-ethyl}-2-oxo-6-phenyl-[1,3]oxazinan-6-yl)-propionitrile was prepared from (S)-6-(2-hydroxy-2-methylpropyl)-3-((S)-1-(4-(1-methyl-2-oxo-1,2-dihydropyridin-4-yl)phenyl)ethyl)-6-phenyl-1,3-oxazinan-2-one following procedures analogous to those described in Example 71 Method 2 to prepare 3-((R)-3-((S)-1-(4-bromophenyl)ethyl)-2-oxo-6-phenyl-1,3-oxazinan-6-yl)-2,2-dimethylpropanenitrile. The starting compound, (S)-6-(2-hydroxy-2-methyl-propyl)-3-{(S)-1-[4-(1-methyl-2-oxo-1,2-dihydro-pyridin-4-yl)-phenyl]-ethyl}-6-phenyl-[1,3]oxazinan-2-one, is obtained from coupling (S)-6-(2-hydroxy-2-methylpropyl)-6-phenyl-3-[(S)-1-(4-(4,4,5,5-tetramethyl-1,3,2-dioxaborolan-2-yl)phenyl)ethyl]-1,3-oxazinan-2-one with trifluoro-methanesulfonic acid 1-methyl-2-oxo-1,2-dihydro-pyridin-4-ylester employing the standard conditions, Pd(dppf)Cl$_2$*CH$_2$Cl$_2$, 2 M aqueous Na$_2$CO$_3$ solution, DMF, 90° C., 2 h. The compound that had been obtained as a resin was dissolved in a small amount of EtOAc and stirred overnight at rt. The solid was filtered by suction, washed with a small amount of diethylether and dried. Melting point: 195-198° C.

Example 51

4108.1002-007 Example 603

2,2-dimethyl-3-((R)-3-((S)-1-(4-(1-methyl-2-oxo-1,2-dihydropyridin-4-yl)phenyl)ethyl)-2-oxo-6-phenyl-1,3-oxazinan-6-yl)propanamide

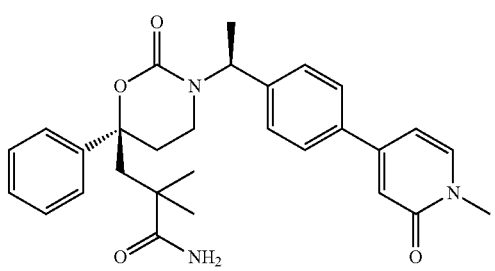

The title compound was prepared from 2,2-dimethyl-3-((R)-2-oxo-6-phenyl-3-((S)-1-(4-(4,4,5,5-tetramethyl-1,3,2-dioxaborolan-2-yl)phenyl)ethyl)-1,3-oxazinan-6-yl)propanenitrile and 4-bromo-1-methylpyridin-2(1H)-one following a procedure analogous to that described in Example 6 Step 1, followed by treatment with H$_2$O$_2$, K$_2$CO$_3$. LC-MS Method 2 t$_R$=1.133 min, m/z=488.1; $^1$H NMR (CDCl$_3$) 1.12 (s, 3H), 1.19 (s, 3H), 1.49 (d, 3H), 2.09-2.28 (m, 3H), 2.32-2.58 (m, 2H), 2.89 (m, 1H), 3.59 (s, 3H), 5.61 (m, 1H), 6.54 (m, 1H), 6.88 (m, 1H), 6.97-7.10 (m, 2H), 7.28 (m, 6H), 7.42 (m, 1H), 7.53 (m, 1H).

Example 52

4108.1002-007 Example 614

(S)-3-((S)-1-(4-(1-ethyl-6-oxo-1,6-dihydropyridin-3-yl)phenyl)propyl)-6-(2-hydroxy-2-methylpropyl)-6-phenyl-1,3-oxazinan-2-one

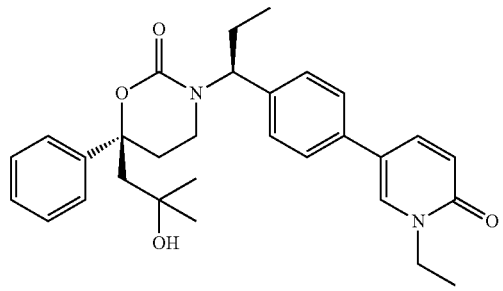

The title compound was prepared from (R)-6-allyl-3-((S)-1-(4-bromophenyl)propyl)-6-phenyl-1,3-oxazinan-2-one following a procedure analogous to that described in Example 32 Method 2 using 5-bromo-1-ethylpyridin-2(1H)-one in Step 4. LC-MS Method 2 t$_R$=1.732 min, m/z=475.1; $^1$H NMR (CDCl$_3$) 0.95 (s, 3H), 1.01 (t, 3H), 1.26 (s, 3H), 1.38 (t, 3H), 2.06 (m, 2H), 2.18-2.31 (m, 3H), 2.36 (m, 1H), 2.55 (m, 1H), 3.04 (m, 1H), 4.11 (m, 2H), 5.37 (m, 1H), 6.66 (d, 1H), 7.11 (m, 2H), 7.20-7.33 (m, 7H), 7.76 (d, 1H), 7.88 (s, 1H).

Example 53

4108.1002-007 Example 615

(S)-3-((S)-1-(4-(1-ethyl-6-oxo-1,6-dihydropyridin-3-yl)phenyl)ethyl)-6-(2-hydroxy-2-methylpropyl)-6-phenyl-1,3-oxazinan-2-one

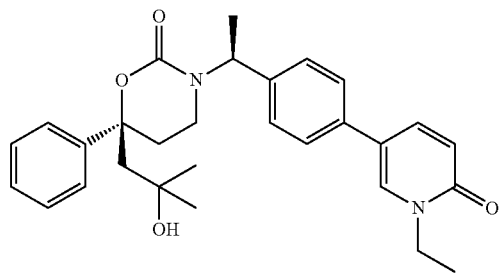

The title compound was prepared from (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one and 5-bromo-1-ethylpyridin-2(1H)-one following a procedure analogous to that described in Example 6 Step 1. LC-MS Method 2 t$_R$=1.224 min, m/z=475.1; $^1$H NMR (CDCl$_3$) 1.11 (s, 3H), 1.19 (s, 3H), 1.39 (t, 3H), 1.56 (d, 3H), 2.20 (s, 2H), 2.26 (m, 1H), 2.36-2.57 (m, 2H), 2.87 (m, 1H), 4.03 (m, 2H), 5.69 (m, 1H), 6.62 (d, 1H), 7.00 (d, 2H), 7.17 (d, 2H), 7.28-7.51 (m, 6H), 7.50 (d, 1H). Recrystallization from isopropyl acetate following a procedure analogous to that described for Example 37 in Recrystallization Method B afforded a crystalline solid with mp 167-168° C.

Example 54

4108.1002-007 Example 616

(S)-6-(2-hydroxy-2-methylpropyl)-3-((S)-1-(4-(1-methyl-6-oxo-1,6-dihydropyridin-3-yl)phenyl)propyl)-6-phenyl-1,3-oxazinan-2-one

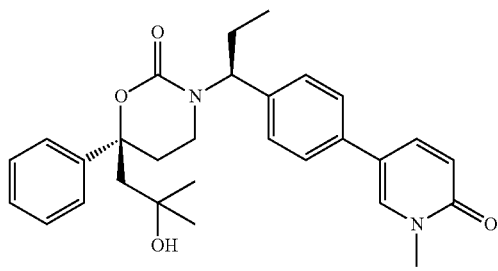

The title compound was prepared from (R)-6-allyl-3-((S)-1-(4-bromophenyl)propyl)-6-phenyl-1,3-oxazinan-2-one following a procedure analogous to that described in Example 32 Method 2 using 5-bromo-1-methylpyridin-2(1H)-one in Step 4. LC-MS Method 2 $t_R$=1.746 min, m/z=475.2; $^1$H NMR (CD$_3$OD) 1.04 (t, 3H), 1.11 (s, 3H), 1.24 (s, 3H), 1.95-2.04 (m, 2H), 2.13-2.26 (m, 4H), 2.44 (m, 1H), 2.91 (m, 1H), 3.61 (s, 3H), 5.36 (m, 1H), 6.67 (d, 1H), 7.10-7.33 (m, 8H), 7.42 (s, 1H), 7.55 (d, 1H).

Example 55

4108.1002-007 Example 618

(S)-6-(2-hydroxy-2-methylpropyl)-3-((S)-1-(4-(1-methyl-2-oxo-1,2-dihydropyridin-4-yl)phenyl)propyl)-6-phenyl-1,3-oxazinan-2-one

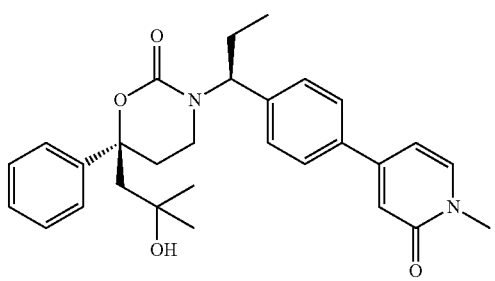

The title compound was prepared from (S)-6-(2-hydroxy-2-methylpropyl)-6-phenyl-3-((S)-1-(4-(4,4,5,5-tetramethyl-1,3,2-dioxaborolan-2-yl)phenyl)propyl)-1,3-oxazinan-2-one and 4-bromo-1-methylpyridin-2(1H)-one following a procedure analogous to that described in Example 59 Step 2. LC-MS Method 2 $t_R$=1.203 min, m/z=971.4; $^1$H NMR (CDCl$_3$) 0.97 (t, 3H), 1.12 (s, 3H), 1.19 (s, 3H), 1.79-2.02 (m, 2H), 2.11-2.24 (m, 4H), 2.29-2.42 (m, 1H), 2.81 (m, 1H), 3.50 (s, 3H), 5.40 (m, 1H), 6.28 (d, 1H), 6.64 (s, 1H), 7.02 (d, 2H), 7.18 (m, 3H), 7.20 (m, 2H), 7.28 (m, 3H).

Example 56

4108.1002-007 Example 622

(R)-6-ethyl-3-((S)-1-(4-(1-methyl-6-oxo-1,6-dihydropyridin-3-yl)phenyl)propyl)-6-phenyl-1,3-oxazinan-2-one

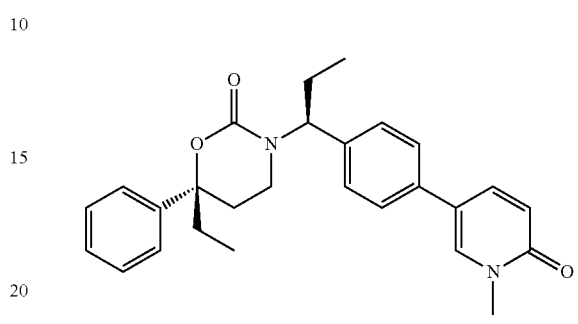

The title compound was prepared from (R)-3-((S)-1-(4-bromophenyl)propyl)-6-ethyl-6-phenyl-1,3-oxazinan-2-one following procedures analogous to those described in Example 32 Method 2 Steps 3 and 4. LC-MS Method 1 $t_R$=1.6 min, m/z=431 (M+1).

(R)-3-((S)-1-(4-bromophenyl)propyl)-6-ethyl-6-phenyl-1,3-oxazinan-2-one was prepared from 1-chloro-3-phenylpentan-3-ol and (S)-1-(4-bromophenyl)propan-1-amine following a procedure analogous to that described in Example 71 Step 2.

1-chloro-3-phenylpentan-3-ol was prepared from 3-chloro-1-phenylpropan-1-one and ethylmagnesium bromide following a procedure analogous to that described in Preparation 1 Method 1 Step 2.

Example 57

4108.1002-007 Example 623

(R)-6-ethyl-3-((S)-1-(4-(1-ethyl-6-oxo-1,6-dihydropyridin-3-yl)phenyl)propyl)-6-phenyl-1,3-oxazinan-2-one

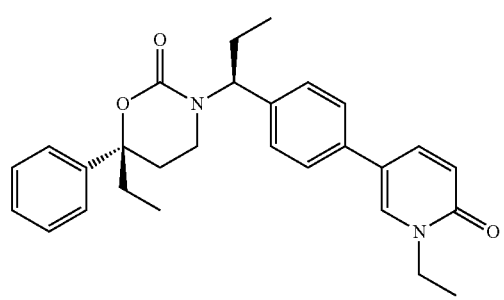

The title compound was prepared from (R)-3-((S)-1-(4-bromophenyl)propyl)-6-ethyl-6-phenyl-1,3-oxazinan-2-one following procedures analogous to those described in Example 32 Method 2 Steps 3 and 4 using 5-bromo-1-ethylpyridin-2(1H)-one in Step 4. LC-MS Method 1 $t_R$=1.68 min, m/z=445 (M+1).

Example 58

4108.1002-007 Example 624

(R)-6-ethyl-3-((S)-1-(4-(1-methyl-2-oxo-1,2-dihydropyridin-4-yl)phenyl)propyl)-6-phenyl-1,3-oxazinan-2-one

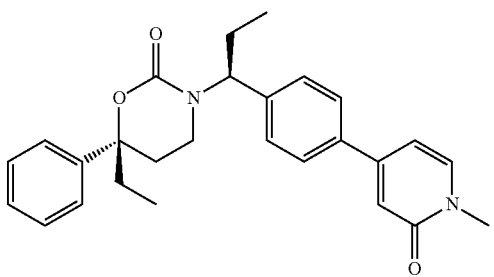

The title compound was prepared from (R)-3-((S)-1-(4-bromophenyl)propyl)-6-ethyl-6-phenyl-1,3-oxazinan-2-one following procedures analogous to those described in Example 32 Method 2 Steps 3 and 4 using 4-iodo-1-methylpyridin-2(1H)-one in Step 4. LC-MS Method 1 $t_R$=1.58 min, m/z=431 (M+1); $^1$H NMR (CDCl$_3$) 7.33 (1H, d, J=7.03 Hz), 7.29-7.21 (7H, m), 7.01 (2H, d, J=8.20 Hz), 6.75 (1H, d, J=2.05), 6.39 (1H, dd, J=2.05, 7.03), 5.48 (1H, ap dd, J=6.44, 9.66), 3.58 (3H, s), 2.95-2.87 (1H, m), 2.37-2.14 (3H, m), 2.06-1.81 (m, 4H), 1.00 (3H, t, J=7.32), 082 (3H, t, J=7.61).

Example 59

4108.1002-007 Example 628

(S)-6-(2-hydroxy-2-methylpropyl)-3-((S)-1-(4-(1-isopropyl-6-oxo-1,6-dihydropyridin-3-yl)phenyl)ethyl)-6-phenyl-1,3-oxazinan-2-one

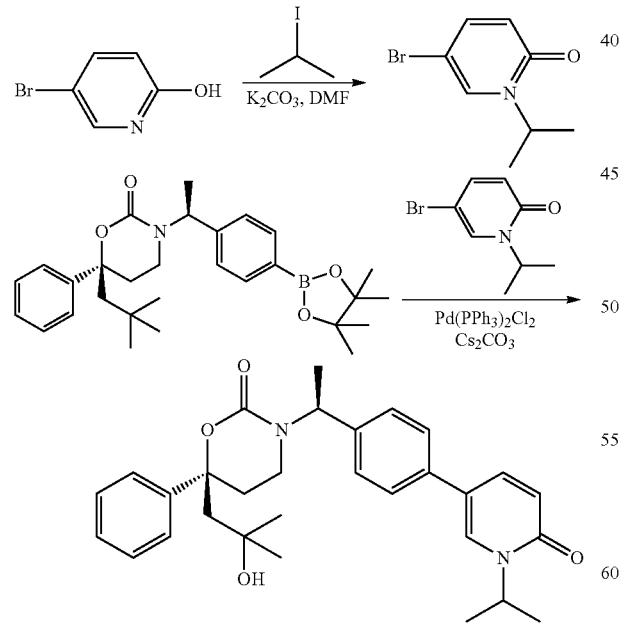

Step 1
To a solution of 5-bromopyridin-2-ol (1 g, 5.75 mmol) in DMF (10 mL) were added 2-iodopropane (4.9 g, 28.75 mmol) and K$_2$CO$_3$ (4 g, 28.75 mmol). The mixture was stirred at rt overnight. The mixture was diluted with water (20 mL) extracted with EtOAc (3×25 mL), the combined organic phase was washed with brine, dried over Na$_2$SO$_4$, concentrated and purified by prep TLC to give 5-bromo-1-isopropylpyridin-2(1H)-one (380 mg, 31%). $^1$H NMR (CDCl$_3$): 1.35 (d, 6H), 5.65-5.75 (m, 1H), 6.48 (d, 1H), 7.30 (m, 1H), 7.41 (d, 1H).

Step 2
To a solution of (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one (100 mg, 0.21 mmol) in 1,4-dioxane (2 mL) was added 5-bromo-1-isopropylpyridin-2(1H)-one (54.2 mg, 0.25 mmol). Then catalysts of Pd(PPh$_3$)$_2$Cl$_2$ (14 mg, 0.02 mmol), Cs$_2$CO$_3$ (1 mL, 2 M) were added. The vessel was sealed with a septum and placed into the microwave cavity. Microwave irradiation of 100 W was used, the temperature being ramped from room temperature to 120° C. Once this temperature was reached, the reaction mixture was held at this temperature for 30 min. After the mixture cooled to rt, the mixture was filtered. The filtrate was extracted with EtOAc (20 mL×4), the organic layer was washed with brine, dried over Na$_2$SO$_4$ and concentrated to give the crude product which was purified by preparative HPLC to give (S)-6-(2-hydroxy-2-methylpropyl)-3-((S)-1-(4-(1-isopropyl-6-oxo-1,6-dihydropyridin-3-yl)phenyl)ethyl)-6-phenyl-1,3-oxazinan-2-one (22 mg, 21%). $^1$H NMR (CDCl$_3$): 1.13 (s, 3H), 1.19 (s, 3H), 1.40 (6H), 1.53 (d, 3H), 2.18-2.30 (m, 4H), 2.40 (m, 1H), 2.88 (m, 1H), 5.31 (m, 1H), 5.70 (m, 1H), 6.73 (d, 1H), 7.02 (d, 2H), 7.15 (d, 2H), 7.27-7.38 (m, 5H), 7.43 (d, 1H), 7.50 (d, 1H).

Example 60

4108.1002-007 Example 630

(R)-6-ethyl-3-((S)-1-(4-(1-isopropyl-6-oxo-1,6-dihydropyridin-3-yl)phenyl)propyl)-6-phenyl-1,3-oxazinan-2-one

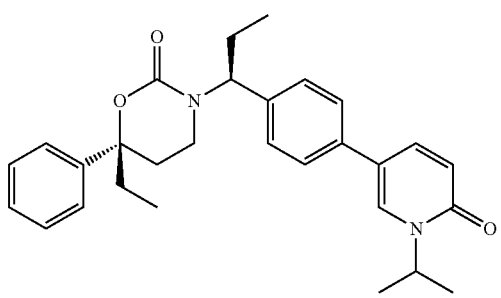

The title compound was prepared from (R)-3-((S)-1-(4-bromophenyl)propyl)-6-ethyl-6-phenyl-1,3-oxazinan-2-one following procedures analogous to those described in Example 32 Method 2 Steps 3 and 4 using 5-bromo-1-isopropylpyridin-2(1H)-one in Step 4. LC-MS Method 1 $t_R$=1.75 min, m/z=459 (M+1); $^1$H NMR (CDCl$_3$) 7.49, (1H, dd, J=2.34, 9.37 Hz), 7.42 (1H, d, J=2.34 Hz), 7.32-7.24 (5H, m), 7.13 (1H, d, J=8.20), 7.04 (1H, d, J=8.49), 6.66 (1H, d, J=9.37), 5.49 (1H, aq q, J=6.44, 9.37), 5.33 (1H, m), 2.96-2.91 (1H, m), 2.39-2.32 (1H, m), 2.29-2.17 (2H, m), 2.05-1.85 (m, 4H), 1.41 (6H, dd, J=1.17, 6.73), 1.01 (3H, t, J=7.32 Hz), 0.832 (3H, t, J=7.32 Hz).

5-bromo-1-isopropylpyridin-2(1H)-one was prepared from 5-bromopyridin-2(1H)-one and isopropyl iodide following a procedure analogous to that described in Example 59 Step 1.

Example 61

4108.1002-007 Example 637

(S)-3-((S)-1-(4-(1,5-dimethyl-6-oxo-1,6-dihydropyridin-3-yl)phenyl)ethyl)-6-(2-hydroxy-2-methylpropyl)-6-phenyl-1,3-oxazinan-2-one

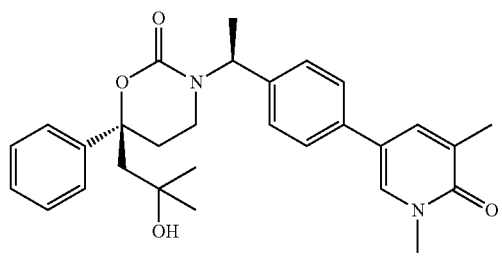

The title compound was prepared following a procedure analogous to that described in Example 59 using 1 5-bromo-3-methylpyridin-2(1H)-one and methyl iodide in Step 1. LC-MS Method 2 $t_R$=1.197 min, m/z=475.1; $^1$H NMR (CDCl$_3$) 1.04 (s, 3H), 1.11 (s, 3H), 1.46 (d, 3H), 2.18 (m, 5H), 2.21 (m, 1H), 2.29-2.40 (m, 1H), 2.80 (m, 1H), 3.41 (s, 3H), 3.56 (s, 3H), 5.60 (m, 1H), 6.91 (d, 2H), 7.07 (d, 2H), 7.21-7.40 (m, 7H).

Example 62

4108.1002-007 Example 638

(S)-3-((S)-1-(4-(1-ethyl-6-oxo-1,6-dihydropyridin-3-yl)phenyl)ethyl)-6-(4-fluorophenyl)-6-(2-hydroxy-2-methylpropyl)-1,3-oxazinan-2-one

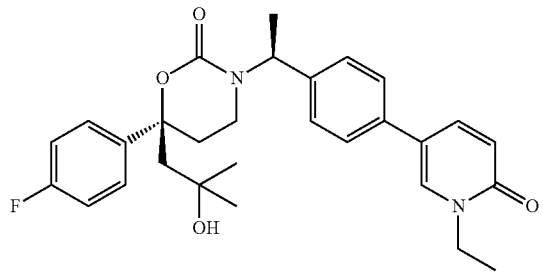

The title compound was prepared following a procedure analogous to that described in Example 59, using 5-bromopyridin-2(1H)-one and ethyl iodide in Step 1 and (S)-6-(4-fluorophenyl)-6-(2-hydroxy-2-methylpropyl)-3-((S)-1-(4-(4,4,5,5-tetramethyl-1,3,2-dioxaborolan-2-yl)phenyl)ethyl)-1,3-oxazinan-2-one in Step 2. LC-MS Method 2 $t_R$=1.205 min, m/z=493.2; $^1$H NMR (CDCl$_3$) 1.16 (d, 6H), 1.39 (t, 3H), 1.52 (d, 3H), 2.19 (s, 4H), 2.20-2.31 (m, 2H), 2.38-2.50 (m, 1H), 2.90 (m, 1H), 4.04 (m, 2H), 5.69 (m, 1H), 6.66 (d, 1H), 7.00 (m, 4H), 7.18 (d, 2H), 7.30 (m, 2H), 7.41 (s, 1H), 7.51 (d, 1H). Recrystallization from isopropyl acetate following a procedure analogous to that described for Example 37 in Recrystallization Method B afforded a crystalline solid with mp 172-173.6° C.

Example 63

4108.1002-007 Example 639

(R)-6-methyl-3-((S)-1-(4-(1-methyl-2-oxo-1,2-dihydropyridin-4-yl)phenyl)propyl)-6-phenyl-1,3-oxazinan-2-one

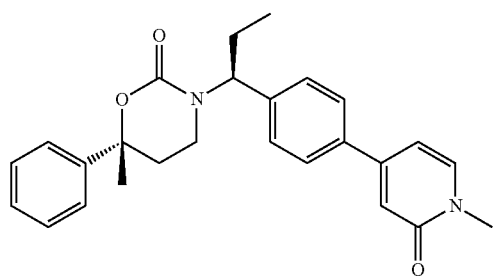

The title compound was prepared from (R)-3-((S)-1-(4-bromophenyl)propyl)-6-methyl-6-phenyl-1,3-oxazinan-2-one following procedures analogous to those described in Example 32 Method 2 Steps 3 and 4 using 4-iodo-1-methylpyridin-2(1H)-one in Step 4. LC-MS Method 1 $t_R$=1.55 min, m/z=417 (M+1); $^1$H NMR (CDCl$_3$) 7.41 (1H, d, J=7.03 Hz), 7.33 (2H, d, J=8.20 Hz), 7.29-7.19 (5H, m), 7.10 (1H, d, J=8.20), 6.95 (1H, d=1.76), 6.55 (1H, dd, J=2, 7.03 Hz), 5.51 (1H, q, J=6.49, 9.66 Hz), 3.65 (3H, s), 3.00-2.95 (1H, m), 2.44-2.36 (1H, m), 2.33-2.15 (2H, m), 2.06-1.86 (2H, m), 1.64 (3H, s), 1.02 (3H, t, J=7.32 Hz).

(R)-3-((S)-1-(4-bromophenyl)propyl)-6-methyl-6-phenyl-1,3-oxazinan-2-one was prepared from 4-chloro-2-phenylbutan-2-ol and (S)-1-(4-bromophenyl)propan-1-amine following a procedure analogous to that described in Example 71 Step 2.

4-chloro-2-phenylbutan-2-ol was prepared from 3-chloro-1-phenylpropan-1-one and methylmagnesium bromide following a procedure analogous to that described in Preparation 1 Method 1 Step 2.

Example 64

4108.1002-007 Example 641

(S)-3-((S)-1-(4-(1,6-dimethyl-2-oxo-1,2-dihydropyridin-4-yl)phenyl)ethyl)-6-(2-hydroxy-2-methylpropyl)-6-phenyl-1,3-oxazinan-2-one

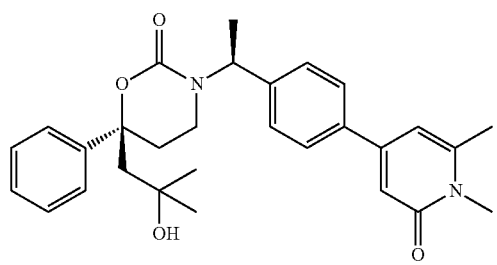

The title compound was prepared from (S)-6-(2-hydroxy-2-methylpropyl)-6-phenyl-3-((S)-1-(4-(4,4,5,5-tetramethyl- 1,3,2-dioxaborolan-2-yl)phenyl)propyl)-1,3-oxazinan-2-one and 4-bromo-1,6-dimethylpyridin-2(1H)-one following a procedure analogous to that described in Example 6 Step 1. LC-MS Method 2 $t_R$=1.173 min, m/z=475.2; $^1$H NMR (CDCl$_3$) 1.10 (s, 3H), 1.16 (s, 3H), 1.51 (d, 3H), 2.18 (m, 3H), 2.21 (m, 1H), 2.42 (m, 4H), 2.86 (m, 1H), 3.54 (s, 3H), 5.66 (m, 1H), 6.21 (s, 1H), 6.60 (s, 1H), 6.97 (m, 2H), 7.23-7.34 (m, 7H).

4-bromo-1,6-dimethylpyridin-2(1H)-one was prepared by methylation of 4-bromo-6-methylpyridin-2(1H)-one with methyl iodide using K$_2$CO$_3$ following a procedure analogous to that described in Example 59 Step 1.

Example 65

4108.1002-007 Example 642

(S)-3-((S)-1-(4-(1-ethyl-2-oxo-1,2-dihydropyridin-4-yl)phenyl)ethyl)-6-(2-hydroxy-2-methylpropyl)-6-phenyl-1,3-oxazinan-2-one

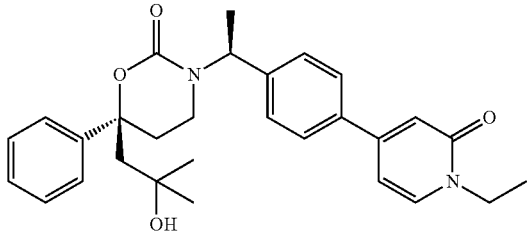

The title compound was prepared from (S)-6-(2-hydroxy-2-methylpropyl)-6-phenyl-3-((S)-1-(4-(4,4,5,5-tetramethyl-1,3,2-dioxaborolan-2-yl)phenyl)propyl)-1,3-oxazinan-2-one and 1-ethyl-4-iodopyridin-2(1H)-one following a procedure analogous to that described in Example 6 Step 1. LC-MS Method 2 $t_R$=1.228 min, m/z=971.4; $^1$H NMR (CDCl$_3$) 1.10 (s, 3H), 1.14 (s, 3H), 1.36 (m, 3H), 1.53 (d, 3H), 2.17 (s, 2H), 2.21-2.32 (m, 2H), 2.32-2.48 (m, 1H), 2.88 (m, 1H), 4.00 (m, 2H), 5.68 (m, 1H), 6.39 (d, 1H), 6.78 (s, 1H), 6.99 (d, 2H), 7.27-7.38 (m, 8H).

1-ethyl-4-iodopyridin-2(1H)-one was prepared from 4-iodopyridin-2(1H)-one and ethyl iodide following a procedure analogous to that described in Example 59 Step 1.

Example 66

4108.1002-007 Example 643

(S)-6-(2-hydroxy-2-methylpropyl)-3-((S)-1-(4-(2-oxo-1-(2,2,2-trifluoroethyl)-1,2-dihydropyridin-4-yl)phenyl)ethyl)-6-phenyl-1,3-oxazinan-2-one

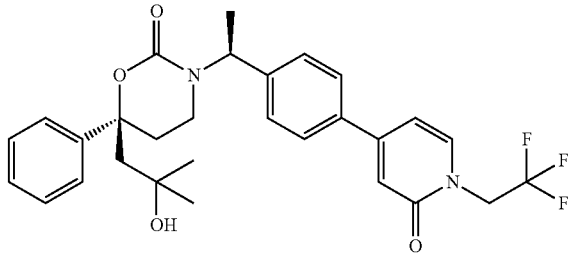

The title compound was prepared from (S)-6-(2-hydroxy-2-methylpropyl)-6-phenyl-3-((S)-1-(4-(4,4,5,5-tetramethyl-1,3,2-dioxaborolan-2-yl)phenyl)propyl)-1,3-oxazinan-2-one and 4-iodo-1-(2,2,2-trifluoroethyl)pyridin-2(1H)-one following a procedure analogous to that described in Example 6 Step 1. LC-MS Method 2 $t_R$=1.871 min, m/z=471.1; $^1$H NMR (CDCl$_3$) 1.11 (s, 3H), 1.17 (s, 3H), 1.53 (d, 3H), 2.16-2.33 (m, 4H), 2.35-2.47 (m, 1H), 2.89 (m, 1H), 4.58-4.70 (m, 2H), 5.69 (m, 1H), 6.71 (s, 1H), 7.00 (d, 2H), 7.19-7.38 (m, 8H). Recrystallization from isopropyl acetate following a procedure analogous to that described for Example 37 in Recrystallization Method B afforded a crystalline solid with mp 144-145.5° C.

4-iodo-1-(2,2,2-trifluoroethyl)pyridin-2(1H)-one was prepared from 4-iodopyridin-2(1H)-one and 2,2,2-trifluoroethyl trifluoromethanesulfonate following a procedure analogous to that described in Example 59 Step 1.

Example 67

4108.1002-007 Example 646

(S)-6-(2-hydroxy-2-methylpropyl)-3-((S)-1-(4-(6-oxo-1-(2,2,2-trifluoroethyl)-1,6-dihydropyridin-3-yl)phenyl)ethyl)-6-phenyl-1,3-oxazinan-2-one

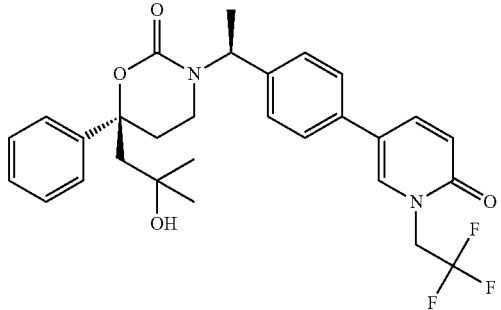

The title compound was prepared from (S)-6-(2-hydroxy-2-methylpropyl)-6-phenyl-3-((S)-1-(4-(4,4,5,5-tetramethyl-1,3,2-dioxaborolan-2-yl)phenyl)propyl)-1,3-oxazinan-2-one and 5-bromo-1-(2,2,2-trifluoroethyl)pyridin-2(1H)-one following a procedure analogous to that described in Example 6 Step 1. LC-MS Method 2 $t_R$=1.323 min, m/z=471.1; $^1$H NMR (CDCl$_3$) 1.13 (s, 3H), 1.19 (s, 3H), 1.53 (d, 3H), 2.19-2.30 (m, 4H), 2.40 (m, 1H), 2.89 (m, 1H), 4.67 (m, 2H), 5.69 (m, 1H), 6.70 (d, 1H), 7.03 (d, 2H), 7.13 (d, 2H), 7.29-7.38 (m, 6H), 7.55 (d, 1H).

5-bromo-1-(2,2,2-trifluoroethyl)pyridin-2(1H)-one was prepared from 5-bromopyridin-2(1H)-one and 2,2,2-trifluoroethyl trifluoromethanesulfonate following a procedure analogous to that described in Example 59 Step 1.

Example 68

4108.1002-007 Example 647

(S)-6-(2-hydroxy-2-methylpropyl)-3-((S)-1-(4-(1-isopropyl-2-oxo-1,2-dihydropyridin-4-yl)phenyl)ethyl)-6-phenyl-1,3-oxazinan-2-one

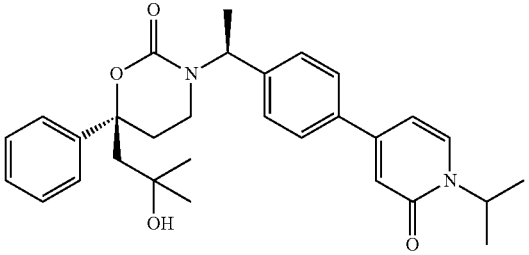

The title compound was prepared from (S)-6-(2-hydroxy-2-methylpropyl)-6-phenyl-3-((S)-1-(4-(4,4,5,5-tetramethyl-1,3,2-dioxaborolan-2-yl)phenyl)propyl)-1,3-oxazinan-2-one and 4-iodo-1-isopropylpyridin-2(1H)-one following a procedure analogous to that described in Example 6 Step 1. LC-MS Method 2 $t_R$=1.846 min, m/z=489.2; $^1$H NMR (CDCl$_3$) 1.10 (s, 3H), 1.24 (s, 3H), 1.39 (d, 6H), 1.52 (d, 3H), 2.17-2.31 (m, 4H), 2.35-2.46 (m, 1H), 2.88 (m, 1H), 5.27 (m, 1H), 5.69 (m, 1H), 6.49 (d, 1H), 6.88 (s, 1H), 7.00 (d, 2H), 7.29-7.38 (m, 7H), 7.40 (d, 1H). Recrystallization from isopropyl acetate following a procedure analogous to that described for Example 37 in Recrystallization Method B afforded a crystalline solid with mp 134-139° C.

4-iodo-1-isopropylpyridin-2(1H)-one was prepared from 4-iodopyridin-2(1H)-one and isopropyl iodide following a procedure analogous to that described in Example 59 Step 1.

Example 69

4108.1002-007 Example 651

3-((R)-6-(4-fluorophenyl)-3-((S)-1-(4-(1-methyl-6-oxo-1,6-dihydropyridin-3-yl)phenyl)ethyl)-2-oxo-1,3-oxazinan-6-yl)-2,2-dimethylpropanenitrile

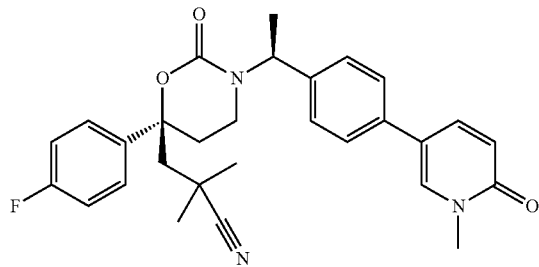

The title compound was prepared from 3-((R)-6-(4-fluorophenyl)-2-oxo-3-((S)-1-(4-(4,4,5,5-tetramethyl-1,3,2-dioxaborolan-2-yl)phenyl)ethyl)-1,3-oxazinan-6-yl)-2,2-dimethylpropanenitrile and 5-bromo-1-methylpyridin-2(1H)-one following a procedure analogous to that described in Example 3 Step 2. LC-MS Method 1 $t_R$=1.45 min, m/z=488; $^1$H NMR (CDCl$_3$) 7.68 (dd, 1H), 7.52 (d, 1H), 7.32 (q, 2H), 7.17 (d, 2H), 7.06 (t, 2H), 6.97 (d, 2H), 6.91 (d, 1H), 5.66 (q, 1H), 3.72 (s, 3H), 2.99 (dt, 1H), 2.48 (dd, 2H), 2.27 (m, 1H), 2.11 (s, 2H), 1.55 (d, 3H), 1.44 (s, 3H), 1.34 (s, 3H).

Example 70

4108.1002-007 Example 655

(S)-3-((S)-1-(4-(1-ethyl-5-methyl-6-oxo-1,6-dihydropyridin-3-yl)phenyl)ethyl)-6-(2-hydroxy-2-methylpropyl)-6-phenyl-1,3-oxazinan-2-one

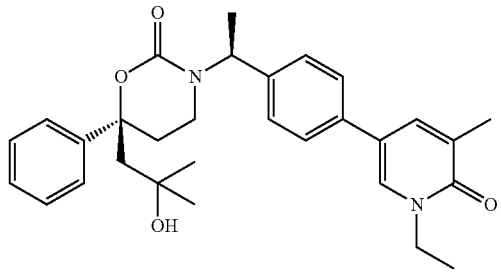

The title compound was prepared from (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one and 5-bromo-1-ethyl-3-methylpyridin-2(1H)-one following a procedure analogous to that described in Example 6 Step 1. LC-MS Method 2 $t_R$=1.314 min, m/z=489; $^1$H NMR (CDCl$_3$) 1.09 (s, 3H), 1.15 (s, 3H), 1.35 (t, 3H), 1.50 (d, 3H), 2.15-2.25 (m, 7H), 2.35 (m, 1H), 2.86 (m, 1H), 4.03 (m, 2H), 5.66 (q, 1H), 6.96 (d, 2H), 7.13 (d, 2H), 7.25-7.36 (m, 7H).

5-Bromo-1-ethyl-3-methylpyridin-2(1H)-one was prepared by alkylation of 5-bromo-3-methylpyridin-2(1H)-one with ethyl iodide following a procedure analogous to that described in Example 59 Step 1.

Example 71

4108.1002-007 Example 658

2,2-dimethyl-3-((R)-2-oxo-3-((S)-1-(4-(6-oxo-1,6-dihydropyridin-3-yl)phenyl)ethyl)-6-phenyl-1,3-oxazinan-6-yl)propanenitrile Method 1

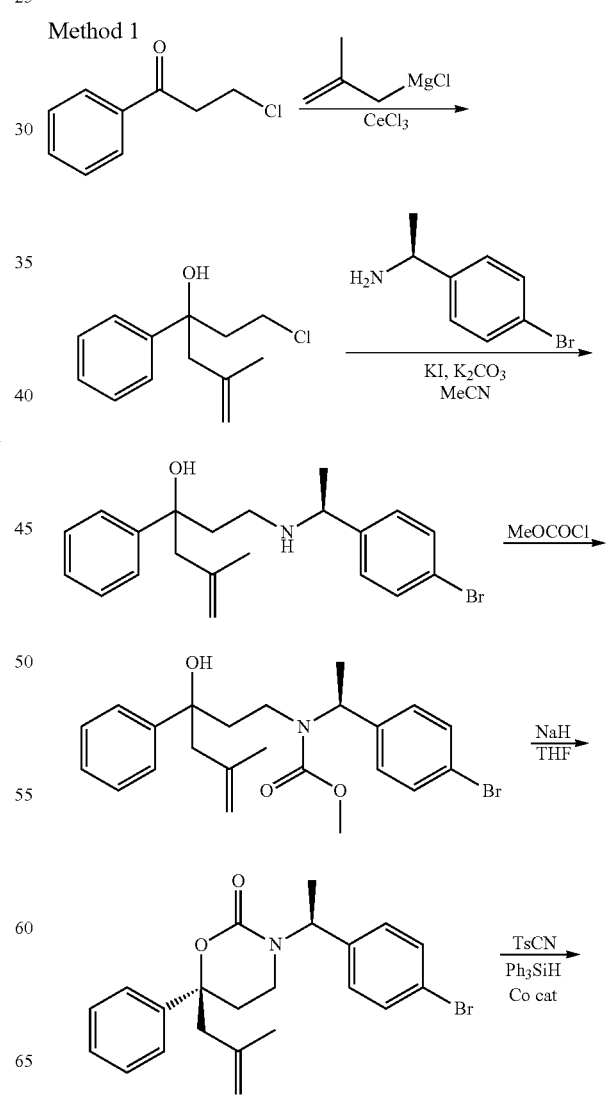

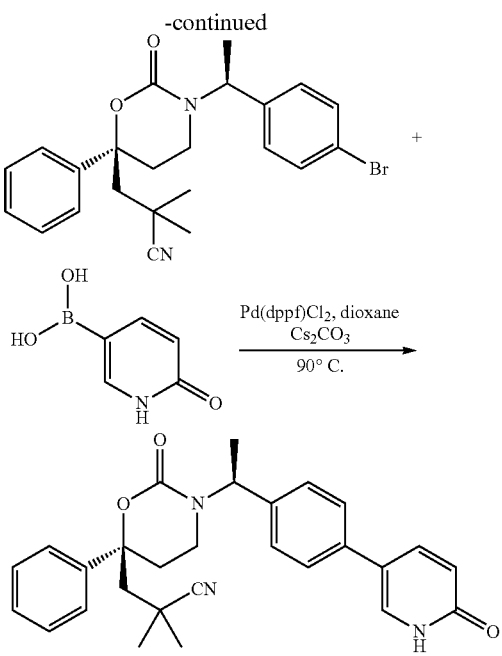

Step 1

A 250 mL flask was charged with anhydrous CeCl₃ (7.1890 g, 29.2 mmol) and THF (55 mL). The mixture was vigorously stirred for 2 h at rt. The suspension was then cooled to −78° C. and a solution of 2-methylallylmagnesium chloride (0.5 M in THF, 56 mL, 28.0 mmol) was added. After stirring for 2 h at −78° C., a solution of 3-chloropropiophenone (3.350 g, 19.8 mmol) in THF (30 mL) was added via cannula. The reaction mixture was allowed to slowly warm to 8° C. while stirring overnight (18 h). The reaction was then quenched with satd aq NaHCO₃, extracted with EtOAc, and dried over Na₂SO₄. After the solvents were evaporated, the crude 1-chloro-5-methyl-3-phenylhex-5-en-3-ol was directly used in the next step without further purification. LC-MS Method 1 $t_R$=1.91 min, m/z 248, 207 (M-OH)⁺; ¹H NMR (400 MHz, CDCl₃) δ 7.39-7.22 (m, 5H), 4.92 (m, 1H), 4.77 (m, 1H), 3.60-3.53 (m, 1H), 3.17-3.10 (m, 1H), 2.67 (d, J=13.2 Hz, 1H), 2.55 (d, J=13.2 Hz, 1H), 2.41-2.25 (m, 2H), 1.29 (s, 3H); ¹³C NMR (100 MHz, CDCl₃) δ 144.55, 141.72, 128.32, 126.88, 125.07, 116.50, 74.44, 51.46, 46.34, 40.19, 24.22.

Step 2

1-chloro-5-methyl-3-phenylhex-5-en-3-ol (1.28 g, 5.7 mmol), (S)-1-(4-bromophenyl)ethanamine (1.37 g, 1.2 equiv), KI (995 mg, 1.05 equiv), K₂CO₃ (1.57 g, 2 equiv) were mixed with acetonitrile (15 mL) and heated to reflux (oil bath 96° C.) for overnight. After being cooled to rt, the mixture was filtered, concentrated, and purified by chromatography on a 40-g silica gel column, eluted with 0~8% MeOH in CH₂Cl₂, to afford 1-((S)-1-(4-bromophenyl)ethylamino)-5-methyl-3-phenylhex-5-en-3-ol (1.33 g, 60%).

Step 3

To a solution of 1-((S)-1-(4-bromophenyl)ethylamino)-5-methyl-3-phenylhex-5-en-3-ol (1.33 g, 3.43 mmol) in CH₂Cl₂ (100 mL) was added pyridine (277 μL, 1 equiv) and triethylamine (717 μL, 1.5 equiv). The mixture was cooled to 0° C. Methyl chloroformate (397 μL, 1.5 equiv) was added slowly. After 15 min, the mixture was warmed to rt slowly and stirred for 3 h. The mixture was then diluted with ether (200 mL), washed with 5% aq HCl (2×25 mL), satd aq NaHCO₃ (25 mL) and brine (20 mL), and dried over Na₂SO₄. After filtration and concentration, the crude methyl(S)-1-(4-bromophenyl)ethyl(3-hydroxy-5-methyl-3-phenylhex-5-enyl)carbamate was used for next steps without further purification.

Step 4

The crude methyl(S)-1-(4-bromophenyl)ethyl(3-hydroxy-5-methyl-3-phenylhex-5-enyl)carbamate from above procedure was dissolved in dry THF (75 mL), NaH (60% in mineral oil, 274 mg, 2 equiv) was added slowly at rt. After 10 min, the mixture was heated to reflux for 2 h. LC-MS found reaction completed. The mixture was cooled to 0° C., quenched with satd aq NH₄Cl (10 mL), diluted with ether (100 mL), washed with 1% aq HCl (25 mL) and brine (15 mL), and dried over Na₂SO₄. After filtration and concentration, the crude product was purified by chromatography on a 40-g silica gel column, eluted with 10~35% EtOAc in hexanes. The second UV active peak was collected to afford (R)-3-((S)-1-(4-bromophenyl)ethyl)-6-(2-methylallyl)-6-phenyl-1,3-oxazinan-2-one (490 mg 34.5% overall yield for Steps 3 and 4).

Step 5

A mixture of (R)-3-((S)-1-(4-bromophenyl)ethyl)-6-(2-methylallyl)-6-phenyl-1,3-oxazinan-2-one (490 mg, 1.18 mmol), TsCN (257 mg, 1.2 equiv), PhSiH₃ (157 μL, 1.07 equiv) and the cobalt N,N'-bis(3,5-di-tert-butylsalicylidene)-1,1,2,2-tetr amethylethenediamine catalyst prepared as described in Preparation 3 (7.5 mg, 0.01 equiv) and ethanol (20 mL) was stirred 4 h at rt. LC-MS found the reaction completed. The mixture was concentrated and purified by ISCO (40 g column, 25~80% EtOAc in Hexanes) to afford 267 mg product (51% yield). LC-MS Method 1 $t_R$=1.89 min., m/z 441, 443 (M+1).

Step 6

To a solution of 3-((R)-3-((S)-1-(4-bromophenyl)ethyl)-2-oxo-6-phenyl-1,3-oxazinan-6-yl)-2,2-dimethylpropanenitrile (208 mg, 0.47 mmol) in 1,4-dioxane (5 mL) were added 6-oxo-1,6-dihydropyridin-3-ylboronic acid (98 mg, 1.5 equiv), 2.0 M aq Cs₂CO₃ solution (500 μL), and Pd(dppf)Cl₂ (20 mg, 0.06 equiv). The mixture was degassed and refilled with N₂ gas 3 times, before being heated to 90° C. (oil bath) for 3 h. LC-MS found the reaction was complete. The mixture was cooled to rt, diluted with EtOAc (25 mL), and washed with water (10 mL). The aqueous layer was extracted with EtOAc (2×10 mL). The combined organic layers were washed with water (10 mL) and brine (8 mL), and dried over Na₂SO₄. After filtration and concentration, the residue was purified by chromatography (12-g silica gel cartridge, 0~10% MeOH in CH₂Cl₂, major UV peak) to afford 2,2-dimethyl-3-((R)-2-oxo-3-((S)-1-(4-(6-oxo-1,6-dihydropyridin-3-yl)phenyl)ethyl)-6-phenyl-1,3-oxazinan-6-yl)propanenitrile (202 mg, 94%) as a brown oil. LC-MS Method 1 $t_R$=1.34 min, m/z=456 (M+1); ¹H NMR (CDCl₃) 8.01 (d, 1H), 7.80 (s, 1H), 7.36 (dt, 6H), 7.19 (d, 2H), 6.98 (m, 3H), 5.65 (d, 1H), 2.98 (d, 1H), 2.50 (m, 2H), 2.32 (m, 1H), 2.17 (s, 2H), 1.57 (d, 3H), 1.40 (s, 3H), 1.32 (s, 3H).

Method 2

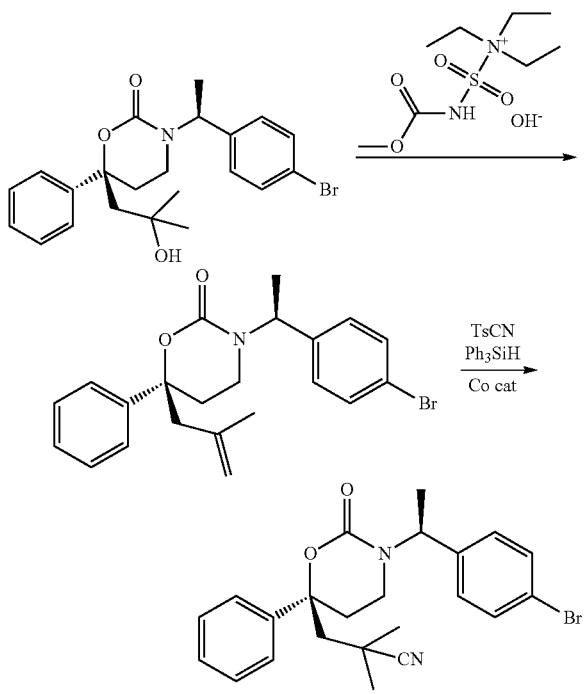

Step 1. 3-[(S)-1-(4-Bromo-phenyl)-ethyl]-(S)-6-(2-methyl-allyl)-6-phenyl-[1,3]oxazinan-2-one (Methoxycarbonylsulfamoyl)triethylammonium hydroxide (1.38 g) was added to 3-[(S)-1-(4-bromo-phenyl)-ethyl]-(S)-6-(2-hydroxy-2-methyl-propyl)-6-phenyl-[1,3]oxazinan-2-one (2.0 g) dissolved in tetrahydrofuran (30 mL) and toluene (15 mL). The resulting solution was stirred at room temperature for 0.5 h and at 75° C. for 1 h. After cooling to room temperature, the solution was concentrated and ethyl acetate was added to the residue. The resulting mixture was washed with aqueous NaHCO₃ solution and brine and dried (MgSO₄). The title compound was obtained after removal of the solvent. Yield: 1.9 g (quantitative). Mass spectrum (ESI⁺): m/z=414/416 (Br) [M+H]⁺

Step 2. 3-{3-[(S)-1-(4-Bromo-phenyl)-ethyl]-2-oxo-(S)-6-phenyl-[1,3]oxazinan-6-yl}-2,2-dimethyl-propionitrile 3-[(S)-1-(4-Bromo-phenyl)-ethyl]-(S)-6-(2-methyl-allyl)-6-phenyl-[1,3]oxazinan-2-one (0.21 g), p-toluenesulfonyl cyanide (143 mg), tert-BuOOH (5.5 M in decane, 27 μL), and phenylsilane (64 μL) were added in the given order to a flask charged with a stir bar, (1R,2R)-(−)-1,2-cyclohexanediamino-N,N'-bis(3,5-di-tert-butylsalicyliden)cobalt(II) (3 mg) and ethanol (15 mL) in argon atmosphere. The resulting solution was stirred at room temperature for 3 h and then concentrated under reduced pressure. The residue was purified by chromatography on silica gel (cyclohexane/ethyl acetate 60:40->0:100) to afford the title compound as a resin-like solid. Yield: 0, 16 g (70% of theory). Mass spectrum (ESI⁺): m/z=441/443 (Br) [M+H]⁺

Example 72

4108.1002-007 Example 659

(S)-3-((S)-1-(4-(1-ethyl-6-methyl-2-oxo-1,2-dihydropyridin-4-yl)phenyl)ethyl)-6-(2-hydroxy-2-methylpropyl)-6-phenyl-1,3-oxazinan-2-one

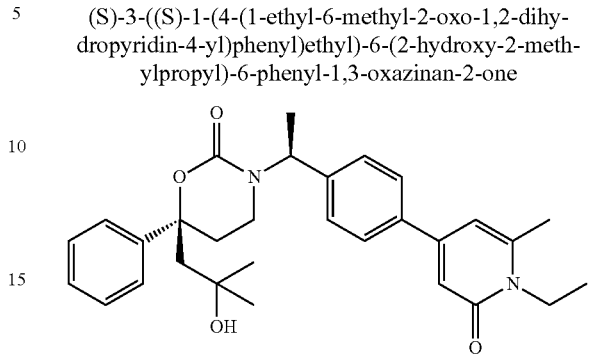

The title compound was prepared from (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one and 4-bromo-1-ethyl-6-methylpyridin-2(1H)-one following a procedure analogous to that described in Example 6 Step 1. LC-MS Method 2 t$_R$=1.211 min, m/z=489.2; ¹H NMR (CDCl₃) 1.10 (s, 3H), 1.17 (s, 3H), 1.49 (s, 9H), 1.57 (d, 3H), 2.22 (m, 4H), 2.37 (m, 1H), 2.84 (m, 1H), 5.60 (m, 1H), 5.91 (s, 1H), 7.06 (d, 2H), 7.27-7.40 (m, 5H), 7.68 (d, 1H), 7.24 (d, 2H), 8.09 (d, 1H), 8.90 (s, 1H).

4-bromo-1-ethyl-6-methylpyridin-2(1H)-one was prepared by alkylation of 4-bromo-6-methylpyridin-2(1H)-one with ethyl iodide using K₂CO₃ following a procedure analogous to that described in Example 59 Step 1.

Example 73

4108.1002-007 Example 664

(S)-6-(2-hydroxy-2-methylpropyl)-6-phenyl-3-((S)-1-(4-(1,5,6-trimethyl-2-oxo-1,2-dihydropyridin-4-yl)phenyl)ethyl)-1,3-oxazinan-2-one

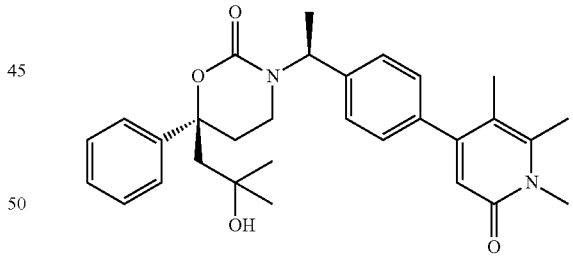

The title compound was prepared from (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one and 4-bromo-1,5,6-trimethylpyridin-2(1H)-one following a procedure analogous to that described in Example 6 Step 1. LC-MS Method 2 t$_R$=1.187 min, m/z=489.2; ¹H NMR (CDCl₃) 1.10 (s, 3H), 1.15 (s, 3H), 1.32 (m, 3H), 1.52 (m, 3H), 1.72 (s, 1H), 2.18 (m, 3H), 2.19 (m, 1H), 2.42 (m, 4H), 2.86 (m, 1H), 4.12 (m, 2H), 5.66 (m, 1H), 6.16 (s, 1H), 6.53 (s, 1H), 6.98 (m, 2H), 7.23-7.34 (m, 7H).

4-bromo-1,5,6-trimethylpyridin-2(1H)-one was prepared by alkylation of 4-bromo-5,6-dimethylpyridin-2(1H)-one with methyl iodide using K₂CO₃ following a procedure analogous to that described in Example 59 Step 1. 4-bromo- 5,6-dimethylpyridin-2(1H)-one was prepared following the procedure described in McElroy, W. T. and DeShong, P. *Org. Lett.* 2003, 5, 4779.

Example 74

4108.1002-007 Example 690

3-((R)-3-((S)-1-(4-(1-isopropyl-6-oxo-1,6-dihydro-pyridin-3-yl)phenyl)ethyl)-2-oxo-6-phenyl-1,3-oxazinan-6-yl)-2,2-dimethylpropanenitrile

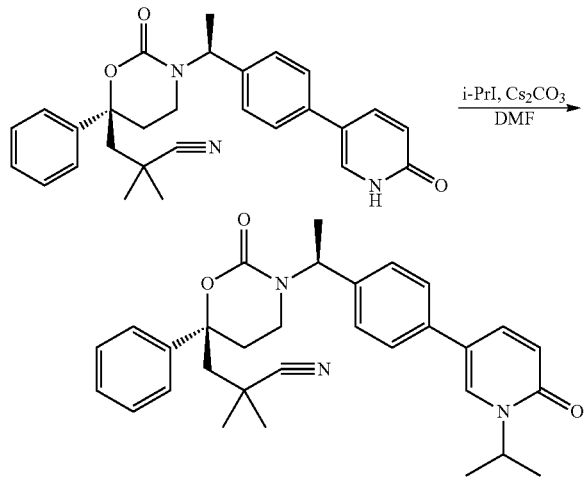

2,2-dimethyl-3-((R)-2-oxo-3-((S)-1-(4-(6-oxo-1,6-dihydropyridin-3-yl)phenyl)ethyl)-6-phenyl-1,3-oxazinan-6-yl)propanenitrile (6 mg, 0.013 mmol) was dissolved in DMF (2.5 mL). Cs$_2$CO$_3$ (c.a. 15 mg, excess) and i-PrI (100 μL, excess) were added. The mixture was stirred for 3 h at rt. LC-MS found the reaction was complete. The mixture was purified by prep HPLC to afford 3-((R)-3-((S)-1-(4-(1-isopropyl-6-oxo-1,6-dihydropyridin-3-yl)phenyl)ethyl)-2-oxo-6-phenyl-1,3-oxazinan-6-yl)-2,2-dimethylpropanenitrile (1.99 mg, 30%). LC-MS Method 1 t$_R$=2.03 min, m/z=498; $^1$H NMR (CDCl$_3$) 8.35 (d, 1H), 7.80 (dd, 1H), 7.37 (m, 5H), 7.22 (d, 2H), 6.92 (d, 2H), 6.83 (d, 1H), 5.66 (q, 1H), 5.22 (m, 1H), 2.93 (m, 1H), 2.16 (s, 2H), 1.55 (d, 3H), 1.46 (s, 3H), 1.40 (d, 6H), 1.33 (s, 3H).

Example 75

4108.1002-007 Example 674

3-{(S)-1-[4-(1-Cyclopropyl-2-oxo-1,2-dihydro-pyridin-4-yl)-phenyl]-ethyl}-(S)-6-(2-hydroxy-2-methyl-propyl)-6-phenyl-[1,3]oxazinan-2-one

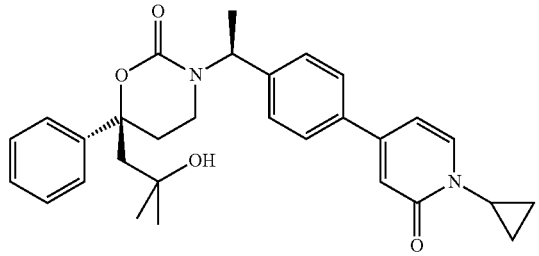

Method 1

2 M aqueous Na$_2$CO$_3$ solution (0.23 mL) was added to a solution of (S)-6-(2-hydroxy-2-methylpropyl)-6-phenyl-3-[(S)-1-(4-(4,4,5,5-tetramethyl-1,3,2-dioxaborolan-2-yl)phenyl)ethyl]-1,3-oxazinan-2-one (0.11 g) and trifluoro-methanesulfonic acid 1-cyclopropyl-2-oxo-1,2-dihydro-pyridin-4-yl ester (74 mg; alternatively, 4-bromo-1-cyclopropyl-1H-pyridin-2-one was used) in dimethylformamide (3 mL). The resulting mixture was sparged with argon for 15 min, before [1,1'-bis(diphenylphosphino)-ferrocene]-dichloropalladium (II) dichloromethane complex (10 mg) was added. The mixture was heated to 100° C. and stirred at this temperature overnight. After cooling to ambient temperature, water was added and the resulting mixture was extracted with ethyl acetate. The combined organic extracts were washed with brine, dried (MgSO$_4$), and concentrated. The residue was purified by chromatography on silica gel (CH$_2$Cl$_2$/MeOH 99:1->90:10) to afford the title compound as a foam-like solid which was crystallized with little ethyl acetate. Yield: 30 mg (27% of theory); Mass spectrum (ESI$^+$): m/z=487 [M+H]$^+$. The compound (1.3 g) was recrystallized from 30 mL of isopropyl acetate. The hot solution, while being stirred, was slowly cooled down to room temperature overnight in the oil bath to yield the crystalline monohydrate. Mp 108-110° C.

The compound of Example 75 (2.0 g) was also recrystallized from a mixture of 30 mL of tert.butyl methylether and 15 mL of isopropanol. The solid was filtered by suction, washed with tert.butyl methylether and dried at 45° C. and then at 65° C. overnight. 100 mg of this solid was stirred in 3 mL of water to first form a resinous material that later on converts into a white solid. This was stirred for another hour, filtered by suction and dried overnight at room temperature and then at 65° C. for 3 hours in a circulating air drier to yield a crystalline monohydrate. Mp 102-108° C.

Intermediate XX

1-Cyclopropyl-4-(4-methoxy-benzyloxy)-1H-pyridin-2-one

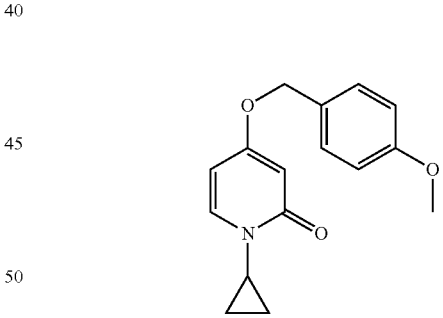

A microwave-suited vessel charged with a stir bar, 4-(4-methoxy-benzyloxy)-1H-pyridin-2-one (0.60 g), cyclopropylboronic acid (0.45 g), pyridine (1.50 mL), triethylamine (1.50 mL), and toluene (4 mL) was sparged with argon for 5 min. Then, Cu(OAc)$_2$ (0.94 g) was added and the mixture was stirred in a microwave oven under microwave irradiation at 140° C. for 45 min. Then, the solvent was evaporated and water was added. The resultant mixture was extracted with ethyl acetate and the combined organic extracts were washed with water and aqueous NaHCO$_3$ solution. After drying (MgSO$_4$) and removing the solvent, the residue was purified by chromatography on silica gel (CH$_2$Cl$_2$/MeOH 99:1->95:5) to afford the title compound as a solid. Yield: 0.17 g (25% of theory); Mass spectrum (ESI$^+$): m/z=272 [M+H]$^+$.

Intermediate XXI

1-Cyclopropyl-4-hydroxy-1H-pyridin-2-one

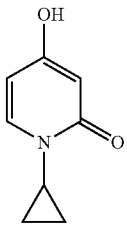

Trifluoroacetic acid (1 mL) was added to a flask charged with a stir bar and 1-cyclopropyl-4-(4-methoxy-benzyloxy)-1H-pyridin-2-one (0.17 g) and chilled in an ice/EtOH bath. The resulting mixture was stirred with cooling for 1.5 h and at ambient temperature for another 4.5 h. Then, the solution was concentrated under reduced pressure and the residue was triturated with tert-butyl methyl ether and dried to give the title compound as a solid. Yield: 0.10 g (quantitative). Mass spectrum (ESI$^+$): m/z=152 [M+H]$^+$.

Intermediate XXII

Trifluoro-methanesulfonic acid 1-cyclopropyl-2-oxo-1,2-dihydro-pyridin-4-yl ester

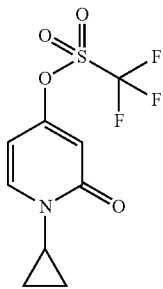

Trifluoromethanesulfonic anhydride (0.12 mL) was added to a flask charged with a stir bar, 1-cyclopropyl-4-hydroxy-1H-pyridin-2-one (0.10 g), NEt$_3$ (0.24 mL), and dichloromethane (8 mL) and chilled in an ice/EtOH bath. The resulting mixture was stirred with cooling for 2 h and at ambient temperature for another 2 h. Then, the solution was diluted with dichloromethane and washed in succession with water, aqueous NaHCO$_3$ solution, and water. The organic solution was dried (MgSO$_4$), the solvent was removed, and the residue was purified by chromatography on silica gel (dichloromethane/methanol 99:1->90:10) to afford the title compound as a resin-like solid. Yield: 0.07 g (36% of theory). Mass spectrum (ESI$^+$): m/z=284 [M+H]$^+$.

Intermediate XXIII

4-Bromo-1-cyclopropyl-1H-pyridin-2-one

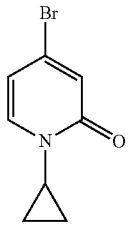

A flask charged with a stir bar, 4-bromo-1H-pyridin-2-one (1.80 g), cyclopropylboronic acid (2.00 g), Cu(OAc)$_2$ (2.00 g), 2,2'-bipyridine (1.70 g), Na$_2$CO$_3$ (2.47 g), and 1,2-dichloroethane (75 mL) was heated to 70° C. and the mixture was stirred at this temperature in air overnight. Then, another portion of cyclopropylboronic acid (0.50 g) and Na$_2$CO$_3$ (0.55 g) were added and the mixture was further stirred at reflux temperature for another 4 h. After cooling to ambient temperature, aqueous NH$_4$Cl solution was added and the resultant mixture was extracted with dichloromethane. The combined organic extracts were dried (MgSO$_4$) and the solvent was evaporated. The residue was purified by chromatography on silica gel (cyclohexane/ethyl acetate 50:50->35:65) to afford the title compound as an oil that crystallized on standing. Yield: 0.82 g (37% of theory); Mass spectrum (ESI$^+$): m/z=214/216 (Br) [M+H]$^+$.

Method 2

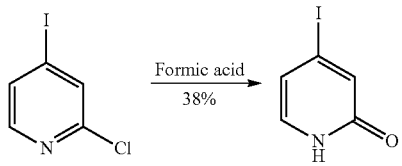

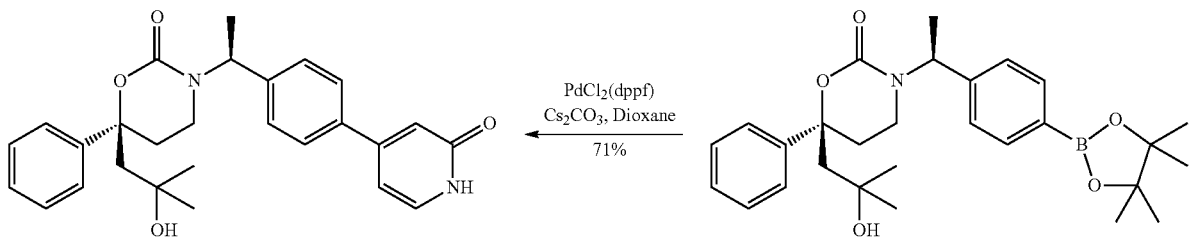

-continued

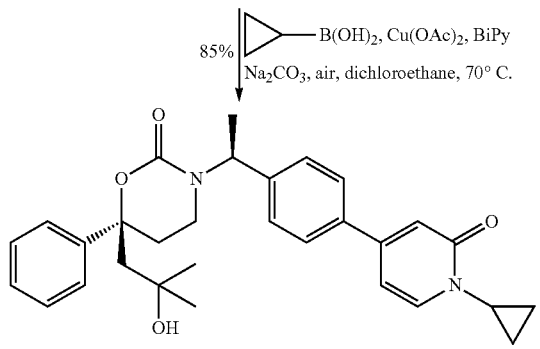

Step 1. 4-Iodopyridin-2(1H)-one

A mixture of 2-chloro-4-iodopyridine (4.943 g, 20.6 mmol) and formic acid (88%, 10 mL) was stirred at 105° C. for 21 h. The excess of formic acid was removed in vacuo, and the mixture was quenched with 2 M aq $Na_2CO_3$, extracted with $CH_2Cl_2$, dried over $Na_2SO_4$. After the solvent was removed under reduced pressure, the residue was purified by chromatography on silica gel eluted with $CH_2Cl_2$/MeOH to afford 1.716 g (38%) of 4-iodopyridin-2(1H)-one as a solid. LC-MS Method 1 $t_R$=0.82 min, m/z=222 (MH$^+$); $^1$H NMR (400 MHz, $(CD_3)_2SO$) δ 7.14 (d, J=6.5 Hz, 1H), 6.87 (s, 1H), 6.49 (d, J=7.0 Hz, 1H).

Step 2. (S)-6-(2-hydroxy-2-methylpropyl)-3-((S)-1-(4-(2-oxo-1,2-dihydropyridin-4-yl)phenyl)ethyl)-6-phenyl-1,3-oxazinan-2-one To a solution of (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one (2.646 g, 5.52 mmol) in 1,4-dioxane (60 mL) were added 4-iodopyridin-2(1H)-one (1.200 g, 5.43 mmol), 2 M $Cs_2CO_3$ (14.5 mL), and $PdCl_2$(dppf).$CH_2Cl_2$ (0.230 g, 0.28 mmol). The mixture was degassed and heated, under a nitrogen atmosphere, at 120° C. for 15 h. The mixture was diluted with $CH_2Cl_2$, dried over $Na_2SO_4$. After the solvents were evaporated, the residue was purified by chromatography on silica gel eluted with MeOH/$CH_2Cl_2$ to afford 1.717 g (71%) of (S)-6-(2-hydroxy-2-methylpropyl)-3-((S)-1-(4-(2-oxo-1,2-dihydropyridin-4-yl)phenyl)ethyl)-6-phenyl-1,3-oxazinan-2-one. LC-MS Method 1 $t_R$=1.23 min, mit 389, 447 (MH$^+$); $^1$H NMR (400 MHz, $CD_3OD$) δ 7.40 (d, J=6.7 Hz, 1H), 7.31 (d, J=8.2 Hz, 2H), 7.29-7.20 (m, 5H), 6.96 (d, J=8.2 Hz, 2H), 6.57-6.52 (m, 2H), 5.49 (q, J=7.0 Hz, 1H), 2.98-2.93 (m, 1H), 2.47-2.34 (m, 2H), 2.16-2.09 (m, 1H), 2.07 (s, 2H), 1.45 (d, J=7.0 Hz, 3H), 1.19 (s, 3H), 0.87 (s, 3H).

Step 3. (S)-3-((S)-1-(4-(1-cyclopropyl-2-oxo-1,2-dihydropyridin-4-yl)phenyl)ethyl)-6-(2-hydroxy-2-methylpropyl)-6-phenyl-1,3-oxazinan-2-one A mixture of (S)-6-(2-hydroxy-2-methylpropyl)-3-((S)-1-(4-(2-oxo-1,2-dihydropyridin-4-yl)phenyl)ethyl)-6-phenyl-1,3-oxazinan-2-one (1.683 g, 3.77 mmol, 1.0 equiv), $Cu(OAc)_2$ (0.692 g, 3.81 mmol, 1.01 equiv), bipyridine (0.599 g, 3.83 mmol, 1.02 equiv), cyclopropylboronic acid (0.681 g, 7.93 mmol, 2.10 equiv) and $Na_2CO_3$ (0.890 g, 8.40 mmol, 2.23 equiv) in dichloroethane (40 mL) was stirred at 70° C. for 22 h under air. The reaction mixture was quenched with satd aq $NH_4Cl$, diluted with $CH_2Cl_2$, dried over $Na_2SO_4$. After the solvent was removed under reduced pressure, the residue was purified by chromatography on silica gel eluted with MeOH/$CH_2Cl_2$ to afford 1.560 g (85%) of (S)-3-((S)-1-(4-(1-cyclopropyl-2-oxo-1,2-dihydropyridin-4-yl)phenyl)ethyl)-6-(2-hydroxy-2-methylpropyl)-6-phenyl-1,3-oxazinan-2-one. LC-MS $t_R$=1.41 min in 3 min chromatography, m/z 429, 487 (MH$^+$); $^1$H NMR (400 MHz, $CD_3OD$) δ 7.52 (d, J=7.0 Hz, 1H), 7.29-7.18 (m, 7H), 6.92 (d, J=8.2 Hz, 2H), 6.54 (d, J=1.8 Hz, 1H), 6.47 (dd, J=7.3, 1.8 Hz, 1H), 5.47 (q, J=7.0 Hz, 1H), 3.27-3.21 (m, 1H), 2.95-2.91 (m, 1H), 2.48-2.33 (m, 2H), 2.15-2.08 (m, 1H), 2.07 (s, 2H), 1.42 (d, J=7.0 Hz, 3H), 1.20 (s, 3H), 1.05-1.00 (m, 2H), 0.87 (s, 3H), 0.83-0.79 (m, 2H); $^{13}$C NMR (100 MHz, $CD_3OD$) δ 166.17, 155.63, 152.88, 144.03, 142.27, 138.90, 136.91, 129.71, 128.70, 128.58, 127.67, 126.09, 116.08, 107.10, 85.19, 71.49, 55.13, 54.62, 37.44, 33.24, 32.71, 31.86, 30.03, 15.60, 7.27. (S)-3-((S)-1-(4-(1-cyclopropyl-2-oxo-1,2-dihydropyridin-4-yl)phenyl)ethyl)-6-(2-hydroxy-2-methylpropyl)-6-phenyl-1,3-oxazinan-2-one (ca. 1.5 g) and isopropyl acetate (30 mL) was heated in a 120° C. oil bath, affording a homogeneous solution. Heating was discontinued and the resulting solution was slowly stirred while slowly cooling to rt in the oil bath overnight. The solids were filtered and washed with isopropyl acetate, dried at room temperature under high vacuum affording crystalline solid Mp 91-94° C.

Example 76

4108.1002-007 Example 676

3-{(S)-1-[4-(1-Cyclopropylmethyl-6-oxo-1,6-dihydro-pyridin-3-yl)-phenyl]-ethyl}-(S)-6-(2-hydroxy-2-methyl-propyl)-6-phenyl-[1,3]oxazinan-2-one

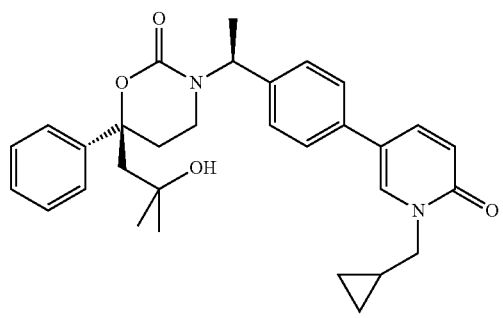

2 M aqueous Na₂CO₃ solution (0.84 mL) was added to a solution of (S)-6-(2-hydroxy-2-methylpropyl)-6-phenyl-3-[(S)-1-(4-(4,4,5,5-tetramethyl-1,3,2-dioxaborolan-2-yl)phenyl)ethyl]-1,3-oxazinan-2-one (0.40 g) and 5-bromo-1-cyclopropylmethyl-1H-pyridin-2-one (0.24 g) in dimethylformamide (4 mL). The resulting mixture was sparged with argon for 10 min, before [1,1'-bis(diphenylphosphino)ferrocene]-dichloropalladium(II) dichloromethane complex (34 mg) was added. The mixture was heated to 100° C. and stirred at this temperature for 4 h. After cooling to ambient temperature, water was added and the resulting mixture was extracted with ethyl acetate. The combined organic extracts were washed with brine, dried (MgSO₄), and concentrated. The residue was purified by chromatography on silica gel (dichloromethane/methanol 99:1->95:5) to afford the title compound that was crystallized with little ethyl acetate. Yield: 0.19 g (46% of theory); Mass spectrum (ESI⁺): m/z=501 [M+H]⁺.

Intermediate XXIV

5-Bromo-1-cyclopropylmethyl-1H-pyridin-2-one

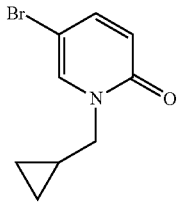

KOᵗBu (0.68 g) was added to a solution of 5-bromo-1H-pyridin-2-one (1.00 g) in tetrahydrofuran (20 mL) at room temperature. After stirring for 30 min, cyclopropylmethyl bromide (0.77 mL) and dimethylformamide (3 mL) were added to the suspension and the resulting mixture was warmed to 70° C. After stirring the mixture at 70° C. for 2 h, the reaction was complete. The mixture was cooled to room temperature, diluted with ethyl acetate (50 mL), and washed with water (2×20 mL) and brine (20 mL). Then, the solution was dried (MgSO₄) and the solvent was removed to give the title compound as a colorless oil. Yield: 1.18 g (90% of theory). Mass spectrum (ESI⁺): m/z=228/230 (Br) [M+H]⁺

Example 77

4108.1002-007 Example 678

(R)-6-Methoxymethyl-3-{(S)-1-[4-(1-methyl-6-oxo-1,6-dihydro-pyridin-3-yl)-phenyl]-ethyl}-6-phenyl-[1,3]oxazinan-2-one

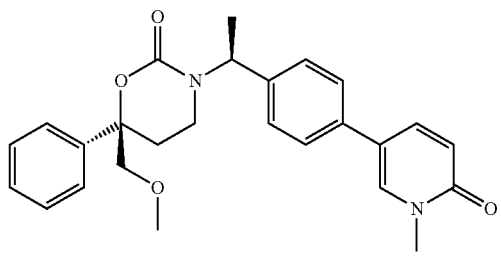

The title compound was prepared from (R)-6-(methoxymethyl)-6-phenyl-3-((S)-1-(4-(4,4,5,5-tetramethyl-1,3,2-dioxaborolan-2-yl)phenyl)ethyl)-1,3-oxazinan-2-one and 5-bromo-1-methylpyridin-2(1H)-one following a procedure analogous to that described in Example 76. Mass spectrum (ESI⁺): m/z=433 [M+H]⁺

Example 78

4108.1002-007 Example 679

(R)-6-Methoxymethyl-3-{(S)-1-[4-(1-methyl-2-oxo-1,2-dihydro-pyridin-4-yl)-phenyl]-ethyl}-6-phenyl-[1,3]oxazinan-2-one

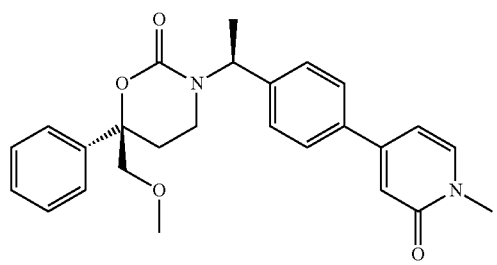

The title compound was prepared from (R)-6-(methoxymethyl)-6-phenyl-3-((S)-1-(4-(4,4,5,5-tetramethyl-1,3,2-dioxaborolan-2-yl)phenyl)ethyl)-1,3-oxazinan-2-one and trifluoro-methanesulfonic acid 1-methyl-2-oxo-1,2-dihydropyridin-4-yl ester following a procedure analogous to that described in Example 76. Mass spectrum (ESI⁺): m/z=433 [M+H]⁺.

Example 79

3-{(S)-1-[4-(5-Fluoro-1-methyl-2-oxo-1,2-dihydropyridin-4-yl)-phenyl]-ethyl}-(S)-6-(2-hydroxy-2-methyl-propyl)-6-phenyl-[1,3]oxazinan-2-one

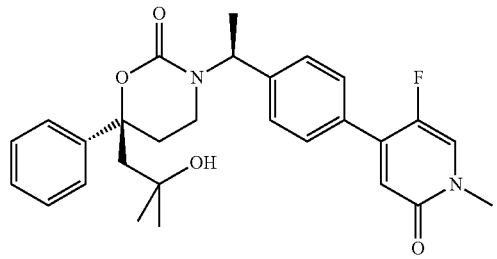

The title compound was prepared from (S)-6-(2-hydroxy-2-methylpropyl)-6-phenyl-3-[(S)-1-(4-(4,4,5,5-tetramethyl-1,3,2-dioxaborolan-2-yl)phenyl)ethyl]-1,3-oxazinan-2-one and 4-bromo-5-fluoro-1-methyl-1H-pyridin-2-one following a procedure analogous to that described in Example 76. Mass spectrum (ESI⁺): m/z=479 [M+H]⁺. The compound that had been obtained as an oil crystallized on standing. The solid was dried at 80° C. under vacuum. Melting points: 120-125° C. with evolution of gas followed by recrystallization and melting at 183-184° C.

Intermediate XXV

4-Bromo-5-fluoro-1-methyl-1H-pyridin-2-one

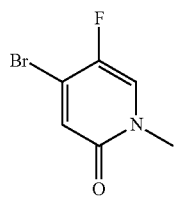

Methyl iodide (0.9 mL) was added to a mixture of potassium carbonate (2.34 g) and 4-bromo-5-fluoro-1H-pyridin-2-one (2.50 g) in dimethylformamide (25 mL) at room temperature. The mixture was stirred at room temperature overnight and then water was added. The resulting mixture was extracted with ethyl acetate and the combined extracts were washed with brine and dried (MgSO$_4$). The solvent was evaporated to afford the crude title compound that was recrystallized from Et$_2$O. Yield: 1.22 g (45% of theory); Mass spectrum (ESI$^+$): m/z=206/208 (Br) [M+H]$^+$.

Example 80

(S)-6-(2-Hydroxy-2-methyl-propyl)-3-((S)-1-{4-[1-(2-hydroxy-2-methyl-propyl)-2-oxo-1,2-dihydro-pyridin-4-yl]-phenyl}ethyl)-6-phenyl-[1,3]oxazinan-2-one

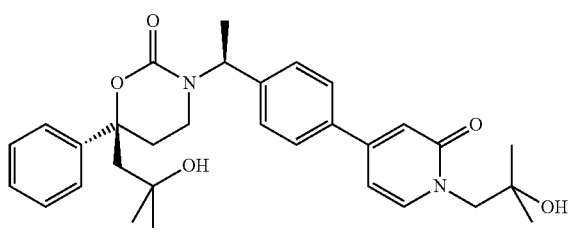

The title compound was prepared from (S)-6-(2-hydroxy-2-methylpropyl)-6-phenyl-3-[(S)-1-(4-(4,4,5,5-tetramethyl-1,3,2-dioxaborolan-2-yl)phenyl)ethyl]-1,3-oxazinan-2-one and 4-bromo-1-(2-hydroxy-2-methyl-propyl)-1H-pyridin-2-one following a procedure analogous to that described in Example 75. Mass spectrum (ESI$^+$): m/z=519 [M+H]$^+$.

Intermediate XXVI

4-Bromo-1-(2-hydroxy-2-methyl-propyl)-1H-pyridin-2-one

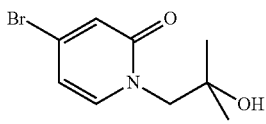

A mixture of 4-bromo-1H-pyridin-2-one (0.25 g), 2,2-dimethyl-oxirane (0.26 mL), and potassium carbonate (0.40 g) in dimethylformamide (2.5 mL) was stirred under microwave irradiation at 120° C. for 30 min. After cooling to ambient temperature, the mixture was concentrated and purified by HPLC on reversed phase (acetonitrile/water) to afford the title compound. Yield: 0.34 g (96% of theory); Mass spectrum (ESI$^+$): m/z=246/248 (Br) [M+H]$^+$.

Example 81

(S)-6-(2-Hydroxy-2-methyl-propyl)-3-((S)-1-{4-[1-(3-methoxy-2-methyl-propyl)-2-oxo-1,2-dihydro-pyridin-4-yl]-phenyl}-ethyl)-6-phenyl-[1,3]oxazinan-2-one

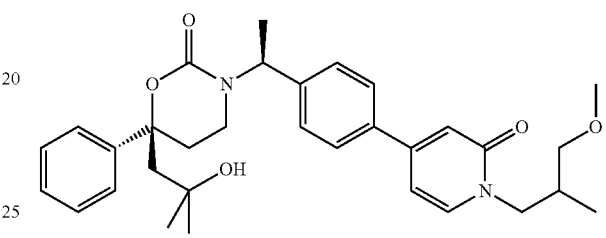

The title compound was prepared from (S)-6-(2-hydroxy-2-methylpropyl)-6-phenyl-3-[(S)-1-(4-(4,4,5,5-tetramethyl-1,3,2-dioxaborolan-2-yl)phenyl)ethyl]-1,3-oxazinan-2-one and 4-bromo-1-(3-methoxy-2-methyl-propyl)-1H-pyridin-2-one following a procedure analogous to that described in Example 75 Method 1. Mass spectrum (ESI$^+$): m/z=533 [M+H]$^+$.

Intermediate XXVII 3-(4-Bromo-2-oxo-2H-pyridin-1-yl)-2-methyl-propionic acid methyl ester

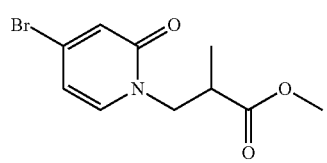

A mixture of 4-bromo-1H-pyridin-2-one (0.50 g), methyl 2-bromoisobutyrate (0.45 mL), and potassium carbonate (0.68 g) in dimethylformamide (5 mL) was stirred at 60° C. for 3 h. After cooling to ambient temperature, water was added and the resulting mixture was extracted with ethyl acetate. The combined extracts were washed with brine, dried (MgSO$_4$), and concentrated. The residue was purified by chromatography on silica gel (cyclohexane/ethyl acetate 70:30->50:50) to afford the title compound. Yield: 0.53 g (67% of theory); Mass spectrum (ESI$^+$): m/z=274/276 (Br) [M+H]$^+$. Additionally 2-(4-bromo-pyridin-2-yloxy)-2-methyl-propionic acid methyl ester was obtained {Yield: 0.15 g; Mass spectrum (ESI$^+$): m/z=274/276 (Br) [M+H]$^+$}

Intermediate XXVIII

4-Bromo-1-(3-hydroxy-2-methyl-propyl)-1H-pyridin-2-one

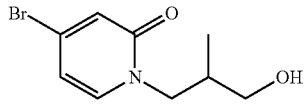

LiAlH₄ (1 M solution in tetrahydrofuran, 1.16 mL) was added to a solution of 3-(4-bromo-2-oxo-2H-pyridin-1-yl)-2-methyl-propionic acid methyl ester (0.53 g) in tetrahydrofuran (6 mL) chilled in an ice bath. After stirring the solution with cooling for 2 h, another portion of LiAlH₄ (1 M in tetrahydrofuran, 0.29 mL) was added. After stirring with cooling for 1 more hour, the reaction was quenched by the addition of water. The resulting mixture was extracted with ethyl acetate and the combined organic extracts were washed with brine and dried (MgSO₄). The solvent was evaporated to give the title compound. Yield: 0.37 g (78% of theory); Mass spectrum (ESI⁺): m/z=246/248 (Br) [M+H]⁺.

Intermediate XXIX

4-Bromo-1-(3-methoxy-2-methyl-propyl)-1H-pyridin-2-one

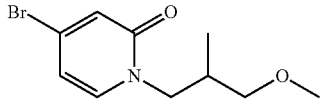

NaH (60% in mineral oil, 57 mg) was added to a solution of 4-bromo-1-(3-hydroxy-2-methyl-propyl)-1H-pyridin-2-one (0.53 g) in dimethylformamide (6 mL) chilled in an ice bath. After stirring the solution with cooling for 0.5 h, methyl iodide (110 µL) was added. The cooling bath was removed and the solution was stirred at room temperature overnight. Then, the solution was concentrated under reduced pressure and the residue was diluted with water. The resulting mixture was extracted with ethyl acetate and the combined organic extracts were washed with brine and dried (MgSO₄). The solvent was evaporated and the residue was purified by HPLC on reversed phase (acetonitrile/water) to give the title compound as an oil. Yield: 70 mg (30% of theory); Mass spectrum (ESI⁺): m/z=260/262 (Br) [M+H]⁺.

Example 82

(S)-6-(2-Hydroxy-2-methyl-propyl)-3-((S)-1-{4-[1-(3-hydroxy-2-methyl-propyl)-2-oxo-1,2-dihydro-pyridin-4-yl]-phenyl}-ethyl)-6-phenyl-[1,3]oxazinan-2-one

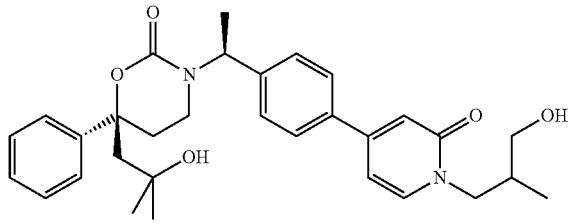

The title compound was prepared from (S)-6-(2-hydroxy-2-methylpropyl)-6-phenyl-3-[(S)-1-(4-(4,4,5,5-tetramethyl-1,3,2-dioxaborolan-2-yl)phenyl)ethyl]-1,3-oxazinan-2-one and 4-bromo-1-(3-hydroxy-2-methyl-propyl)-1H-pyridin-2-one following a procedure analogous to that described in Example 75. Mass spectrum (ESI⁺): m/z=519 [M+H]⁺.

Example 83

(S)-6-(2-Hydroxy-2-methyl-propyl)-3-(1-{4-[1-(2-methoxy-2-methyl-propyl)-2-oxo-1,2-dihydro-pyridin-4-yl]-phenyl}-ethyl)-6-phenyl-[1,3]oxazinan-2-one

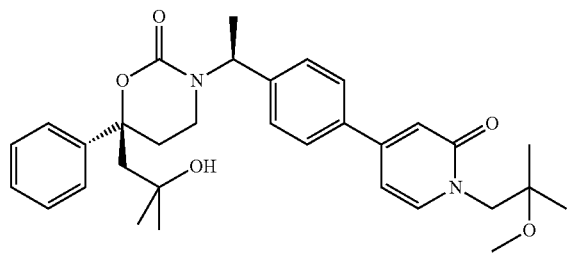

The title compound was prepared from (S)-6-(2-hydroxy-2-methylpropyl)-6-phenyl-3-[(S)-1-(4-(4,4,5,5-tetramethyl-1,3,2-dioxaborolan-2-yl)phenyl)ethyl]-1,3-oxazinan-2-one and 4-bromo-1-(2-methoxy-2-methyl-propyl)-1H-pyridin-2-one following a procedure analogous to that described in Example 75 Method 1. Mass spectrum (ESI⁺): m/z=533 [M+H]⁺.

Intermediate XXX

4-Bromo-1-(2-methoxy-2-methyl-propyl)-1H-pyridin-2-one

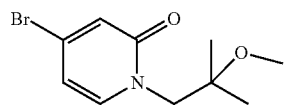

The title compound was prepared from 4-bromo-1-(2-hydroxy-2-methyl-propyl)-1H-pyridin-2-one and methyl iodide following a procedure analogous to that described in Intermediate XXIX. Mass spectrum (ESI⁺): m/z=260/262 (Br) [M+H]⁺.

Example 84

6-(3-hydroxy-3-methylbutyl)-6-isopropyl-3-((S)-1-(4-(1-methyl-2-oxo-1,2-dihydropyridin-4-yl)phenyl)ethyl)-1,3-oxazinan-2-one

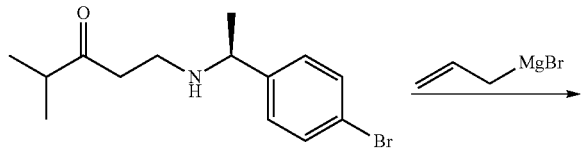

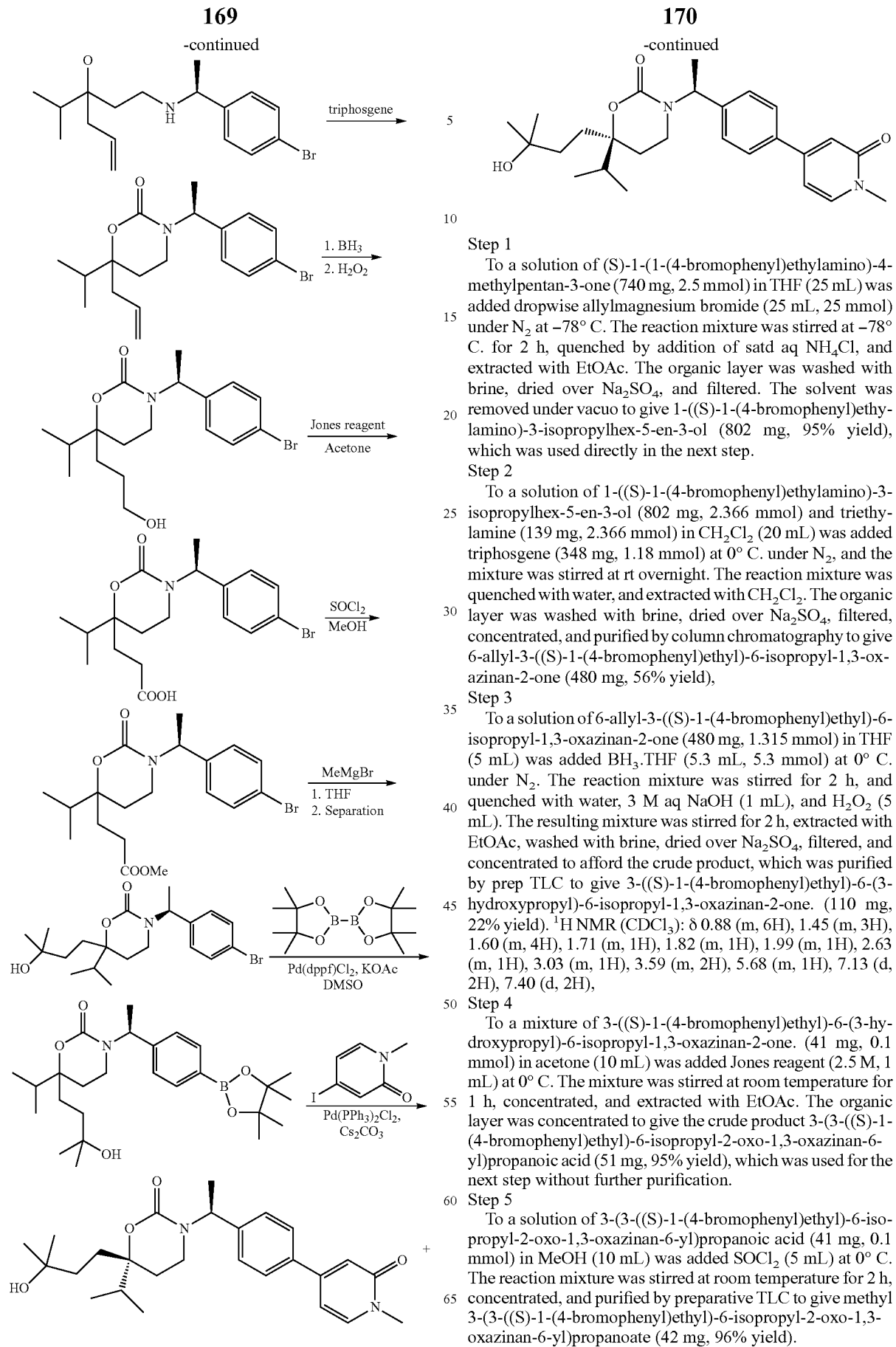

Step 1

To a solution of (S)-1-(1-(4-bromophenyl)ethylamino)-4-methylpentan-3-one (740 mg, 2.5 mmol) in THF (25 mL) was added dropwise allylmagnesium bromide (25 mL, 25 mmol) under $N_2$ at −78° C. The reaction mixture was stirred at −78° C. for 2 h, quenched by addition of satd aq $NH_4Cl$, and extracted with EtOAc. The organic layer was washed with brine, dried over $Na_2SO_4$, and filtered. The solvent was removed under vacuo to give 1-((S)-1-(4-bromophenyl)ethylamino)-3-isopropylhex-5-en-3-ol (802 mg, 95% yield), which was used directly in the next step.

Step 2

To a solution of 1-((S)-1-(4-bromophenyl)ethylamino)-3-isopropylhex-5-en-3-ol (802 mg, 2.366 mmol) and triethylamine (139 mg, 2.366 mmol) in $CH_2Cl_2$ (20 mL) was added triphosgene (348 mg, 1.18 mmol) at 0° C. under $N_2$, and the mixture was stirred at rt overnight. The reaction mixture was quenched with water, and extracted with $CH_2Cl_2$. The organic layer was washed with brine, dried over $Na_2SO_4$, filtered, concentrated, and purified by column chromatography to give 6-allyl-3-((S)-1-(4-bromophenyl)ethyl)-6-isopropyl-1,3-oxazinan-2-one (480 mg, 56% yield), Step 3

To a solution of 6-allyl-3-((S)-1-(4-bromophenyl)ethyl)-6-isopropyl-1,3-oxazinan-2-one (480 mg, 1.315 mmol) in THF (5 mL) was added $BH_3 \cdot THF$ (5.3 mL, 5.3 mmol) at 0° C. under $N_2$. The reaction mixture was stirred for 2 h, and quenched with water, 3 M aq NaOH (1 mL), and $H_2O_2$ (5 mL). The resulting mixture was stirred for 2 h, extracted with EtOAc, washed with brine, dried over $Na_2SO_4$, filtered, and concentrated to afford the crude product, which was purified by prep TLC to give 3-((S)-1-(4-bromophenyl)ethyl)-6-(3-hydroxypropyl)-6-isopropyl-1,3-oxazinan-2-one. (110 mg, 22% yield). $^1H$ NMR ($CDCl_3$): δ 0.88 (m, 6H), 1.45 (m, 3H), 1.60 (m, 4H), 1.71 (m, 1H), 1.82 (m, 1H), 1.99 (m, 1H), 2.63 (m, 1H), 3.03 (m, 1H), 3.59 (m, 2H), 5.68 (m, 1H), 7.13 (d, 2H), 7.40 (d, 2H), Step 4

To a mixture of 3-((S)-1-(4-bromophenyl)ethyl)-6-(3-hydroxypropyl)-6-isopropyl-1,3-oxazinan-2-one. (41 mg, 0.1 mmol) in acetone (10 mL) was added Jones reagent (2.5 M, 1 mL) at 0° C. The mixture was stirred at room temperature for 1 h, concentrated, and extracted with EtOAc. The organic layer was concentrated to give the crude product 3-(3-((S)-1-(4-bromophenyl)ethyl)-6-isopropyl-2-oxo-1,3-oxazinan-6-yl)propanoic acid (51 mg, 95% yield), which was used for the next step without further purification.

Step 5

To a solution of 3-(3-((S)-1-(4-bromophenyl)ethyl)-6-isopropyl-2-oxo-1,3-oxazinan-6-yl)propanoic acid (41 mg, 0.1 mmol) in MeOH (10 mL) was added $SOCl_2$ (5 mL) at 0° C. The reaction mixture was stirred at room temperature for 2 h, concentrated, and purified by preparative TLC to give methyl 3-(3-((S)-1-(4-bromophenyl)ethyl)-6-isopropyl-2-oxo-1,3-oxazinan-6-yl)propanoate (42 mg, 96% yield).

Step 6

To a solution of methyl 3-(3-((S)-1-(4-bromophenyl)ethyl)-6-isopropyl-2-oxo-1,3-oxazinan-6-yl)propanoate (42 mg, 0.1 mmol) in dry THF (5 mL) was added MeMgBr (2.5 mL, 2.5 mmol, 1 M in THF) at −78° C. The mixture was stirred at rt for 0.5 h, quenched with satd aq NH$_4$Cl, and extracted with EtOAc. The organic layer was concentrated, and to afford crude 3-((S)-1-(4-bromophenyl)ethyl)-6-(3-hydroxy-3-methylbutyl)-6-isopropyl-1,3-oxazinan-2-one.

The two isomers could be separated by preparative HPLC.

Isomer 1: (1.1 mg, 12% yield), $^1$H NMR (CDCl$_3$): δ0.91 (m, 6H), 1.25 (m, 6H), 1.44 (d, 3H), 1.70 (m, 4H), 1.85 (m, 2H), 2.01 (m, 1H), 2.74 (m, 1H), 3.18 (m, 1H), 5.79 (m, 1H), 7.24 (d, 2H), 7.50 (d, 2H), Isomer 2: (0.9 mg, 10% yield), $^1$H NMR (CDCl$_3$): δ0.89 (m, 6H), 1.15 (s, 6H), 1.45 (m, 5H), 1.55 (m, 3H), 1.85 (m, 1H), 1.99 (m, 1H), 2.64 (m, 1H), 2.99 (m, 1H), 5.72 (m, 1H), 7.17 (d, 2H), 7.40 (d, 2H), Step 7

To a solution of compound 3-((S)-1-(4-bromophenyl)ethyl)-6-(3-hydroxy-3-methylbutyl)-6-isopropyl-1,3-oxazinan-2-one (105 mg, 0.255 mmol) in DMSO (8 mL) was added compound 4,4,4',4',5,5,5',5'-octamethyl-2,2'-bi(1,3,2-dioxaborolane) (198.5 mg, 0.781 mmol), KOAc (351.6 mg, 3.587 mmol), and Pd(dppf)Cl$_2$ (21.9 mg, 0.027 mmol) under N$_2$. The reaction mixture was stirred at 90° C. for 3.5 h added H$_2$O, and extracted with ethyl acetate. The organic layer was washed with water and brine, dried over Na$_2$SO$_4$, concentrated, and purified by preparative TLC to give the two isomers of 6-(3-hydroxy-3-methylbutyl)-6-isopropyl-3-((S)-1-(4-(4,4,5,5-tetramethyl-1,3,2-dioxaborolan-2-yl)phenyl)ethyl)-1,3-oxazinan-2-one Isomer 1 (17 mg, 15%).
Isomer 2 (10.3 mg, 9%).

Step 8

To a solution of compound 4-iodo-1-methylpyridin-2(1H)-one (17 mg, 0.074 mmol) in DME (4.6 mL) was added Pd(PPh$_3$)$_4$ (6.7 mg, 0.007 mmol) under nitrogen. The mixture was stirred at room temperature for 1 h, and a solution of compound 6-(3-hydroxy-3-methylbutyl)-6-isopropyl-3-((S)-1-(4-(4,4,5,5-tetramethyl-1,3,2-dioxaborolan-2-yl)phenyl)ethyl)-1,3-oxazinan-2-one isomer 1 (17 mg, 0.037 mmol) in EtOH (2 mL) and satd aq NaHCO$_3$ (1.5 mL) were added. The mixture was stirred at 100° C. for 2 h, quenched with water, and extracted with EtOAc. The combined organic layer was dried over anhydrous Na$_2$SO$_4$ and concentrated to give the compound 6-(3-hydroxy-3-methylbutyl)-6-isopropyl-3-((S)-1-(4-(1-methyl-2-oxo-1,2-dihydropyridin-4-yl)phenyl)ethyl)-1,3-oxazinan-2-one isomer 1 (10.73 mg, 65.8%). LC-MS Method 2 Method 2 $t_R$=1.03 min, m/z=463, 441; $^1$H NMR (CD$_3$OD): δ 0.89 (m, 6H), 1.11 (s, 6H), 1.42 (m, 2H), 1.51 (m, 3H), 1.60 (m, 2H), 1.82-2.02 (m, 2H), 2.69 (m, 1H), 3.03 (m, 1H), 3.51 (s, 3H), 5.79 (m, 3H), 6.35 (d, 1H), 6.72 (s, 1H), 7.28 (d, 1H), 7.39 (d, 2H), 7.49 (m, 2H).

6-(3-hydroxy-3-methylbutyl)-6-isopropyl-3-((S)-1-(4-(1-methyl-2-oxo-1,2-dihydropyridin-4-yl)phenyl)ethyl)-1,3-oxazinan-2-one isomer 2 was prepared from 6-(3-hydroxy-3-methyl butyl)-6-isopropyl-3-((S)-1-(4-(4,4,5,5-tetramethyl-1,3,2-dioxaborolan-2-yl)phenyl)ethyl)-1,3-oxazinan-2-one isomer following a procedure analogous to that described in Step 8 immediately above. LC-MS Method 2 Method 2 $t_R$=1.00 min, m/z=463, 441; $^1$H NMR (CD$_3$OD): δ 0.89 (m, 6H), 1.18 (m, 6H), 1.43 (m, 1H), 1.51 (m, 3H), 1.63 (m, 2H), 1.76 (m, 2H), 1.92 (m, 1H), 2.61 (m, 1H), 3.12 (m, 1H), 3.51 (s, 3H), 5.79 (m, 1H), 6.37 (d, 1H), 6.72 (s, 1H), 7.28 (d, 1H), 7.35 (d, 2H), 7.51 (m, 2H).

Example 85

(S)-3-((S)-1-(4-(1-cyclopropyl-2-oxo-1,2-dihydropyridin-4-yl)phenyl)ethyl)-6-(2-hydroxy-2-methylpropyl)-6-isopropyl-1,3-oxazinan-2-one

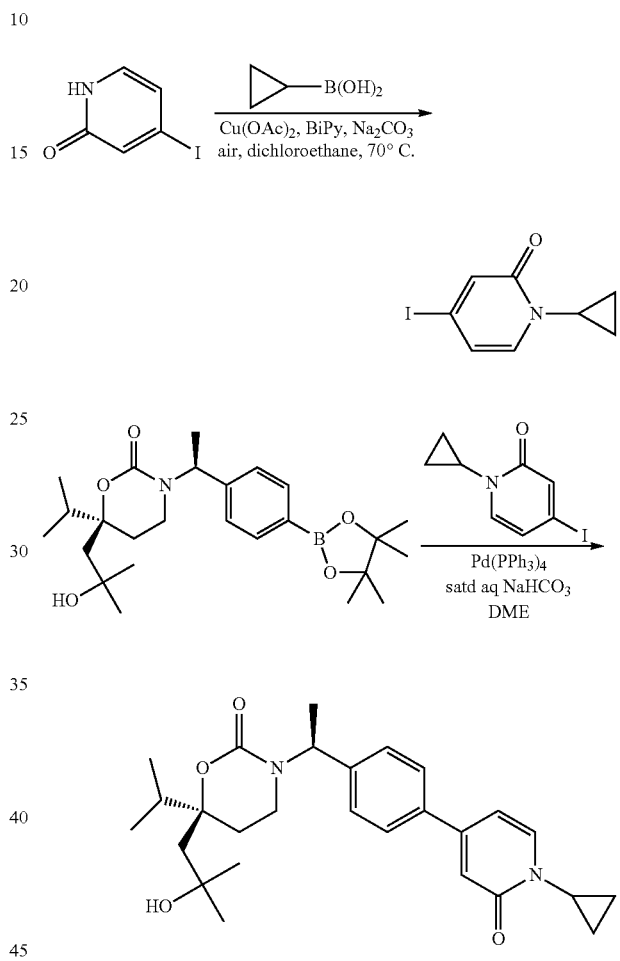

Step 1

A mixture of 4-iodopyridin-2(1H)-one (0.2425 g, 1.10 mmol, 1.0 equiv), Cu(OAc)$_2$ (0.2146 g, 1.18 mmol, 1.07 equiv), bipyridine (0.1832 g, 1.17 mmol, 1.07 equiv), cyclopropylboronic acid (0.2122 g, 2.47 mmol, 2.25 equiv) and Na$_2$CO$_3$ (0.2638 g, 2.49 mmol, 2.27 equiv) in dichloroethane (10 mL) was stirred at 70° C. for 18 h. The reaction mixture was quenched with satd aq NH$_4$Cl, diluted with CH$_2$Cl$_2$, and dried over Na$_2$SO$_4$. After the solvent was removed under reduced pressure, the residue was purified by chromatography on silica gel eluted with hexanes/ethyl acetate to afford 0.2309 g (81%) of 1-cyclopropyl-4-iodopyridin-2(1H)-one.

Step 2

To a solution of compound 2-cyclopropyl-4-iodopyridin-2 (1H)-one (17.60 mg, 0.067 mmol) in DME (2.5 mL) was added Pd(PPh$_3$)$_4$ (6.12 mg, 0.006 mmol) under nitrogen. The mixture was stirred at rt for 1 h. A solution of compound (S)-6-(2-hydroxy-2-methylpropyl)-6-isopropyl-3-((S)-1-(4-(4,4,5,5-tetramethyl-1,3,2-dioxaborolan-2-yl)phenyl)ethyl)-1,3-oxazinan-2-one (15 mg, 0.034 mmol) in EtOH (1 mL) and satd aq NaHCO$_3$ (1 mL) were added. The mixture was stirred at 100° C. for 2 h, quenched with water and extracted with EtOAc. The combined organic layer was dried over anhydrous Na₂SO₄ and concentrated to give the final crude product, which was purified by preparative HPLC to afford the compound (S)-3-((S)-1-(4-(1-cyclopropyl-2-oxo-1,2-dihydropyridin-4-yl)phenyl)ethyl)-6-(2-hydroxy-2-methylpropyl)-6-isopropyl-1,3-oxazinan-2-one (6.50 mg, 43%). LC-MS Method 2 $t_R$=1.00 min, m/z=453; ¹H NMR (CD₃OD): δ0.82 (d, 3H), 0.89 (m, 2H), 0.99 (d, 3H), 1.17 (m, 2H), 1.35 (m, 6H), 1.58 (d, 3H), 1.62 (m, 2H), 1.85 (m, 1H), 1.96 (d, 1H), 2.09-2.18 (m, 2H), 2.68-2.78 (m, 1H), 3.11 (m, 1H), 3.37 (m, 1H), 5.81 (m, 1H), 6.40 (d, 2H), 6.78 (s, 1H), 7.31-7.42 (m, 3H), 7.58 (d, 2H).

Example 86

(S)-6-(2-hydroxy-2-methylpropyl)-3-((S)-1-(4-(1-(2-hydroxyethyl)-6-oxo-1,6-dihydropyridin-3-yl)phenyl)ethyl)-6-phenyl-1,3-oxazinan-2-one The title compound was prepared from (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one and 5-bromo-1-(2-hydroxyethyl)pyridin-2(1H)-one following a procedure analogous to that described in Example 20 Step 2. LC-MS Method 2 $t_R$=1.08 min, m/z=513, 491; ¹H NMR (CD₃OD) δ 0.95 (s, 3H), 1.24 (s, 3H), 1.26 (s, 1H), 1.52 (d, 3H), 2.12 (s, 2H), 2.18 (m, 1H), 2.40-2.53 (m, 2H), 3.02 (m, 1H), 3.52 (m, 0.5H), 3.64 (m, 0.5H), 3.83 (t, 1H), 4.15 (t, 1H), 5.53 (m, 1H), 6.61 (m, 1H), 7.01 (d, 2H), 7.25-7.40 (m, 7H), 7.79 (m, 2H).

5-Bromo-1-(2-hydroxyethyl)pyridin-2(1H)-one was prepared from 5-bromopyridin-2(1H)-one and 2-iodoethanol following a procedure analogous to that described in Example 20 Step 1.

Example 87

(S)-3-((S)-1-(4-(1-(2-fluoroethyl)-6-oxo-1,6-dihydropyridin-3-yl)phenyl)ethyl)-6-(2-hydroxy-2-methylpropyl)-6-phenyl-1,3-oxazinan-2-one

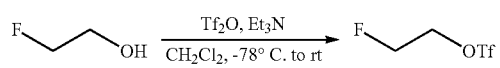

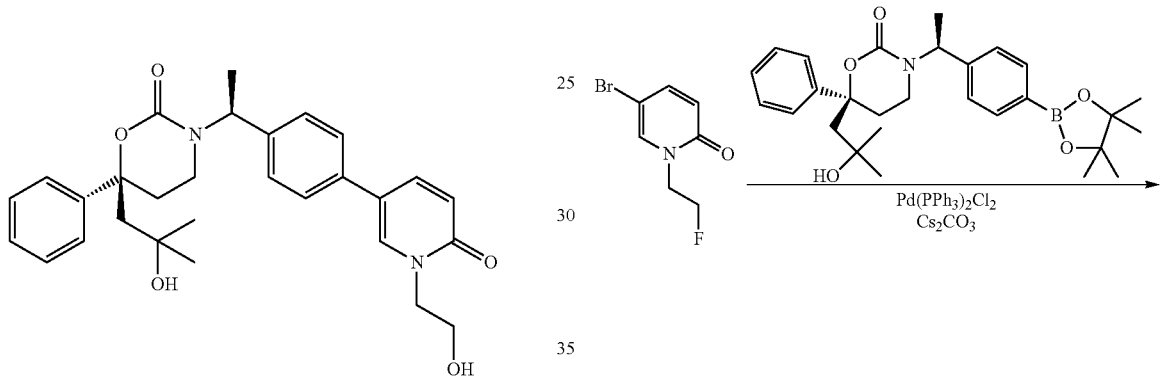

Step 1

To a solution of 2-fluoroethanol (3.2 g, 50 mmol) and triethylamine (5.5 g, 55 mmol) in dichloromethane (60 mL) was added dropwise (CF₃SO₂)₂O (15.5 g, 55 mmol) at −78° C. under N₂. The mixture was stirred at 10~20° C. for 1 h, and treated with water (100 mL). The organic layer was washed with satd aq NaHCO₃ (100 mL) and brine (100 mL), dried, and concentrated to give 2-fluoroethyl trifluoromethanesulfonate (8 g, yield 82%).

Step 2

A solution of 5-bromopyridin-2(1H)-one (100 mg, 0.58 mmol), 2-fluoroethyl trifluoromethanesulfonate (1.1 g, 5.8 mmol), and K₂CO₃ (800 mg, 5.8 mmol) in DMF (3 mL) was stirred at rt overnight. 2-Fluoroethyl trifluoromethanesulfonate (1.1 g, 5.8 mmol) and K₂CO₃ (800 mg, 5.8 mmol) were added, and the mixture was treated with ethyl acetate (20 mL) and water (20 mL). The organic layer was washed with water (2×20 mL) and brine (20 mL), dried over Na₂SO₄, concentrated, and purified by preparative, TLC (1:1 petroleum ether/EtOAc) to give two isomers.

5-bromo-1-(2-fluoroethyl)pyridin-2(1H)-one (30 mg, yield 24%). ¹H NMR (CD₃OD): δ 4.25 (t, 1H), 4.32 (t, 1H), 4.62 (t, 1H), 4.74 (t, 1H), 6.52 (d, 1H), 7.61 (dd, 1H), 7.85 (s, 1H).

5-bromo-2-(2-fluoroethoxy)pyridine (30 mg, yield 24%). ¹H NMR (CD₃OD): δ4.46 (t, 1H), 4.53 (t, 1H), 4.64 (t, 1H), 4.76 (t, 1H), 6.79 (d, 1H), 7.79 (dd, 1H), 8.18 (s, 1H), Step 3

To a solution of (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one (20 mg, 0.041 mmol), 5-bromo-1-(2-fluoroethyl)pyridin-2(1H)-one (9.2 mg, 0.041 mmol), and Cs₂CO₃ (2 N, 0.2 mL, 0.41 mmol) in 1,4-dioxane (2 mL) was added Pd(PPh₃)₂Cl₂ (3 mg, 0.0041 mmol) under N₂. The mixture was refluxed for 2 h, treated with EtOAc (10 mL) and water (10 mL). The organic layer was dried over Na₂SO₄, concentrated, and purified by preparative HPLC to give (S)-3-((S)-1-(4-(1-(2-fluoroethyl)-6-oxo-1,6-dihydropyridin-3-yl)phenyl)ethyl)-6-(2-hydroxy-2-methylpropyl)-6-phenyl-1,3-oxazinan-2-one (4.20 mg, 20%). LC-MS Method 2 $t_R$=1.01 min, m/z=515, 493; ¹H NMR (CD₃OD): δ 0.97 (s, 3H), 1.28 (s, 3H), 1.56 (d, 3H), 2.18 (s, 2H), 2.22 (m, 1H), 2.49 (m, 2H), 3.05 (m, 1H), 4.37 (t, 1H), 4.43 (t, 1H), 4.69 (t, 1H), 4.81 (t, 1H), 5.59 (q, 1H), 6.66 (d, 1H), 7.05 (d, 2H), 7.33 (m, 7H), 7.82 (m, 2H).

Example 88

(S)-3-((S)-1-(4-(1-cyclopropyl-2-oxo-1,2-dihydropyridin-4-yl)phenyl)ethyl)-6-(2-fluorophenyl)-6-(2-hydroxy-2-methylpropyl)-1,3-oxazinan-2-one

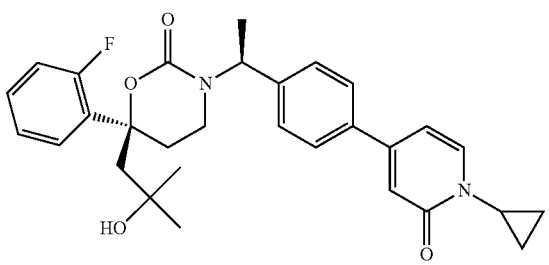

The title compound was prepared from (S)-6-(2-fluorophenyl)-6-(2-hydroxy-2-methylpropyl)-3-((S)-1-(4-(4,4,5,5-tetramethyl-1,3,2-dioxaborolan-2-yl)phenyl)ethyl)-1,3-oxazinan-2-one and 1-cyclopropyl-4-iodopyridin-2(1H)-one following a procedure analogous to that described in Example 23 Step 9. LC-MS Method 2 $t_R$=1.05 min, m/z=505; ¹H NMR (CDCl₃) δ 0.88 (m, 2H), 1.12 (s, 3H), 1.15 (s, 1H), 1.17 (s, 1H), 1.21 (s, 3H), 2.18-2.29 (m, 2H), 2.30-2.34 (m, 1H), 2.42 (d, 1H), 2.54 (d, 1H), 2.90 (m, 1H), 3.35 (m, 1H), 5.70 (m, 1H), 6.32 (m, 1H), 6.68 (m, 1H), 6.98 (m, 1H), 7.09 (d, 2H), 7.18 (t, 1H), 7.25-7.36 (m, 4H), 7.50 (t, 1H).

Example 89

(S)-6-(2-hydroxy-2-methylpropyl)-3-((S)-1-(4-(1-(2-hydroxy-2-methylpropyl)-6-oxo-1,6-dihydropyridin-3-yl)phenyl)ethyl)-6-phenyl-1,3-oxazinan-2-one

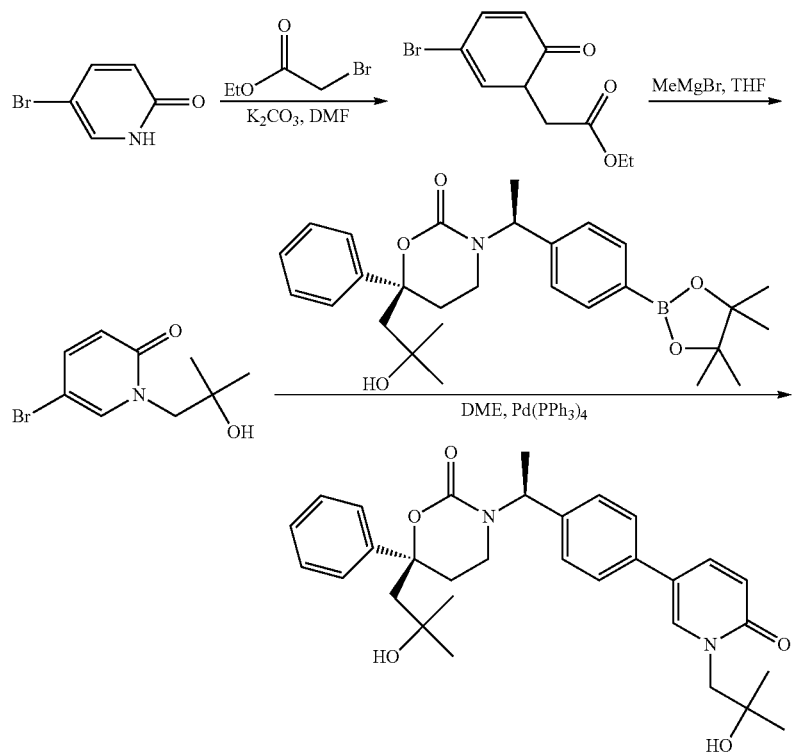

Step 1

To a solution of compound 5-bromopyridin-2(1H)-one (348 mg, 2.0 mmol) and $K_2CO_3$ (830 mg, 6.0 mmol) in DMF (15 mL) was added ethyl bromoacetate dropwise. The mixture was stirred at room temperature for 2 h, filtered, and the filtrate was concentrated in vacuo. The residue was purified by prep TLC (1:1 PE/EtOAc) to afford ethyl 2-(5-bromo-2-oxopyridin-1(2H)-yl)acetate (300 mg, 57.7%). $^1$H NMR $CDCl_3$: δ 7.41-7.26 (m, 2H), 6.53-6.5 (d, 1H), 4.59 (s, 2H), 4.28-4.21 (q, 2H), 1.32-1.23 (q, 3H).

Step 2

To a solution of ethyl 2-(5-bromo-2-oxopyridin-1(2H)-yl) acetate (130 mg, 0.5 mmol) in anhydrous THF (5 mL) was added 1 M MeMgBr (5 mL, 5 mmol) dropwise with stirring at −78° C. The reaction mixture was stirred at −78° C. for 1 h, quenched with aq $NH_4Cl$ (5 mL), and extractde with EtOAc (3×10 mL). The combined organic layer was dried and concentrated to give the crude final product, which was purified by preparative TLC (1:1 PE/EtOAc) to afford the 5-bromo-1-(2-hydroxy-2-methylpropyl)pyridin-2(1H)-one (65 mg, 52.9%).

Step 3

To a solution of 5-bromo-1-(2-hydroxy-2-methylpropyl) pyridin-2(1H)-one (20 mg, 81.3 mmol) in DME (6 mL) was added $Pd(PPh_3)_4$ (10 mg) under nitrogen. The mixture was stirred for 1 h at rt, and a solution of (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one (38.95 mg, 81.3 mmol) in EtOH (2 mL) and satd aq $NaHCO_3$ (2 mL) were added. The resulting mixture was stirred at 100° C. for 2 h, quenched with water, and extracted with EtOAc. The combined organic layer was dried over anhydrous $Na_2SO_4$ and concentrated to give the crude product, which was purified by preparative TLC and preparative HPLC to afford (S)-6-(2-hydroxy-2-methylpropyl)-3-((S)-1-(4-(1-(2-hydroxy-2-methylpropyl)-6-oxo-1,6-dihydropyridin-3-yl) phenyl)ethyl)-6-phenyl-1,3-oxazinan-2-one (6.5 mg, 15.5%). LC-MS Method 2 $t_R$=0.99 min, m/z=519; $^1$H NMR ($CDCl_3$): δ 7.60-7.57 (d, 1H), 7.43 (s, 1H), 7.36-7.26 (m, 5H), 7.15 (d, 2H), 7.01 (d, 2H), 6.70 (d, 1H), 2.85 (m, 1H), 5.69-5.66 (m, 1H), 4.13-4.09 (s, 2H), 4.05-3.98 (s, 1H), 2.89-2.86 (m, 1H), 2.44-2.36 (m, 1H), 2.28-2.16 (m, 5H), 1.58-1.53 (d, 3H), 1.33-1.30 (s, 6H), 1.19 (s, 3H), 1.12 (s, 3H).

Example 90

3-((S)-1-{4-[1-(3-Hydroxy-2,2-dimethyl-propyl)-2-oxo-1,2-dihydro-pyridin-4-yl]-phenyl}-ethyl)-(S)-6-(2-hydroxy-2-methyl-propyl)-6-phenyl-[1,3]oxazinan-2-one

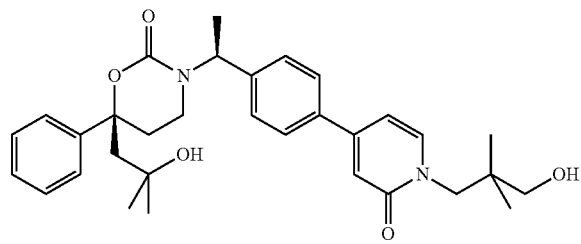

2 M aqueous $Na_2CO_3$ solution (0.32 mL) was added to a mixture of 4-bromo-1-(3-hydroxy-2,2-dimethyl-propyl)-1H-pyridin-2-one (0.13 g) and (S)-6-(2-hydroxy-2-methylpropyl)-6-phenyl-3-[(S)-1-(4-(4,4,5,5-tetramethyl-1,3,2-dioxaborolan-2-yl)phenyl)ethyl]-1,3-oxazinan-2-one (0.15 g) in N,N-dimethylformamide (3 mL). The resulting mixture was sparged with argon for 5 min, before [1,1'-bis(diphenylphosphino)-ferrocene]dichloro-palladium(II) dichloromethane complex (26 mg) was added. The mixture was heated to 100° C. and stirred at this temperature for 4 h. After cooling to ambient temperature, water was added and the resulting mixture was extracted with ethyl acetate. The combined organic extracts were washed with water and brine and dried ($MgSO_4$). The solvent was evaporated and the residue was purified by HPLC on reversed phase (methanol/water/ $NH_4OH$) to afford the title compound as a beige solid. Yield: 0.10 g (60% of theory); Mass spectrum ($ESI^+$): m/z=533 $[M+H]^+$.

3-(4-Bromo-2-oxo-2H-pyridin-1-yl)-2,2-dimethyl-propionic acid methyl ester

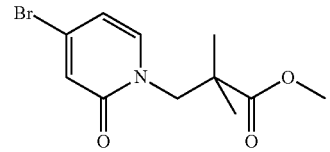

3-Bromo-2,2-dimethyl-propionic acid methyl ester (0.75 g) was added to a mixture of 4-bromo-1H-pyridin-2-one (0.55 g) and potassium carbonate (0.75 g) in N,N-dimethylformamide (10 mL) at room temperature. The mixture was heated to 60° C. and stirred at this temperature overnight. After stirring at 80° C. for another 8 h, the mixture was cooled to room temperature and water was added. The resultant mixture was extracted with ethyl acetate and the combined organic extracts were washed with brine and dried ($MgSO_4$). The solvent was evaporated and the residue was purified by chromatography on silica gel (cyclohexane/ethyl acetate 4:1) to afford the title compound; 3-(4-bromo-pyridin-2-yloxy)-2,2-dimethyl-propionic acid methyl ester (0.35 g) was also obtained from this reaction. Yield: 0.29 g (32% of theory); Mass spectrum ($ESI^+$): m/z=288/300 (Br) $[M+H]^+$.

4-Bromo-1-(3-hydroxy-2,2-dimethyl-propyl)-1H-pyridin-2-one

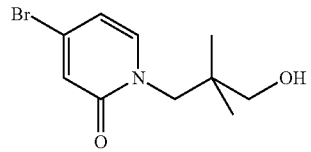

Lithium borohydride (25 mg) was added to a solution of 3-(4-bromo-2-oxo-2H-pyridin-1-yl)-2,2-dimethyl-propionic acid methyl ester (0.29 g) in tetrahydrofuran (3 mL) chilled in an ice bath. Then methanol (45 μL) was added and the mixture was stirred in the cooling bath for 1 h and at room temperature overnight. The mixture was diluted with tetrahydrofuran and $MgSO_4$ was added. The mixture was filtered and the filtrate was concentrated. The residue was purified by chromatography on silica gel (cyclohexane/ethyl acetate 1:1) to afford the

Example 91

3-((S)-1-(4-(1-cyclopropyl-2-oxo-1,2-dihydropyridin-4-yl)phenyl)ethyl)-6-(2-hydroxy-2-methylpropyl)-6-(tetrahydro-2H-pyran-4-yl)-1,3-oxazinan-2-one

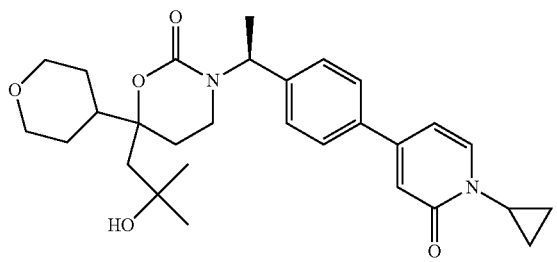

The title compound was prepared following procedures analogous to those described in Example 23 with the following changes. In Step 1 tetrahydro-2H-pyran-4-carboxylic acid and carbonyl diimidazole were used in place of 2-fluorobenzoyl chloride and in Step 9 1-cyclopropyl-4-iodopyridin-2(1H)-one was used in place of 5-bromo-1-methylpyridin-2(1H)-one. Two isomers were isolated.

Isomer 1. LC-MS Method 2 $t_R$=0.95 min, m/z=495.
Isomer 2. LC-MS Method 2 $t_R$=0.93 min, m/z=495.

Example 92

(S)-6-(2-hydroxy-2-methylpropyl)-3-((S)-1-(4-(1-trideuteromethyl-2-oxo-1,2-dihydropyridin-4-yl)phenyl)ethyl)-6-phenyl-1,3-oxazinan-2-one

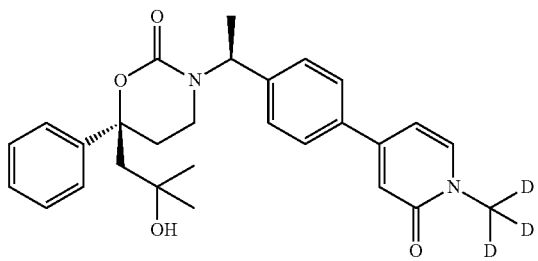

The title compound was prepared following procedures analogous to those described in Example 48 Method 2 with the following changes. In Step 1 trideuteromethyl iodide was used in place of methyl iodide and in Step 2 $PdCl_2(dppf)$ was used in place of $PdCl_2(PPh_3)_2$. LC-MS Method 1 $t_R$=1.30 min, m/z=464.

Biological Test Example 1

The inhibition of a microsomal preparation of 11β-HSD1 by compounds of the invention was measured essentially as previously described (K. Solly, S. S. Mundt, H. J. Zokian, G. J. Ding, A. Hermanowski-Vosatka, B. Strulovici, and W. Zheng, High-Throughput Screening of 11-Beta-Hydroxyseroid Dehydrogenase Type 1 in Scintillation Proximity Assay Format. Assay Drug Dev Technol 3 (2005) 377-384). All reactions were carried out at rt in 96 well clear flexible PET Microbeta plates (PerkinElmer). The assay begins by dispensing 49 μl of substrate solution (50 mM HEPES, pH 7.4, 100 mM KCl, 5 mM NaCl, 2 mM $MgCl_2$, 2 mM NADPH and 160 nM [$^3$H]cortisone (1 Ci/mmol)) and mixing in 1 μL of the test compounds in DMSO previously diluted in half-log increments (8 points) starting at 0.1 mM. After a 10 minute pre-incubation, 50 μL of enzyme solution containing microsomes isolated from CHO cells overexpressing human 11β-HSD1 (10-20 μg/ml of total protein) was added, and the plates were incubated for 90 minutes at rt. The reaction was stopped by adding 50 μl of the SPA beads suspension containing 10 μM 18β-glycyrrhetinic acid, 5 mg/ml protein A coated YSi SPA beads (GE Healthcare) and 3.3 μg/ml of anti-cortisol antibody (East Coast Biologics) in Superblock buffer (Bio-Rad). The plates were shaken for 120 minutes at rt, and the SPA signal corresponding to [$^3$H]cortisol was measured on a Microbeta plate reader.

Biological Test Example 2

The inhibition of 11β-HSD1 by compounds of this invention was measured in whole cells as follows. Cells for the assay were obtained from two sources: fully differentiated human omental adipocytes from Zen-Bio, Inc.; and human omental pre-adipocytes from Lonza Group Ltd. Pre-differentiated omental adipocytes from Zen-Bio Inc. were purchased in 96-well plates and were used in the assay at least two weeks after differentiation from precursor preadipocytes. Zen-Bio induced differentiation of pre-adipocytes by supplementing medium with adipogenic and lipogenic hormones (human insulin, dexamethasone, isobutylmethylxanthine and PPAR-gamma agonist). The cells were maintained in full adipocyte medium (DMEM/Ham's F-12 (1:1, v/v), HEPES pH 7.4, fetal bovine serum, penicillin, streptomycin and Amphotericin B, supplied by Zen-Bio, Inc.) at 37° C., 5% $CO_2$.

Pre-adipocytes were purchased from Lonza Group Ltd. and placed in culture in Preadipocyte Growth Medium-2 supplemented with fetal bovine serum, penicillin, and streptomycin (supplied by Lonza) at 37° C., 5% $CO_2$. Pre-adipocytes were differentiated by the addition of insulin, dexamethasone, indomethacin and isobutyl-methylxanthine (supplied by Lonza) to the Preadipocyte Growth Medium-2. Cells were exposed to the differentiating factors for 7 days, at which point the cells were differentiated and ready for the assay. One day before running the assay, the differentiated omental adipocytes were transferred into serum- and phenol-red-free medium for overnight incubation. The assay was performed in a total volume of 200 μL. The cells were pre-incubated with serum-free, phenol-red-free medium containing 0.1% (v/v) of DMSO and various concentrations of the test compounds at least 1 h before [$^3$H] cortisone in ethanol (50Ci/mmol, ARC, Inc.) was added to achieve a final concentration of cortisone of 100 nM. The cells were incubated for 3-4 hrs at 37° C., 5% $CO_2$. Negative controls were incubated without radioactive substrate and received the same amount of [$^3$H] cortisone at the end of the incubation. Formation of [$^3$H] cortisol was monitored by analyzing 25 μL of each supernatant in a scintillation proximity assay (SPA). (Solly, K.; Mundt, S. S.; Zokian, H. J.; Ding, G. J.; Hermanowski-Vosatka, A.; Strulovici, B.; Zheng, W. Assay Drug Dev. Technol. 2005, 3, 377-384). Many compounds of the invention showed significant activity in this assay.

TABLE OF BIOLOGICAL ASSAY RESULTS

Biological Test Example 1

| Compound | IC$_{50}$ Range$^a$ | Average % inhibition at 100 nM |
|---|---|---|
| EXAMPLE 1 | ++ | 90.3 |
| EXAMPLE 2 | ++ | 89.1 |
| EXAMPLE 3 | ++ | 95.6 |
| EXAMPLE 4 | ++ | 95.2 |
| EXAMPLE 5 | ++ | 95.6 |
| EXAMPLE 6 | ++ | 92.6 |
| EXAMPLE 7 | ++ | 75.9 |
| EXAMPLE 8 | ++ | 84.5 |
| EXAMPLE 9 | ++ | 86.2 |
| EXAMPLE 10 | ++ | 95.8 |
| EXAMPLE 11 | ++ | 84.1 |
| EXAMPLE 12 | ++ | 84.2 |
| EXAMPLE 13 | ++ | 90.0 |
| EXAMPLE 14 | ++ | 91.0 |
| EXAMPLE 15 | ++ | 92.9 |
| EXAMPLE 16 | ++ | 95.6 |
| EXAMPLE 17 Isomer 1 | ++ | 54.0 |
| EXAMPLE 17 Isomer 2 | # | 14.8 |
| EXAMPLE 18 Isomer 1 | # | 23.7 |
| EXAMPLE 18 Isomer 2 | ++ | 42.6 |
| EXAMPLE 19 | ++ | 36.5 |
| EXAMPLE 20 | ++ | 90.9 |
| EXAMPLE 21 Isomer 1 | ++ | 103.5 |
| EXAMPLE 21 Isomer 2 | ++ | 88.8 |
| EXAMPLE 22 Isomer 1 | ++ | 82.5 |
| EXAMPLE 22 Isomer 2 | ++ | 88.7 |
| EXAMPLE 23 | ++ | 88.2 |
| EXAMPLE 24 | ++ | 87.9 |
| EXAMPLE 25 | ++ | 93.9 |
| EXAMPLE 26 | ++ | 94.7 |
| EXAMPLE 27 | ++ | 92.0 |
| EXAMPLE 28 Isomer 1 | ++ | 86.9 |
| EXAMPLE 28 Isomer 2 | # | 42.9 |
| EXAMPLE 29 | ++ | 94.1 |
| EXAMPLE 30 | ++ | 96.7 |
| EXAMPLE 31 | ++ | 90.1 |
| EXAMPLE 32 | ++ | 96.4 |
| EXAMPLE 33 | ++ | 95.9 |
| EXAMPLE 34 | ++ | 95.0 |
| EXAMPLE 35 | ++ | 95.8 |
| EXAMPLE 36 | ++ | 95.0 |
| EXAMPLE 37 | ++ | 96.5 |
| EXAMPLE 38 | ++ | 74.3 |
| EXAMPLE 39 | ++ | 99.1 |
| EXAMPLE 40 | ++ | 95.9 |
| EXAMPLE 41 | ++ | 88.7 |
| EXAMPLE 42 | ++ | 88.4 |
| EXAMPLE 43 | ++ | 96.6 |
| EXAMPLE 44 | ++ | 102.0 |
| EXAMPLE 45 | ++ | 97.9 |
| EXAMPLE 46 | ++ | 94.8 |
| EXAMPLE 47 | ++ | 100.1 |
| EXAMPLE 48 | ++ | 95.0 |
| EXAMPLE 49 | ++ | 97.4 |
| EXAMPLE 50 | ++ | 97.1 |
| EXAMPLE 51 | ++ | 93.4 |
| EXAMPLE 52 | ++ | 95.4 |
| EXAMPLE 53 | ++ | 96.6 |
| EXAMPLE 54 | ++ | 96.0 |
| EXAMPLE 55 | ++ | 96.6 |
| EXAMPLE 56 | ++ | 102.8 |
| EXAMPLE 57 | ++ | 102.2 |
| EXAMPLE 58 | ++ | 104.7 |
| EXAMPLE 59 | ++ | 95.9 |
| EXAMPLE 60 | ++ | 94.5 |
| EXAMPLE 61 | ++ | 96.2 |
| EXAMPLE 62 | ++ | 96.9 |
| EXAMPLE 63 | ++ | 96.2 |
| EXAMPLE 64 | ++ | 94.9 |
| EXAMPLE 65 | ++ | 96.1 |
| EXAMPLE 66 | ++ | 96.0 |
| EXAMPLE 67 | ++ | 97.7 |
| EXAMPLE 68 | ++ | 95.6 |
| EXAMPLE 69 | ++ | 98.1 |
| EXAMPLE 70 | ++ | 96.5 |
| EXAMPLE 71 | ++ | 92.2 |
| EXAMPLE 72 | ++ | 95.6 |
| EXAMPLE 73 | ++ | 99.2 |
| EXAMPLE 74 | ++ | 95.0 |
| EXAMPLE 75 | ++ | 87.4 |
| EXAMPLE 84 Isomer 1 | # | 16.2 |
| EXAMPLE 84 Isomer 2 | # | 8.0 |
| EXAMPLE 85 | ++ | 68.4 |
| EXAMPLE 86 | ++ | 87.7 |
| EXAMPLE 87 | ++ | 107.5 |
| EXAMPLE 88 | ++ | 92.4 |
| EXAMPLE 89 | ++ | 92.6 |
| EXAMPLE 91 Isomer 1 | # | 22.5 |
| EXAMPLE 91 Isomer 2 | # | 13.8 |
| EXAMPLE 92 | ++ | 93.7 |

$^a$++ means IC$_{50}$ = <100 nM, + means IC$_{50}$ = 100-1000 nM, # means IC$_{50}$ > 100 nM, − means IC$_{50}$ > 1000 nM.

Biological Test Example 3

In vitro inhibition of 11β-HSD1 by test compounds was determined with HTRF (Homogeneous Time-Resolved Fluorescence) technology (cisbio international, France) detecting cortisol generated from cortisterone by human liver microsomes. Briefly, compounds were incubated for 1 hour at 37° C. in Tris buffer (20 mM tris, 5 mM EDTA, pH 6.0) containing NADPH (200 μM) and cortisone (80 nM). Cortisol generated in the reaction is then detected with a competitive immunoassay, involving two HTRF conjugates: cortisol linked to XL665 and anti-cortisol antibody labeled with Europium cryptate. The incubation period for detection reaction was typically 2 hours. The amount of cortisol was determined by reading the time-resolved fluorescence of the wells (Ex 320/75 nm; Em 615/8.5 nm and 665/7.5 nm). The ratio of the two emission signals was then calculated (Em665*10000/Em615). Each assay contained incubations with vehicle controls instead of compound as controls for non-inhibited cortisol generation (100% CTL; 'high values') and incubations with carbenoxolone as controls for fully inhibited enzyme and cortisol background (0% CTL; 'low values'). Each assay also contained a calibration curve with cortisol to transform the fluorescent data into cortisol concentrations. Percent inhibition of each compound was determined relative to the carbenoxolone signal.

In following table the 11β-HSD 1 inhibitory activities, determined as described above, wherein 100% indicates no inhibition and a value of zero or below zero indicates complete inhibition.

TABLE OF BIOLOGICAL ASSAY RESULTS
FOR BIOLOGICAL TEST 3

| Example | Average % control inhibition at 100 nM |
|---|---|
| 75 | −14 |
| 76 | 17 |
| 77 | 59 |
| 78 | 58 |
| 79 | 15 |
| 80 | 37 |
| 81 | 11 |
| 82 | −12 |
| 83 | 54 |
| 90 | 4 |

Biological Test Example 4

The inhibition of a microsomal preparation of 11β-HSD1 in the presence of 50% human plasma by compounds of the invention was measured as follows. Microsomes from CHO cells overexpressing human 11β-HSD1 were diluted into reaction buffer consisting of 25 mM HEPES, pH 7.4, 50 mM KCl, 2.5 mM NaCl, 1 mM MgCl2, and 50% (v/v) human plasma (BioChemed). The assay began by dispensing 49 μl of microsome solution into 96-well polypropylene plates and adding 1 μl of the test compounds in DMSO, previously diluted in half-log increments (8 points) starting at 1.0 mM. The reaction was initiated with the addition of 50 μl substrate solution consisting of reaction buffer with 2 mM NADPH and 160 nM [3-H]cortisone (1 Ci/mmol). The plates were incubated for 120 minutes at rt, and the reaction was quenched with the addition of 100 μl acetonitrile with 20 mM cortisone and 20 mM cortisol. After a ten minute incubation at rt, 100 μl of each well was filtered through a MultiScreen HTS, HV filter plate (Millipore) and diluted with 100 μl of reaction buffer without human plasma. [$^3$-H]cortisone and [$^3$-H]cortisol were separated by HPLC on a Zorbax SB-C8 column (4.6×250 mm, Agilent) with an isocratic elution at 25% acetonitrile in water with 0.01% trifluoroacetic acid, and radioactivity was quantified with an in-line β-RAM (IN/US Systems, Inc.).

Biological Test Example 5

Fraction Unbound in Human Plasma

Plasma protein binding of compounds was determined with Equilibrium Dialysis of spiked plasma against compound free dextrane buffer using a dialysis membrane with mass cutoff of 5000 Da. Compound concentrations in plasma and buffer after incubation were measured using HPLC/Mass spectrometry.

Biological Test Example 6

CYP3A4 Inhibition

The assay was based on a method published by Moody et al. (Xenobiotica 1999). The inhibition of cytochrome P450 3A4-isoenzyme catalysed N-demethylation of [N-methyl-14C]-Erythromycin by the test compound was assayed at 37° C. with human recombinant cytochrome P450 3A4. All assays were carried out on a robotic system in 96 well plates. The final incubation volume of 200 μl contained TRIS buffer (0.1 M), MgCl$_2$ (5 mM), recombinant protein (40 μmol/ml), Erythromycin (50 μM) and the test compound either at four different concentrations in duplicate (e.g. highest concentration 10-50 μM with subsequent serial 1:5 dilutions) or at a concentration of 10 μM in triplicate. Following a short pre-incubation period, reactions were started with the cofactor (NADPH, 1 mM) and stopped by addition of 50 μl aqueous trichloroacetic acid (10%; w/v). An aliquot of the incubate was transferred to 96 well solid phase extraction (SPE) plates and extracted on the cartridge. The resultant [$^{14}$C]-formaldehyde/formic acid was not retained on the cartridge and was therefore separated from the unmetabolized substrate by washing the SPE plates with water. An aliquot of the eluates was transferred into well plates suitable for liquid scintillation counting. The rate of formation of [$^{14}$C]-formaldehyde/formic acid in these incubations was compared to a control activity containing no test compound. If the compound was tested at four concentrations, experimental IC$_{50}$ values were calculated.

Biological Test Example 7

CYP2C9 Inhibition

Using a procedure similar to that described in Biological Test Example 6, the inhibition of cytochrome P450 2C9-isoenzyme catalysed O-demethylation of [O-methyl-$^{14}$C]-Naproxen by the test compound was assayed at 37° C. with human recombinant cytochrome P450 2C9. The experimental IC$_{50}$ was calculated based on % control at four different concentrations.

Biological Test Example 8

CYP2C19 Inhibition

Using a procedure similar to that described in Biological Test Example 6, the inhibition of cytochrome P450 2C19-isoenzyme catalysed N-demethylation of [N-methyl-$^{14}$C]-Diazepam by the test compound was assayed at 37° C. with human recombinant cytochrome P450 2C19. The experimental IC$_{50}$ was calculated based on % control at four different concentrations.

Biological Test Example 9

CYP2C9 Inhibition

The inhibition of recombinant CYP2C9 by compounds of the invention was measured using a commercial kit from Invitrogen (cat #2859). Supplied microsomes isolated from insect cells infected with a baculovirus engineered to express human CYP2C9 were diluted to 10 mM in reaction buffer (100 mM potassium phosphate buffer, pH 8.0) with an NADPH generation system (3.33 mM glucose-6-phosphate and 0.4 U/ml glucose-6-phosphate dehydrogenase). 89 μl of this dilution were dispensed to each well of a 96-well, black, polystyrene plate and mixed with 1 μl of test compound previously diluted in DMSO in half log increments starting at 3 mM. The assay was initiated by adding 10 μl of fluorogenic substrate n-octyloxymethylresorufin (OOMR, 20 μM.) with NADP (100 μM) diluted in reaction buffer. The plate was immediately placed in a Perkin Elmer Fusion plate reader. Reaction progress was monitored by measuring fluorescence every two minutes for a total of twenty minutes (530 nM excitation filter/605 nM emission filter).

TABLE OF BIOLOGICAL ASSAY RESULTS FOR
BIOLOGICAL TESTS 1, 4 AND 5

| EXAMPLE | Biological Test Example 1 IC$_{50}$ (nM) | Biological Test Example 4[a] IC$_{50}$ (nM) | Shift[b] | Biological Test Example 5 (%) |
|---|---|---|---|---|
| 1 | 1.51 | 2.84 | 1.88 | |
| 2 | 0.31 | 15.54 | 50.94 | |
| 3 | 1.59 | 3.85 | 2.42 | |
| 4 | 1.80 | 5.60 | 3.12 | |
| 5 | 1.25 | 3.80 | 3.04 | |
| 6 | 2.36 | 4.07 | 1.72 | |
| 7 | 35.07 | nt | | |
| 8 | 18.33 | nt | | |
| 9 | 4.29 | 13.12 | 3.06 | |
| 10 | 2.91 | 13.13 | 4.51 | |
| 11 | 5.94 | 13.51 | 2.27 | |
| 12 | 5.38 | 31.75 | 5.90 | |
| 13 | 7.22 | nt | 0.00 | |
| 14 | 1.11 | 2.88 | 2.59 | |
| 15 | 0.58 | 2.15 | 3.70 | |
| 16 | 0.90 | 2.00 | 2.23 | |
| 17 Isomer 1 | 75.98 | nt | | |
| 17 Isomer 2 | >100.00 | nt | | |
| 18 Isomer 1 | >100.00 | nt | | |
| 18 Isomer 2 | 97.49 | nt | | |
| 19 | 95.38 | nt | | |
| 20 | 4.28 | 7.61 | 1.78 | |
| 21 Isomer 1 | 3.89 | 4.72 | 1.21 | |
| 21 Isomer 2 | 7.21 | 9.58 | 1.33 | |
| 22 Isomer 1 | 14.87 | 75.86 | 5.10 | |
| 22 Isomer 2 | 6.60 | 20.11 | 3.05 | |
| 23 | 1.99 | 4.17 | 2.10 | |
| 24 | 3.70 | 8.28 | 2.24 | |
| 25 | 2.34 | 5.44 | 2.32 | |
| 26 | 1.49 | 8.05 | 5.39 | |
| 27 | 3.49 | 8.41 | 2.41 | |
| 28 Isomer 1 | >100.00 | nt | | |
| 28 Isomer 2 | 8.89 | nt | | |
| 29 | 1.39 | 2.76 | 1.99 | |
| 30 | 1.44 | 3.42 | 2.37 | 13.9 |
| 31 | 9.01 | 25.42 | 2.82 | |
| 32 | 3.58 | 11.48 | 3.20 | 12.3 |
| 33 | 2.23 | 3.69 | 1.66 | |
| 34 | 3.19 | 8.85 | 2.78 | |
| 35 | 2.97 | nt | | |
| 36 | 2.03 | 13.62 | 6.72 | |
| 37 | 1.67 | 6.44 | 3.85 | 14.6 |
| 38 | 5.18 | nt | | |
| 39 | 1.31 | 5.10 | 3.89 | |
| 40 | 1.86 | 7.01 | 3.77 | |
| 41 | 9.28 | 38.06 | 4.10 | |
| 42 | 6.70 | 53.38 | 7.97 | |
| 43 | 2.23 | 3.51 | 1.57 | |
| 44 | 1.08 | 5.60 | 5.19 | |
| 45 | 1.58 | 11.85 | 7.52 | |
| 46 | 4.24 | 16.97 | 4.00 | |
| 47 | 0.96 | 6.75 | 7.03 | |
| 48 | 1.62 | 5.54 | 3.41 | 8.7 |
| 49 | 1.03 | 2.96 | 2.86 | |
| 50 | 0.61 | 1.97 | 3.23 | |
| 51 | 5.46 | 7.89 | 1.45 | |
| 52 | 3.24 | 14.09 | 4.35 | 9.0 |
| 53 | 1.35 | 4.19 | 3.10 | 12.8 |
| 54 | 2.40 | 7.05 | 2.94 | 9.1 |
| 55 | 1.66 | 7.18 | 4.31 | 7.1 |
| 56 | 1.03 | 13.19 | 12.81 | |
| 57 | 1.26 | 12.45 | 9.92 | |
| 58 | 0.87 | 8.98 | 10.32 | |
| 59 | 1.53 | 4.02 | 2.63 | 11.7 |
| 60 | 0.75 | 7.00 | 9.40 | |
| 61 | 1.40 | 6.99 | 4.99 | |
| 62 | 2.48 | 11.96 | 4.82 | |
| 63 | 3.85 | 102.97 | 26.73 | |
| 64 | 1.64 | 9.62 | 5.87 | |
| 65 | 0.80 | 4.64 | 5.82 | |
| 66 | 1.47 | 6.71 | 4.58 | 5.5 |
| 67 | 2.01 | 7.29 | 3.63 | |
| 68 | 0.96 | 4.39 | 4.59 | |
| 69 | 0.72 | 3.89 | 5.42 | |
| 70 | 1.01 | 2.63 | 2.60 | |
| 71 | 0.65 | 3.96 | 6.09 | |
| 72 | 4.04 | 8.23 | 2.04 | |
| 73 | 1.99 | 33.08 | 16.62 | |
| 74 | 1.21 | 8.76 | 7.24 | |
| 75 | 1.40 | 2.80 | 2.00 | 15.6 |
| 84 Isomer 1 | >100 | nt | | |
| 84 Isomer 2 | >100 | nt | | |
| 85 | 42.9 | nt | | |
| 86 | 12.1 | 24.5 | 2.0 | |
| 87 | 1.4 | 3.2 | 2.2 | |
| 88 | 1.3 | | | |
| 89 | 2.8 | | | |
| 91 Isomer 1 | >100 | | | |
| 91 Isomer 2 | >100 | | | |
| 92 | 1.8 | | | |

[a]nt means not tested;
[b]Shift is the IC$_{50}$ determined in Biological Test Example 4 divided by the IC$_{50}$ determined in Biological Test Example 1.

TABLE OF BIOLOGICAL ASSAY RESULTS FOR
BIOLOGICAL TESTS 6-9

| EXAMPLE | Biological Test Example 6 CYP3A4, IC$_{50}$ [μM] | Biological Test Example 7 CYP2C9, IC$_{50}$ [μM] | Biological Test Example 8 CYP2C19, IC$_{50}$ [μM] | Biological Test Example 9 CYP2C9 IC$_{50}$ [uM] |
|---|---|---|---|---|
| 1 | | | | |
| 2 | | | | |
| 3 | 44 | 38 | >50 | |
| 4 | 21 | 17 | 22 | |
| 5 | 29 | 37 | 22 | |
| 6 | | | | |
| 7 | | | | |
| 8 | | | | |
| 9 | | | | |
| 10 | | | | 30.0 |
| 11 | | | | 16.1 |
| 12 | | | | 12.1 |
| 13 | | | | |
| 14 | 25 | 18 | 24 | |
| 15 | | | | |
| 16 | | | | |
| 17 Isomer 1 | | | | |
| 17 Isomer 2 | | | | |
| 18 Isomer 1 | | | | |
| 18 Isomer 2 | | | | |
| 19 | | | | |
| 20 | | | | |
| 21 Isomer 1 | | | | |
| 21 Isomer 2 | | | | |
| 22 Isomer 1 | | | | |
| 22 Isomer 2 | | | | |
| 23 | >50 | >50 | 44 | |
| 24 | | | | |
| 25 | 33 | 30 | 22 | |
| 26 | >50 | >50 | >50 | |
| 27 | | | | |
| 28.1 | | | | |
| 28.2 | | | | |

TABLE OF BIOLOGICAL ASSAY RESULTS FOR BIOLOGICAL TESTS 6-9 -continued

| EXAMPLE | Biological Test Example 6 CYP3A4, IC$_{50}$ [µM] | Biological Test Example 7 CYP2C9, IC$_{50}$ [µM] | Biological Test Example 8 CYP2C19, IC$_{50}$ [µM] | Biological Test Example 9 CYP2C9 IC$_{50}$ [uM] |
|---|---|---|---|---|
| 29 | | | | 7.5 |
| 30 | >50 | >50 | 27 | 14.3 |
| 31 | | | | |
| 32 | >50 | >50 | >50 | 28.7 |
| 33 | >50 | 43 | 17 | 24.6 |
| 34 | | | | |
| 35 | | | | |
| 36 | | | | |
| 37 | 48 | 43 | >50 | 24.8 |
| 38 | | | | 30.0 |
| 39 | | | | |
| 40 | >50 | >50 | 13 | 27.9 |
| 41 | | | | |
| 42 | | | | |
| 43 | | | | 10.5 |
| 44 | | | | |
| 45 | | | | 15.2 |
| 46 | | | | |
| 47 | | | | 12.1 |
| 48 | >50 | >50 | >50 | 30.0 |
| 49 | 32 | 29 | 46 | 14.8 |
| 50 | 14 | 11 | 27 | 5.1 |
| 51 | | | | |
| 52 | 48 | 14 | 8 | 20.3 |
| 53 | >50 | >50 | >50 | 30.0 |
| 54 | >50 | >50 | 18 | |
| 55 | >50 | 29 | 13 | 24.3 |
| 56 | | | | |
| 57 | | | | |
| 58 | 8 | 3 | 2 | |
| 59 | >50 | >50 | 37 | 17.7 |
| 60 | | | | |
| 61 | >50 | 40 | 18 | |
| 62 | 48 | >50 | 38 | |
| 63 | | | | |
| 64 | >50 | 33 | 17 | |
| 65 | >50 | >50 | 25 | |
| 66 | 18 | 10 | 11 | |
| 67 | 28 | 41 | 34 | |
| 68 | 43 | 47 | 28 | |
| 69 | 23 | 38 | >50 | |
| 70 | 28 | >50 | 23 | |
| 71 | 6 | 17 | 24 | |
| 72 | 41 | 35 | 8 | |
| 73 | | | | |
| 74 | | | | |
| 75 | 23 | 19 | 24 | |
| 76 | 10 | 4 | 9 | |
| 77 | >50 | >50 | 34 | |
| 78 | 47 | 39 | 40 | |
| 79 | >50 | >50 | >50 | |
| 80 | >50 | >50 | 38 | |
| 81 | >50 | 30 | 12 | |
| 82 | >50 | 48 | 29 | |
| 83 | >50 | 14 | 10 | |
| 84 Isomer 1 | | | | |
| 84 Isomer 2 | | | | |
| 85 | | | | |
| 86 | | | | |
| 87 | | | | |
| 88 | | | | |
| 89 | | | | |

TABLE OF BIOLOGICAL ASSAY RESULTS FOR COMPARATOR COMPOUNDS IN BIOLOGICAL TESTS 1, 4 AND 5

| Comparator Compound | Biological Test Example 1 IC$_{50}$ (nM) | Biological Test Example 4[a] IC$_{50}$ (nM) | Shift[b] | Biological Test Example 5 (%) |
|---|---|---|---|---|
| 1 | 0.77 | 11.97 | 15.51 | |
| 2 | 1.80 | 14.16 | 7.88 | |
| 3 | 0.75 | 17.74 | 23.63 | 0.3 |
| 4 | 1.44 | 15.24 | 10.57 | |
| 5 | 0.51 | 18.50 | 36.10 | |
| 6 | 1.48 | 37.58 | 25.39 | |
| 7 | 0.99 | 41.90 | 42.43 | |
| 8 | 0.72 | 17.85 | 24.74 | |
| 9 | 0.55 | 11.86 | 21.45 | 0.3 |
| 10 | 1.79 | 53.49 | 29.91 | |
| 11 | 0.55 | 13.40 | 24.59 | 0.7 |
| 12 | 1.08 | 19.54 | 18.12 | 0.4 |
| 13 | 0.76 | 6.32 | 8.30 | |
| 14 | 1.30 | 8.94 | 6.90 | |
| 15 | 0.79 | 8.94 | 11.32 | |

[a]nt means not tested;
[b]Shift is the IC$_{50}$ determined in Biological Test Example 4 divided by the IC$_{50}$ determined in Biological Test Example 1.

TABLE OF BIOLOGICAL ASSAY RESULTS FOR COMPARATOR COMPOUNDS IN BIOLOGICAL TESTS 6-9

| Comparator Compound | Biological Test Example 6 CYP3A4, IC$_{50}$ [µM] | Biological Test Example 7 CYP2C9, IC$_{50}$ [µM] | Biological Test Example 8 CYP2C19, IC$_{50}$ [µM] | Biological Test Example 9 CYP2C9 IC$_{50}$ [µM] |
|---|---|---|---|---|
| 1 | | | | 27.0 |
| 2 | | | | 1.4 |
| 3 | 7.4 | 4.1 | 5.7 | 4.9 |
| 4 | | | | 5.1 |
| 5 | 9.9 | 5.1 | 8.3 | 3.7 |
| 6 | 4.4 | 2.3 | 8.6 | 5.0 |
| 7 | | | | 4.0 |
| 8 | 5.3 | 2.4 | 5.6 | 3.0 |
| 9 | 7.0 | 3.1 | 9.3 | 2.5 |
| 10 | | | | 3.6 |
| 11 | 14.1 | 6.3 | 12.5 | 5.5 |
| 12 | 4.9 | 4.6 | 9.5 | 2.5 |
| 12 | 4.9 | 3.9 | 10.1 | |
| 13 | 4.4 | 5.6 | <0.4 | 7.3 |
| 14 | 19.7 | 25.9 | 6.4 | 24.6 |
| 15 | 3.1 | 7.7 | <0.4 | 9.5 |

Comparator 1

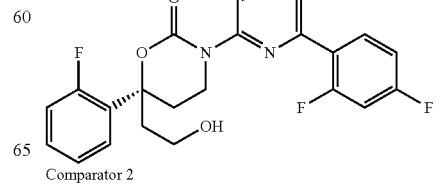

Comparator 2

TABLE OF BIOLOGICAL ASSAY RESULTS FOR COMPARATOR COMPOUNDS IN BIOLOGICAL TESTS 6-9

| Comparator Compound | Biological Test Example 6 CYP3A4, IC$_{50}$ [μM] | Biological Test Example 7 CYP2C9, IC$_{50}$ [μM] | Biological Test Example 8 CYP2C19, IC$_{50}$ [μM] | Biological Test Example 9 CYP2C9 IC$_{50}$ [uM] |
|---|---|---|---|---|

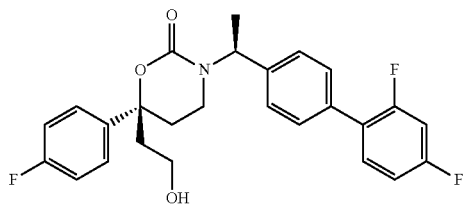

Comparator 3

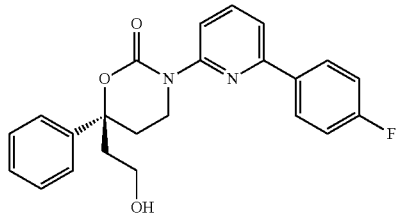

Comparator 4

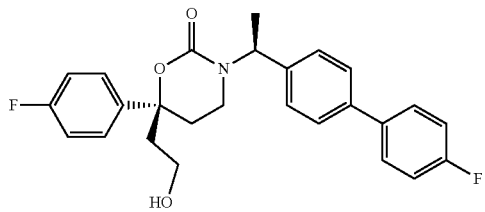

Comparator 5

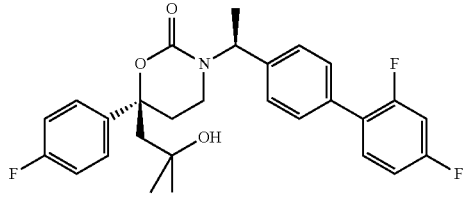

Comparator 6

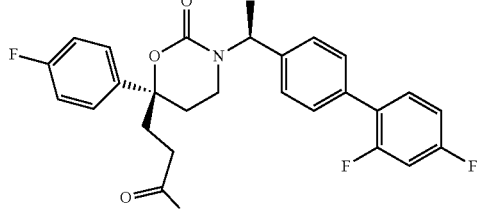

Comparator 7

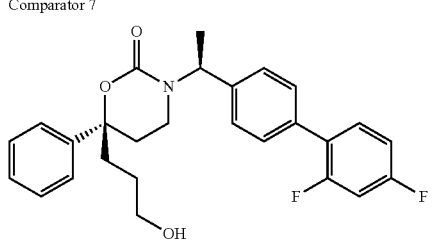

Comparator 8

TABLE OF BIOLOGICAL ASSAY RESULTS FOR COMPARATOR COMPOUNDS IN BIOLOGICAL TESTS 6-9

| Comparator Compound | Biological Test Example 6 CYP3A4, IC$_{50}$ [μM] | Biological Test Example 7 CYP2C9, IC$_{50}$ [μM] | Biological Test Example 8 CYP2C19, IC$_{50}$ [μM] | Biological Test Example 9 CYP2C9 IC$_{50}$ [uM] |
|---|---|---|---|---|

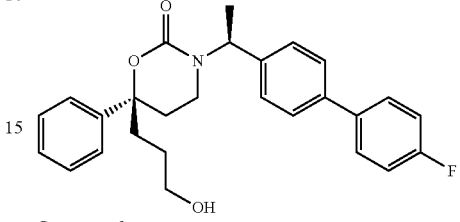

Comparator 9

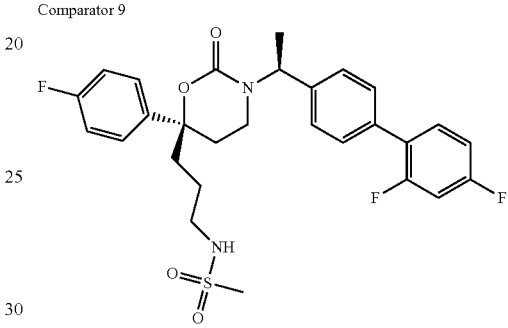

Comparator 10

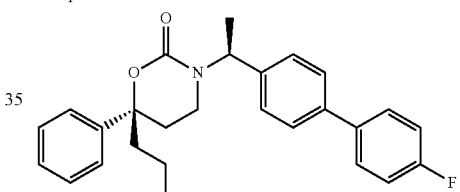

Comparator 11

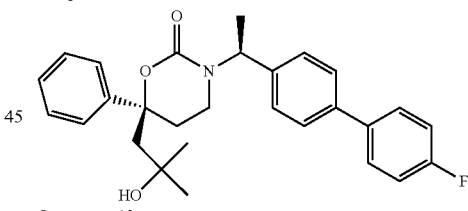

Comparator 12

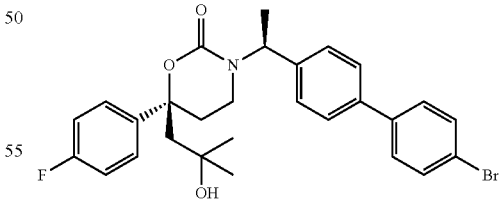

Comparator 13

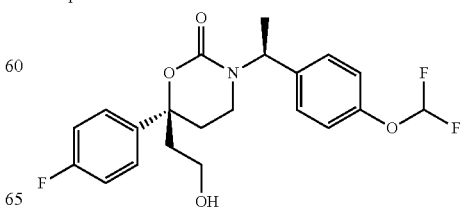

Comparator 14

-continued

TABLE OF BIOLOGICAL ASSAY RESULTS FOR COMPARATOR COMPOUNDS IN BIOLOGICAL TESTS 6-9

| Comparator Compound | Biological Test Example 6 CYP3A4, IC$_{50}$ [μM] | Biological Test Example 7 CYP2C9, IC$_{50}$ [μM] | Biological Test Example 8 CYP2C19, IC$_{50}$ [μM] | Biological Test Example 9 CYP2C9 IC$_{50}$ [uM] |
|---|---|---|---|---|

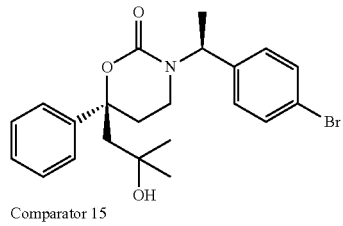

Comparator 15

The compounds of the invention are useful for ameliorating or treating disorders or diseases in which decreasing the level of cortisol is effective in treating a disease state. Thus, the compounds of the invention can be used in the treatment or prevention of diabetes mellitus (e.g., type II diabetes), obesity, symptoms of metabolic syndrome, glucose intolerance, hyperglycemica, hypertension, hyperlipidemia, insulin resistance, cardiovascular disease, dyslipidemia, atherosclerosis, lipodystrophy, osteoporosis, glaucoma, Cushing's syndrome, Addison's Disease, visceral fat obesity associated with glucocorticoid therapy, depression, anxiety, Alzheimer's disease, dementia, cognitive decline (including age-related cognitive decline), polycystic ovarian syndrome, infertility and hypergonadism. The compounds of the invention can be used as therapeutic agents for pseudo Cushing's Syndrome associated with alcoholic liver disease. In addition, the compounds modulate the function of B and T cells of the immune system and can therefore be used to treat diseases such as tuberculosis, leprosy and psoriasis. They can also be used to promote wound healing, particularly in diabetic patients.

Additional diseases or disorders that are related to 11β-HSD1 activity include those selected from the group consisting of lipid disorders, hypertriglyceridemia, hypercholesterolemia, low HDL levels, high LDL levels, vascular restenosis, pancreatitis, abdominal obesity, neurodegenerative disease, retinopathy, nephropathy, neuropathy, diabetes, coronary heart disease, stroke, peripheral vascular disease, Cushing's syndrome, hyperinsulinemia, viral diseases, and Syndrome X. A further disease related to 11β-HSD1 activity is pseudo Cushing's Syndrome associated with alcoholic liver disease.

A pharmaceutical composition of the invention may, alternatively or in addition to an 11β-HSD1 inhibitor of the invention, comprise a pharmaceutically acceptable salt of a an 11β-HSD1 inhibitor of the invention and one or more pharmaceutically acceptable carriers therefore. Alternatively, a pharmaceutical composition of the invention may comprise a compound of an 11β-HSD1 inhibitor of the invention or a pharmaceutical salt thereof as the only pharmaceutically active agent in the pharmaceutical composition. The disclosed 11β-HSD1 inhibitors can be used alone or in a combination therapy with one or more additional agents for the treatment of diabetes, dyslipidemia, cardiovascular disease, hypertension, obesity, cancer or glaucoma.

The compositions of the invention are 11β-HSD1 inhibitors. Said compositions contain compounds having a mean inhibition constant (IC$_{50}$) against 11β-HSD1 of below about 1,000 nM; preferably below about 100 nM; more preferably below about 50 nM; even more preferably below about 5 nM; and most preferably below about 1 nM.

The invention includes a therapeutic method for treating or ameliorating an 11β-HSD1 mediated disorder in a subject in need thereof comprising administering to a subject in need thereof an effective amount of an 11β-HSD1 inhibitor of the invention, or an enantiomer, diastereomer, or pharmaceutically acceptable salt thereof or composition thereof. As used herein, "treating" or "treatment" includes both therapeutic and prophylactic treatment. Therapeutic treatment includes reducing the symptoms associated with a disease or condition and/or increasing the longevity of a subject with the disease or condition. Prophylactic treatment includes delaying the onset of a disease or condition in a subject at risk of developing the disease or condition or reducing the likelihood that a subject will then develop the disease or condition in a subject that is at risk for developing the disease or condition.

An embodiment of the invention includes administering an 11β-HSD1 inhibiting compound of the invention or composition thereof in a combination therapy with one or more additional agents for the treatment of diabetes, dyslipidemia, cardiovascular disease, hypertension, obesity, cancer or glaucoma. Agents for the treatment of diabetes include insulins, such as Humulin® (Eli Lilly), Lantus® (Sanofi Aventis), Novolin (Novo Nordisk), and Exubera® (Pfizer); PPAR gamma agonists, such as Avandia® (rosiglitzone maleate, GSK) and Actos® (pioglitazone hydrochloride, Takeda/Eli Lilly); sulfonylureas, such as Amaryl® (glimepiride, Sanofi Aventis), Diabeta® (glyburide, Sanofi Aventis), Micronase®/Glynase® (glyburide, Pfizer), and Glucotrol®/Glucotrol XL® and (glipizide, Pfizer); meglitinides, such as Prandin®/NovoNorm® (repaglinide, Novo Nordisk), Starlix® (nateglinide, Novartis), and Glufast® (mitiglinide, Takeda); biguanides, such as Glucophase®/Glucophase XR® (metformin HCl, Bristol Myers Squibb) and Glumetza (metformin HCl, Depomed); thiazolidinediones; amylin analogs, GLP-1 analogs; DPP-IV inhibitors; PTB-1B inhibitors; protein kinase inhibitors (including AMP-activated protein kinase inhibitors); glucagon antagonists, glycogen synthase kinase-3 beta inhibitors; glucose-6-phoshatase inhibitors; glycogen phosphorylase inhibitors; sodium glucose co-transporter inhibitors, and alpha-glucosidase inhibitors, such as Precose®/Glucobay®/Prandase®/Glucor® (acarbose, Bayer) and Glyset® (miglitol, Pfizer). Agents for the treatment of dyslipidemia and cardiovascular disease include statins, fibrates, and ezetimbe. Agents for the treatment of hypertension include alpha-blockers, beta-blockers, calcium channel blockers, diuretics, angiotensin converting enzyme (ACE) inhibitors, dual ACE and neutral endopeptidase (NEP) inhibitors, angiotensin-receptor blockers (ARBs), aldosterone synthase inhibitors, aldosterone-receptor antagonists, or endothelin receptor antagonist. Agents for the treatment of obesity include orlistat, phentermine, sibutramine and rimonabant.

An embodiment of the invention includes administering an 11β-HSD1 inhibiting compound of the invention or composition thereof in a combination therapy with one or more other 11β-HSD1 inhibitors, or with combination products, such as Avandamet® (metformin HCl and rosiglitazone maleate, GSK); Avandaryl® (glimepiride and rosiglitazone maleate, GSK); Metaglip® (glipizide and metformin HCl, Bristol Myers Squibb); and Glucovance® (glyburide and metformin HCl, Bristol Myers Squibb).

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Additionally, the compounds of the present invention can be administered intranasally or transdermally. It will be obvious to those skilled in the art that the following dosage forms may comprise as the active ingredient, either compounds or a corresponding pharmaceutically acceptable salt of a compound of the present invention.

For preparing pharmaceutical compositions from the compounds of the present invention, pharmaceutically acceptable carriers can either be solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material. In powders, the carrier is a finely divided solid which is in a mixture with the finely divided active ingredient.

In tablets, the active ingredient is mixed with the carrier having the necessary binding properties in suitable proportions and compacted in the shape and size desired.

The powders and tablets preferably contain from about one to about seventy percent of the active ingredient. Suitable carriers are magnesium carbonate, magnesium stearate, talc, sugar, lactose, pectin, dextrin, starch, gelatin, tragacanth, methylcellulose, sodium caboxymethylcellulose, a low-melting wax, cocoa butter, and the like. Tablets, powders, cachets, lozenges, fast-melt strips, capsules and pills can be used as solid dosage forms containing the active ingredient suitable for oral administration.

For preparing suppositories, a low-melting wax, such as a mixture of fatty acid glycerides or cocoa butter, is first-melted and the active ingredient is dispersed homogeneously therein, as by stirring. The molten homogeneous mixture is then poured into convenient sized molds, allowed to cool, and thereby to solidify.

Liquid form preparations include solutions, suspensions, retention enemas, and emulsions, for example, water or water propylene glycol solutions. For parenteral injection, liquid preparations can be formulated in solution in aqueous polyethylene glycol solution.

Aqueous solutions suitable for oral administration can be prepared by dissolving the active ingredient in water and adding suitable colorants, flavors, stabilizing, and thickening agents as desired. Aqueous suspensions for oral administration can be prepared by dispersing the finely divided active ingredient in water with viscous material, such as natural or synthetic gums, resins, methylcellulose, sodium carboxymethylcellulose, and other well-known suspending agents.

The pharmaceutical composition is preferably in unit dosage form. In such form, the composition is subdivided into unit doses containing appropriate quantities of the active ingredient. The unit dosage form can be a packaged preparation, the package containing discrete quantities of, for example, tablets, powders, and capsules in vials or ampules. Also, the unit dosage form can be a tablet, cachet, capsule, or lozenge itself, or it can be the appropriate amount of any of these in packaged form.

The quantity of active ingredient in a unit dose preparation may be varied or adjusted from about 0.1 mg to about 1000.0 mg, preferably from about 0.1 mg to about 100 mg. The dosages, however, may be varied depending upon the requirements of the patient, the severity of the condition being treated, and the compound being employed. Determination of the proper dosage for a particular situation is within the skill in the art. Also, the pharmaceutical composition may contain, if desired, other compatible therapeutic agents.

In therapeutic treatment or as a method-of-use as an inhibitor of 11β-HSD1 or an inhibitor in the production of cortisol in the cell, the active ingredient is preferably administered orally in a solid dosage form as disclosed above in an amount of about 0.1 mg to about 100 mg per daily dose where the dose is administered once or more than once daily.

All publications, patents and patent applications mentioned in this specification are herein incorporated by reference to the same extent as if each individual publication or patent application were specifically and individually designated as having been incorporated by reference. It is understood that the examples and embodiments described herein are for illustrative purposes only, and it will be appreciated that the invention is susceptible to modification, variation and change without departing from the proper scope or fair meaning of the appended claims.

While this invention has been particularly shown and described with references to example embodiments thereof, it will be understood by those skilled in the art that various changes in form and details may be made therein without departing from the scope of the invention encompassed by the appended claims.

What is claimed is:

1. A compound of the following formula:

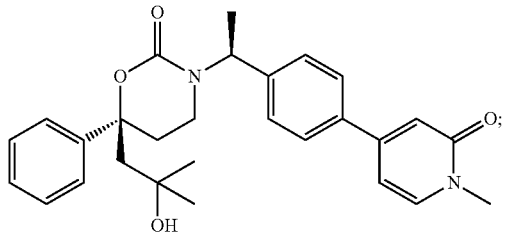

or a pharmaceutically acceptable salt or hydrate thereof.

2. A method of treating a human with a disease or condition selected from Type II diabetes mellitus, obesity, glucose intolerance, hyperglycemica, hyperlipidemia, insulin resistance and dyslipidemia comprising the step of administering to the human with the disease or condition an effective amount of a compound of the following formula:

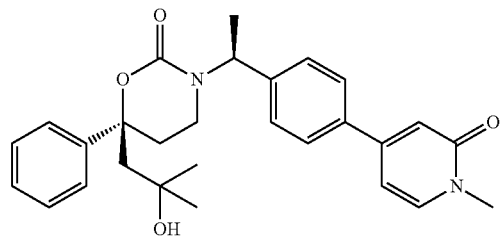

or a pharmaceutically acceptable salt or hydrate thereof.

3. The method of claim 2, wherein the disease or condition is Type II diabetes mellitus.

4. A pharmaceutical composition comprising: i) a pharmaceutically acceptable carrier or diluent; and ii) a compound of the following formula:

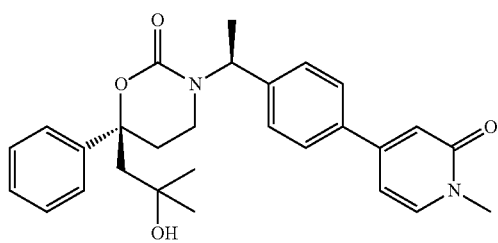

or a pharmaceutically acceptable salt or hydrate thereof.

5. A compound of the following formula:

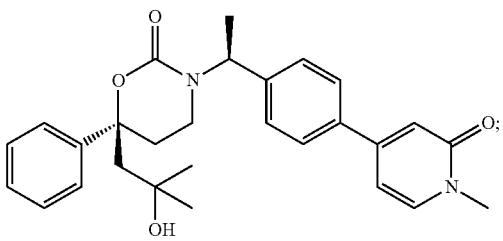

or a pharmaceutically acceptable salt thereof.

6. A pharmaceutical composition comprising: i) a pharmaceutically acceptable carrier or diluent; and ii) a compound of the following formula:

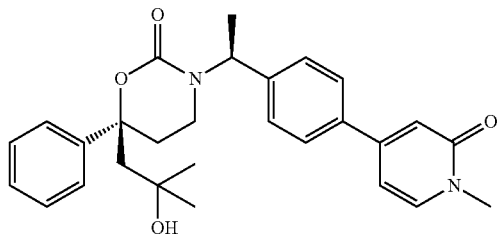

or a pharmaceutically acceptable salt thereof.

7. A method of treating a human with a disease or condition selected from Type II diabetes mellitus, obesity, glucose intolerance, hyperglycemica, hyperlipidemia, insulin resistance and dyslipidemia comprising the step of administering to the human with the disease or condition an effective amount of a compound of the following formula:

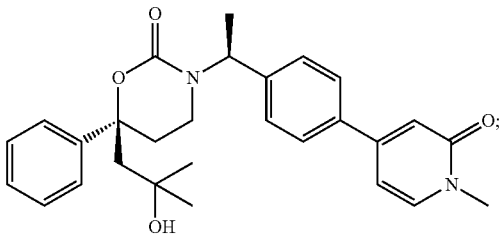

or a pharmaceutically acceptable salt thereof.

8. The method of claim 7 wherein the disease or condition is Type II diabetes mellitus.

9. A monohydrate of a compound of the following formula:

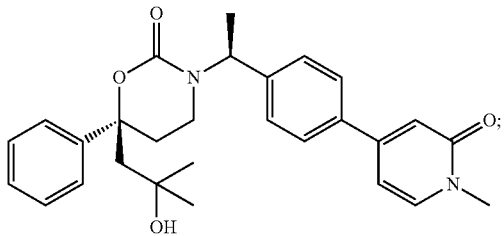

or a pharmaceutically acceptable salt thereof.

10. A pharmaceutical composition comprising: i) a pharmaceutically acceptable carrier or diluent; and ii) a monohydrate of a compound of the following formula:

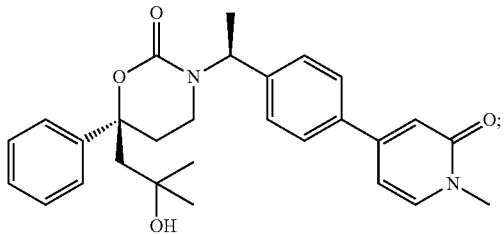

or a pharmaceutically acceptable salt thereof.

11. A method of treating a human with a disease or condition selected from Type II diabetes mellitus, obesity, glucose intolerance, hyperglycemica, hyperlipidemia, insulin resistance and dyslipidemia comprising the step of administering to the human with the disease or condition an effective amount of a monohydrate of a compound of the following formula:

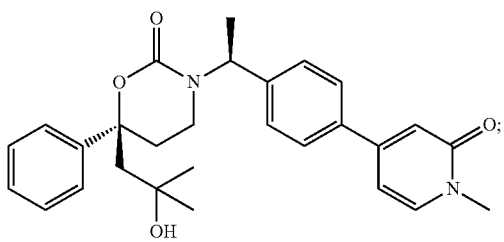

or a pharmaceutically acceptable salt thereof.

12. The method of claim 11 wherein the disease or condition is Type II diabetes mellitus.

13. A monohydrate of a compound of the following formula:

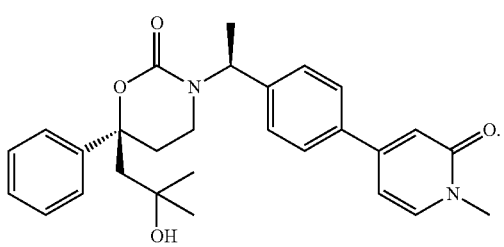

14. A pharmaceutical composition comprising: i) a pharmaceutically acceptable carrier or diluent; and ii) a monohydrate of a compound of the following formula:

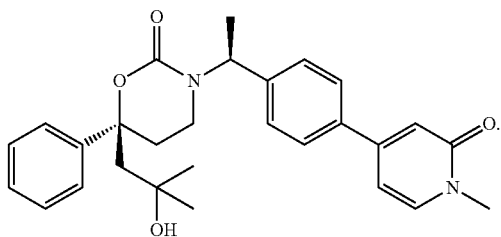

15. A method of treating a human with a disease or condition selected from Type II diabetes mellitus, obesity, glucose intolerance, hyperglycemica, hyperlipidemia, insulin resistance and dyslipidemia comprising the step of administering to the human with the disease or condition an effective amount of a monohydrate of a compound of the following formula:

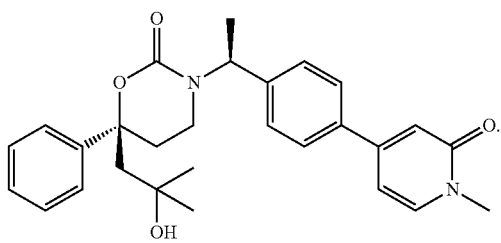

16. The method of claim 15 wherein the disease or condition is Type II diabetes mellitus.

17. A hydrate of a compound of the following formula:

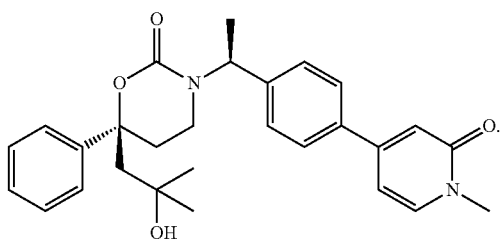

18. A pharmaceutical composition comprising: i) a pharmaceutically acceptable carrier or diluent; and ii) a hydrate of a compound of the following formula:

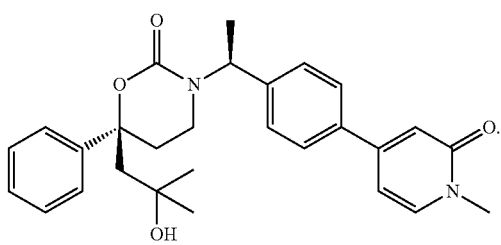

19. A method of treating a human with a disease or condition selected from Type II diabetes mellitus, obesity, glucose intolerance, hyperglycemica, hyperlipidemia, insulin resistance and dyslipidemia comprising the step of administering to the human with the disease or condition an effective amount of a hydrate of a compound of the following formula:

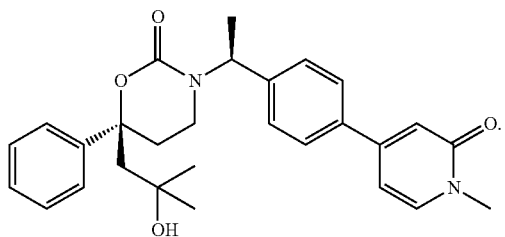

20. The method of claim 19 wherein the disease or condition is Type II diabetes mellitus.

21. A hydrate of a compound of the following formula:

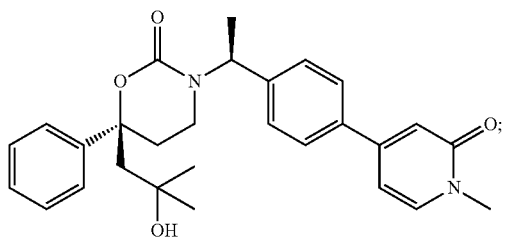

or a pharmaceutically acceptable salt thereof.

22. A pharmaceutical composition comprising: i) a pharmaceutically acceptable carrier or diluent; and ii) a hydrate of a compound of the following formula:

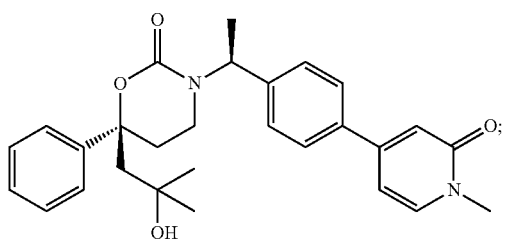

or a pharmaceutically acceptable salt thereof.

23. A method of treating a human with a disease or condition selected from Type II diabetes mellitus, obesity, glucose intolerance, hyperglycemica, hyperlipidemia, insulin resistance and dyslipidemia comprising the step of administering to the human with the disease or condition an effective amount of a hydrate of a compound of the following formula:

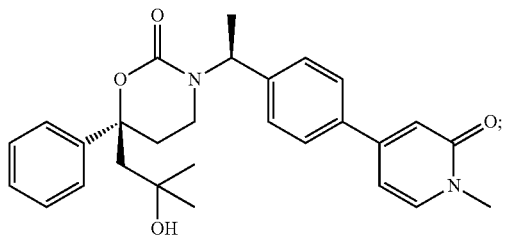

or a pharmaceutically acceptable salt thereof.

24. The method of claim 23 wherein the disease or condition is Type II diabetes mellitus.

* * * * *

UNITED STATES PATENT AND TRADEMARK OFFICE
CERTIFICATE OF CORRECTION

| | | |
|---|---|---|
| PATENT NO. | : 8,138,178 B2 | Page 1 of 1 |
| APPLICATION NO. | : 12/741522 | |
| DATED | : March 20, 2012 | |
| INVENTOR(S) | : David Claremon | |

It is certified that error appears in the above-identified patent and that said Letters Patent is hereby corrected as shown below:

In the Specification:

Column 191, line 26: delete "hyperglycemica" and insert --hyperglycemia--

In the Claims:

Column 194, Claim 2, line 44: delete "hyperglycemica" and insert --hyperglycemia--
Column 194, Claim 2, line 54: insert --;-- after structure
Column 195, Claim 4, line 6: insert --;-- after structure
Column 195, Claim 6, line 38: insert --;-- after structure
Column 195, Claim 7, line 48: delete "hyperglycemica" and insert --hyperglycemia--
Column 196, Claim 11, line 31: delete "hyperglycemica" and insert --hyperglycemia--
Column 197, Claim 15, line 14: delete "hyperglycemica" and insert --hyperglycemia--
Column 197, Claim 19, line 64: delete "hyperglycemica" and insert --hyperglycemia--
Column 198, Claim 23, line 47: delete "hyperglycemica" and insert --hyperglycemia--

Signed and Sealed this
Eighteenth Day of September, 2012

David J. Kappos
*Director of the United States Patent and Trademark Office*